US008980545B2

(12) United States Patent
Delwart et al.

(10) Patent No.: US 8,980,545 B2
(45) Date of Patent: Mar. 17, 2015

(54) DIVERGENT PICORNAVIRUS: COSAVIRUS

(75) Inventors: Eric Delwart, San Francisco, CA (US); Amit Kapoor, Pacifica, CA (US); Joseph Victoria, San Francisco, CA (US)

(73) Assignee: Blood Systems, Inc., Scottsdale, AZ (US)

( * ) Notice: Subject to any disclaimer, the term of this patent is extended or adjusted under 35 U.S.C. 154(b) by 1240 days.

(21) Appl. No.: 12/407,675

(22) Filed: Mar. 19, 2009

(65) Prior Publication Data

US 2012/0107357 A1    May 3, 2012

Related U.S. Application Data

(60) Provisional application No. 61/038,375, filed on Mar. 20, 2008.

(51) Int. Cl.
| | | |
|---|---|---|
| C12Q 1/70 | (2006.01) | |
| C12Q 1/68 | (2006.01) | |
| C12N 7/01 | (2006.01) | |
| C12N 5/00 | (2006.01) | |
| C12N 5/02 | (2006.01) | |
| C12N 7/00 | (2006.01) | |

(52) U.S. Cl.
CPC ...... *C12Q 1/701* (2013.01); *C12N 7/00* (2013.01); *C12N 2770/32021* (2013.01); *C12N 2770/32022* (2013.01)
USPC .............. 435/5; 435/6.1; 435/6.11; 435/6.12; 435/235.1; 435/320.1; 435/325; 536/23.72; 536/24.32; 536/24.33

(58) Field of Classification Search
None
See application file for complete search history.

(56) References Cited

U.S. PATENT DOCUMENTS

| | | | |
|---|---|---|---|
| 5,986,171 A | 11/1999 | Abe et al. | |
| 7,745,391 B2 * | 6/2010 | Mintz et al. | 514/19.3 |
| 2006/0159659 A1 | 7/2006 | Hallenbeck et al. | |
| 2006/0240466 A1 | 10/2006 | Hyoty et al. | |
| 2012/0107357 A1 * | 5/2012 | Delwart et al. | 424/216.1 |

FOREIGN PATENT DOCUMENTS

| | | | |
|---|---|---|---|
| WO | WO 98/14611 | 4/1998 | |
| WO | WO 2006/076423 | * 7/2006 | A01H 5/00 |

OTHER PUBLICATIONS

Kapoor et al., "Chacterization of a highly divergent picornavirus prevalent in stool samples of children with acute flaccid paralysis", *International Conference of Emerging Infectious Diseases 2008 Slide sessions and Poster Abstracts* (Mar. 17, 2008).

Parshionikar et al., "Development of homologous viral internal controls for use in RT-PCR assays of waterborne enteric viruses", *J. Virological Methods*, 121(1):39-48, 2004.
Swennen et al., "Oral poliomyelitis vaccine: time to change?", *Vaccine* 19(17-19):2262-2267, 2001.
Supplementary European Search Report, Application No. 09721869. 7-1222/2274447 (PCT/US2009037726), Blood Systems, Inc.
International Search Report (ISR) from WO 2009/117615 A3, filed Dec. 30, 2009, Blood Systems, Inc.
Allander et al., "A virus discovery method incorporating DNase treatment and its application to the identification of two bovine parvovirus species", *Proc. Natl. Acad. Sci. U.S.A.*, 98(20):11609-11614 (2001).
Allander et al., "Cloning of a human parvovirus by molecular screening of respiratory tract samples", *Proc. Natl. Acad. Sci. U.S.A.*, 102(36):12891-12896 (2005).
Breitbart et al., "Genomic analysis of uncultured marine viral communities", *Proc. Natl. Acad. Sci. U.S.A.*, 99(22):14250-14255 (2002).
Breitbart et al., "Metagenomic analyses of an uncultured viral community from human feces", *J Bacteriol.*, 185(20):6220-6223 (2003).
Cox-Foster et al., "A metagenomic survey of microbes in honey bee colony collapse disorder", *Science* (New York, N.Y.), 318(5848):283-287 (2007).
Culley et al., "High diversity of unknown picorna-like viruses in the sea", *Nature*, 424(6952):1054-1057 (2003).
Duke et al., "Sequence and structural elements that contribute to efficient encephalomyocarditis virus RNA translation", *J Virol.*, 66(3):1602-1609 (1992).
Edwards & Rohwer, "Viral metagenomics", *Nat. Rev. Microbiol.*, 3(6):504-510 (2005).
Fauquet et al., "Virus taxonomy", *8th reports of the International Committee on Taxonomy of Viruses* (Academic Press), p. 1162 (2005).
Feng et al., "Clonal integration of a polyomavirus in human Merkel cell carcinoma", *Science* (New York, N.Y.), 319(5866):1096-1100 (2008).
Finkbeiner et al., "Metagenomic analysis of human diarrhea: viral detection and discovery", *PLoS Pathogens*, 4(2):e 1000011 (2008).
GenBank: DQ401688.1. Theiler's encephalomyelitis virus, complete genome (Mar. 2, 2007). Retrieved from the Internet Aug. 17, 2009 at:<http://www.ncbi.nlm.nih.gov/nuccore/89280778> (nucleotides 5192-5206; 6924-6939; 7227-7239; 7304-7317).
Hales et al., "Complete genome sequence analysis of Seneca Valley virus-001, a novel oncolytic picornavirus", *The Journal of General Virology*, 89(Pt 5):1265-1275 (2008).
Hellen & de Breyne, "A distinct group of hepacivirus/pestivirus-like internal ribosomal entry sites in members of diverse picornavirus genera: evidence for modular exchange of functional noncoding RNA elements by recombination", *J. Virol.*, 81(11):5850-5863 (2007).
Hinton & Crabb, "The novel picornavirus Equine rhinitis B virus contains a strong type U internal ribosomal entry site which functions similarly to that of Encephalomyocarditis virus", *The Journal of general virology*, 82(Pt 9):2257-2269 (2001).
Hinton et al., "Internal ribosomal entry site-mediated translation initiation in equine rhinitis A virus: similarities to and differences from that of foot-and-mouth disease virus", *J. Virol.*, 74(24):11708-11716 (2000).

(Continued)

*Primary Examiner* — Shanon A Foley
(74) *Attorney, Agent, or Firm* — DLA Piper LLP (US)

(57) ABSTRACT

Presented herein is the discovery of a new human picornavirus, Cosavirus (previously termed Dekavirus), methods of detecting the Cosavirus and diagnosing Cosavirus infection, methods of treating or preventing Cosavirus infection, and methods for identifying anti-Cosavirus compounds.

14 Claims, 54 Drawing Sheets

(56) References Cited

OTHER PUBLICATIONS

Holtz et al., "Identification of a novel picornavirus related to cosaviruses in a child with acute diarrhea", *Virology Journal*, 2008, 5:159 (http://www.virologyj.com/content/5/1/159).

Jones et al., "New DNA viruses identified in patients with acute viral infection syndrome", *J. Virol.*, 79(13):8230-8236 (2005).

Jones et al., "Discovery of a novel human picornavirus in a stool sample from a pediatric patient presenting with fever of unknown origin", *Journal of Clinical Microbiology*, 45(7):2144-2150 (2007).

Kapoor et al., "A highly divergent picornavirus in a marine mammal", *J. Virol.*, 82(1):311-320 (2008).

Kapoor et al., "A highly prevalent and genetically diversified Picornaviridae genus in South Asian children", *Proc. Natl. Acad. Sci. U.S.A.*, 105(51):20482-20487 (2008).

Kistler et al., "Pan-viral screening of respiratory tract infections in adults with and without asthma reveals unexpected human coronavirus and human rhinovirus diversity", *The Journal of Infectious Diseases*, 196(6):817-825 (2007).

Koonin & Dolja, "Evolution and taxonomy of positive-strand RNA viruses: implications of comparative analysis of amino acid sequences", *Crit. Rev. Biochem. Mol. Biol.*, 28(5):375-430 (1993).

Kozak M., "Point mutations define a sequence flanking the AUG initiator codon that modulates translation by eukaryotic ribosomes", *Cell*, 44(2):283-292 (1986).

Lamson et al., "MassTag polymerase-chain-reaction detection of respiratory pathogens, including a new rhinovirus genotype, that caused influenza-like illness in New York State during 2004-2005", *The Journal of Infectious Diseases*, 194(10):1398-1402 (2006).

Lopez de Quinto & Martinez-Salas, "Interaction of the eIF4G initiation factor with the aphthovirus IRES is essential for internal translation initiation in vivo", *RNA* (New York, N.Y.), 6(10):1380-1392 (2000).

Martinez-Salas et al., "New insights into internal ribosome entry site elements relevant for viral gene expression", *The Journal of General Virology*, 89(Pt 3):611-626 (2008).

Mason et al., "Identification and characterization of a cis-acting replication element (cre) adjacent to the internal ribosome entry site of foot-and-mouth disease virus", *J. Virol.*, 76(19):9686-9694 (2002).

Modlin J.F., "Enterovirus déjà vu", *The New England Journal of Medicine*, 356(12):1204-1205 (2007).

Morens & Pallansch, "Human enterovirus infections", *Epidemiology*, ed Rotbart HA (ASM Press, Washington, D.C.), pp. 3-23 (1995).

Oberste et al., "Molecular evolution of the human enteroviruses: correlation of serotype with VP1 sequence and application to picornavirus classification", *J. Virol.*, 73(3):1941-1948 (1999).

Palacios et al., "A new arenavirus in a cluster of fatal transplant-associated diseases", *The New England Journal of Medicine*, 358(10):991-998 (2008).

Pallansch & Roos, "Enteroviruses: polioviruses, coxsackieviruses, echoviruses, and newer enteroviruses", *Fields Virology* (Lippincott Williams and Wilkins, Philadelphia, PA) 4th Ed. pp. 723-775 (2001).

Saeed et al., "Epidemiology and clinical findings associated with enteroviral acute flaccid paralysis in Pakistan", *BMC Infectious Diseases*, 7:6 (2007).

Saleh et al., "Functional interaction of translation initiation factor eIF4G with the foot-and-mouth disease virus internal ribosome entry site", *The Journal of General Virology*, 82(Pt 4):757-763 (2001).

Simmonds et al., "Detection of genome-scale ordered RNA structure (GORS) in genomes of positive-stranded RNA viruses: Implications for virus evolution and host persistence", *RNA* (New York, N.Y.), 10(9)1337-1351 (2004).

Solomon & Willison, "Infectious causes of acute flaccid paralysis", *Current Opinion in Infectious Diseases*, 16(5):375-381 (2003).

Strikas et al., "Temporal and geographic patterns of isolates of nonpolio enterovirus in the United States, 1970-1983", *The Journal of Infectious Diseases*, 153(2):346-351 (1986).

van den Hoogen et al., "A newly discovered human pneumovirus isolated from young children with respiratory tract disease", *Nat. Med.*, 7(6):719-724 (2001).

van Der Hoek et al., "Identification of a new human coronavirus", *Nat. Med.*, 10(4):368-373 (2004).

Welch et al., "Detection of enterovirus viraemia in blood donors", *Vox Sanguinis*, 80(4):211-215 (2001).

Witso et al., "High prevalence of human enterovirus a infections in natural circulation of human enteroviruses", *Journal of Clinical Microbiology*, 44(11):4095-4100 (2006).

Zhang et al., "RNA Viral Community in Human Feces: Prevalence of Plant Pathogenic Viruses", *PLoS Biology*, 4(I):e3 (2005).

\* cited by examiner

TTCTGAGACCGGCACGGTCAACCCGACTCATTTACGAGTTACTCATTTATTTTG
AAACATCATAAAGAACGTGAACCGCTCTTTGTTTCTTTAAGGAATTTAGAGTAG
AAAACATTTGAGATGAGGCCCGGTTGAACTCCGGGCGCTTTCCATCCGCTGTG
ATGGGCTCACTCCTGTACACCGTGAGTCCGCGCAGTGCTGACTTAACACTTAA
GTAATGTATAGGCCGAGGATTACACCGCTCGGCTCCCACCTTTCACCACCGTG
GGATTAACAGGTTCAATGCACAAATTCCTGTCCTTGGCTATGTCAAAGCAATAC
AGTGTGTACATGGCGTGCACGCTCAAAGCGGAGACTTAGGCCTCACAGATTGT
GTTTTGTGTTATTGGATGCTGGATGGTCACGTTGGAGACTGCATGTGGCAGTCT
TGAAACGTGTGGTTTGACGTCTATCCATTATGGCAGTGGGTGGAGTACTGCAA
AGATGTCACCGTGCTTTACACGGTTTTTGAACCCCACACCGGCTGTTTGGCGCT
TGCAGGACAGCAGGTTTATTTTCTTATGTTCTCCATTTCTAGCCAACAGGGTTC
TATCCTGTTGGGCGGAGTGATACTCCCGTTCCTTCTTGGACAGATTGCCTCCAC
GTTCTTTGTGGATCTCAAGGTGATCAAGTCACTGGTGAATAGAGCGAAGGTTG
AGGAGACCTGAGGAATTTCCATGTGGCTTTGCCAGGAGTTGTAGCGATGCTGT
GTGTGTGTGCGGATTTCCCCTCATGGCAACATGAGCCTCACAGGCCAAAAGCC
CTGTCCGAAAGGACCCACACAGTGGAGCAACCCCAGCTCCCTCCTACAAAGCT
TTGTGAGAATGAACTCAAGTTTATTCTACTTTATTCTCTATTTACATCAGGCCCC
AAAGATGTCCTGAAGGTACCTTGTGTATCTGGGCACGAGCACCATCAGCTACC
CGGACTTGTATTTCGGTACAGACACATGTGGTGACCCAGCCCCTCTGCTTCGG
CAGGGGGGCTTTCGCTCGCTCAGCACGAGATCTGATCAGGAGCCCCTCCCAGT
GTGCTTTACACCTGGCGAGGGGTTAAAAATTGCCCAAGGCCTGGCAAAACAAC
CTAGGGGACTAGGTTTTCCTTTTATTAATAATATCTGTCATTATGGGTGCAAAT
AATAGCAAAGAATCTGTGTCCAGCAATGGCAACGAGGGAACAATTGTTAATAA
CTTTTATTCAAACCAGTATTATGCTTCTATTGATGCTTCTGCCCAAGGTGTTGG
GACCTCTACTACTCCTGAAAACGGCAACGTATCTGGCTTTCTTGGACTTGCAGG
TAGTGCTTTTAATGCTCTCTCTCTTCTCGCCTCACCACGAACCGAGACAGGAAT
GATGATGGAAGATCGTGTCCTTTCCCGTACTGCCGGTAATACATCTGTAAACTC
TCAAGCTGCTGAAGGGGTTTTGCAGGCATATGGGACTGAGACAGACAGCAATT
CGCCCACTTCGTGTGGCGACGATCCTAGCAAGGGTACACACGCAACAGACAGA
GCCTTTGTAATACAATTGCTTCCATGGAAACAGACAACAAATTCATACTTTGCT

FIG. 1-1

```
CAATGGGTAAGACTCACACAGAAACTGTCAAACAATTTGCATGGAAATGTTATG
GCCAAAAACATTAAATCACATGCTTTTGCCAAAATGGGCTTTGAAGTAATGTTA
CAGGCAAACACCTCGCCTTTCCATAATGGCATACTGGGTCTTTTCTTGGTACCG
GAGTTTGTTAGAAAGGGTGAAATTACAGATGAGTGGATTGACCTCACACCTAC
CTCTTCTTTAGTTTCAAACACTGAGTTGTACAACCCCCAGACTTATGCAAATTTT
CCATTTGATGCTAAACATAGTTTTGATTATTCTGATATTACACCAGAACAATTTA
TGATTTTCCCTCACCAACTTATAAATCCTAAAGACACAAATGTTGCCACAGTAC
GTGTGCCGTACATTAATATTGCTCCAACAAATGATACTACAGTACATACAGTAT
GGACAGCTGTTGTTATGGTTCTTGTACCTCTTAACTTTTCTTCTGGTGCTTCAC
CAACTGTATCTTTAACATTAACTATAACTCCAATAAACTCAGTTTTTAATGGATT
ACATCACACCGCACAGGGGCCTATCCCTGTGCGACCTTTCCATAATTTCCAGCA
GTTTAGCACTACTGTCCCTCTGCGCACTGAACCATGTTACGGCATGACAGTGAC
TCCTCCAGTTGATTACATGCCCTTACCCATTACAGATTTAGTTGAGCTTGCTAA
AGTGCCCAGTTTTGTTACTGTGGCAAACAGTGACACGACTAGCGAGCGTAGTT
TCCCTTATTTCTCTGTTAGTAACACAGAACAAGGCAGAAATCTTTTCAAATCCA
GTGTAGTTCTCAGCGACTTACACTACCAGCACACTCTTGTAGCAAATTTGGCCC
GTTACTTTTGCAACTACAGAGGTAGTCTACAGTTTGATTTTATAGCTGCAACAA
CTGCAATGACAAGAGGCAAATTGCTCATTAGCTACACCCCACCAGGGGCTGGT
GAGCCACAATCAATTGATCAGGCAATGATGGGAACTTATGCTATCTGGGATTTG
GGATTACAATCAACCTTCAATTTTGTAGTCCCTTTTATATCTGCTTCTGACTTCA
GATTTAACACCTCTTCTGTATCTAATGCTTTGAACTCTGATGGTTGGATCACAG
TGTGGCTTATGAACCCTCTAACATATCCTCCCAGTACACCTCCTACCCAACAGA
TATTGATGTTGATGTCAGCTGGCAGTGACTTTTCTTACCGGTTGCCCATTTCGC
CCGGTTTCGCCGAGGGGGAAACGAGCGAACATCCAATGGACAACGCTGAGTGC
GGGAAAATTGATGACAAAGACGCAGGAATGTTTTCCGGACACTCTGTTGGGCT
GCCTACTCCCCACACCTCGACTTCTTTCTTCTATGACAGGTACAGATTCGTAGG
AATTGTAAAGAGTGTAGTGAATAATACTCCCAAACCAGTCAACATTTATGATGA
TACAGGAAAAGTTAAGAACCTACAACAGGTTTTTCCAACTTCAGACACACTACT
GCCCCACTCTTTGATGTCCCTTTCTCCCTGTGCGTCAGTGTGTGGCCAGCCTAT
CTCTTCCTTCCTGTTTGCTCAACGAGCGAATCCCAAGAAAACTCTAAAGCTGCG
CTCAGGTGATGAATTCTTGTATAGATGTTGCCCTTTTCTTACATTAAATGTGA
```

FIG. 1-2

```
CCTTGAGTTTACTGTGGTCCCCCCTGCGAATTCTACTAGAGATTATATTGTGCA
CTGGTACCCGCCAGGGGCCACCCTGGATGCTGGAGAAGTAGCCGTGGGTAATA
CATCAGGTAGCAATGGCTTTGATGATAATGGGATGAACGCTGGTTCTAGTCTGT
TTTCTTACAATCCTACTTTCCACGCAAGAGCTCCGTCAAAAGTCTCAGCTGTTA
TACCTTTTTGCTTACCCGTTTCTCTATTACCTCTATATTTTGATGGCTTTCCCGA
TTACAGTACTACAAAAGGAATGTATGGATGCTCCCCTTCTTTTAGTTTTGGAAC
CATATACATTGAATCTGGACTCCAAGAAACTTATTCAGTTTACATTAGATACAA
GGATTTTAAGGGTTATGCTCCCAGACCGCTCATTCGGACACCACACATTAGGCT
ATCAGAAAGAGCTAGATATATTATGGCAGACTCGGTGCTTCCACGCCCTCTCAC
ACGCGCTGAACGTGATGTGGCGCGTGATTTGCTGCTCATTGCTGGGGATATTG
AATCAAATCCAGGACCTGCATTTAATCCAGAATATACAGCTCATGGCCCAGTTA
CTGAATTGATTCAATTGGCAAGGAAACCAGAAACTGTAGATAATGTAAATAGGC
TTCTCACAACCCTGAATACTCTTATGGCTAAATGGAACAATCTCAAGGATACTG
TTACAGATGCTGTGTTTCTTAGAGACATGGTATGTCTTCTTGTGAAGCTTACTT
CTCTTATGTACTTGGTTCATGGACAGGGACCAGGTGCTTACTTTGCTGCTGCCT
CCATTCTTCTTGCTGATGGCATAACTTTCTTTGATTGGTACGAGAAAATCAAGA
TTTTCATGGCTAGAAAACTCAGAGTTTCCCCTCCCTTCTTCCCCGCTGCCCAGG
GGCCGGACCTTAGAGACTTTGTGACCTTTTTCAACGCAGCGCGCGGAGCGCAA
TGGATGATTGATTCTCTCAAATCCCTTATAACTTGTATCAAACAATGGCTTGAA
CTTGAAGAGGAAAATGAAGCAGTACAACTTGAAAAGATGTTAATAGACTCTCCC
AGACATTGCAAGGCAATAAATGACTACAACAGAGGTGACTCCTTTCAGAGACC
GACCAACTCTTTTGAATTCATGGACAGACTTGTGGAATGTGCTACCAAGCTTGG
GAAAGTCCAAATTGCAACTTATTTCAGAAATTTTACTACAGCTGATTCTGATAC
AAGCAGACCAGAGCCAGTTGTTGTTGTTTTGCGCGGGAAACCAGGCGTAGGCA
AATCTGCTGCAGCTACTGTTATGGCAGCTGCAGTATCTAAATTGTTGGTAGGAA
GTCAATCAGTGTACACCCTTTCCCCAGATACGGAACATATGGATGGATATCACG
GACAGTTTGTGACTTTGATGGATGACCTTGGACAAAACCCAGACGGAGAAGAC
TTCAGATGTTTCTGTCAAATGGTTTCTTGTGCTCAGTACAGACCTGCTATGGCT
GACCTTAAAGACAAAGGAATCCTGTTTACATCCAGACTGTTGATTGCTACTACT
AATCTCCCAGATTTTAACCCTGTTACTATCTCTGATCCGCGAGCTTTAGATCGT
CGGATCACTTTTGATATTCTTGTCACTCCAGGTTCTGCCGCCACCAAGAATGGG
```

FIG. 1-3

```
AAACTTGACTTGGCCGCTGCTCTCAAACCAGATGGACCGGGAGAACACCCTTA
CACTTCTGATTGCCCTATTCTCCACACCACTGGACTCCTCCTGAAGAACCTCAG
AAACAACCAGACCATGAACTTGAAAGACCTAGTGGACATGATTGTTAAGAGAAT
TAAACACAAGAAGAAGTTGGAAATATGCTTGACTCTCTTGTTGCTCAGGGACC
TACTATGATTGTTGGCTATACCAAAGACGATGATGGTATCGCTATTGTGGACTG
CTTGGAAGAATGGAACAAGATAAAGGACAAGAAGAAGAAACAGCTTGCTTTGG
AAATGGTTGCTCAAGAACTTAAGGACAAACATGAAGAACATAAAGGCACAATC
AAATTACTCAAAATGTTTGTTACTGGCCTTGGAGTGGTTGCCGCTGTTGCAGGC
GCGTATGCCACAATGAAATACTTTACAAAGGACAAACCCAAGGAAGAAGAAGA
AGAGCCAGAAGAAAGAAAGAGAAGAAAACAGAAGAATCCAAAGAGGCTGCAG
GACCATACAACGGACCTACAAAGAAAGAAATTAAAACATTGAAGTTAAAGGCC
CAGAGTCCACTTATGGATATGGAAAGAAAATTGCCCAGAATGTCATGCCCTTC
CAGATTTTCTATAATGGAAAAAGATACACCCAGTCTTGTCTGGCAATTGGAAAA
AGAGTTATTCTTGTGAACAAACATGCTTTTGAATCAGTTGAACACAAATTTGTT
GTTGACCAAAAGGAATACACATTGGACCAGGTTACAGCTATTTCCCTTGACTGC
GGATCAGGTGTCACGGATGTGTGTGCTGTATGTTTGCCCCCAGGCCCAGACTT
CAAATCAATAAAGAAACATTTCCTACCCTTCAACACTACCATGTTTCCAGGAAC
CAGACTGACCATCCTCTCGAATGACCACTACCCTATGTCCAGAGAAGGCTCTTT
CCTCAGATTTGAGGATGAGGTACCGACTAATGTAGGTAACATGCCCTTTGTAAT
GCTTTACAAATCAACCTCTTATTTTGGAATGTGTGGCTCAGTTGTATGTAGCAG
ATTTGTTGATGGTGGAGGAATAATTGGAATGCACTGCGCAGGTGGAGGCGGAG
TCAGTGTTGGAACTCGTTTGACTGCTAGAATGATTGAATCAGTTTTTGATTACT
TCTACCCCCCAGTAGCCCAGGGAATAATTGAAAACACAGAGACAGGACCCCGT
GTACATGTGCCCAGAACTTCCAAACTCAAAAGAACAAACGCCACTTATCCGGCA
ACGGAAAAGTATGGCCCAGCTGCTCTTTCGCGGTATGATCCGCGATTAAATGA
GGGAGTCAACTTGGATGAGGTGATCTTCTCAAAACATACTCAAAACACTCTTGT
TGAGAAAGGATCCACTTTCAGAAGCGCCCTTGACATGGCAGCAGAAATTTATG
GTGAAAAGTTTAGAGGAAATGATTTCTCTCCCCTTTCAGTTGAAGATGCAATTC
TTGGAATTCCCGGACTTGACAGACTTGACCCGAATACTGCTTCTGGATTGCCCT
ACACTAAAACCAGACGACAGATGATTGACTTCAACACAGGACAGATTTTGGAC
GACACTCTTAAGTGTCGACTTGGACAATGGCTTGCAGGACGACCCCCCCAGGA
```

FIG. 1-4

AGTACATTACCAGACATTTCTTAAGGATGAAATCAGGCCCATTGAAAAGGTCAA
AGCAGGAAAGACTAGAATAATTGATGTTCCTCCTCTTGATCATGTCATCGCTTT
TAGAATGCTCTTTGGCAGATTCATTGCCCACTACCACTTAAACTTTGGCTTCAA
AACAGGCTCTGCTATTGGTTGTGACCCAGATGTCGCTTGGGCTTCTTTTGGCTT
TGAACTCAGTGGCTTTCCTTATCTGTATGATTTTGATTACTCAAACTTTGATGCT
TCTCACAGTACTTCAATATTTGAAATCTTAGAACAGAAATTCTTTTCCCCAGAAT
TAGGTTTTGATCCTAGATGCTCACTTCTCTTGAAATCCCTTGCAGTTTCAACCC
ACTGTTATGAGAACAAGAGACTCCAGATTGCTGGAGGACTTCCCTCTGGCACG
GCAGGTACCTCAGTACTGAACACCGTGATAAACAACATTATCTTTCACGGTGCA
CTATACCACACTTACACTAATTTTGAGCGGGATGACATCAGTATGTTAGCCTAT
GGCGACGACATTGTTGTTGCCTCCAAATTTGAACTTGACTTGGTTATGGTTAAG
GCTTTCATGAACCGGATTGGCTATAAGATTACCCCTGCAGACAAAAGTGATGAA
TTCAGACCAAAGTGTATGGATGACATTTGCTTCTTAAAGAGGCGTTTTGTTAAA
GTTGCTGGAGTTTGGGCTCCAGTGATGGAAACTGAAACCTCGAGGCAATGTT
GTCTTGGTACAAACCAGGAACTCTTAATGAAAGCTCCAGAGTGTCTCAAGACT
TGCCCACTTCTCAGGACGTGACGTGTATGACCACCTTTTCAAGCCCTTCATTCG
TGATGGGTTTGATGTCACACCTTGGAAACAGTTACACTTGGAATGGCTTAATAA
GTTATCAGCTTAAAGAATTTTGAATTGGCATTTCAGATTTATTTTGAATTTGGCT
TTTAATTCGGCTTTAATTTGGTTATTTATTGGGTATATTCAAATCTAATGACC

FIG. 1-5

MGANNSKESVSSNGNEGTIVNNFYSNQYYASIDASAQGVGTSTTPENGNVSGFLGL
AGSAFNALSLLASPRTETGMMMEDRVLSRTAGNTSVNSQAAEGVLQAYGTETDSN
SPTSCGDDPSKGTHATDRAFVIQLLPWKQTTNSYFAQWVRLTQKLSNNLHGNVMA
KNIKSHAFAKMGFEVMLQANTSPFHNGILGLFLVPEFVRKGEITDEWIDLTPTSSLV
SNTELYNPQTYANFPFDAKHSFDYSDITPEQFMIFPHQLINPKDTNVATVRVPYINIA
PTNDTTVHTVWTAVVMVLVPLNFSSGASPTVSLTLTITPINSVFNGLHHTAQGPIPV
RPFHNFQQFSTTVPLRTEPCYGMTVTPPVDYMPLPITDLVELAKVPSFVTVANSDTT
SERSFPYFSVSNTEQGRNLFKSSVVLSDLHYQHTLVANLARYFCNYRGSLQFDFIAA
TTAMTRGKLLISYTPPGAGEPQSIDQAMMGTYAIWDLGLQSTFNFVVPFISASDFRF
NTSSVSNALNSDGWITVWLMNPLTYPPSTPPTQQILMLMSAGSDFSYRLPISPGFAE
GETSEHPMDNAECGKIDDKDAGMFSGHSVGLPTPHTSTSFFYDRYRFVGIVKSVVN
NTPKPVNIYDDTGKVKNLQQVFPTSDTLLPHSLMSLSPCASVCGQPISSFLFAQRAN
PKKTLKLRSGDEFLYRCCPFSYIKCDLEFTVVPPANSTRDYIVHWYPPGATLDAGE
VAVGNTSGSNGFDDNGMNAGSSLFSYNPTFHARAPSKVSAVIPFCLPVSLLPLYFDG
FPDYSTTKGMYGCSPSFSFGTIYIESGLQETYSVYIRYKDFKGYAPRPLIRTPHIRLSE
RARYIMADSVLPRPLTRAERDVARDLLLIAGDIESNPGPAFNPEYTAHGPVTELIQL
ARKPETVDNVNRLLTTLNTLMAKWNNLKDTVTDAVFLRDMVCLLVKLTSLMYLV
HGQGPGAYFAAASILLADGITFFDWYEKIKIFMARKLRVSPPFFPAAQGPDLRDFVT
FFNAARGAQWMIDSLKSLITCIKQWLELEEENEAVQLEKMLIDSPRHCKAINDYNR
GDSFQRPTNSFEFMDRLVECATKLGKVQIATYFRNFTTADSDTSRPEPVVVVLRGK
PGVGKSAAATVMAAAVSKLLVGSQSVYTLSPDTEHMDGYHGQFVTLMDDLGQNP
DGEDFRCFCQMVSCAQYRPAMADLKDKGILFTSRLLIATTNLPDFNPVTISDPRALD
RRITFDILVTPGSAATKNGKLDLAAALKPDGPGEHPYTSDCPILHTTGLLLKNLRNN
QTMNLKDLVDMIVKRIKHKKEVGNMLDSLVAQGPTMIVGYTKDDDGIAIVDCLEE
WNKIKDKKKKQLALEMVAQELKDKHEEHKGTIKLLKMFVTGLGVVAAVAGAYA
TMKYFTKDKPKEEEEEPEEKKEKKTEESKEAAGPYNGPTKKEIKTLKLKAQSPLM
DMEKKIAQNVMPFQIFYNGKRYTQSCLAIGKRVILVNKHAFESVEHKFVVDQKEY
TLDQVTAISLDCGSGVTDVCAVCLPPGPDFKSIKKHFLPFNTTMFPGTRLTILSNDH
YPMSREGSFLRFEDEVPTNVGNMPFVMLYKSTSYFGMCGSVVCSRFVDGGGIIGM

FIG. 2-1

HCAGGGGVSVGTRLTARMIESVFDYFYPPVAQGIIENTETGPRVHVPRTSKLKRTN
ATYPATEKYGPAALSRYDPRLNEGVNLDEVIFSKHTQNTLVEKGSTFRSALDMAAE
IYGEKFRGNDFSPLSVEDAILGIPGLDRLDPNTASGLPYTKTRRQMIDFNTGQILDD
TLKCRLGQWLAGRPPQEVHYQTFLKDEIRPIEKVKAGKTRIIDVPPLDHVIAFRML
FGRFIAHYHLNFGFKTGSAIGCDPDVAWASFGFELSGFPYLYDFDYSNFDASHSTSIF
EILEQKFFSPELGFDPRCSLLLKSLAVSTHCYENKRLQIAGGLPSGTAGTSVLNTVIN
NIIFHGALYHTYTNFERDDISMLAYGDDIVVASKFELDLVMVKAFMNRIGYKITPAD
KSDEFRPKCMDDICFLKRRFVKVAGVWAPVMETENLEAMLSWYKPGTLNEKLQS
VSRLAHFSGRDVYDHLFKPFIRDGFDVTPWKQLHLEWLNKLSA

FIG. 2-2

|         | SEQ ID NO'S 18-22<br>L/1A | SEQ ID NO'S 23-28<br>1A/1B | SEQ ID NO'S 29-34<br>1B/1C |
|---------|---------------------------|----------------------------|----------------------------|
| EMCV    | <61>VVFELQ\|GNSTSS        | <58>MLPLLA\|DQNTEE         | <244>ETLSRQ\|SPIPVT        |
| Mengo   | <61>VVFETQ\|GNSTSS        | <58>MLPLLA\|DQNTEE         | <244>EVLSRQ\|SPIPVT        |
| Saffold | <65>VLMEPQ\|GNSNSS        | <60>IAPLLM\|DQNTEE         | <257>SVLEAD\|SPIPVT        |
| HCoSV   |                           | <62>ALSLLA\|SPRTET         | <253>LHHTAQ\|GPIPVR        |
| FMDV    | <193>AGLFLR\|GAGHSS       | <73>FGALLA\|DKKTEE         | <207>EKPAKQ\|GIIPVA        |
| ERV-2   | <213>RDSQCR\|GAGHSR       | <58>QSLALL\|DQDTEE         | <244>RQTVSE\|GIPGTQ        |

|         | SEQ ID NO'S 35-40<br>1C/1D | SEQ ID NO'S 41-46<br>1D/2A | SEQ ID NO'S 47-52<br>2A/2B |
|---------|---------------------------|----------------------------|----------------------------|
| EMCV    | <219>APWSPQ\|GVENAE       | <265>GVLMLE\|SPNALD        | <131>IETNPG\|PFMFRP        |
| Mengo   | <219>APWSPQ\|GVENAE       | <265>GVLMLE\|SPNPLD        | <131>VETNPG\|PFTFKP        |
| Saffold | <219>TKYTPQ\|GVDNAE       | <263>QILELQ\|DPISIY        | <121>VETNPG\|PVQSVF        |
| HCoSV   | <233>GFAEGE\|TSEHPM       | <279>RYIMAD\|SVLPRP        | <18> IESNPG\|PAFNPE        |
| FMDV    | <210>VDPVRQ\|TTSSGE       | <204>VKKQLC\|NFDLLK        | <4>  VESNPG\|PFFFSD        |
| ERV-2   | <218>TYPRVE\|GTENME       | <307>LSQGAT\|NFDLLK        | <4>  VESNPG\|PTIWSM        |

|         | SEQ ID NO'S 53-58<br>2B/2C | SEQ ID NO'S 59-64<br>2C/3A | SEQ ID NO'S 65-70<br>3A/3B |
|---------|---------------------------|----------------------------|----------------------------|
| EMCV    | <138>SLFQQQ\|SPLKQV       | <313>QTLVAQ\|APVDEV        | <76> LDEQEQ\|GPYNETA       |
| Mengo   | <139>SLFQQQ\|SPLKQV       | <313>QTLVAQ\|GPVDEV        | <76> LDEQEQ\|GPYNETT       |
| Saffold | <124>PLLQQQ\|SPIREA       | <313>NTLVAQ\|SPGNDM        | <74> LSEGEQ\|AAYSGGK       |
| HCoSV   | <109>FFPAAQ\|GPDLRD       | <309>DSLVAQ\|GPTMIV        | <96> ESKEAA\|GPYNGPT       |
| FMDV    | <142>ERAEKQ\|LKARDI       | <306>HPIFKQ\|ISIPSQ        | <140>EKPQAE\|GPYAGPL       |
| ERV-2   | <271>QALLSE\|GISSTL       | <305>GGIFAQ\|SRDRYY        | <120>DSIFEQ\|SRAYNIP       |

|         | SEQ ID NO'S 71-76<br>3B/3C | SEQ ID NO'S 77-82<br>3C/3D |
|---------|---------------------------|----------------------------|
| EMCV    | <7>  QLLDIQ\|GPNPVM       | <193>NAFEPQ\|GALERL<454>   |
| Mengo   | <7>  QLLDVQ\|GPNPTM       | <193>QAFEPQ\|GALERL<454>   |
| Saffold | <7>  QVLDVQ\|GGGKIV       | <205>DCLTPQ\|GAIVEI<455>   |
| HCoSV   | <6>  LKLKAQ\|SPLMDM       | <191>YPPVAQ\|GIIENT<457>   |
| FMDV    | <58>APIVTE\|SGCPPT        | <201>PPPHTE\|GLVVDT<464>   |
| ERV-2   | <27>EAHIPQ\|GPVCEV        | <222>GEPVAQ\|GWTYFD<462>   |

FIG. 3

>HCoSV-D-5004

AATAGCAAGGAGAGTGTGTCCAGCAATGGCAATCAGGGTACTATTGTCAATAATTTTTATGCTAACTCATATTATGCTTC
TATTGACGCTTCTGCCTCCTCAGTCGGGGGCGATACTCCTGCTGAAAATGGTACTGTATCTGGCATTCTCGGAAGTTTTG
CTTCTGCTTTCACTTCCGCTGCACTACTAGCAAAACCAAAAGTTGAAAATGACACAAACATGGAAGACAGAGTAATAACA
CTCAAAGCAGGAAATACAATTGTCAATTCTCAGGCTTCTGAAGGTGTTCTACATGGTTATGGCATTGGAACAAACACACA
GAGACCCTCTTCATGTGGTGATGACCCCTCAATTGCGACGCACTGTATTGAGCGAGGGTTTACCATCAATTTGGCTGACT
GGGACAAATCCAAGGAATCATGGCAGGCACTTGTTTACAGACTCTCAGATCATTTGAAAGATGATACAGTAGGTAACATG
TTTTCCAAGACTTTGGGAACCCACGCTTATACTAAGTGTGGTTACAGAGTCAGTCTGCAAATTAACACATCTCCCTTTCA
CTCCGGTCTTATTGGCTTATTCTTAGTTCCAGAGTGTTGTATACCTGCTAGCTTGAATATGGATTGGATTGATTTAAAAA
CTCAGCTACCATTACTGACAAGCAGCTCGCACTACCAGGGTTTAGGTCTTTCAACAGGTCAAGGGACAATATCTGAAAAG
GGTTCTATTGATGCTGCTGGTACAATTCCTCAACAACTCTTCATATATCCACACCAGTTGATTAACCCAAAAGACACAAA
CATAGCCTCAGTTGAAGTTCCTTATGTAAATTGTGCTCCCACCTCAGATCCAATGATACACAACATTTGGACTGCTCTTG
TAGTAGTTATAGCTCCTCTCCAGTCTAATGCATCAGCTTCTCCTACTGTAGCAATGTCTATGACTGTAACTCCAGTGGGT
GCTGTCTTTAACGGACTAAGACACCCTGCTCCTAATGTACAAACAGCAATACCTGTTAGAATGACACAAAATTCTGGACA
GTTTTCCACAACTCTTCCTGCTAGAATGGAACCATGTTATGGCTTAACTCCCAACCCCACCAGAGACTTTCTTCCCCCAG
TAGTCGAAGATTTACTCAGCATAGCAAAAGTCCCTTGTTTCCTGCTGGCAGATGAAGATACCACAAAACAGAAACCCTAT
TTTCTTATTTCAAATGCCTCTTCAACTCAAACAGCTGTTTTTGAAATGAATGTCATACTCAGTGAATATGCGCTCCAGCG
CACCTTTGTGTCAATGTTTGGAAAGTTTTTCTGTAACTACAGAGGCAGTATACAGATTACCGCCTGGGCAGCTGTGACAG
CAATGACTAGGGGAAAGTTGCTCTTCTCTTACACACCACCAGGTGCAGGTAAACCACAAAACATAAAACAAGCAATGATG
GGTACCTACACCATATGGGACTTGGGTCTCCAATCCACTCTTAATTTCACCATTCCTTACATCTCCAGTGTAGACTTTAG
AATTAACTCTAGGGCTGTTGCTTCTGCCTTGAATGCTGACGGGTGGCTTACTATTTGGATCCTCAATCCTATAACTTATC
CTCCACAGACTCCTCCACAACAAGCCATTTTGTTAATGGCTTCTGCAGGTTCTGATTTTTCATACAGATTGCCTATAAAC
CCTCCCTTCGTCCAAGGAGATATCCATGACAACGCAGAAAAGGGACTCACTGAAACAACTGATGCAACCCAGTTCTGTGG
TGCCGCTGTTGGGTACACAACAAATCATTCAAATTGTGAATTCTTCTTTGATAGATATAGATTTGTAGGTTTTATAGATG
CTGTTAGAAACAACAAAAGAAGTGTGATTTCTGTTTTTGACTCAAACAACAAAGTCAAGAGAATTGCTGAATTGTTTAAA
GAACCAAACAAACCAGGTAATTATTTCACTTTATCACCAAACCCAGCAATTTCGACAACTCCTATGTCAGCTTACATTGT
CATAGATCATCCTTCTTCAACTTCAAGCCCTTACACTCAGTATGCTATTGCAACAACTGGTGATCCCTTCTTTCTAAGAT
CTTGCCCCTTCACATACTTTCACTGTGATTTAGAGGTAACAATAAAACCAGAAAATGCAGTTTCAGGTGTTTGGCGCGCC
ACTTGGTATCCACCAGGCTCGGACTTAAAAGAAGATGAGGTTGTTCCAAGTTTTAGGACTACAGGTGAATCTGGTAATAT
GTCTCTTACTGTAAACAATAGAGAGAGGTCAACAATATATAATACTTATCCCACCTTTTACTCTAGGGATGGTCAGTGTG
TTTCTTTTAACATACCCTACACCTCACCTCTTAGTGTTATTCCTACCAGATTTGATGGTTATCCTGACTATTCAAGGACT
GTTGGTGCATACGGTGTGGCCCCTGCAAACCACTTTGGCACTTTGACTGTAGCTGCTAATGATGAAGGTTACAAATTCTT
TGTTTATGTTAGATACAAAAACTTCAAAGGGTATGTCCCCAAGACCCTACCTCCACAACCACTGTTTTTAAAGAATTCCA
GAAGTTTGACTAATGAAACAATAATAGCAAGACCTTACATTAGAGAGAGCAGCAATGTCTCTAGATTAAAGCTCCTACTT
TCAGGTGACATTGAAACAAATCCTGGACCTAATCACTCTAAATTTCAGGTACAAGGATCCATGTCAGATTTTTTAAATGT
GGCCAGAAAACCAGAAACATTGGATAATGTGACCAGGCTTTTAACTACTTTAAATAATCTAATGAATAAATGGAACAATG
TTAAACATATGTGTACTGATTCTTATTTTCTAAGAGATATTCTGTGCTTGCTTGTTAAGCTTACATCACTCTCATACCTT
GTTGCAGGACAGGGACCTTCTGCTTACTTAGCTGCTTCCGCTGTGCTCATTGCGGACGGCATTTCTTTCCTTGACTGGTA
TGAAAAAATAAAAAGATTTCTTGGTTCTCGTTTTCGAGTTCCACCTCCTATCTTCACTCTTGCCCAAGGACCAGATCTTA
GAGACTTAGTTACTTTCTTTAATGCTGCTAGGGGCGCACAGTGGATGGTTGATTCCATCCGTGGACTGATTTCATGGATC
AAACAATGGCTTGAACTGGAAGAAGCAAACGAAGCTGTCCAATTCGAAAGACTGTTGATAGAAAGTCCCAAGCACTGCAA
GGCAATAAATGACTACAATGTTGGAAAAAGCTTTATTAGACCAGAGAACTCCTTTGACTTCATGGAAAAACTTGTGGATT
CTGCCACAAAACTTGGAAAAGTGAACATTGCAGGTTATTTCAGATCTTTTACCTCGGTTGACACAGATACAGCAAGAATG
GAACCAGTTGTCTTGGTACTACGTGGCAAACCAGGAGCTGGAAAATCAGCAGCAGCTACTATCATCACAGCTGCTGTCTC
CAAAATTTTGACAGGAACTCAATCTGTTTATTCTCTCTCCCCTGACACTGAACACATGGACGGATATCACGGCCAGTTTG
CAATGATCATGGATGATTTAGGACAAAACCCAGATGGAGAAGACTTTAGAACTTTCTGTCAAATGATTTCAGTTGCACAA
TACAGACCTTCAATGGCTGACTTAAAGGACAAAGGCATTTTGTTTAAATCCCAGTTTATTGTTGCAACAACAAATTTACC
AGAGTTTAGACCTTTGACTGTTTCTGATCGCGGAGCTGTTGACCGCAGAATAACATTTGATATTGGTGTGACCCCAGGTA
CTGCTGTAACAAAAAATGGAAAGCTTGACCTTGCCATGGCTTTGAAACCAGACGGTGAGGGAGAGTTCCCTTACTCGTGT
GATTGCCAGATATTACACACTACTGGACTTGCTCTACAGAACCTCAGAACAGGCAAAACAATGAACATCAAGGAATTAGT
TGATTTAATTGTAAAGAAAATCAAGAGCAAAAGGACTACAAGCGGAATGCTTGAAGGACTGGTGGTGCAGTCGCCCAAAA
TTGTAGGCTACACCAAGGACGACGAGGGCGTCGTCATTGTTGACTGTCTCGAGGATTGGCACAGAATTCGAGACAAGAAA
AGAAAGCAACAGGCTCTTGAGATGGTTGCAGAGGAGATGCAAATTCAACATGACAAACATTCTCAGACCATTTCCTTGAT
AAAACAGTTTCTCTCAGGGCTCGGTGTGGTGGCTGCTGTTGGAGCCGCCTTTGCCGCAGGCAAGGTACTGAAAAACATGA
TGACCTCAGACCGGGCACAGGATGAACCAGACTCTGAATCCCAGGAGAAGACTGAAGAAAAACAAAAAGCTGAAGGACCA
TACAATGGACCAACAAAGAAGGAACTGAAAACTCTAAAGCTGAAAGCCCAGGGCCCCTTGTTGGATCTTGAAAAGAAGGT
CCTCGCTAACGTGCAGCCTTTCATTTTGCGCGTTGCTGGTAGAGACTACATTCAATCTTGTCTCTTTGTTGGAAAAAGGG
TTTTCCTTGTGAACAAACATGCAATTGACTCAGTTGAACAAAAATTTCAAGTTGCAGGAAAAACATATGACTTGGATGAT
GTTGATGTGGCAATTCTTGACACGGAATATGGACTTACGGATGTTGCAGCTGTCAAGCTCAACACAGGCCCAGAATGGAA

FIG. 4-1

```
AAACCTTTCAAAACTCTTTGTTTCACTGGACACGACTCTACACCCAGGAACCAGGATAACGATTTTGTCTAACGACCAAC
TTAACATGGTGAGAGAGGGTAGTTTTCTCAGAAATGAGGATGACATACCCACCAATATTGGCCCAATACCTTTTGTCATG
CTTTATAAGGCTTCCTCTTACTTTGGTATGTGTGGTTCTGCTGTTGTGACCAGAATTGGTGATTGTCCCGGAATTCTTGG
TCTCCATTGTGCTGGCGGTGGGGGTGTGTGTGTGGCTTCCAGAGTTACAAAAAGAATGGTAGAAACTGTCCTAAAATACT
TTTATCCACCTCAGGTACAGGGACAAATTATAAACACAGAAAATGGACCCCGTGTGCATGTTCCCAGACAGTCTAAGCTC
AAAAGAACAAATGCTGTTTATCCTGCTACTCCAAAATATGGACCTGCTGTGCTTTCTAAGAATGATCCCAGGCTTGACCC
AGATGTGGACTTTGACAAAGTAATTTTCTCAAAACATGTTGCCAACGTGGTTATTGATGAGGACACTAGTTTCTGGAATG
CCCTAAAAATGTCTGCCCAAATATACGCAGAAAAATTCAAAGGTGTTGACTTCTCCCCTCTCACTGTAGAGGAAGCAATT
CTTGGAATTCCAGGACTTGACCGGATGGACCCCAATACTGCTTCAGGATTACCCTATACTAAAACTAGAAGACAGATGAT
TGATTTTCAGGAAGGGAAAATACTTGACCCAGAACTCCAATCCAGACTTGACACTTGGCTTTCAAATAAACAACCAGAAA
TGCTCTACCAAACATTTTTAAAAGATGAAATCAGACCAATTGAAAAAGTAAAAGCTGGTAAAACCAGAATTATTGATGTG
ACCCCCCTTGACCATGTTTTGGCATTCAGAATTGTTCTAGGCAGATTCATGGCTCATTTTCACAATAATTATGGTTTTAA
TCTTGGTTCTGCTGTTGGATGCGATCCCGACGTTGCTTGGGCCAACTTTGGCTTTGCTCTTTCTTCTAAGAAGTACCAGT
ATGACTTTGATTACTCAAACTTTGATGCTTCTCATTCAGAGTCCATCTTTGAACTTCTTAAACAGTTTGTTTTCACCAAA
GACAATGGTTTTGATCACAGATGCTCTCTCATGATTGATTCTCTGGTTACCTCGACCCACTGCTATGAGCAACAAAGAAT
GACCATTCGCGGCGGCCTCCC
```

FIG. 4-2

>HCoSV-D-5004
NSKESVSSNGNQGTIVNNFYANSYYASIDASASSVGGDTPAENGTVSGILGSFASAFTSA
ALLAKPKVENDTNMEDRVITLKAGNTIVNSQASEGVLHGYGIGTNTQRPSSCGDDPSIAT
HCIERGFTINLADWDKSKESWQALVYRLSDHLKDDTVGNMFSKTLGTHAYTKCGYRVSLQ
INTSPFHSGLIGLFLVPECCIPASLNMDWIDLKTQLPLLTSSSHYQGLGLSTGQGTISEK
GSIDAAGTIPQQLFIYPHQLINPKDTNIASVEVPYVNCAPTSDPMIHNIWTALVVVIAPL
QSNASASPTVAMSMTVTPVGAVFNGLRHPAPNVQTAIPVRMTQNSGQFSTTLPARMEPCY
GLTPNPTRDFLPPVVEDLLSIAKVPCFLLADEDTTKQKPYFLISNASSTQTAVFEMNVIL
SEYALQRTFVSMFGKFFCNYRGSIQITAWAAVTAMTRGKLLFSYTPPGAGKPQNIKQAMM
GTYTIWDLGLQSTLNFTIPYISSVDFRINSRAVASALNADGWLTIWILNPITYPPQTPPQ
QAILLMASAGSDFSYRLPINPPFVQGDIHDNAEKGLTETTDATQFCGAAVGYTTNHSNCE
FFFDRYRFVGFIDAVRNNKRSVISVFDSNNKVKRIAELFKEPNKPGNYFTLSPNPAISTT
PMSAYIVIDHPSSTSSPYTQYAIATTGDPFFLRSCPFTYFHCDLEVTIKPENAVSGVWRA
TWYPPGSDLKEDEVVPSFRTTGESGNMSLTVNNRERSTIYNTYPTFYSRDGQCVSFNIPY
TSPLSVIPTRFDGYPDYSRTVGAYGVAPANHFGTLTVAANDEGYKFFVYVRYKNFKGYVP
KTLPPQPLFLKNSRSLTNETIIARPYIRESSNVSRLKLLLSGDIETNPGPNHSKFQVQGS
MSDFLNVARKPETLDNVTRLLTTLNNLMNKWNNVKHMCTDSYFLRDILCLLVKLTSLSYL
VAGQGPSAYLAASAVLIADGISFLDWYEKIKRFLGSRFRVPPPIFTLAQGPDLRDLVTFF
NAARGAQWMVDSIRGLISWIKQWLELEEANEAVQFERLLIESPKHCKAINDYNVGKSFIR
PENSFDFMEKLVDSATKLGKVNIAGYFRSFTSVDTDTARMEPVVLVLRGKPGAGKSAAAT
IITAAVSKILTGTQSVYSLSPDTEHMDGYHGQFAMIMDDLGQNPDGEDFRTFCQMISVAQ
YRPSMADLKDKGILFKSQFIVATTNLPEFRPLTVSDRGAVDRRITFDIGVTPGTAVTKNG
KLDLAMALKPDGEGEFPYSCDCQILHTTGLALQNLRTGKTMNIKELVDLIVKKIKSKRTT
SGMLEGLVVQSPKIVGYTKDDEGVVIVDCLEDWHRIRDKKRKQQALEMVAEEMQIQHDKH
SQTISLIKQFLSGLGVVAAVGAAFAAGKVLKNMMTSDRAQDEPDSESQEKTEEKQKAEGP
YNGPTKKELKTLKLKAQGPLLDLEKKVLANVQPFILRVAGRDYIQSCLFVGKRVFLVNKH
AIDSVEQKFQVAGKTYDLDDVDVAILDTEYGLTDVAAVKLNTGPEWKNLSKLFVSLDTTL
HPGTRITILSNDQLNMVREGSFLRNEDDIPTNIGPIPFVMLYKASSYFGMCGSAVVTRIG
DCPGILGLHCAGGGGVCVASRVTKRMVETVLKYFYPPQVQGQIINTENGPRVHVPRQSKL
KRTNAVYPATPKYGPAVLSKNDPRLDPDVDFDKVIFSKHVANVVIDEDTSFWNALKMSAQ
IYAEKFKGVDFSPLTVEEAILGIPGLDRMDPNTASGLPYTKTRRQMIDFQEGKILDPELQ
SRLDTWLSNKQPEMLYQTFLKDEIRPIEKVKAGKTRIIDVTPLDHVLAFRIVLGRFMAHF
HNNYGFNLGSAVGCDPDVAWANFGFALSSKKYQYDFDYSNFDASHSESIFELLKQFVFTK
DNGFDHRCSLMIDSLVTSTHCYEQQRMTIRGGL

FIG. 5

>HCoSV-C-5152-1
CGTGTATCTAGGGATGAGCAACCCACCAACTACCGGGACTTACAGTTTAAGCTGTAG
ACACATGTGGTAACCCAGCCCCTTCCCTGACGGGAGAGGGGGCTTTTGCTCACCTAG
CACAGGATCTGATCAGGAGACTCCCTCACAGTGCTTTACACTGTTGTGGGAGTTTAA
AAATTGCCCAAGGCCTGGCACACAACCTAGGGGGACTAGGTTTTCCTTTTATTTGA
AGTTGTCAATATGGGTGCAAACAACAGCAAAGAGAGTGTTTCTAGCAATGGCAATC
AGGGTACTATTGTTAACAATTTTTATGCTAATTCTTACTATGCTTCTATTGACGCTTC
TGCCTCCTCGGTCGGGGGCGACACTCCTGCTGAAAACGGTACTGTCACTGGTCTTCT
GGGAAATATTGCTTCTGCTTTCACTTCCGCTGCACTCTTGGCCAAACCAACTGTAGA
AAATGAAACCGGTATGGAAGATAGGGTAATTTCTCTCAAGGCAGGCAATACTTTGG
TTAACTCACAGGCTTCAGAAGGGCTGTTATATGGATATGGCAAGGAAAGTGATAAA
AACCCCCCAACATCATGCGGTGATGATCCATCTGAAACACAACACTGCATACAGAG
AGGTTTTACTATTCCTTTGACTGATTGGACCAGAACCCAAGATCCATGGCAAGCTCT
TGTATACAAACTTTCAGATCAGTTTAAAAATGAAAGCAAGGGAAACATGTTTTCCAA
GGGAATGAAAACACATGCTTTTACCAAAACTGGCTACAGGGTATCTCTTCAGGTTAA
CACTTCTCCTTTCCACTCTGGCCTTTTAGGCCTATTTCTTGTCCCAGAGTGTAGTATA
CCTGCATCTACGTCACTGGATTGGATTGACTTGAAGACAGATGCTCCTCTTTTAAAG
AGCACAAACTATTACARGGGTCTTGGACTACAGCAACAATCTTCAGCCGCTGGAAA
CAAGTATGCAGACAACTGTATCATAGACTCCTCAGCAATAACTCCTCAGCAGCTCTT
TATATATCCTCACCAACTTATAAACCCCAAAGAAACTAACATTGCCTCAGTTGCAGT
TCCTTATGTGAACTGTGCTCCAACATCTGATCCTCAGATCCACAACATCTGGACTGC
CTTGGTAGTGATAATTTCACCCCTCCAGTTTGCTAATGGTGCTTCTCCTAATGTAACC
ATGTCACTTACAGTAACCCCTCTTAACACTGTTTCAATGGCTTACGCCATGCTCTGC
CTGCTACGCAAGGCCCTATACCAGTTAGGTGTATGCAGAATTCTTACCAGTTCTCAA
CCACACTTCCCGCAACCGCAGAACCGTGTTACGGTTGCACAGTGAACCCGCCCAGA
GACTACTTGCCTCCTGCTATCGAGGATTTGCTTTCTTTGGCTAAAGTTCCTTCTTTTCT
GCTTTGTAGCGAAGACACCGCTAAACAGGTGCCATATGTGAAGGTTACAAACACTC
AAACACAGCACAACTCTATCTTTTCAATGAATGTAGTTTTGTCAGATTATGCACTTCA
GAGGACCATGGTTTCACAGCTGGGAACATTTTTCTGTAATTATAGAGGAAGCATTC

>HCoSV-C-5152-2
TTTCAGTCACACAGTACAGACCTGCTATGGCTTCCCTTGAGGACAAAGGAATACTTT
TCTCTTCTAGATTAATAATTGCAACAACAAATCTTGTAGATTTCAACCCCGTCACCAT
TTCTGACCCTCGTGCTTTAGACAGAAGAATAACATTTGATTTGTGTGTTACCCCTGGT
TCTGCCGCAACAACATCTAAGGGCAAACTTGACCTTAAGAAGGCATTACAACCTGAT
GGACCTGGCTTTGGACCTTACACAACAGACTGCTCTCTCCTGCATACGACTGGGCTA
AATCTCAAGAATCTCAGAAACAATAGGGTTTACAGCATAGTTGATTTGGTTGAAGAG
GTAGTGGCCAATATGAACAAGAAAAAAGCTGTGAATGTCATGCTAGAAGGACTTGT
GGCACAGACTGGAAAAGTAGTTGGTTATACCAAAGATGACGATGGAGTTGTCATCG
TAGATTCAATGGATGAATGGCACAAAATACTAGACAAGAAAAGGAAACAGGAAGT
GTTAGAAGTGATTGCCCAAGAAATACAGGTAAGACATGATGAACACAAGGAGTTTA
CTCAGATTGTCACCAAATTTTTAACAGCCCTAGGCGTAATTGTTGCTGTAGGTGCTG
CTTTAATTGGATACAAGTATTTGACATCCGGCCCTGACAAAGAAAAGGAATCAACTG

FIG. 6-1

```
AGGAGCCAGAAAAACAAGAAGAGAAAGAAGAACAAAAGAAAGCTGAGGGACCTTA
CGAGGGACCCTCCAAGAAAGAGCTAAAAACACTCAAACTGCGCATTCAGTGCCCAG
TTAAAGACTGTGAGAAAAACTTTTGAATGCAATACACCCCTTTGTAATTCACTATG
ATAAAAGAAAGTACACACAGTCATGTATAGCTCTAGGTAAAAGGTTAATAATGGTA
AACAAACATGCAATGGAAACACTGGACAGATATGTTACCATAGCTGGAAAGATGTA
TGAGATTGATGATTGGACTGGGTTAACCTTGAAACCTCCCATGGAGAAACTGACGT
CTCCATAGTGAAACTGCCCCCCGGACCGGAATTCAAGAATATAGTTAGAAATTTTG
TTCACAAGACATAACTCTCATGCCTGGCACTAGAATGATGATCTTGTCTAATGATGA
CTTTTCTATGGTTAGGGAAGGCTCTTTTCTGAGATTTGAGGATTCTGTACCAACAAAT
ATCGGACCTATTCCATTTACCTTACTATACAAGTCCTCCTCTTATTTCGGAATGTGTG
GCTCGGCTGTTGTGTGCAGAACATCTGGCGAAACTGGCATAGTGGGAATGCACTGTG
CAGGTGGAGGCGGAGTTTCTGTCGCATGTCGCGTCACTAGAAAAATGGTAGAAGCT
GCTGTCATGTATTTTTTAATCCTTCTAATAGTTCAAGGCATGATTGTGTCAACTGAAA
CATGTGACCCAATTCACGTTCCTAGAAAAACAAAGTACAAGAGAACTAATGCTGAT
TATCCTTCTACTAAGAATTATGCCCCAGCTGTTTATCTAGAAATGACCCCAGACTTG
ACCCTGATGTTGATTTGATACTGTTTTGTTCTCCAAACACACTGAAAATGTCATCAT
CCCTCCTGACACACTGGCTTACGATAGTCTCCTGAAGGCTACACAGGTTTACGCTTG
TAAGTTTAATGGCAATTTTGAACCTTTAACTGTGGAAGAGGCAATTTTGGGAATACC
TGGCTTGGACAGGATGGATCCTAATACATCATCTGGCCTGCCTTATACTAAAACAAG
AAGACAGCTCATAGATTTTGTCAATGGAAAAATTTTGGACACACAATTACAGGAAA
GACTCGACATGTGGCTGAGTGGAAAACAACCTGAAACTTATTACCAAACTTTCCTAA
AAGATGAAATTAGGCATATTGACAAAGTGAGAAGAGGGAAAACTCGCATTATCGAT
GTGACTCCCTTAGATCATGTTTGGCTTTCAGAATTCTATTTGGCAGATTCATGGCAC
ATTACCACCTAAACCCTGGCTTTGATTTAGGCAGCGCTATTGGATGTGACCCAGAAG
TTGCTTGGAATCAGTTTGGTTATCATCTTACTAAGTATAAAAATCTCTATGACTTTGA
TTACTCAAACTTTGATTCTTCTCATTCTAAGTCTATCTTTGAGATTCTGAAAGATCAT
TTCTTCACCACAACCAACGGTTTTGATTCTCGTTGCGCCTTGCTACTAGATTCTCTGG
CTGTCTCCAAACACAAATATGACAACAAAGTGATGACTATAGTGGGCGGCCTC
```

FIG. 6-2

\>HCoSV-C-5152-1
MGANNSKESVSSNGNQGTIVNNFYANSYYASIDASASSVGG
DTPAENGTVTGLLGNIASAFTSAALLAKPTVENETGMEDRVISLKAGNTLVNSQASEGLL
YGYGKESDKNPPTSCGDDPSETQHCIQRGFTIPLTDWTRTQDPWQALVYKLSDQFKNESK
GNMFSKGMKTHAFTKTGYRVSLQVNTSPFHSGLLGLFLVPECSIPASTSLDWIDLKTDAP
LLKSTNYYXGLGLQQQSSAAGNKYADNCIIDSSAITPQQLFIYPHQLINPKETNIASVAV
PYVNCAPTSDPQIHNIWTALVVIISPLQFANGASPNVTMSLTVTPLNTVFNGLRHALPAT
QGPIPVRCMQNSYQFSTTLPATAEPCYGCTVNPPRDYLPPAIEDLLSLAKVPSFLLCSED
TAKQVPYVKVTNTQTQHNSIFSMNVVLSDYALQRTMVSQLGTFFCNYRGSI

\>HCoSV-C-5152-2
SVTQYRPAMASLEDKGILFSSRLIIATTNLVDFNPVTISDPRALDRRITFDLCVTPGSAA
TTSKGKLDLKKALQPDGPGFGPYTTDCSLLHTTGLNLKNLRNNRVYSIVDLVEEVVANMN
KKKAVNVMLEGLVAQTGKVVGYTKDDDGVVIVDSMDEWHKILDKKRKQEVLEVIAQEIQV
RHDEHKEFTQIVTKFLTALGVIVAVGAALIGYKYLTSGPDKEKESTEEPEKQEEKEEQKK
AEGPYEGPSKKELKTLKLRIQCPVKDCEKKLLNAIHPFVIHYDKRKYTQSCIALGKRLIM
VNKHAMETLDRYVTIAGKMYEIDDLDWVNLETSHGETDVSIVKLPPGPEFKNIVRNFCSQ
DITLMPGTRMMILSNDDFSMVREGSFLRFEDSVPTNIGPIPFTLLYKSSSYFGMCGSAVV
CRTSGETGIVGMHCAGGGGVSVACRVTRKMVEAAVMYFLILLIVQGMIVSTETCDPIHVP
RKTKYKRTNADYPSTKNYAPAVLSRNDPRLDPDVDFDTVLFSKHTENVIIPPDTLAYDSL
LKATQVYACKFNGNFEPLTVEEAILGIPGLDRMDPNTSSGLPYTKTRRQLIDFVNGKILD
TQLQERLDMWLSGKQPETYYQTFLKDEIRHIDKVRRGKTRIIDVTPLDHVLAFRILFGRF
MAHYHLNPGFDLGSAIGCDPEVAWNQFGYHLTKYKNLYDFDYSNFDSSHSKSIFEILKDH
FFTTTNGFDSRCALLLDSLAVSKHKYDNKVMTIVGGL

FIG. 7

| | | |
|---|---|---|
| HCoSV-1 | MGANNSKESVSSNGNEGTIVNNFYSNQYYASIDASAQGVGTSTTPENGNVSGFLGLAGSA | 60 |
| HCoSV-5004 | ----NSKESVSSNGNQGTIVNNFYANSYYASIDASASSVGGDTPAENGTVSGILGSFASA | 56 |
| | \*\*\*\*\*\*\*\*\*\*\*:\*\*\*\*\*\*\*\*:\*.\*\*\*\*\*\*\*\*..\*\* .\*..\*\*\*.\*\*\*.\*\* .\*\* | |
| | | |
| HCoSV-1 | FNALSLLASPRTETGMMMEDRVLSRTAGNTSVNSQAAEGVLQAYGTETDSNSPTSCGDDP | 120 |
| HCoSV-5004 | FTSAALLAKPKVENDTNMEDRVITLKAGNTIVNSQASEGVLHGYGIGTNTQRPSSCGDDP | 116 |
| | \*.: :\*\*\*.\*:.\*.. \*\*\*\*\*:: .\*\*\*\* \*\*\*\*\*.\*\*\*\*:.\*\* \*:::. \*::\*\*\*\*\*\* | |
| | | |
| HCoSV-1 | SKGTHATDRAFVIQLLPWKQTTNSYFAQWVRLTQKLSNNLHGNVMAKNIKSHAFAKMGFE | 180 |
| HCoSV-5004 | SIATHCIERGFTINLADWDKSKESWQALVYRLSDHLKDDTVGNMFSKTLGTHAYTKCGYR | 176 |
| | \* .\*\*. :\*.\*.\*:\* \*.::..\*: \* \*\*::\*.:: \*\*:::\*.: :\*\*::\* \*:. | |
| | | |
| HCoSV-1 | VMLQANTSPFHNGILGLFLVPEFVRKGEITDEWIDLTPTSSLVSNTELYN--PQTYANFP | 238 |
| HCoSV-5004 | VSLQINTSPFHSGLIGLFLVPECCIPASLNMDWIDLKTQLPLLTSSSHYQGLGLSTGQGT | 236 |
| | \* \*\* \*\*\*\*\*\*.\*::\*\*\*\*\*\*\* ..:. :\*\*\*\*.. .\*:::.. \*: : .:. . | |
| | | |
| HCoSV-1 | FDAKHSFDYSDITPEQFMIFPHQLINPKDTNVATVRVPYINIAPTNDTTVHTVWTAVVMV | 298 |
| HCoSV-5004 | ISEKGSIDAAGTIPQQLFIYPHQLINPKDTNIASVEVPYVNCAPTSDPMIHNIWTALVVV | 296 |
| | :.. \* \*:\* :.. \*:\*::\*:\*\*\*\*\*\*\*\*\*\*:\*:\*.\*\*\*.\*. :\*.:\*\*\*:\*:\* | |
| | | |
| HCoSV-1 | LVPLNFSSGASPTVSLTLTITPINSVFNGLHHTA---QGPIPVRPFHNFQQFSTTVPLRT | 355 |
| HCoSV-5004 | IAPLQSNASASPTVAMSMTVTPVGAVFNGLRHPAPNVQTAIPVRMTQNSGQFSTTLPARM | 356 |
| | :.\*\*: :..\*\*\*\*\*:::\*:\*\*:..:\*\*\*\*\*:\*.\* \* .\*\*\*\* :\* \*\*\*\*\*:\* \* | |
| | | |
| HCoSV-1 | EPCYGMTVTPPVDYMPLPITDLVELAKVPSFVTVANSDTTSERSFPYFSVSNTEQGR-NL | 414 |
| HCoSV-5004 | EPCYGLTPNPTRDFLPPVVEDLLSIAKVPCFL-LADEDTTKQK--PYFLISNASSTQTAV | 413 |
| | \*\*\*\*\*:\* .\*. \*::\* : \*\*:.:\*\*\*\*.\*: :\*:.\*\*\*.:: \*\*\* :\*\*:.. : : | |
| | | |
| HCoSV-1 | FKSSVVLSDLHYQHTLVANLARYFCNYRGSLQFDFIAATTAMTRGKLLISYTPPGAGEPQ | 474 |
| HCoSV-5004 | FEMNVILSEYALQRTFVSMFGKFFCNYRGSIQITAWAAVTAMTRGKLLFSYTPPGAGKPQ | 473 |
| | \*: .\*:\*\*: \*:.\*:\*: :..::\*\*\*\*\*\*\*:\*: \*\*.\*\*\*\*\*\*\*\*\*:\*\*\*\*\*\*\*\*:\*\* | |
| | | |
| HCoSV-1 | SIDQAMMGTYAIWDLGLQSTFNFVVPFISASDFRFNTSSVSNALNSDGWITVWLMNPLTY | 534 |
| HCoSV-5004 | NIKQAMMGTYTIWDLGLQSTLNFTIPYISSVDFRINSRAVASALNADGWLTIWILNPITY | 533 |
| | .\*.\*\*\*\*\*\*\*:\*\*\*\*\*\*\*\*.\*\*.:\*:\*\*: \*\*\*.\*: :\*:.\*\*\*:\*\*\*.\*:\*::\*\*:\*\* | |
| | | |
| HCoSV-1 | PPSTPPTQQILMLMSAGSDFSYRLPISPGFAEGETSEHPMDNAECGKIDDKDAGMFSGHS | 594 |
| HCoSV-5004 | PPQTPPQQAILLMASAGSDFSYRLPINPPFVQGDIHDN----AEKGLTETTDATQFCGAA | 589 |
| | \*\*.\*\*\* \* \*\*::.\*\*\*\*\*\*\*\*\*\*\*\*.\* \*.:\*: :: \*\* \* . \*\* \*.\* : | |
| | | |
| HCoSV-1 | VGLPTPHTSTSFFYDRYRFVGIVKSVVNNTPKPVNIYDDTGKVKNLQQVFPTSDTLLPHS | 654 |
| HCoSV-5004 | VGYTTNHSNCEFFFDRYRFVGFIDAVRNNKRSVISVFDSNNKVKRIAELFKEPN--KPGN | 647 |
| | \*\* .\* \*: .\*\*:\*\*\*\*\*\*\*::..\* \*\*. . :.::\*...\*\*\*.: ::\* .: \* . | |
| | | |
| HCoSV-1 | LMSLSPCASVCGQPISSFLFAQRANPKKTLKLR-----SGDEFLYRCCPFSYIKCDLEFT | 709 |
| HCoSV-5004 | YFTLSPNPAISTTPMSAYIVIDHPSSTSSPYTQYAIATTGDPFFLRSCPFTYFHCDLEVT | 707 |
| | ::\*\*\* .::. \*:\*::\*. ::......: : :\*\* \*: \*.\*\*\*:\*\*::\*\*\*\*.\* | |
| | | |
| HCoSV-1 | VVPPANSTRDYIVHWYPPGATLDAGEVAVGN-TSGSNGFDDNGMN--AGSSLFSYNPTFH | 766 |
| HCoSV-5004 | IKPENAVSGVWRATWYPPGSDLKEDEVVPSFRTTGESGNMSLTVNNRERSTIYNTYPTFY | 767 |
| | : \* : : . \*\*\*\*\*: \*. .\*\* . . \*:\*..\* . :\* \*:::. \*\*\*: | |
| | | |
| HCoSV-1 | ARAPSKVSAVIPFCLPVSLLPLYFDGFPDYSTTKGMYGCSPSFSFGTIYIESG-LQETYS | 825 |
| HCoSV-5004 | SRDGQCVSFNIPYTSPLSVIPTRFDGYPDYSRTVGAYGVAPANHFGTLTVAANDEGYKFF | 827 |
| | :\* . \*\* \*\*. \*:.\*:.\*\* \*\*\*:\*\*\*\* \* \*\* \*\*: \*\*\*: :. ..: | |
| | | |
| HCoSV-1 | VYIRYKDFKGYAPRPLIRTPHIRLSERARYIMADSVLPRPLTRAERDVARDLLLIAGDIE | 885 |
| HCoSV-5004 | VYVRYKNFKGYVPKTLP--PQPLFLKNSRSLTNETIIARPYIRESSNVSRLKLLLSGDIE | 885 |
| | \*\*:\*\*\*:\*\*\*\*.\*:.\* \*: : :..:\* : ::::.\*\* \* . :\*:\* \*\*::\*\*\*\* | |
| | | |
| HCoSV-1 | SNPGPAFNPEYTAHGPVTELIQLARKPETVDNVNRLLTTLNTLMAKWNNLKDTVTDAVFL | 945 |
| HCoSV-5004 | TNPGPNHS-KFQVQGSMSDFLNVARKPETLDNVTRLLTTLNNLMNKWNNVKHMCTDSYFL | 944 |
| | :\*\*\*\* .. :: ..\*.:\*.:::\*\*\*\*\*\*.\*\*\*.\*\*\*\*\*\*\*.\*\* \*\*:. \*\*: \*\* | |

FIG. 8-1

```
HCoSV-1    RDMVCLLVKLTSLMYLVHGQGPGAYFAAASILLADGITFFDWYEKIKIFMARKLRVSPPF 1005
HCoSV-5004 RDILCLLVKLTSLSYLVAGQGPSAYLAASAVLIADGISFLDWYEKIKRFLGSRFRVPPPI 1004
           **:.********* *** ****.**:**:::*:****:*:****** *:.. ::**.**:

HCoSV-1    FPAAQGPDLRDFVTFFNAARGAQWMIDSLKSLITCIKQWLELEEENEAVQLEKMLIDSPR 1065
HCoSV-5004 FTLAQGPDLRDLVTFFNAARGAQWMVDSIRGLISWIKQWLELEEANEAVQFERLLIESPK 1064
           *. ********:***********:**::.**: ********* *****:*::**:**:

HCoSV-1    HCKAINDYNRGDSFQRPTNSFEFMDRLVECATKLGKVQIATYFRNFTTADSDTSRPEPVV 1125
HCoSV-5004 HCKAINDYNVGKSFIRPENSFDFMEKLVDSATKLGKVNIAGYFRSFTSVDTDTARMEPVV 1124
           ********* .** ** ***:**::**:.********:**.****.**:.*:**:* ****

HCoSV-1    VVLRGKPGVGKSAAATVMAAAVSKLLVGSQSVYTLSPDTEHMDGYHGQFVTLMDDLGQNP 1185
HCoSV-5004 LVLRGKPGAGKSAAATIITAAVSKILTGTQSVYSLSPDTEHMDGYHGQFAMIMDDLGQNP 1184
           :*******.*******::.*****:*.*:****:**************.. :*******

HCoSV-1    DGEDFRCFCQMVSCAQYRPAMADLKDKGILFTSRLLIATTNLPDFNPVTISDPRALDRRI 1245
HCoSV-5004 DGEDFRTFCQMISVAQYRPSMADLKDKGILFKSQFIVATTNLPEFRPLTVSDRGAVDRRI 1244
           ****** ****:*.*****:***********.*:::.******:*.*:*.** *:****

HCoSV-1    TFDILVTPGSAATKNGKLDLAAALKPDGPGEHPYTSDCPILHTTGLLLKNLRNNQTMNLK 1305
HCoSV-5004 TFDIGVTPGTAVTKNGKLDLAMALKPDGEGEFPYSCDCQILHTTGLALQNLRTGKTMNIK 1304
           **** ****:*.********* ******.**:**:.** *******:*:***..:***:*

HCoSV-1    DLVDMIVKRIKHKKEVGNMLDSLVAQGPTMIVGYTKDDDGIAIVDCLEEWNKIKDKKKKQ 1365
HCoSV-5004 ELVDLIVKKIKSKRTTSGMLEGLVVQSP-KIVGYTKDDEGVVIVDCLEDWHRIRDKKRKQ 1363
           :***:***:**.*:...**:.**.*.*  ********:*::******:*::*:***:**

HCoSV-1    LALEMVAQELKDKHEEHKGTIKLLKMFVTGLGVVAAVAGAYATMKYFTKDKPKE-EEEEP 1424
HCoSV-5004 QALEMVAEEMQIQHDKHSQTISLIKQFLSGLGVVAAVGAAFAAGKVLKNMMTSDRAQDEP 1423
            ******:*:: . :*::*. **.*:* *:.*********..*:*: *  :.:  ::**

HCoSV-1    EEKKEKKTEESKEAAGPYNGPTKKEIKTLKLKAQSPLMDMEKKIAQNVMPFQIFYNGKRY 1484
HCoSV-5004 DSESQEKTEEKQKAEGPYNGPTKKELKTLKLKAQGPLLDLEKKVLANVQPFILRVAGRDY 1483
           :.:.::****.::* ********** ********.**:*:***: ***:**: :  *:*

HCoSV-1    TQSCLAIGKRVILVNKHAFESVEHKFVVDQKEYTLDQVTAISLDCGSGVTDVCAVCLPPG 1544
HCoSV-5004 IQSCLFVGKRVFLVNKHAIDSVEQKFQVAGKTYDLDDVDVAILDTEYGLTDVAAVKLNTG 1543
            ****  :****:******::***:** * * *  **:* .  ** *:***.** * .*

HCoSV-1    PDFKSIKKHFLPFNTTMFPGTRLTILSNDHYPMSREGSFLRFEDEVPTNVGNMPFVMLYK 1604
HCoSV-5004 PEWKNLSKLFVSLDTTLHPGTRITILSNDQLNMVREGSFLRNEDDIPTNIGPIPFVMLYK 1603
           *::*.::.* *:.::**:.****:*****:  * ******* **::****:.*:*******

HCoSV-1    STSYFGMCGSVVCSRFVDGGGIIGMHCAGGGGVSVGTRLTARMIESVFDYFYPPVAQGII 1664
HCoSV-5004 ASSYFGMCGSAVVTRIGDCPGILGLHCAGGGGVCVASRVTKRMVETVLKYFYPPQVQGQI 1663
           ::********.* :* .*  **:*:*******.*.:*:*.**:*:*::.****  **  *

HCoSV-1    ENTETGPRVHVPRTSKLKRTNATYPATEKYGPAALSRYDPRLNEGVNLDEVIFSKHTQNT 1724
HCoSV-5004 INTENGPRVHVPRQSKLKRTNAVYPATPKYGPAVLSKNDPRLDPDVDFDKVIFSKHVANV 1723
            ***.******** ********.**** *****.**:.****:  *::*:******.:*.

HCoSV-1    LVEKGSTFRSALDMAAEIYGEKFRGNDFSPLSVEDAILGIPGLDRLDPNTASGLPYTKTR 1784
HCoSV-5004 VIDEDTSFWNALKMSAQIYAEKFKGVDFSPLTVEEAILGIPGLDRMDPNTASGLPYTKTR 1783
           ::::::::*  .**.*:::**:***:*.* ******:**:*************:*************

HCoSV-1    RQMIDFNTGQILDDTLKCRLGQWLAGRPPQEVHYQTFLKDEIRPIEKVKAGKTRIIDVPP 1844
HCoSV-5004 RQMIDFQEGKILDPELQSRLDTWLSNKQP-EMLYQTFLKDEIRPIEKVKAGKTRIIDVTP 1842
           ******:: *:*** *:. **. **:.: *  *:**********************.*
```

FIG. 8-2

```
HCoSV-1     LDHVIAFRMLFGRFIAHYHLNFGFKTGSAIGCDPDVAWASFGFELSGFPYLYDFDYSNFD  1904
HCoSV-5004  LDHVLAFRIVLGRFMAHFHNNYGFNLGSAVGCDPDVAWANFGFALSSKKYQYDFDYSNFD  1902
            ****:***:::***:**:* *:**: ***:**********.*** **.  * *********

HCoSV-1     ASHSTSIFEILEQKFFSPELGFDPRCSLLLKSLAVSTHCYENKRLQIAGGLPSGTAGTSV  1964
HCoSV-5004  ASHSESIFELLKQFVFTKDNGFDHRCSLMIDSLVTSTHCYEQQRMTIRGGL--------  1953
            **** ****:*:* .*: : *** ****::.**..******::*: * ***
```

FIG. 8-3

```
HCoSV-1          MGANNSKESVSSNGNEGTIVNNFYSNQYYASIDASAQGVGTSTTPENGNVSGFLGLAGSA 60
HCoSV-aa1-5152   MGANNSKESVSSNGNQGTIVNNFYANSYYASIDASASSVGGDTPAENGTVTGLLGNIASA 60
                ***************:********:*.*********..** .*..***.*:*:**   .**

HCoSV-1          FNALSLLASPRTETGMMMEDRVLSRTAGNTSVNSQAAEGVLQAYGTETDSNSPTSCGDDP 120
HCoSV-aa1-5152   FTSAALLAKPTVENETGMEDRVISLKAGNTLVNSQASEGLLYGYGKESDKNPPTSCGDDP 120
                 *.: :***.* .*.    *****:* .**** *****:**:* .**.*:*.*.********

HCoSV-1          SKGTHATDRAFVIQLLPWKQTTNSYFAQWVRLTQKLSNNLHGNVMAKNIKSHAFAKMGFE 180
HCoSV-aa1-5152   SETQHCIQRGFTIPLTDWTRTQDPWQALVYKLSDQFKNESKGNMFSKGMKTHAFTKTGYR 180
                 *:   *. :*.*.* *   *.:* :.: *    :*::::.*: :**:::*.:*:***:* *:.

HCoSV-1          VMLQANTSPFHNGILGLFLVPEFVRKGEITDEWIDLTPTSSLVSNTELY------NPQTY 234
HCoSV-aa1-5152   VSLQVNTSPFHSGLLGLFLVPECSIPASTSLDWIDLKTDAPLLKSTNYYXGLGLQQQSSA 240
                 * **.******.*:********     .. : :****.. :.*:..*: *       : .:

HCoSV-1          ANFPFDAKHSFDYSDITPEQFMIFPHQLINPKDTNVATVRVPYINIAPTNDTTVHTVWTA 294
HCoSV-aa1-5152   AGNKYADNCIIDSSAITPQQLFIYPHQLINPKETNIASVAVPYVNCAPTSDPQIHNIWTA 300
                 *.   :   :  :* * ***:*::*:********:**:*:* ***:* ***.*. :*.:***

HCoSV-1          VVMVLVPLNFSSGASPTVSLTLTITPINSVFNGLHHTA---QGPIPVRPFHNFQQFSTTV 351
HCoSV-aa1-5152   LVVIISPLQFANGASPNVTMSLTVTPLNTVFNGLRHALPATQGPIPVRCMQNSYQFSTTL 360
                 :*::: **:*:.****.*:::**:**:*:*****:*:     ******* ::*  *****:

HCoSV-1          PLRTEPCYGMTVTPPVDYMPLPITDLVELAKVPSFVTVANSDTTSERSFPYFSVSNTEQG 411
HCoSV-aa1-5152   PATAEPCYGCTVNPPRDYLPPAIEDLLSLAKVPSFLLCS---EDTAKQVPYVKVTNTQTQ 417
                 *  :***** **.** **:* .* **:.*******:  :     : :..**..*:**:

HCoSV-1          RN-LFKSSVVLSDLHYQHTLVANLARYFCNYRGSLQFDFIAATTAMTRGKLLISYTPPGA 470
HCoSV-aa1-5152   HNSIFSMNVVLSDYALQRTMVSQLGTFFCNYRGSI------------------------- 452
                 :* :*. .*****   *:*:*::*. :*******:
```

FIG. 9

```
HCoSV-1           QYRPAMADLKDKGILFTSRLLIATTNLPDFNPVTISDPRALDRRITFDILVTPGSAATKN 1260
HCoSV-aa2-5152    QYRPAMASLEDKGILFSSRLIIATTNLVDFNPVTISDPRALDRRITFDLCVTPGSAATTS 63
                  *******.*:******:***:****** ********************: ********..

HCoSV-1           -GKLDLAAALKPDGPGEHPYTSDCPILHTTGLLLKNLRNNQTMNLKDLVDMIVKRIKHKK 1319
HCoSV-aa2-5152    KGKLDLKKALQPDGPGFGPYTTDCSLLHTTGLNLKNLRNNRVYSIVDLVEEVVANMNKKK 123
                   *****  **:*****  ***:**.:****** *******:. .: ***: :* .:::**

HCoSV-1           EVGNMLDSLVAQGPTMIVGYTKDDDGIAIVDCLEEWNKIKDKKKKQLALEMVAQELKDKH 1379
HCoSV-aa2-5152    AVNVMLEGLVAQ-TGKVVGYTKDDDGVVIVDSMDEWHKILDKKRKQEVLEVIAQEIQVRH 182
                   *. **:.****  . :*********:.***.::**:** ***:** .**::***:: :*

HCoSV-1           EEHKGTIKLLKMFVTGLGVVAAVAGAYATMKYFTKDKPKEEEEEPEEKKEKKTEESKEAA 1439
HCoSV-aa2-5152    DEHKEFTQIVTKFLTALGVIVAVGAALIGYKYLTSGPDKEKESTEEPEKQEEKEEQKKAE 242
                  :***   :::. *:*.***:.**..*    **:*..  **:*.  * :*:::.**.*:*

HCoSV-1           GPYNGPTKKEIKTLKLKAQSPLMDMEKKIAQNVMPFQIFYNGKRYTQSCLAIGKRVILVN 1499
HCoSV-aa2-5152    GPYEGPSKKELKTLKLRIQCPVKDCEKKLLNAIHPFVIHYDKRKYTQSCIALGKRLIMVN 302
                  ***:**:***:*****: *.*: * ***: : : ** *.*: ::*****:*:***:*:**

HCoSV-1           KHAFESVEHKFVVDQKEYTLDQVTAISLDCGSGVTDVCAVCLPPGPDFKSIKKHFLPFNT 1559
HCoSV-aa2-5152    KHAMETLDRYVTIAGKMYEIDDLDWVNLETSHGETDVSIVKLPPGPEFKNIVRNFCSQDI 362
                  ***:*:::: ..:  * * :*::  :.*: . * ***. * *****:**.* ::* . :

HCoSV-1           TMFPGTRLTILSNDHYPMSREGSFLRFEDEVPTNVGNMPFVMLYKSTSYFGMCGSVVCSR 1619
HCoSV-aa2-5152    TLMPGTRMMILSNDDFSMVREGSFLRFEDSVPTNIGPIPFTLLYKSSSYFGMCGSAVVCR 422
                  *::****: *****.:.* **********.****:* :**.:****:********.* .*

HCoSV-1           FVDGGGIIGMHCAGGGGVSVGTRLTARMIESVFDYFYPP-VAQGIIENTETGPRVHVPRT 1678
HCoSV-aa2-5152    TSGETGIVGMHCAGGGGVSVACRVTRKMVEAAVMYFLILLIVQGMIVSTETCDPIHVPRK 482
                    .  **:************. *:* :*:*:.. **    :.**:* .***   :****.

HCoSV-1           SKLKRTNATYPATEKYGPAALSRYDPRLNEGVNLDEVIFSKHTQNTLVEKGSTFRSALDM 1738
HCoSV-aa2-5152    TKYKRTNADYPSTKNYAPAVLSRNDPRLDPDVDFDTVLFSKHTENVIIPPDTLAYDSLLK 542
                  :* ***** **:*::*.**.*** ****: .*::* *:*****:*.::  .:   .:*

HCoSV-1           AAEIYGEKFRGNDFSPLSVEDAILGIPGLDRLDPNTASGLPYTKTRRQMIDFNTGQILDD 1798
HCoSV-aa2-5152    ATQVYACKFNGN-FEPLTVEEAILGIPGLDRMDPNTSSGLPYTKTRRQLIDFVNGKILDT 601
                  *:::*. **.** *.**:**:**********:****:***********:*** .*:***

HCoSV-1           TLKCRLGQWLAGRPPQEVHYQTFLKDEIRPIEKVKAGKTRIIDVPPLDHVIAFRMLFGRF 1858
HCoSV-aa2-5152    QLQERLDMWLSGKQP-ETYYQTFLKDEIRHIDKVRRGKTRIIDVTPLDHVLAFRILFGRF 660
                   *: **. **:*: * *.:********** *:**: ********.*****:***:*****

HCoSV-1           IAHYHLNFGFKTGSAIGCDPDVAWASFGFELSGFPYLYDFDYSNFDASHSTSIFEILEQK 1918
HCoSV-aa2-5152    MAHYHLNPGFDLGSAIGCDPEVAWNQFGYHLTKYKNLYDFDYSNFDSSHSKSIFEILKDH 720
                  :****** **. ********:*** .**:.*: :  **********:***.******:::

HCoSV-1           FFSPELGFDPRCSLLLKSLAVSTHCYENKRLQIAGGLPSGTAGTSVLNTVINNIIFHGAL 1978
HCoSV-aa2-5152    FFTTTNGFDSRCALLLDSLAVSKHKYDNKVMTIVGGL----------------------- 757
                  **:.  ***.**:***.*****.* *:** : *.***
```

FIG. 10

```
HCoSV-C2-5005    ----------------------------------------------------------
HCoSV-C-5152-2   ----------------------------------------------------------
HCoSV-B-2263     ----------------------------------------------------------
HCoSV-1          MGANNSKESVSSNGNEGTIVNNFYSNQYYASIDASAQGVGTSTTPENGNVSGFLGLAGSA
HCoSV-A-6344     MGANNSKESVSSNGNEGTIVNNFYSNQYYASIDASAQGVGTSTTPENGNVSGFLGLASSA
HCoSV-C-5152-1   MGANNSKESVSSNGNQGTIVNNFYANSYYASIDASASSVGGDTPAENGTVTGLLGNIASA
HCoSV-D-5004     ----NSKESVSSNGNQGTIVNNFYANSYYASIDASASSVGGDTPAENGTVSGILGSFASA

HCoSV-C2-5005    ----------------------------------------------------------
HCoSV-C-5152-2   ----------------------------------------------------------
HCoSV-B-2263     ----------------------------------------------------------
HCoSV-1          FNALSLLASPRTETGMMMEDRVLSRTAGNTSVNSQAAEGVLQAYGTETDSNSPTSCGDDP
HCoSV-A-6344     FNALSLLASPRVENSRYQEDRLLTRKAGNTSINSQAAEGVLCAYGKESDSRSPTSCGDAP
HCoSV-C-5152-1   FTSAALLAKPTVENETGMEDRVISLKAGNTLVNSQASEGLLYGYGKESDKNPPTSCGDDP
HCoSV-D-5004     FTSAALLAKPKVENDTNMEDRVITLKAGNTIVNSQASEGVLHGYGIGTNTQRPSSCGDDP

HCoSV-C2-5005    ----------------------------------------------------------
HCoSV-C-5152-2   ----------------------------------------------------------
HCoSV-B-2263     ----------------------------------------------------------
HCoSV-1          SKGTHATDRAFVIQLLPWKQTTNSYFAQWVRLTQKLSNNLHGNVMAKNIKSHAFAKMGFE
HCoSV-A-6344     SNGTPATDRGFVFQLLPWQKTNKAYDAQWIRITAGLLQNNKANVFAKNLKAHSYLRAGYE
HCoSV-C-5152-1   SETQHCIQRGFTIPLTDWTRTQDPWQALVYKLSDQFKNESKGNMFSKGMKTHAFTKTGYR
HCoSV-D-5004     SIATHCIERGFTINLADWDKSKESWQALVYRLSDHLKDDTVGNMFSKTLGTHAYTKCGYR

HCoSV-C2-5005    ----------------------------------------------------------
HCoSV-C-5152-2   ----------------------------------------------------------
HCoSV-B-2263     ----------------------------------------------------------
HCoSV-1          VMLQANTSPFHNGILGLFLVPEFVRKGEITDEWIDLTPTSSLVSNTELYN--------PQ
HCoSV-A-6344     VTLQVNTSPFHIGLIGLFLVPEFTRPGPENLEWRDLTEMKRILNDTNIYN--------SQ
HCoSV-C-5152-1   VSLQVNTSPFHSGLLGLFLVPECSIPASTSLDWIDLKTDAPLLKSTNYYXGLGL---QQQ
HCoSV-D-5004     VSLQINTSPFHSGLIGLFLVPECCIPASLNMDWIDLKTQLPLLTSSSHYQGLGLSTGQGT

HCoSV-C2-5005    ----------------------------------------------------------
HCoSV-C-5152-2   ----------------------------------------------------------
HCoSV-B-2263     ----------------------------------------------------------
HCoSV-1          TYA-NFPFDAKHSFDYSDITPEQFMIFPHQLINPKDTNVATVRVPYINIAPTNDTTVHTV
HCoSV-A-6344     TLPGSFSFDSDHSFDLGDFTPEQFLLFPHQLINPKDNNIATVRVPYVNIAPTSDTTVHNI
HCoSV-C-5152-1   SSAAGNKYADNCIIDSSAITPQQLFIYPHQLINPKETNIASVAVPYVNCAPTSDPQIHNI
HCoSV-D-5004     ISEKG-------SIDAAGTIPQQLFIYPHQLINPKDTNIASVEVPYVNCAPTSDPMIHNI

HCoSV-C2-5005    ----------------------------------------------------------
HCoSV-C-5152-2   ----------------------------------------------------------
HCoSV-B-2263     ----------------------------------------------------------
HCoSV-1          WTAVVMVLVPLNFSSGASPTVSLTLTITPINSVFNGLHHTA---QGPIPVRPFHNFQQFS
HCoSV-A-6344     WTAVVMVVSPLDFATGASPQVGMVLTITPVNSVFNGLHHTA---QGPIPTRPFHNFNQFN
HCoSV-C-5152-1   WTALVVIISPLQFANGASPNVTMSLTVTPLNTVFNGLRHALPATQGPIPVRCMQNSYQFS
HCoSV-D-5004     WTALVVVIAPLQSNASASPTVAMSMTVTPVGAVFNGLRHPAPNVQTAIPVRMTQNSGQFS

HCoSV-C2-5005    ----------------------------------------------------------
HCoSV-C-5152-2   ----------------------------------------------------------
HCoSV-B-2263     ----------------------------------------------------------
HCoSV-1          TTVPLRTEPCYGMTVTPPVDYMPLPITDLVELAKVPSFVTVANSDTTSERSFPYFS---V
```

FIG. 11-1

```
HCoSV-A-6344      TTVPLRTEPCYGMTLTPXVDYMPKPIDDLVSLVKVPSFITNSGSDTPTGRSFPYFS---V
HCoSV-C-5152-1    TTLPATAEPCYGCTVNPPRDYLPPAIEDLLSLAKVPSFLLCSEDTAKQVPYVKVT-----
HCoSV-D-5004      TTLPARMEPCYGLTPNPTRDFLPPVVEDLLSIAKVPCFLLADEDTTKQKPYFLIS--NAS

HCoSV-C2-5005     ------------------------------------------------------------
HCoSV-C-5152-2    ------------------------------------------------------------
HCoSV-B-2263      ------------------------------------------------------------
HCoSV-1           SNTEQGRNLFKSSVVLSDLHYQHTLVANLARYFCNYRGSLQFDFIAATTAMTRGKLLISY
HCoSV-A-6344      SSSTQGEKLFSSGVVLSDKHYQHTLLSNLADFFCNYRGSLQFDLVAVTTAMTRGKLLLAY
HCoSV-C-5152-1    NTQTQHNSIFSMNVVLSDYALQRTMVSQLGTFFCNYRGSIQI------------------
HCoSV-D-5004      STQTAV---FEMNVILSEYALQRTFVSMFGKFFCNYRGSIQITAWAAVTAMTRGKLLFSY

HCoSV-C2-5005     ------------------------------------------------------------
HCoSV-C-5152-2    ------------------------------------------------------------
HCoSV-B-2263      ------------------------------------------------------------
HCoSV-1           TPPGAGEPQSIDQAMMGTYAIWDLGLQSTFNFVVPFISASDFRFNTSSVSNALNSDGWIT
HCoSV-A-6344      TPPGAGEPTTIDQAMMGTYTIWDLGLQSTVNFVVPFISASDFRYNSVSVSSALNSDGWFT
HCoSV-C-5152-1    ------------------------------------------------------------
HCoSV-D-5004      TPPGAGKPQNIKQAMMGTYTIWDLGLQSTLNFTIPYISSVDFRINSRAVASALNADGWLT

HCoSV-C2-5005     ------------------------------------------------------------
HCoSV-C-5152-2    ------------------------------------------------------------
HCoSV-B-2263      ------------------------------------------------------------
HCoSV-1           VWLMNPLTYPPSTPPTQQILMLMSAGSDFSYRLPISPGFAEGETSEHPMDNAECGKIDDK
HCoSV-A-6344      VWLLNPLTYPPGSPPTQQIVVMLSAGEDFSYRLPISPGMAQTDGASGPHDNVECGVTDDA
HCoSV-C-5152-1    ------------------------------------------------------------
HCoSV-D-5004      IWILNPITYPPQTPPQQAILLMASAGSDFSYRLPINPPFVQGDIHDNAEKGLTETTDATQ

HCoSV-C2-5005     ------------------------------------------------------------
HCoSV-C-5152-2    ------------------------------------------------------------
HCoSV-B-2263      ------------------------------------------------------------
HCoSV-1           DAGMFSGHSVGLPTPHTSTSFFYDRYRFVGIVKSVVNNTPKPVNIYDDTGKVKNLQQVFP
HCoSV-A-6344      DADLNSGHSVSLPTPHTHTGFFYDRYRFIGAMKSNALDGPKPVSYLDTSKKVKTLNKVFQ
HCoSV-C-5152-1    ------------------------------------------------------------
HCoSV-D-5004      FCGAAVGYTTNHSNCEFFFDRYRFVGFIDAVRNNKRSVISVFDSNNKVKRIAELFKEPNK

HCoSV-C2-5005     ------------------------------------------------------------
HCoSV-C-5152-2    ------------------------------------------------------------
HCoSV-B-2263      ------------------------------------------------------------
HCoSV-1           TSDTLLPHSLMSLSPCASVCGQPISSFLFAQRANPKKTLKLRSGDEFLYRCCPFSYIKCD
HCoSV-A-6344      TNNELKPYSVLSLSPYPSICGVPISSFVYG-KASTRKYIRIMTGDDLLYKSCPFTYYKCD
HCoSV-C-5152-1    ------------------------------------------------------------
HCoSV-D-5004      PGNYFTLSPNPAISTTPMSAYIVIDHPSSTSSPYTQYAIATTGDPFFLRSCPFTYFHCDL

HCoSV-C2-5005     ------------------------------------------------------------
HCoSV-C-5152-2    ------------------------------------------------------------
HCoSV-B-2263      ------------------------------------------------------------
HCoSV-1           LEFTVVPPANSTRDYIVHWYPPGATLDAGEVAVGNT-SGSNGFDDNGMNAGSSLFS-YNP
HCoSV-A-6344      LEFTVVPPPGFDRDYVVHWYPPGSTLDSAKVMYGMTGNPDNGFDDNGENHGSGMLN-VNP
HCoSV-C-5152-1    ------------------------------------------------------------
HCoSV-D-5004      EVTIKPENAVSGVWRATWYPPGSDLKEDEVVPSFRTTGESGNMSLTVNNRERSTIYNTYP
```

FIG. 11-2

```
HCoSV-C2-5005    ------------------------------------------------------------
HCoSV-C-5152-2   ------------------------------------------------------------
HCoSV-B-2263     ------------------------------------------------------------
HCoSV-1          TFHARAPSKVSAVIPFCLPVSLLPLYFDGFPDYSTTKGMYGCSPSFSFG--TIYIESGLQ
HCoSV-A-6344     SFYARGTTKVSAVVPFCAPTSLLPLYFDGYPDYSRTPGYYGVSPATSFGSLTVETTAGNE
HCoSV-C-5152-1   ------------------------------------------------------------
HCoSV-D-5004     TFYSRDGQCVSFNIPYTSPLSVIPTRFDGYPDYSRTVGAYGVAPANHFGTLTVAANDEGY

HCoSV-C2-5005    ------------------------------------------------------------
HCoSV-C-5152-2   ------------------------------------------------------------
HCoSV-B-2263     ------------------------------------------------------------
HCoSV-1          ETYSVYIRYKDFKGYAPRPLIRTPHIRLSERARYIMADSVLPRPLTRAERDVARDLLLIA
HCoSV-A-6344     DLFSVYIRYKNFKGYLPRPVIRRPHTAVSGRSKLVMSDSVLPRSLTREEREVARLLLKIS
HCoSV-C-5152-1   ------------------------------------------------------------
HCoSV-D-5004     KFFVYVRYKNFKG----YVPKTLPPQPLFLKNSRSLTNETIIARPYIRESSNVSRLKLLL

HCoSV-C2-5005    ------------------------------------------------------------
HCoSV-C-5152-2   ------------------------------------------------------------
HCoSV-B-2263     ------------------------------------------------------------
HCoSV-1          GDIESNPGPAFNPEYTAHGPVTELIQLARKPETVDNVNRLLTTLNTLMAKWNNLKDTVTD
HCoSV-A-6344     GDVESNPGPAFNPEYTAHGPVTELIQLARKPETVDNVNRLLTTLNTLMAKWNNLKDTVTD
HCoSV-C-5152-1   ------------------------------------------------------------
HCoSV-D-5004     SGDIETNPGPNHSKFQVQGSMSDFLNVARKPETLDNVTRLLTTLNNLMNKWNNVKHMCTD

HCoSV-C2-5005    ------------------------------------------------------------
HCoSV-C-5152-2   ------------------------------------------------------------
HCoSV-B-2263     ------------------------------------------------------------
HCoSV-1          AVFLRDMVCLLVKLTSLMYLVHGQGPGAYFAAASILLADGITFFDWYEKIKIFMARKLRV
HCoSV-A-6344     AVFLRDMVCLLVKLTSLMYLVHGQGPGAYFAAASILLADGITFFDWYEKIKIFMARKLRV
HCoSV-C-5152-1   ------------------------------------------------------------
HCoSV-D-5004     SYFLRDILCLLVKLTSLSYLVAGQGPSAYLAASAVLIADGISFLDWYEKIKRFLGSRFRV

HCoSV-C2-5005    ------------------------------------------------------------
HCoSV-C-5152-2   ------------------------------------------------------------
HCoSV-B-2263     ------------------------------------------------------------
HCoSV-1          SPPFFPAAQGPDLRDFVTFFNAARGAQWMIDSLKSLITCIKQWLELEEENEAVQLEKMLI
HCoSV-A-6344     SPPFFPAAQGPDLRDFVTFFNAARGAQWMIDSLKSLITWIKQWLELEEENEAVQLEKMLI
HCoSV-C-5152-1   ------------------------------------------------------------
HCoSV-D-5004     PPPIFTLAQGPDLRDLVTFFNAARGAQWMVDSIRGLISWIKQWLELEEANEAVQFERLLI

HCoSV-C2-5005    ------------------------------------------------------------
HCoSV-C-5152-2   ------------------------------------------------------------
HCoSV-B-2263     ------------------------------------------------------------
HCoSV-1          DSPRHCKAINDYNRGDSFQRPTNSFEFMDRLVECATKLGKVQIATYFRNFTTADSDTSRP
HCoSV-A-6344     DSPRHCKAINDYNRGDSFQRPTNSFEFMDRLVECATKLGKVQIATYFRNFTTADSDTSRP
HCoSV-C-5152-1   ------------------------------------------------------------
HCoSV-D-5004     ESPKHCKAINDYNVGKSFIRPENSFDFMEKLVDSATKLGKVNIAGYFRSFTSVDTDTARM

HCoSV-C2-5005    ------------------------------------------------------------
HCoSV-C-5152-2   ------------------------------------------------------------
HCoSV-B-2263     ------------------------------------------------------------
```

FIG. 11-3

```
HCoSV-1           EPVVVVLRGKPGVGKSAAATVMAAAVSKLLVGSQSVYTLSPDTEHMDGYHGQFVTLMDDL
HCoSV-A-6344      EPVVVVLRGKPGAGKSAAATVMAAAVSKLLVGSQSVYTLSPDTEHMDGYHGQFVTLMDDL
HCoSV-C-5152-1    ------------------------------------------------------------
HCoSV-D-5004      EPVVLVLRGKPGAGKSAAATIITAAVSKILTGTQSVYSLSPDTEHMDGYHGQFAMIMDDL

HCoSV-C2-5005     ------------------------------------------------------------
HCoSV-C-5152-2    ---------------SVTQYRPAMASLEDKGILFSSRLIIATTNLVDFNPVTISDPRAL
HCoSV-B-2263      ------------------------------------------------------------
HCoSV-1           GQNPDGEDFRCFCQMVSCAQYRPAMADLKDKGILFTSRLLIATTNLPDFNPVTISDPRAL
HCoSV-A-6344      GQNPDGEDFRCFCQMVSCAQYRPAMADLKDKGILFTSRLLIATTNLPDFNPVTISDPRAL
HCoSV-C-5152-1    ------------------------------------------------------------
HCoSV-D-5004      GQNPDGEDFRTFCQMISVAQYRPSMADLKDKGILFKSQFIVATTNLPEFRPLTVSDRGAV

HCoSV-C2-5005     ------------------------------------------------------------
HCoSV-C-5152-2    DRRITFDLCVTPGSAATTSKGKLDLKKALQPDGPGFGPYTTDCSLLHTTGLNLKNLRNNR
HCoSV-B-2263      ------------------------------------------------------------
HCoSV-1           DRRITFDILVTPGSAAT-KNGKLDLAAALKPDGPGEHPYTSDCPILHTTGLLLKNLRNNQ
HCoSV-A-6344      DRRITFDVLVTPGSAAT-KNGKLDLAAALKPDGPGEHPYTSDCPILHTTGLLLKNLRNNQ
HCoSV-C-5152-1    ------------------------------------------------------------
HCoSV-D-5004      DRRITFDIGVTPG-TAVTKNGKLDLAMALKPDGEGEFPYSCDCQILHTTGLALQNLRTGK

HCoSV-C2-5005     ------------------------------------------------------------
HCoSV-C-5152-2    VYSIVDLVEEVVANMNKKKAVNVMLEGLVAQ-TGKVVGYTKDDDGVVIVDSMDEWHKILD
HCoSV-B-2263      ------------------------------------------------------------
HCoSV-1           TMNLKDLVDMIVKRIKHKKEVGNMLDSLVAQGPTMIVGYTKDDDGIAIVDCLEEWNKIKD
HCoSV-A-6344      TMNLKDLVDMIVKRIKHKKEVGNMLDSLVAQGPTMIVGYTKDDDGIAIVDCLEEWNKIKD
HCoSV-C-5152-1    ------------------------------------------------------------
HCoSV-D-5004      TMNIKELVDLIVKKIKSKRTTSGMLEGLVVQSPKIVG-YTKDDEGVVIVDCLEDWHRIRD

HCoSV-C2-5005     ------------------------------------------------------------
HCoSV-C-5152-2    KKRKQEVLEVIAQEIQVRHDEHKEFTQIVTKFLTALGVIVAVGAALIGYKYLT-SGPDKE
HCoSV-B-2263      ------------------------------------------------------------
HCoSV-1           KKKKQLALEMVAQELKDKHEEHKGTIKLLKMFVTGLGVVAAVAGAYATMKYFT-KDKPKE
HCoSV-A-6344      KKKKQLALEMVAQELKDKHEEHKGTIKLLKMFVTGLGVVAAVAGAYATMKYFT-KDKPKE
HCoSV-C-5152-1    ------------------------------------------------------------
HCoSV-D-5004      KKRKQQALEMVAEEMQIQHDKHSQTISLIKQFLSGLGVVAAVGAAFAAGKVLKNMMTSDR

HCoSV-C2-5005     ------------------------------------------------------------
HCoSV-C-5152-2    KESTEEPEKQEEKEEQKKAEGPYEGPSKKELKTLKLRIQCPVKDCEKKLLNAIHPFVIHY
HCoSV-B-2263      ------------------------------------------------------------
HCoSV-1           EEEEPEEKKEKKTEESKEAAGPYNGPTKKEIKTLKLKAQSPLMDMEKKIAQNVMPFQIFY
HCoSV-A-6344      EEEEPEEKKEKKTEESKEAAGPYNGPTKKEIKTLKLKAQSPLMDMEKKIAQNVMPFQIFY
HCoSV-C-5152-1    ------------------------------------------------------------
HCoSV-D-5004      AQDEPDSESQEKTEEKQKAEGPYNGPTKKELKTLKLKAQGPLLDLEKKVLANVQPFILRV

HCoSV-C2-5005     ------------------------------------------------------------
HCoSV-C-5152-2    DKRKYTQSCIALGKRLIMVNKHAMETLDRYVTIAGKMYEIDDLDWVNLETSHGETDVSIV
HCoSV-B-2263      ------------------------------------------------------------
HCoSV-1           NGKRYTQSCLAIGKRVILVNKHAFESVEHKFVVDQKEYTLDQVTAISLDCGSGVTDVCAV
HCoSV-A-6344      NGKRYTQSCLAIGKRVILVNKHAFESVEHKFVVDQREYTLDQVTAISLDCGSGVTDVCAV
HCoSV-C-5152-1    ------------------------------------------------------------
HCoSV-D-5004      AGRDYIQSCLFVGKRVFLVNKHAIDSVEQKFQVAGKTYDLDDVDVAILDTEYGLTDVAAV
```

FIG. 11-4

```
HCoSV-C2-5005   ----------------------------------------------------------
HCoSV-C-5152-2  KLPPGPEFKNIVRNFCSQDITLMPGTRMMILSNDDFSMVREGSFLRFEDSVPTNIGPIPF
HCoSV-B-2263    ----------------------------------------------------------
HCoSV-1         CLPPGPDFKSIKKHFLPFNTTMFPGTRLTILSNDHYPMSREGSFLRFEDEVPTNVGNMPF
HCoSV-A-6344    CLPPGPDFKSIKKHFLPFNTTMFPGTRLTILSNDHYPMSREGSFLRFEDEVPTNVGNMPF
HCoSV-C-5152-1  ----------------------------------------------------------
HCoSV-D-5004    KLNTGPEWKNLSKLFVSLDTTLHPGTRITILSNDQLNMVREGSFLRNEDDIPTNIGPIPF

HCoSV-C2-5005   ----------------------------------------------------------
HCoSV-C-5152-2  TLLYKSSSYFGMCGSAVVCRTSGETGIVGMHCAGGGGVSVACRVTRKMVEAAVMYFLILL
HCoSV-B-2263    ----------------------------------------------------------
HCoSV-1         VMLYKSTSYFGMCGSVVCSRFVDGGGIIGMHCAGGGGVSVGTRLTARMIESVFDYFYPP-
HCoSV-A-6344    VMLYKSTSYFGMCGSVVCSRFVDGGGIIGMHCAGGGGVSVGTRLTARMVESVFDYFYPP-
HCoSV-C-5152-1  ----------------------------------------------------------
HCoSV-D-5004    VMLYKASSYFGMCGSAVVTRIGDCPGILGLHCAGGGGVCVASRVTKRMVETVLKYFYPPQ

HCoSV-C2-5005   ----------------------------------------------------------
HCoSV-C-5152-2  IVQGMIVSTETCDPIHVPRKTKYKRTNADYPSTKNYAPAVLSRNDPRLDPDVDFDTVLFS
HCoSV-B-2263    ----------------------------------------------------------
HCoSV-1         VAQGIIENTETGPRVHVPRTSKLKRTNATYPATEKYGPAALSRYDPRLNEGVNLDEVIFS
HCoSV-A-6344    IAQGIIENTETGPRVHVPRTSKLKRTNATYPATDKYGPAALSRYDPRLNEGVNLDEVIFS
HCoSV-C-5152-1  ----------------------------------------------------------
HCoSV-D-5004    VQGQIIN-TENGPRVHVPRQSKLKRTNAVYPATPKYGPAVLSKNDPRLDPDVDFDKVIFS

HCoSV-C2-5005   ----------------------------------------------------------
HCoSV-C-5152-2  KHTENVIIPPDTLAYDSLLKATQVYACKFNGN-FEPLTVEEAILGIPGLDRMDPNTSSGL
HCoSV-B-2263    ----------------------------------------------------------
HCoSV-1         KHTQNTLVEKGSTFRSALDMAAEIYGEKFRGNDFSPLSVEDAILGIPGLDRLDPNTASGL
HCoSV-A-6344    KHTQNTLVEKGSTFRSALDMAAEIYGEKFRGNDFSPLSVEDAILGIPGLDRLDPNTASGL
HCoSV-C-5152-1  ----------------------------------------------------------
HCoSV-D-5004    KHVANVVIDEDTSFWNALKMSAQIYAEKFKGVDFSPLTVEEAILGIPGLDRMDPNTASGL

HCoSV-C2-5005   ----------------------------------------------------------
HCoSV-C-5152-2  PYTKTRRQLIDFVNGKILDTQLQERLDMWLSGKQP-ETYYQTFLKDEIRHIDKVRRGKTR
HCoSV-B-2263    ----------------------------------------------------------
HCoSV-1         PYTKTRRQMIDFNTGQILDDTLKCRLGQWLAGRPPQEVHYQTFLKDEIRPIEKVKAGKTR
HCoSV-A-6344    PYTKTRRQMIDFNTGQILDDTLKCRLGQWLAGRPPQDVHYQTFLKDEIRPIEKVKAGKTR
HCoSV-C-5152-1  ----------------------------------------------------------
HCoSV-D-5004    PYTKTRRQMIDFQEGKILDPELQSRLDTWLSNKQPEMLYQT-FLKDEIRPIEKVKAGKTR

HCoSV-C2-5005   -------DHVIAFRVLFGRFMAYYHLNPGFELGSAIGCDPEIAWTHFGYHLSGFRNLYDF
HCoSV-C-5152-2  IIDVTPLDHVLAFRILFGRFMAHYHLNPGFDLGSAIGCDPEVAWNQFGYHLTKYKNLYDF
HCoSV-B-2263    -------DHVLAFRMLFGRFMAYYHLNPGFKIGSAIGCDPETAWNGFGYTLSSKQYKYDF
HCoSV-1         IIDVPPLDHVIAFRMLFGRFIAHYHLNFGFKTGSAIGCDPDVAWASFGFELSGFPYLYDF
HCoSV-A-6344    IIDVPPLDHVIAFRMLFGRFIAHYHLNFGFKTGSAIGCDPDVAWASFGFELSGFPYLYDF
HCoSV-C-5152-1  ----------------------------------------------------------
HCoSV-D-5004    IIDVTPLDHVLAFRIVLGRFMAHFHNNYGFNLGSAVGCDPDVAWANFGFALSSKKYQYDF

HCoSV-C2-5005   DYSNFDSSHSVSIFKILKDHFFTPSNGFDSRCTLLLDSLAVSKHKYDNKVMT--------
HCoSV-C-5152-2  DYSNFDSSHSKSIFEILKDHFFTTTNGFDSRCALLLDSLAVSKHKYDNKVMTIVGGL---
```

FIG. 11-5

```
HCoSV-B-2263      DYSNFDASHSTSIFEILEEEFFTPKNGFDVRCSLLLKSLSCSTHCYENKRFT--------
HCoSV-1           DYSNFDASHSTSIFEILEQKFFSPELGFDPRCSLLLKSLAVSTHCYENKRLQIAGGLPSG
HCoSV-A-6344      DYSNFDASHSTSIFEIIEQKFFSPELGFDPRCSLLLKSLAVSTHCYENKRLQ--------
HCoSV-C-5152-1    ------------------------------------------------------------
HCoSV-D-5004      DYSNFDASHSESIFELLKQFVFTKDNGFDHRCSLMIDSLVTSTHCYEQQRMTIRGGL---

HCoSV-C2-5005     ------------------------------------------------------------
HCoSV-C-5152-2    ------------------------------------------------------------
HCoSV-B-2263      ------------------------------------------------------------
HCoSV-1           TAGTSVLNTVINNIIFHGALYHTYTNFERDDISMLAYGDDIVVASKFELDLVMVKAFMNR
HCoSV-A-6344      ------------------------------------------------------------
HCoSV-C-5152-1    ------------------------------------------------------------
HCoSV-D-5004      ------------------------------------------------------------

HCoSV-C2-5005     ------------------------------------------------------------
HCoSV-C-5152-2    ------------------------------------------------------------
HCoSV-B-2263      ------------------------------------------------------------
HCoSV-1           IGYKITPADKSDEFRPKCMDDICFLKRRFVKVAGVWAPVMETENLEAMLSWYKPGTLNEK
HCoSV-A-6344      ------------------------------------------------------------
HCoSV-C-5152-1    ------------------------------------------------------------
HCoSV-D-5004      ------------------------------------------------------------

HCoSV-C2-5005     ---------------------------------------------
HCoSV-C-5152-2    ---------------------------------------------
HCoSV-B-2263      ---------------------------------------------
HCoSV-1           LQSVSRLAHFSGRDVYDHLFKPFIRDGFDVTPWKQLHLEWLNKLSA
HCoSV-A-6344      ---------------------------------------------
HCoSV-C-5152-1    ---------------------------------------------
HCoSV-D-5004      ---------------------------------------------
```

FIG. 11-6

```
HCoSV-1         TTCTGAGACCGGCACGGTCAACCCGACTCATTTACGAGTTACTCATTTATTTTGAAACAT
HCoSV-A-6344    ------------------------------------------------------------
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         CATAAAGAACGTGAACCGCTCTTTGTTTCTTTAAGGAATTTAGAGTAGAAAACATTTGAG
HCoSV-A-6344    ------------------------------------------------------------
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         ATGAGGCCCGGTTGAACTCCGGGCGCTTTCCATCCGCTGTGATGGGCTCACTCCTGTACA
HCoSV-A-6344    ------------------------------------------------------------
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         CCGTGAGTCCGCGCAGTGCTGACTTAACACTTAAGTAATGTATAGGCCGAGGATTACACC
HCoSV-A-6344    ------------------------------------------------------------
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         GCTCGGCTCCCACCTTTCACCACCGTGGGATTAACAGGTTCAATGCACAAATTCCTGTCC
HCoSV-A-6344    ------------------------------------------------------------
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         TTGGCTATGTCAAAGCAATACAGTGTGTACATGGCGTGCACGCTCAAAGCGGAGACTTAG
HCoSV-A-6344    ------ATGTCAAAGCAATACAGTATGTACACAGTGTACACGCTCAAGGCGGAGATTTAG
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         GCCTCACAGATTGTGTTTTGTGTTATTGGATGCTGGATGGTCACGTTGGAGACTGCATGT
HCoSV-A-6344    GCCTCACAGATTGTGTTTTGTGTTATTGGATGCTGGATGGTCACGTTGGAGACTGCATGT
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------
```

FIG. 12-1

```
HCoSV-1         GGCAGTCTTGAAACGTGTGGTTTGACGTCTATCCATTATGGCAGTGGGTGGAGTACTGCA
HCoSV-A-6344    GGCAGTCTTGAAACGTGTGGTTTGACGTCTATCCGTTATGGCAGTGGGTGGAGCACTGCA
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         AAGATGTCACCGTGCTTTACACGGTTTTTGAACCCCACACCGGCTGTTTGGCGCTTGCAG
HCoSV-A-6344    AAGACGTCACCGTGCTTTACACGGTTTTTGAACCCCACACCGGCTGTTTGGCGCTTGCAG
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         GACAGCAGGTTTATTTTCTTATGTTCTCCATTTCTAGCCAACAGGGTTCTATCCTGTTGG
HCoSV-A-6344    GACAGCAGGTTTATTTTCATATGTTCTTTATTTCTAGCCAACAGGGTTCTATCCTGTTGG
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         GCGGAGTGATACTCCCGTTCCTTCTTGGACAGATTGCCTCCACGTTCTTTGTGGATCTCA
HCoSV-A-6344    GCGGAGTGATACTCCCGTTCCTTCTTGGACAGATTGCCTCCACGATCTTTGTGGACCTTA
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         AGGTGATCAAGTCACTGGTGAATAGAGCGAAGGTTGAGGAGACCTGAGGAATTTCCATGT
HCoSV-A-6344    AGGTGATCAAGTCACTGGTGAATTGAGCGAAGGTTGAGGAAGCCTGAGGAATTTCCATGT
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         GGCTTTGCCAGGAGTTGTAGCGATGCTGTGTGTGTGCGGATTTCCCCTCATGGCAACA
HCoSV-A-6344    GGCTTTGCCAGGAGTTGTAGCGATGCTGTGTGTGTGCGGATTTCCCCTCATGGCAACA
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         TGAGCCTCACAGGCCAAAAGCCCTGTCCGAAAGGACCCACACAGTGGAGCAACCCCAGCT
HCoSV-A-6344    TGAGCCTCACAGGCCAAAAGCCCCGTCCGAAAGGACCCACACAGTGGAGCAACCCCAGCT
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------
```

FIG. 12-2

```
HCoSV-1        CCCTCCTACAAAGCTTTGTGAGAATGAACTCAAGTTTATTCTACTTTATTCTCTATTTAC
HCoSV-A-6344   CCCTCCTACAAAGCTTTGTGTGAATGAACTCATGTTTATTCTTCTTTATTCTCTATTTAC
HCoSV-B-2263   ------------------------------------------------------------
HCoSV-D-5004   ------------------------------------------------------------
HCoSV-C-5152-2 ------------------------------------------------------------
HCoSV-C2-5005  ------------------------------------------------------------

HCoSV-1        ATCAGGCCCCAAAGATGTCCTGAAGGTACCTTGTGTATCTGGGCACGAGCACCATCAGCT
HCoSV-A-6344   ATCAGGCCCCAAAGATGTCCTGAAGGTACCTTGTGTATCTGGGCGTGAGCACCATCAACT
HCoSV-B-2263   ------------------------------------------------------------
HCoSV-D-5004   ------------------------------------------------------------
HCoSV-C-5152-2 ------------------------------------------------------------
HCoSV-C2-5005  ------------------------------------------------------------

HCoSV-1        ACCCGGACTTGTATTTCGGTACAGACACATGTGGTGACCCAGCCCCTCTGCTTCGGCAGG
HCoSV-A-6344   ACCCGGACTTGCACTTTGGTGCAGACGCATGTGGTGACCCAGCCCCTCTGCTTCGGCGGA
HCoSV-B-2263   ------------------------------------------------------------
HCoSV-D-5004   ------------------------------------------------------------
HCoSV-C-5152-2 ------------------------------------------------------------
HCoSV-C2-5005  ------------------------------------------------------------

HCoSV-1        GGGGCTTTCGCTCGCTCAGCACGAGATCTGATCAGGAGCCCCTCCCAGTGTGCTTTACAC
HCoSV-A-6344   GGGGCTTTTGCTCGCTCAGCACGAGATCTGATCAGGAGTCCCTCCCAGTGTGCTTTACAC
HCoSV-B-2263   ------------------------------------------------------------
HCoSV-D-5004   ------------------------------------------------------------
HCoSV-C-5152-2 ------------------------------------------------------------
HCoSV-C2-5005  ------------------------------------------------------------

HCoSV-1        CTGGCGAGGGGTTAAAAATTGCCCAAGGCCTGGCAAAACAACCTAGGGGACTAGGTTTTC
HCoSV-A-6344   CTGGCGAGGGGTTAAAAATTGCCCAAGGCCTGGCACAACAACCTAGGGGACTAGGTTTTC
HCoSV-B-2263   ------------------------------------------------------------
HCoSV-D-5004   ------------------------------------------------------------
HCoSV-C-5152-2 ------------------------------------------------------------
HCoSV-C2-5005  ------------------------------------------------------------

HCoSV-1        CTTTTATTAATAATATCTGTCATTATGGGTGCAAATAATAGCAAAGAATCTGTGTCCAGC
HCoSV-A-6344   CTTTTATTAACAATGTCTGTCAATATGGGTGCAAACAACAGCAAAGAATCAGTGTCTAGC
HCoSV-B-2263   ------------------------------------------------------------
HCoSV-D-5004   ---------------------------------AATAGCAAGGAGAGTGTGTCCAGC
HCoSV-C-5152-2 ------------------------------------------------------------
HCoSV-C2-5005  ------------------------------------------------------------

HCoSV-1        AATGGCAACGAGGGAACAATTGTTAATAACTTTTATTCAAACCAGTATTATGCTTCTATT
HCoSV-A-6344   AATGGCAACGAGGGAACTATTGTTAATAACTTTTATTCAAACCAGTACTATGCTTCTATT
HCoSV-B-2263   ------------------------------------------------------------
HCoSV-D-5004   AATGGCAATCAGGGTACTATTGTCAATAATTTTTATGCTAACTCATATTATGCTTCTATT
HCoSV-C-5152-2 ------------------------------------------------------------
HCoSV-C2-5005  ------------------------------------------------------------
```

FIG. 12-3

```
HCoSV-1        GATGCTTCTGCCCAAGGTGTTGGGACCTCTACTACTCCTGAAAACGGCAACGTATCTGGC
HCoSV-A-6344   GATGCTTCTGCCCAAGGTGTTGGGACCTCTACTACTCCTGAAAATGGTAATGTTTCTGGC
HCoSV-B-2263   ------------------------------------------------------------
HCoSV-D-5004   GACGCTTCTGCCTCCTCAGTCGGGGGCGATACTCCTGCTGAAAATGGTACTGTATCTGGC
HCoSV-C-5152-2 ------------------------------------------------------------
HCoSV-C2-5005  ------------------------------------------------------------

HCoSV-1        TTTCTTGGACTTGCAGGTAGTGCTTTTAATGCTCTCTCTCTTCTCGCCTCACCACGAACC
HCoSV-A-6344   TTTCTTGGACTTGCAAGTAGTGCTTTTAATGCTCTCTCTCTTCTCGCCTCTCCCAGAGTA
HCoSV-B-2263   ------------------------------------------------------------
HCoSV-D-5004   ATTCTCGGAAGTTTTGCTTCTGCTTTCACTTCCGCTGCACTACTAGCAAAACCAAAAGTT
HCoSV-C-5152-2 ------------------------------------------------------------
HCoSV-C2-5005  ------------------------------------------------------------

HCoSV-1        GAGA-CAGGAATGATGATGGAAGATCGTGTCCTTTCCCGTACTGCCGGTAATACATCTGT
HCoSV-A-6344   GAAAACAGTAGATACCA-GGAAGATCGACTCTTGACTCGCAAAGCAGGCAATACATCTAT
HCoSV-B-2263   ------------------------------------------------------------
HCoSV-D-5004   GAAAATGACACAAAC-ATGGAAGACAGAGTAATAACACTCAAAGCAGGAAATACAATTGT
HCoSV-C-5152-2 ------------------------------------------------------------
HCoSV-C2-5005  ------------------------------------------------------------

HCoSV-1        AAACTCTCAAGCTGCTGAAGGGGTTTTGCAGGCATATGGGACTGAGACAGACAGCAATTC
HCoSV-A-6344   AAACTCACAAGCTGCAGAAGGGGTTTTGTGTGCTTATGGTAAAGAGTCAGATTCTAGAAG
HCoSV-B-2263   ------------------------------------------------------------
HCoSV-D-5004   CAATTCTCAGGCTTCTGAAGGTGTTCTACATGGTTATGGCATTGGAACAAACACACAGAG
HCoSV-C-5152-2 ------------------------------------------------------------
HCoSV-C2-5005  ------------------------------------------------------------

HCoSV-1        GCCCACTTCGTGTGGCGACGATCCTAGCAAGGGTACACACGCAACAGACAGAGCCTTTGT
HCoSV-A-6344   TCCCACCTCATGTGGCGATGCACCAAGCAACGGTACACCTGCCACTGATAGAGGTTTTGT
HCoSV-B-2263   ------------------------------------------------------------
HCoSV-D-5004   ACCCTCTTCATGTGGTGATGACCCCTCAATTGCGACGCACTGTATTGAGCGAGGGTTTAC
HCoSV-C-5152-2 ------------------------------------------------------------
HCoSV-C2-5005  ------------------------------------------------------------

HCoSV-1        AATACAATTGCTTCCATGGAAACAGACAACAAATTCATACTTTGCTCAATGGGTAAGACT
HCoSV-A-6344   TTTTCAATTACTACCATGGCAAAAGACAAACAAGGCCTATGACGCACAATGGATCAGAAT
HCoSV-B-2263   ------------------------------------------------------------
HCoSV-D-5004   CATCAATTTGGCTGACTGGGACAAATCCAAGGAATCATGGCAGGCACTTGTTTACAGACT
HCoSV-C-5152-2 ------------------------------------------------------------
HCoSV-C2-5005  ------------------------------------------------------------

HCoSV-1        CACACAGAAACTGTCAAACAATTTGCATGGAAATGTTATGGCCAAAAACATTAAATCACA
HCoSV-A-6344   TACAGCTGGTTTGCTACAGAACAATAAGGCAAATGTGTTTGCAAAGAACTTAAAAGCACA
HCoSV-B-2263   ------------------------------------------------------------
HCoSV-D-5004   CTCAGATCATTTGAAAGATGATACAGTAGGTAACATGTTTTCCAAGACTTTGGGAACCCA
HCoSV-C-5152-2 ------------------------------------------------------------
HCoSV-C2-5005  ------------------------------------------------------------
```

FIG. 12-4

```
HCoSV-1        TGCTTTTGCCAAAATGGGCTTTGAAGTAATGTTACAGGCAAACACCTCGCCTTTCCATAA
HCoSV-A-6344   TTCATACCTGCGGGCAGGCTATGAGGTTACTCTCCAGGTAAATACATCCCCTTTCCACAT
HCoSV-B-2263   ------------------------------------------------------------
HCoSV-D-5004   CGCTTATACTAAGTGTGGTTACAGAGTCAGTCTGCAAATTAACACATCTCCCTTTCACTC
HCoSV-C-5152-2 ------------------------------------------------------------
HCoSV-C2-5005  ------------------------------------------------------------

HCoSV-1        TGGCATACTGGGTCTTTTCTTGGTACCGGAGTTTGTTAGAAAGGGT----GAAATTACAG
HCoSV-A-6344   TGGTTTAATTGGCCTTTTCCTTGTTCCAGAATTTACCCGACCTGGACCCGAAAACTTGGA
HCoSV-B-2263   ------------------------------------------------------------
HCoSV-D-5004   CGGTCTTATTGGCTTATTCTTAGTTCCAGAGTGTTGTATACCTGCTAGCTTGAATATGGA
HCoSV-C-5152-2 ------------------------------------------------------------
HCoSV-C2-5005  ------------------------------------------------------------

HCoSV-1        ATGAGTGGATTGACCTCACACCTACCTCTTCTTTAGTTTCAAACACTGAGTTGTACAACC
HCoSV-A-6344   ATGGAGAGATTTGACTGAAATGAAAAGGATATTAAAT----GACACAAACATTTATAACT
HCoSV-B-2263   ------------------------------------------------------------
HCoSV-D-5004   TTGGATTGATTTAAA-AACTCAGCTACCATTACTGACAAGCAGCTCGCACTACCAGGGTT
HCoSV-C-5152-2 ------------------------------------------------------------
HCoSV-C2-5005  ------------------------------------------------------------

HCoSV-1        CCCAGACT-TATGCAAAT--TTTCCATTTGATGCTAAACATAGTTTTGATTATTCTGATA
HCoSV-A-6344   CTCAGACTCTACCTGGCTCCTTTTCTTTTGATTCGGACCATTCTTTTGATCTTGGTGACT
HCoSV-B-2263   ------------------------------------------------------------
HCoSV-D-5004   TAGGTCTTTCAACAGGTCAAGGGACAATATCTGAAAAGGGTTCTATTGATGCTGCTGGTA
HCoSV-C-5152-2 ------------------------------------------------------------
HCoSV-C2-5005  ------------------------------------------------------------

HCoSV-1        TTACACCAGAACAATTTATGATTTTCCCTCACCAACTTATAAATCCTAAAGACACAAATG
HCoSV-A-6344   TTACACCTGAACAGTTCTTGCTTTTCCCTCATCAGCTGATTAACCCAAAAGACAACAACA
HCoSV-B-2263   ------------------------------------------------------------
HCoSV-D-5004   CAATTCCTCAACAACTCTTCATATATCCACACCAGTTGATTAACCCAAAAGACACAAACA
HCoSV-C-5152-2 ------------------------------------------------------------
HCoSV-C2-5005  ------------------------------------------------------------

HCoSV-1        TTGCCACAGTACGTGTGCCGTACATTAATATTGCTCCAACAAATGATACTACAGTACATA
HCoSV-A-6344   TTGCCACTGTTCGCGTCCCGTACGTAAATATAGCACCCACCAGTGACACTACTGTACACA
HCoSV-B-2263   ------------------------------------------------------------
HCoSV-D-5004   TAGCCTCAGTTGAAGTTCCTTATGTAAATTGTGCTCCCACCTCAGATCCAATGATACACA
HCoSV-C-5152-2 ------------------------------------------------------------
HCoSV-C2-5005  ------------------------------------------------------------

HCoSV-1        CAGTATGGACAGCTGTTGTTATGGTTCTTGTACCTCTTAACTTTTCTTCTGGTGCTTCAC
HCoSV-A-6344   ACATCTGGACAGCTGTGGTGATGGTTGTTTCCCCTCTTGATTTTGCTACTGGTGCATCTC
HCoSV-B-2263   ------------------------------------------------------------
HCoSV-D-5004   ACATTTGGACTGCTCTTGTAGTAGTTATAGCTCCTCTCCAGTCTAATGCATCAGCTTCTC
HCoSV-C-5152-2 ------------------------------------------------------------
HCoSV-C2-5005  ------------------------------------------------------------
```

FIG. 12-5

```
HCoSV-1        CAACTGTATCTTTAACATTAACTATAACTCCAATAAACTCAGTTTTTAATGGATTACATC
HCoSV-A-6344   CCCAGGTAGGTATGGTGTTGACTATCACACCTGTAAACTCTGTATTCAATGGGTTACACC
HCoSV-B-2263   ------------------------------------------------------------
HCoSV-D-5004   CTACTGTAGCAATGTCTATGACTGTAACTCCAGTGGGTGCTGTCTTTAACGGACTAAGAC
HCoSV-C-5152-2 ------------------------------------------------------------
HCoSV-C2-5005  ------------------------------------------------------------

HCoSV-1        ACACCGCAC--------AGGGGCCTATCCCTGTGCGACCTTTCCATAATTTCCAGCAGT
HCoSV-A-6344   ACACCGCTC--------AGGGTCCTATCCCCACTCGTCCTTTCCACAACTTCAATCAGT
HCoSV-B-2263   -----------------------------------------------------------
HCoSV-D-5004   ACCCTGCTCCTAATGTACAAACAGCAATACCTGTTAGAATGACACAAAATTCTGGACAGT
HCoSV-C-5152-2 -----------------------------------------------------------
HCoSV-C2-5005  -----------------------------------------------------------

HCoSV-1        TTAGCACTACTGTCCCTCTGCGCACTGAACCATGTTACGGCATGACAGTGACTCCTCCAG
HCoSV-A-6344   TTAACACTACTGTGCCTCTCAGAACTGAACCTTGTTATGGAATGACTCTCACTCCGCYAG
HCoSV-B-2263   ------------------------------------------------------------
HCoSV-D-5004   TTTCCACAACTCTTCCTGCTAGAATGGAACCATGTTATGGCTTAACTCCCAACCCCACCA
HCoSV-C-5152-2 ------------------------------------------------------------
HCoSV-C2-5005  ------------------------------------------------------------

HCoSV-1        TTGATTACATGCCCTTACCCATTACAGATTTAGTTGAGCTTGCTAAAGTGCCCAGTTTTG
HCoSV-A-6344   TAGACTACATGCCCAAACCTATTGATGATTTAGTTTCTTTGGTCAAGGTGCCCAGCTTTA
HCoSV-B-2263   ------------------------------------------------------------
HCoSV-D-5004   GAGACTTTCTTCCCCAGTAGTCGAAGATTTACTCAGCATAGCAAAAGTCCCTTGTTTC-
HCoSV-C-5152-2 ------------------------------------------------------------
HCoSV-C2-5005  ------------------------------------------------------------

HCoSV-1        TTACTGTGGCAAACAGTGACACGACTAGCGAGCGTAGTTTCCCTTATTTCTCTGTTAGTA
HCoSV-A-6344   TTACTAATTCTGGTTCTGACACTCCGACTGGTAGGTCATTTCCATATTTTTCAGTTAGTT
HCoSV-B-2263   ------------------------------------------------------------
HCoSV-D-5004   CTGCTG--GCAGATGAAGATACCACAAAACAGAAACCCTATTTTCTTATTTCAAATGCCT
HCoSV-C-5152-2 ------------------------------------------------------------
HCoSV-C2-5005  ------------------------------------------------------------

HCoSV-1        ACACAGAACAAGGCAGAAATCTTTTCAAATCCAGTGTAGTTCTCAGCGACTTACACTACC
HCoSV-A-6344   CCTCTACTCAAGGTGAAAAATTGTTTTCCAGTGGCGTTGTGTTGAGTGACAAACATTACC
HCoSV-B-2263   ------------------------------------------------------------
HCoSV-D-5004   CTTCAACTCAA---ACAGCTGTTTTTGAAATGAATGTCATACTCAGTGAATATGCGCTCC
HCoSV-C-5152-2 ------------------------------------------------------------
HCoSV-C2-5005  ------------------------------------------------------------

HCoSV-1        AGCACACTCTTGTAGCAAATTTGGCCCGTTACTTTTGCAACTACAGAGGTAGTCTACAGT
HCoSV-A-6344   AGCACACACTCCTCTCCAATCTGGCCGATTTCTTTTGTAATTACAGAGGTAGCTTACAGT
HCoSV-B-2263   ------------------------------------------------------------
HCoSV-D-5004   AGCGCACCTTTGTGTCAATGTTTGGAAAGTTTTTCTGTAACTACAGAGGCAGTATACAGA
HCoSV-C-5152-2 ------------------------------------------------------------
HCoSV-C2-5005  ------------------------------------------------------------
```

FIG. 12-6

```
HCoSV-1        TTGATTTTATAGCTGCAACAACTGCAATGACAAGAGGCAAATTGCTCATTAGCTACACCC
HCoSV-A-6344   TTGATTTGGTTGCAGTAACAACTGCCATGACCCGTGGCAAGCTTTTACTGGCCTACACGC
HCoSV-B-2263   ------------------------------------------------------------
HCoSV-D-5004   TTACCGCCTGGGCAGCTGTGACAGCAATGACTAGGGGAAAGTTGCTCTTCTCTTACACAC
HCoSV-C-5152-2 ------------------------------------------------------------
HCoSV-C2-5005  ------------------------------------------------------------

HCoSV-1        CACCAGGGGCTGGTGAGCCACAATCAATTGATCAGGCAATGATGGGAACTTATGCTATCT
HCoSV-A-6344   CTCCTGGTGCTGGTGAACCAACAACGATTGACCAGGCTATGATGGGAACATACACCATAT
HCoSV-B-2263   ------------------------------------------------------------
HCoSV-D-5004   CACCAGGTGCAGGTAAACCACAAAACATAAAACAAGCAATGATGGGTACCTACACCATAT
HCoSV-C-5152-2 ------------------------------------------------------------
HCoSV-C2-5005  ------------------------------------------------------------

HCoSV-1        GGGATTTGGGATTACAATCAACCTTCAATTTTGTAGTCCCTTTTATATCTGCTTCTGACT
HCoSV-A-6344   GGGATTTAGGTCTTCAGTCAACTGTAAATTTTGTGGTGCCTTTCATATCAGCTAGTGATT
HCoSV-B-2263   ------------------------------------------------------------
HCoSV-D-5004   GGGACTTGGGGTCTCCAATCCACTCTTAATTTCACCATTCCTTACATCTCCAGTGTAGACT
HCoSV-C-5152-2 ------------------------------------------------------------
HCoSV-C2-5005  ------------------------------------------------------------

HCoSV-1        TCAGATTTAACACCTCTTCTGTATCTAATGCTTTGAACTCTGATGGTTGGATCACAGTGT
HCoSV-A-6344   TTAGATACAATAGTGTTAGTGTGTCCTCAGCTCTGAATTCGGATGGATGGTTTACTGTAT
HCoSV-B-2263   ------------------------------------------------------------
HCoSV-D-5004   TTAGAATTAACTCTAGGGCTGTTGCTTCTGCCTTGAATGCTGACGGGTGGCTTACTATTT
HCoSV-C-5152-2 ------------------------------------------------------------
HCoSV-C2-5005  ------------------------------------------------------------

HCoSV-1        GGCTTATGAACCCTCTAACATATCCTCCCAGTACACCTCCTACCCAACAGATATTGATGT
HCoSV-A-6344   GGCTGCTTAACCCCTTGACTTATCCACCGGGTTCTCCCCCGACCCAGCAAATTGTAGTGA
HCoSV-B-2263   ------------------------------------------------------------
HCoSV-D-5004   GGATCCTCAATCCTATAACTTATCCTCCACAGACTCCTCCACAACAAGCCATTTTGTTAA
HCoSV-C-5152-2 ------------------------------------------------------------
HCoSV-C2-5005  ------------------------------------------------------------

HCoSV-1        TGATGTCAGCTGGCAGTGACTTTTCTTACCGGTTGCCCATTTCGCCCGGTTTCGCCGAGG
HCoSV-A-6344   TGCTTTCTGCCGGGGAAGACTTCTCTTACAGGTTGCCTATTTCTCCCGGTATGGCCCAAA
HCoSV-B-2263   ------------------------------------------------------------
HCoSV-D-5004   TGGCTTCTGCAGGTTCTGATTTTTCATACAGATTGCCTATAAACCCTCCCTTCGTCCAAG
HCoSV-C-5152-2 ------------------------------------------------------------
HCoSV-C2-5005  ------------------------------------------------------------

HCoSV-1        GGGAAACGAGCGAACATCCAATGGACAACGCTGAGTGCGGGAAAATTGATGACAAAGACG
HCoSV-A-6344   CAGATGGAGCTTCAGGTCCCCATGACAACGTCGAGTGCGGCGTGACAGACGACGCTGATG
HCoSV-B-2263   ------------------------------------------------------------
HCoSV-D-5004   GAGATA-----------TCCATGACAACGCAGAAAAGGGACTCACTGAAACAACTGATG
HCoSV-C-5152-2 ------------------------------------------------------------
HCoSV-C2-5005  ------------------------------------------------------------
```

FIG. 12-7

```
HCoSV-1        CAGGAATGTTTTCCGGACACTCTGTTGGGCTGCCTACTCCCCACACCTCGACTTCTTTCT
HCoSV-A-6344   CTGATCTCAACTCTGGTCATAGTGTGTCTCTTCCTACCCCGCACACCCATACTGGCTTCT
HCoSV-B-2263   ------------------------------------------------------------
HCoSV-D-5004   CAACCCAGTTCTGTGGTGCCGCTGTTGGGTACACAACAAATCATTCAAATTGTGAATTCT
HCoSV-C-5152-2 ------------------------------------------------------------
HCoSV-C2-5005  ------------------------------------------------------------

HCoSV-1        TCTATGACAGGTACAGATTCGTAGGAATTGTAAAGAGTGTAGTGAATAATACTCCCAAAC
HCoSV-A-6344   TCTATGATAGATATAGATTCATTGGAGCTATGAAATCCAATGCTTTAGATGGCCCCAAAC
HCoSV-B-2263   ------------------------------------------------------------
HCoSV-D-5004   TCTTTGATAGATATAGATTTGTAGGTTTTATAGATGCTGTTAGAAACAACAAAAGAAGTG
HCoSV-C-5152-2 ------------------------------------------------------------
HCoSV-C2-5005  ------------------------------------------------------------

HCoSV-1        CAGTCAACATTTATGATGATACAGGAAAAGTTAAGAACCTACAACAGGTTTTTCCAACTT
HCoSV-A-6344   CAGTTTCTTATCTTGATACTA-GCAAGAAGGTAAAAACTCTTAACAAAGTTTTCCAGACT
HCoSV-B-2263   ------------------------------------------------------------
HCoSV-D-5004   TGATTTCTGTTTTTGACTCAA-ACAACAAAGTCAAGAGAATTGCTGAATTGTTTAAAGAA
HCoSV-C-5152-2 ------------------------------------------------------------
HCoSV-C2-5005  ------------------------------------------------------------

HCoSV-1        CA-GACACACTACTGCCCCACTCTTTGATGTCCCTTTCTCCC----TGTGCGTCAGTGTG
HCoSV-A-6344   AATAATGAACTGAAACCTTATTCAGTTCTTTCCCTTTCCCCC----TACCCAAGCATTTG
HCoSV-B-2263   ------------------------------------------------------------
HCoSV-D-5004   CCAAACAAACCAGGTAATTATTTCACTTTATCACCAAACCCAGCAATTTCGACAACTCCT
HCoSV-C-5152-2 ------------------------------------------------------------
HCoSV-C2-5005  ------------------------------------------------------------

HCoSV-1        TGGCCAGCCTATCTCTTCCTTCCTG--TTTGCTCAACGAGCGAATCCCAAGA---AAACT
HCoSV-A-6344   TGGTGTCCCTATATCCAGCTT--TG--TCTACGGCAAG-GCATCCACCAGGA---AATAC
HCoSV-B-2263   ------------------------------------------------------------
HCoSV-D-5004   ATGTCAGCTTACATTGTCATAGATCATCCTTCTTCAACTTCAAGCCCTTACACTCAGTAT
HCoSV-C-5152-2 ------------------------------------------------------------
HCoSV-C2-5005  ------------------------------------------------------------

HCoSV-1        CTAAAGCTGCGCTCAGGTGATGAATTCTTGTATAGATGTTGCCCTTTTCTTACATTAAA
HCoSV-A-6344   ATCAGGATAATGACAGGTGATGACTTGCTTTACAAATCATGTCCCTTTACCTACTATAAG
HCoSV-B-2263   ------------------------------------------------------------
HCoSV-D-5004   GCTATTGCAACAACTGGTGATCCCTTCTTTCTAAGATCTTGCCCCTTCACATACTTTCAC
HCoSV-C-5152-2 ------------------------------------------------------------
HCoSV-C2-5005  ------------------------------------------------------------

HCoSV-1        TGTGACCTTGAGTTTACTGTGGTCCCCCCTGCGAATTCTACTAGAGATTATATTGTGCAC
HCoSV-A-6344   TGTGATCTAGAATTTACTGTAGTACCCCCCCTGGCTTTGATAGGGATTACGTGGTTCAT
HCoSV-B-2263   ------------------------------------------------------------
HCoSV-D-5004   TGTGATTTAGAGGTAACAATAAAACCAGAAAATGCAGTTTCAGGTGTTTGGCGCGCCACT
HCoSV-C-5152-2 ------------------------------------------------------------
HCoSV-C2-5005  ------------------------------------------------------------
```

FIG. 12-8

```
HCoSV-1        TGGTACCCGCCAGGGGCCACCCTGGATGCTGGAGAAGTAGCC------GTGGGTAATACA
HCoSV-A-6344   TGGTATCCTCCAGGTTCCACGTTGGATTCGGCAAAAGTTATG------TATGGAATGACA
HCoSV-B-2263   ------------------------------------------------------------
HCoSV-D-5004   TGGTATCCACCAGGCTCGGACTTAAAAGAAGATGAGGTTGTTCCAAGTTTTAGGACTACA
HCoSV-C-5152-2 ------------------------------------------------------------
HCoSV-C2-5005  ------------------------------------------------------------

HCoSV-1        TCAGGT---AGCAATGGCTTTGATGATAATGGGATGAACGCTGGTTCTAGTCTGTTTTCT
HCoSV-A-6344   GGAAATCCAGACAATGGTTTTGATGACAATGGTGAGAATCACGGCTCTGGCATGCTTAAT
HCoSV-B-2263   ------------------------------------------------------------
HCoSV-D-5004   GGTGAATCTGGTAATATGTCTCTTACTGTAAACAATAGAGAGAGGTCAACAATATATAAT
HCoSV-C-5152-2 ------------------------------------------------------------
HCoSV-C2-5005  ------------------------------------------------------------

HCoSV-1        TACAATCCTACTTTCCACGCAAGAGCTCCGTCAAAAGTCTCAGCTGTTATACCTTTTTGC
HCoSV-A-6344   GTGAATCCATCTTTCTATGCCCGCGGTACCACGAAAGTTAGCGCAGTGGTCCCGTTCTGT
HCoSV-B-2263   ------------------------------------------------------------
HCoSV-D-5004   ACTTATCCCACCTTTTACTCTAGGGATGGTCAGTGTGTTTCTTTTAACATACCCTACACC
HCoSV-C-5152-2 ------------------------------------------------------------
HCoSV-C2-5005  ------------------------------------------------------------

HCoSV-1        TTACCCGTTTCTCTATTACCTCTATATTTTGATGGCTTTCCCGATTACAGTACTACAAAA
HCoSV-A-6344   GCACCTACATCTCTTTTACCTTTGTACTTTGATGGCTATCCTGATTATTCTCGCACCCCG
HCoSV-B-2263   ------------------------------------------------------------
HCoSV-D-5004   TCACCTCTTAGTGTTATTCCTACCAGATTTGATGGTTATCCTGACTATTCAAGGACTGTT
HCoSV-C-5152-2 ------------------------------------------------------------
HCoSV-C2-5005  ------------------------------------------------------------

HCoSV-1        GGAATGTATGGATGCTCCCCTTCTTTTAGTTTTGGAACCATATACATTGAATC-----TG
HCoSV-A-6344   GGCTACTACGGGGTATCTCCAGCTACATCTTTCGGCTCACTCACTGTTGAAACAACTGCA
HCoSV-B-2263   ------------------------------------------------------------
HCoSV-D-5004   GGTGCATACGGTGTGGCCCCTGCAAACCACTTTGGCACTTTGACTGTAGCTGCTAATGAT
HCoSV-C-5152-2 ------------------------------------------------------------
HCoSV-C2-5005  ------------------------------------------------------------

HCoSV-1        GACTCCAAGAAACT-TATTCAGTTTACATTAGATACAAGGATTTTAAGGGTTATGCTCCC
HCoSV-A-6344   GGTAATGAGGATCTGTTTTCAGTCTACATTAGGTACAAAAATTTTAAAGGCTATCTTCCT
HCoSV-B-2263   ------------------------------------------------------------
HCoSV-D-5004   GAAGGTTACAAATT---CTTTGTTTATGTTAGATACAAAAACTTCAAAGGGTATGTCCCC
HCoSV-C-5152-2 ------------------------------------------------------------
HCoSV-C2-5005  ------------------------------------------------------------

HCoSV-1        AGACCGCTCATTCGGACACCACACATTAGGCTATCAGAAAGAGCTAGATATATTATGGCA
HCoSV-A-6344   CGACCAGTGATTCGGCGTCCACACACTGCAGTTTCTGGCCGTTCTAAACTTGTCATGTCT
HCoSV-B-2263   ------------------------------------------------------------
HCoSV-D-5004   AAGACCCTACCTCCACAACCAC------TGTTTTTAAAGAATTCCAGAAGTTTGACTAAT
HCoSV-C-5152-2 ------------------------------------------------------------
HCoSV-C2-5005  ------------------------------------------------------------
```

FIG. 12-9

```
HCoSV-1        GACTCGGTGCTTCCACGCCCTCTCACACGCGCTGAACGTGATGTGGCGCGTGATTTGCTG
HCoSV-A-6344   GACTCTGTCTTGCCCCGAAGTCTAACACGAGAGGAGCGAGAGGTTGCACGTCTCCTCCTG
HCoSV-B-2263   ------------------------------------------------------------
HCoSV-D-5004   GAAACAATAATAGCAAGACCTTACATTAGAGAGAGCAGCAATGTCTCTAGATTAAAGCTC
HCoSV-C-5152-2 ------------------------------------------------------------
HCoSV-C2-5005  ------------------------------------------------------------

HCoSV-1        CTCATTGCTGGGGATATTGAATCAAATCCAGGACCTGCATTTAATCCAGAATATACAGCT
HCoSV-A-6344   AAAATATCAGGTGATGTAGAATCCAATCCAGGCCCTGCATTTAACCCAGAATATACTGCT
HCoSV-B-2263   ------------------------------------------------------------
HCoSV-D-5004   CTACTTTCAGGTGACATTGAAACAAATCCTGGACCTAA---TCACTCTAAATTTCAGGTA
HCoSV-C-5152-2 ------------------------------------------------------------
HCoSV-C2-5005  ------------------------------------------------------------

HCoSV-1        CATGGCCCAGTTACTGAATTGATTCAATTGGCAAGGAAACCAGAAACTGTAGATAATGTA
HCoSV-A-6344   CATGGTCCCGTTACTGAACTGATTCAATTGGCCAGAAAACCAGAAACTGTAGATAATGTA
HCoSV-B-2263   ------------------------------------------------------------
HCoSV-D-5004   CAAGGATCCATGTCAGATTTTTTAAATGTGGCCAGAAAACCAGAAACATTGGATAATGTG
HCoSV-C-5152-2 ------------------------------------------------------------
HCoSV-C2-5005  ------------------------------------------------------------

HCoSV-1        AATAGGCTTCTCACAACCCTGAATACTCTTATGGCTAAATGGAACAATCTCAAGGATACT
HCoSV-A-6344   AACAGGCTTTTGACAACTCTCAATACTCTTATGGCAAAATGGAACAACCTTAAGGATACT
HCoSV-B-2263   ------------------------------------------------------------
HCoSV-D-5004   ACCAGGCTTTTAACTACTTTAAATAATCTAATGAATAAATGGAACAATGTTAAACATATG
HCoSV-C-5152-2 ------------------------------------------------------------
HCoSV-C2-5005  ------------------------------------------------------------

HCoSV-1        GTTACAGATGCTGTGTTTCTTAGAGACATGGTATGTCTTCTTGTGAAGCTTACTTCTCTT
HCoSV-A-6344   GTTACAGACGCTGTGTTTCTCAGGGACATGGTATGTCTTCTTGTAAAGCTCACTTCTCTC
HCoSV-B-2263   ------------------------------------------------------------
HCoSV-D-5004   TGTACTGATTCTTATTTTCTAAGAGATATTCTGTGCTTGCTTGTTAAGCTTACATCACTC
HCoSV-C-5152-2 ------------------------------------------------------------
HCoSV-C2-5005  ------------------------------------------------------------

HCoSV-1        ATGTACTTGGTTCATGGACAGGGACCAGGTGCTTACTTTGCTGCTGCCTCCATTCTTCTT
HCoSV-A-6344   ATGTACCTGGTTCACGGACAAGGACCAGGTGCTTACTTTGCTGCTGCCTCTATCCTTCTT
HCoSV-B-2263   ------------------------------------------------------------
HCoSV-D-5004   TCATACCTTGTTGCAGGACAGGGACCTTCTGCTTACTTAGCTGCTTCCGCTGTGCTCATT
HCoSV-C-5152-2 ------------------------------------------------------------
HCoSV-C2-5005  ------------------------------------------------------------

HCoSV-1        GCTGATGGCATAACTTTCTTTGATTGGTACGAGAAAATCAAGATTTTCATGGCTAGAAAA
HCoSV-A-6344   GCTGACGGCATAACCTTCTTTGATTGGTACGAGAAAATTAAAATCTTCATGGCCAGAAAA
HCoSV-B-2263   ------------------------------------------------------------
HCoSV-D-5004   GCGGACGGCATTTCTTTCCTTGACTGGTATGAAAAAATAAAAAGATTTCTTGGTTCTCGT
HCoSV-C-5152-2 ------------------------------------------------------------
HCoSV-C2-5005  ------------------------------------------------------------
```

FIG. 12-10

| | |
|---|---|
| HCoSV-1 | CTCAGAGTTTCCCCTCCCTTCTTCCCCGCTGCCCAGGGGCCGGACCTTAGAGACTTTGTG |
| HCoSV-A-6344 | CTCAGAGTTTCTCCCCCTTTCTTTCCCGCCGCCCAAGGACCGGACCTCAGAGACTTTGTG |
| HCoSV-B-2263 | ------------------------------------------------------------ |
| HCoSV-D-5004 | TTTCGAGTTCCACCTCCTATCTTCACTCTTGCCCAAGGACCAGATCTTAGAGACTTAGTT |
| HCoSV-C-5152-2 | ------------------------------------------------------------ |
| HCoSV-C2-5005 | ------------------------------------------------------------ |

| | |
|---|---|
| HCoSV-1 | ACCTTTTTCAACGCAGCGCGCGGAGCGCAATGGATGATTGATTCTCTCAAATCCCTTATA |
| HCoSV-A-6344 | ACCTTCTTCAATGCTGCGCGCGGAGCGCAATGGATGATTGATTCTCTCAAGTCCCTCATA |
| HCoSV-B-2263 | ------------------------------------------------------------ |
| HCoSV-D-5004 | ACTTTCTTTAATGCTGCTAGGGGCGCACAGTGGATGGTTGATTCCATCCGTGGACTGATT |
| HCoSV-C-5152-2 | ------------------------------------------------------------ |
| HCoSV-C2-5005 | ------------------------------------------------------------ |

| | |
|---|---|
| HCoSV-1 | ACTTGTATCAAACAATGGCTTGAACTTGAAGAGGAAAATGAAGCAGTACAACTTGAAAAG |
| HCoSV-A-6344 | ACTTGGATCAAACAATGGCTTGAACTTGAAGAAGAAAATGAAGCAGTGCAACTTGAAAAG |
| HCoSV-B-2263 | ------------------------------------------------------------ |
| HCoSV-D-5004 | TCATGGATCAAACAATGGCTTGAACTGGAAGAAGCAAACGAAGCTGTCCAATTCGAAAGA |
| HCoSV-C-5152-2 | ------------------------------------------------------------ |
| HCoSV-C2-5005 | ------------------------------------------------------------ |

| | |
|---|---|
| HCoSV-1 | ATGTTAATAGACTCTCCCAGACATTGCAAGGCAATAAATGACTACAACAGAGGTGACTCC |
| HCoSV-A-6344 | ATGCTAATAGACTCTCCTAGACACTGCAAGGCAATAAATGACTACAACAGAGGTGATTCT |
| HCoSV-B-2263 | ------------------------------------------------------------ |
| HCoSV-D-5004 | CTGTTGATAGAAAGTCCCAAGCACTGCAAGGCAATAAATGACTACAATGTTGGAAAAAGC |
| HCoSV-C-5152-2 | ------------------------------------------------------------ |
| HCoSV-C2-5005 | ------------------------------------------------------------ |

| | |
|---|---|
| HCoSV-1 | TTTCAGAGACCGACCAACTCTTTTGAATTCATGGACAGACTTGTGGAATGTGCTACCAAG |
| HCoSV-A-6344 | TTCCAGAGACCGACCAACTCTTTTCGAATTCATGGACAGGCTTGTGGAATGTGCTACTAAA |
| HCoSV-B-2263 | ------------------------------------------------------------ |
| HCoSV-D-5004 | TTTATTAGACCAGAGAACTCCTTTGACTTCATGGAAAAACTTGTGGATTCTGCCACAAAA |
| HCoSV-C-5152-2 | ------------------------------------------------------------ |
| HCoSV-C2-5005 | ------------------------------------------------------------ |

| | |
|---|---|
| HCoSV-1 | CTTGGGAAAGTCCAAATTGCAACTTATTTCAGAAATTTTACTACAGCTGATTCTGATACA |
| HCoSV-A-6344 | CTTGGGAAAGTTCAAATTGCAACTTATTTCAGAAATTTCACCACAGCTGATTCTGACACA |
| HCoSV-B-2263 | ------------------------------------------------------------ |
| HCoSV-D-5004 | CTTGGAAAAGTGAACATTGCAGGTTATTTCAGATCTTTTACCTCGGTTGACACAGATACA |
| HCoSV-C-5152-2 | ------------------------------------------------------------ |
| HCoSV-C2-5005 | ------------------------------------------------------------ |

| | |
|---|---|
| HCoSV-1 | AGCAGACCAGAGCCAGTTGTTGTTGTTTTGCGCGGGAAACCAGGCGTAGGCAAATCTGCT |
| HCoSV-A-6344 | AGTAGACCAGAACCAGTTGTTGTTGTCCTGCGTGGAAAACCAGGCGCAGGTAAATCTGCT |
| HCoSV-B-2263 | ------------------------------------------------------------ |
| HCoSV-D-5004 | GCAAGAATGGAACCAGTTGTCTTGGTACTACGTGGCAAACCAGGAGCTGGAAAATCAGCA |
| HCoSV-C-5152-2 | ------------------------------------------------------------ |
| HCoSV-C2-5005 | ------------------------------------------------------------ |

FIG. 12-11

```
HCoSV-1         GCAGCTACTGTTATGGCAGCTGCAGTATCTAAATTGTTGGTAGGAAGTCAATCAGTGTAC
HCoSV-A-6344    GCAGCTACTGTTATGGCGGCTGCAGTATCTAAATTGTTAGTAGGAAGTCAATCAGTATAT
HCoSV-B-2263    ------------------------------------------------------------
HCoSV-D-5004    GCAGCTACTATCATCACAGCTGCTGTCTCCAAAATTTTGACAGGAACTCAATCTGTTTAT
HCoSV-C-5152-2  ------------------------------------------------------------
HCoSV-C2-5005   ------------------------------------------------------------

HCoSV-1         ACCCTTTCCCCAGATACGGAACATATGGATGGATATCACGGACAGTTTGTGACTTTGATG
HCoSV-A-6344    ACTCTTTCCCCAGACACGGAACACATGGATGGATATCATGGACAGTTTGTGACCTTGATG
HCoSV-B-2263    ------------------------------------------------------------
HCoSV-D-5004    TCTCTCTCCCCTGACACTGAACACATGGACGGATATCACGGCCAGTTTGCAATGATCATG
HCoSV-C-5152-2  ------------------------------------------------------------
HCoSV-C2-5005   ------------------------------------------------------------

HCoSV-1         GATGACCTTGGACAAAACCCAGACGGAGAAGACTTCAGATGTTTCTGTCAAATGGTTTCT
HCoSV-A-6344    GATGACCTTGGACAAAACCCAGACGGTGAAGATTTCAGATGTTTCTGCCAAATGGTTTCT
HCoSV-B-2263    ------------------------------------------------------------
HCoSV-D-5004    GATGATTTAGGACAAAACCCAGATGGAGAAGACTTTAGAACTTTCTGTCAAATGATTTCA
HCoSV-C-5152-2  -------------------------------------------------------TTTCA
HCoSV-C2-5005   ------------------------------------------------------------

HCoSV-1         TGTGCTCAGTACAGACCTGCTATGGCTGACCTTAAAGACAAAGGAATCCTGTTTACATCC
HCoSV-A-6344    TGTGCTCAGTATAGACCTGCTATGGCTGACCTTAAAGACAAAGGAATCCTGTTTACATCC
HCoSV-B-2263    ------------------------------------------------------------
HCoSV-D-5004    GTTGCACAATACAGACCTTCAATGGCTGACTTAAAGGACAAAGGCATTTGTTTAAATCC
HCoSV-C-5152-2  GTCACACAGTACAGACCTGCTATGGCTTCCCTTGAGGACAAAGGAATACTTTTCTCTTCT
HCoSV-C2-5005   ------------------------------------------------------------

HCoSV-1         AGACTGTTGATTGCTACTACTAATCTCCCAGATTTTAACCCTGTTACTATCTCTGATCCG
HCoSV-A-6344    AGATTGTTGATTGCTACTACTAATCTCCCAGATTTTAACCCTGTTACTATCTCTGATCCA
HCoSV-B-2263    ------------------------------------------------------------
HCoSV-D-5004    CAGTTTATTGTTGCAACAACAAATTTACCAGAGTTTAGACCTTTGACTGTTTCTGATCGC
HCoSV-C-5152-2  AGATTAATAATTGCAACAACAAATCTTGTAGATTTCAACCCCGTCACCATTTCTGACCCT
HCoSV-C2-5005   ------------------------------------------------------------

HCoSV-1         CGAGCTTTAGATCGTCGGATCACTTTTGATATTCTTGTCACTCCAGGTTCTGCCGCCACC
HCoSV-A-6344    CGAGCTTTAGATCGTCGGATCACTTTTGACGTTCTTGTCACTCCAGGTTCTGCCGCTACC
HCoSV-B-2263    ------------------------------------------------------------
HCoSV-D-5004    GGAGCTGTTGACCGCAGAATAACATTTGATATTGGTGTGACCCCAGGTACTGCTGTAACA
HCoSV-C-5152-2  CGTGCTTTAGACAGAAGAATAACATTTGATTTGTGTGTTACCCCTGGTTCTGCCGCAACA
HCoSV-C2-5005   ------------------------------------------------------------

HCoSV-1         AAG---AATGGGAAACTTGACTTGGCCGCTGCTCTCAAACCAGATGGACCGGGAGAACAC
HCoSV-A-6344    AAG---AATGGGAAACTTGACTTGGCTGCTGCTCTCAAACCAGATGGACCAGGAGAACAC
HCoSV-B-2263    ------------------------------------------------------------
HCoSV-D-5004    AAA---AATGGAAAGCTTGACCTTGCCATGGCTTTGAAACCAGACGGTGAGGGAGAGTTC
HCoSV-C-5152-2  ACATCAAGGGCAAACTTGACCTTAAGAAGGCATTACAACCTGATGGACCTGGCTTTGGA
HCoSV-C2-5005   ------------------------------------------------------------
```

FIG. 12-12

```
HCoSV-1         CCTTACACTTCTGATTGCCCTATTCTCCACACCACTGGACTCCTCCTGAAGAACCTCAGA
HCoSV-A-6344    CCTTATACTTCTGATTGCCCTATTCTCCACACCACTGGACTCCTCCTGAAGAATCTCAGA
HCoSV-B-2263    ------------------------------------------------------------
HCoSV-D-5004    CCTTACTCGTGTGATTGCCAGATATTACACACTACTGGACTTGCTCTACAGAACCTCAGA
HCoSV-C-5152-2  CCTTACACAACAGACTGCTCTCTCCTGCATACGACTGGGCTAAATCTCAAGAATCTCAGA
HCoSV-C2-5005   ------------------------------------------------------------

HCoSV-1         AACAACCAGACCATGAACTTGAAAGACCTAGTGGACATGATTGTTAAGAGAATTAAACAC
HCoSV-A-6344    AACAACCAGACCATGAACTTGAAAGACCTAGTGGACATGATTGTTAAGAGAATTAAACAC
HCoSV-B-2263    ------------------------------------------------------------
HCoSV-D-5004    ACAGGCAAAACAATGAACATCAAGGAATTAGTTGATTTAATTGTAAAGAAAATCAAGAGC
HCoSV-C-5152-2  AACAATAGGGTTTACAGCATAGTTGATTTGGTTGAAGAGGTAGTGGCCAATATGAACAAG
HCoSV-C2-5005   ------------------------------------------------------------

HCoSV-1         AAGAAAGAAGTTGGAAATATGCTTGACTCTCTTGTTGCTCAGGGACCTACTATGATTGTT
HCoSV-A-6344    AAGAAGGAAGTTGGAAACATGCTTGACTCTCTTGTTGCTCAAGGACCTACCATGATTGTT
HCoSV-B-2263    ------------------------------------------------------------
HCoSV-D-5004    AAAAGGACTACAAGCGGAATGCTTGAAGGACTGGTGGTGCAGTCGCC---CAAAATTGTA
HCoSV-C-5152-2  AAAAAAGCTGTGAATGTCATGCTAGAAGGACTTGTGGCACAGACTGG---AAAAGTAGTT
HCoSV-C2-5005   ------------------------------------------------------------

HCoSV-1         GGCTATACCAAAGACGATGATGGTATCGCTATTGTGGACTGCTTGGAAGAATGGAACAAG
HCoSV-A-6344    GGCTACACTAAAGATGACGATGGCATTGCTATTGTGGACTGCTTGGAAGAATGGAACAAG
HCoSV-B-2263    ------------------------------------------------------------
HCoSV-D-5004    GGCTACACCAAGGACGACGAGGGCGTCGTCATTGTTGACTGTCTCGAGGATTGGCACAGA
HCoSV-C-5152-2  GGTTATACCAAAGATGACGATGGAGTTGTCATCGTAGATTCAATGGATGAATGGCACAAA
HCoSV-C2-5005   ------------------------------------------------------------

HCoSV-1         ATAAAGGACAAGAAGAAGAAACAGCTTGCTTTGGAAATGGTTGCTCAAGAACTTAAGGAC
HCoSV-A-6344    ATAAAGGACAAGAAGAAGAAACAGCTTGCTTTGGAAATGGTTGCTCAAGAACTCAAGGAC
HCoSV-B-2263    ------------------------------------------------------------
HCoSV-D-5004    ATTCGAGACAAGAAAAGAAAGCAACAGGCTCTTGAGATGGTTGCAGAGGAGATGCAAATT
HCoSV-C-5152-2  ATACTAGACAAGAAAAGGAAACAGGAAGTGTTAGAAGTGATTGCCCAAGAAATACAGGTA
HCoSV-C2-5005   ------------------------------------------------------------

HCoSV-1         AAACATGAAGAACATAAAGGCACAATCAAATTACTCAAAATGTTTGTTACTGGCCTTGGA
HCoSV-A-6344    AAACATGAAGAACACAAAGGAACTATAAAGCTGCTCAAGATGTTTGTTACTGGCCTTGGA
HCoSV-B-2263    ------------------------------------------------------------
HCoSV-D-5004    CAACATGACAAACATTCTCAGACCATTTCCTTGATAAAACAGTTTCTCTCAGGGCTCGGT
HCoSV-C-5152-2  AGACATGATGAACACAAGGAGTTTACTCAGATTGTCACCAAATTTTTAACAGCCCTAGGC
HCoSV-C2-5005   ------------------------------------------------------------

HCoSV-1         GTGGTTGCCGCTGTTGCAGGCGCGTATGCCAC-AATGAAATACTTTACAAAGGACAAACC
HCoSV-A-6344    GTGGTTGCCGCTGTTGCAGGCGCGTATGCCAC-GATGAAGTACTTCACAAAAAGACAAACC
HCoSV-B-2263    ------------------------------------------------------------
HCoSV-D-5004    GTGGTGGCTGCTGTTGGAGCCGCCTTTGCCGCAGGCAAGGTACTGAAAAACATGATGACC
HCoSV-C-5152-2  GTAATTGTTGCTGTAGGTGCTGCTTTAATTGGATACAAGTATTTGACATCCGGCCCTGAC
HCoSV-C2-5005   ------------------------------------------------------------
```

FIG. 12-13

```
HCoSV-1         CAAGG--AAGAAGAAGAAGAGCCAGAAGAAAAGAAAGAGAAGAAAACAGAAGAATCCAAA
HCoSV-A-6344    CAAGG--AAGAAGAAGAAGAGCCAGAGGAAAAGAAAGAAAAGAAAACAGAAGAATCCAAA
HCoSV-B-2263    ------------------------------------------------------------
HCoSV-D-5004    TCAGACCGGGCACAGGATGAACCAGACTCTGAATCCCAGGAGAAGACTGAAGAAAAACAA
HCoSV-C-5152-2  AAAGA---AAAGGAATCAACTGAGGAGCCAGAAAAACAAGAAGAGAAAGAAGAACAAAAG
HCoSV-C2-5005   ------------------------------------------------------------

HCoSV-1         GAGGCTGCAGGACCATACAACGGACCTACAAAGAAAGAAATTAAAACATTGAAGTTAAAG
HCoSV-A-6344    GAAGCTGCAGGACCATACAATGGTCCCACAAAGAAAGAAATTAAGACTTTGAAGTTGAAA
HCoSV-B-2263    ------------------------------------------------------------
HCoSV-D-5004    AAAGCTGAAGGACCATACAATGGACCAACAAAGAAGGAACTGAAAACTCTAAAGCTGAAA
HCoSV-C-5152-2  AAAGCTGAGGGACCTTACGAGGGACCCTCCAAGAAAGAGCTAAAAACACTCAAACTGCGC
HCoSV-C2-5005   ------------------------------------------------------------

HCoSV-1         GCCCAGAGTCCACTTATGGATATGGAAAAGAAAATTGCCCAGAATGTCATGCCCTTCCAG
HCoSV-A-6344    GCCCAGAGTCCACTTATGGATATGGAGAAGAAGATTGCTCAGAATGTCATGCCATTTCAG
HCoSV-B-2263    ------------------------------------------------------------
HCoSV-D-5004    GCCCAGGGCCCCTTGTTGGATCTTGAAAAGAAGGTCCTCGCTAACGTGCAGCCTTTCATT
HCoSV-C-5152-2  ATTCAGTGCCCAGTTAAAGACTGTGAGAAAAAACTTTTGAATGCAATACACCCCTTTGTA
HCoSV-C2-5005   ------------------------------------------------------------

HCoSV-1         ATTTTCTATAATGGAAAAAGATACACCCAGTCTTGTCTGGCAATTGGAAAAAGAGTTATT
HCoSV-A-6344    ATTTTCTACAATGGCAAAAGGTACACCCAGTCTTGCTTGGCAATTGGCAAAAGAGTTATT
HCoSV-B-2263    ------------------------------------------------------------
HCoSV-D-5004    TTGCGCGTTGCTGGTAGAGACTACATTCAATCTTGTCTCTTTGTTGGAAAAAGGGTTTTC
HCoSV-C-5152-2  ATTCACTATGATAAAAGAAAGTACACACAGTCATGTATAGCTCTAGGTAAAAGGTTAATA
HCoSV-C2-5005   ------------------------------------------------------------

HCoSV-1         CTTGTGAACAAACATGCTTTTGAATCAGTTGAACACAAATTTGTTGTTGACCAAAAGGAA
HCoSV-A-6344    CTTGTAAACAAACATGCCTTTGAATCAGTTGAGCACAAATTTGTTGTTGACCAAAGAGAA
HCoSV-B-2263    ------------------------------------------------------------
HCoSV-D-5004    CTTGTGAACAAACATGCAATTGACTCAGTTGAACAAAAATTTCAAGTTGCAGGAAAAACA
HCoSV-C-5152-2  ATGGTAAACAAACATGCAATGGAAACACTGGACAGATATGTTACCATAGCTGGAAAGATG
HCoSV-C2-5005   ------------------------------------------------------------

HCoSV-1         TACACATTGGACCAGGTTACAGCTATTTCCCTTGACTGCGGATCAGGTGTCACGGATGTG
HCoSV-A-6344    TACACATTGGACCAGGTTACAGCTATTTCCCTTGACTGTGGATCAGGTGTTACAGATGTG
HCoSV-B-2263    ------------------------------------------------------------
HCoSV-D-5004    TATGACTTGGATGATGTTGATGTGGCAATTCTTGACACGGAATATGGACTTACGGATGTT
HCoSV-C-5152-2  TATGAGATTGATGATTTGGACTGGGTTAACCTTGAAACCTCCCATGGAGAAACTGACGTC
HCoSV-C2-5005   ------------------------------------------------------------

HCoSV-1         TGTGCTGTATGTTTGCCCCCAGGCCCAGACTTCAAATCAATAAAGAAACATTTCCTACCC
HCoSV-A-6344    TGTGCTGTTTGTTTGCCCCCAGGCCCAGACTTCAAATCAATAAAGAAACATTTCCTACCC
HCoSV-B-2263    ------------------------------------------------------------
HCoSV-D-5004    GCAGCTGTCAAGCTCAACACAGGCCCAGAATGGAAAAACCTTTCAAAACTCTTTGTTTCA
HCoSV-C-5152-2  TCCATAGTGAAACTGCCCCCCGGACCGGAATTCAAGAATATAGTTAGAAATTTTTGTTCA
HCoSV-C2-5005   ------------------------------------------------------------
```

FIG. 12-14

```
HCoSV-1        TTCAACACTACCATGTTTCCAGGAACCAGACTGACCATCCTCTCGAATGACCACTACCCT
HCoSV-A-6344   TTCAACACTACCATGTTCCCAGGAACTAGATTGACTATTCTGTCAAATGACCACTACCCT
HCoSV-B-2263   ------------------------------------------------------------
HCoSV-D-5004   CTGGACACGACTCTACACCCAGGAACCAGGATAACGATTTTGTCTAACGACCAACTTAAC
HCoSV-C-5152-2 CAAGACATAACTCTCATGCCTGGCACTAGAATGATGATCTTGTCTAATGATGACTTTTCT
HCoSV-C2-5005  ------------------------------------------------------------

HCoSV-1        ATGTCCAGAGAAGGCTCTTTCCTCAGATTTGAGGATGAGGTACCGACTAATGTAGGTAAC
HCoSV-A-6344   ATGTCCAGAGAAGGCTCTTTCCTCAGATTTGAGGACGAAGTGCCGACTAATGTAGGTAAC
HCoSV-B-2263   ------------------------------------------------------------
HCoSV-D-5004   ATGGTGAGAGAGGGTAGTTTTCTCAGAAATGAGGATGACATACCCACCAATATTGGCCCA
HCoSV-C-5152-2 ATGGTTAGGGAAGGCTCTTTTCTGAGATTTGAGGATTCTGTACCAACAAATATCGGACCT
HCoSV-C2-5005  ------------------------------------------------------------

HCoSV-1        ATGCCCTTTGTAATGCTTTACAAATCAACCTCTTATTTTGGAATGTGTGGCTCAGTTGTA
HCoSV-A-6344   ATGCCCTTTGTAATGCTTTATAAATCAACTTCTTACTTTGGTATGTGTGGTTCAGTTGTG
HCoSV-B-2263   ------------------------------------------------------------
HCoSV-D-5004   ATACCTTTTGTCATGCTTTATAAGGCTTCCTCTTACTTTGGTATGTGTGGTTCTGCTGTT
HCoSV-C-5152-2 ATTCCATTTACCTTACTATACAAGTCCTCCTCTTATTTCGGAATGTGTGGCTCGGCTGTT
HCoSV-C2-5005  ------------------------------------------------------------

HCoSV-1        TGTAGCAGATTTGTTGATGGTGGAGGAATAATTGGAATGCACTGCGCAGGTGGAGGCGGA
HCoSV-A-6344   TGTAGTAGATTTGTTGATGGTGGAGGAATAATTGGAATGCACTGTGCAGGTGGAGGCGGA
HCoSV-B-2263   ------------------------------------------------------------
HCoSV-D-5004   GTGACCAGAATTGGTGATTGTCCCGGAATTCTTGGTCTCCATTGTGCTGGCGGTGGGGGT
HCoSV-C-5152-2 GTGTGCAGAACATCTGGCGAAACTGGCATAGTGGGAATGCACTGTGCAGGTGGAGGCGGA
HCoSV-C2-5005  ------------------------------------------------------------

HCoSV-1        GTCAGTGTTGGAACTCGTTTGACTGCTAGAATGATTGAATCAGTTTTTGATTACTTCTA-
HCoSV-A-6344   GTCAGTGTTGGTACCCGTTTGACTGCTAGAATGGTTGAATCAGTGTTCGACTACTTCTA-
HCoSV-B-2263   ------------------------------------------------------------
HCoSV-D-5004   GTGTGTGTGGCTTCCAGAGTTACAAAAAGAATGGTAGAAACTGTCCTAAAATACTTTTA-
HCoSV-C-5152-2 GTTTCTGTCGCATGTCGCGTCACTAGAAAAATGGTAGAAGCTGCTGTCATGTATTTTTTA
HCoSV-C2-5005  ------------------------------------------------------------

HCoSV-1        --CCCCCCAGTAGCCCAGGGAATAATTGAAAACACAGAGACAGGACCCCGTGTACATGTG
HCoSV-A-6344   --CCCCCCAATAGCTCAGGGAATAATTGAAAACACAGAGACAGGACCCCGTGTGCATGTG
HCoSV-B-2263   ------------------------------------------------------------
HCoSV-D-5004   --TCCACCTCAGGTACAGGGACAAATTATAAACACAGAAAATGGACCCCGTGTGCATGTT
HCoSV-C-5152-2 ATCCTTCTAATAGTTCAAGGCATGATTGTGTCAACTGAAACATGTGACCCAATTCACGTT
HCoSV-C2-5005  ------------------------------------------------------------

HCoSV-1        CCCAGAACTTCCAAACTCAAAAGAACAAACGCCACTTATCCGGCAACGGAAAAGTATGGC
HCoSV-A-6344   CCCAGAACTTCCAAACTCAAAAGAACAAATGCTACTTATCCGGCAACGGATAAGTACGGC
HCoSV-B-2263   ------------------------------------------------------------
HCoSV-D-5004   CCCAGACAGTCTAAGCTCAAAAGAACAAATGCTGTTTATCCTGCTACTCCAAAATATGGA
HCoSV-C-5152-2 CCTAGAAAAACAAAGTACAAGAGAACTAATGCTGATTATCCTTCTACTAAGAATTATGCC
HCoSV-C2-5005  ------------------------------------------------------------
```

FIG. 12-15

```
HCoSV-1         CCAGCTGCTCTTTCGCGGTATGATCCGCGATTAAATGAGGGAGTCAACTTGGATGAGGTG
HCoSV-A-6344    CCAGCTGCTCTTTCGCGTTATGATCCGCGATTAAATGAAGGAGTCAATTTGGATGAGGTG
HCoSV-B-2263    ------------------------------------------------------------
HCoSV-D-5004    CCTGCTGTGCTTTCTAAGAATGATCCCAGGCTTGACCCAGATGTGGACTTTGACAAAGTA
HCoSV-C-5152-2  CCAGCTGTTTTTATCTAGAAATGACCCCAGACTTGACCCTGATGTTGATTTTGATACTGTT
HCoSV-C2-5005   ------------------------------------------------------------

HCoSV-1         ATCTTCTCAAAACATACTCAAAACACTCTTGTTGAGAAAGGATCCACTTTCAGAAGCGCC
HCoSV-A-6344    ATTTTCTCAAAACACACTCAAAACACCCTTGTTGAGAAAGGATCCACTTTCAGAAGCGCT
HCoSV-B-2263    ------------------------------------------------------------
HCoSV-D-5004    ATTTTCTCAAAACATGTTGCCAACGTGGTTATTGATGAGGACACTAGTTTCTGGAATGCC
HCoSV-C-5152-2  TTGTTCTCCAAACACACTGAAAATGTCATCATCCCTCCTGACACACTGGCTTACGATAGT
HCoSV-C2-5005   ------------------------------------------------------------

HCoSV-1         CTTGACATGGCAGCAGAAATTTATGGTGAAAAGTTTAGAGGAAATGATTTCTCTCCCCTT
HCoSV-A-6344    CTTGACATGGCAGCAGAAATTTATGGTGAAAAGTTTAGAGGAAATGATTTCTCTCCCCTT
HCoSV-B-2263    ------------------------------------------------------------
HCoSV-D-5004    CTAAAAATGTCTGCCCAAATATACGCAGAAAAATTCAAAGGTGTTGACTTCTCCCCTCTC
HCoSV-C-5152-2  CTCCTGAAGGCTACACAGGTTTACGCTTGTAAGTTTAATGGCA---ATTTTGAACCTTTA
HCoSV-C2-5005   ------------------------------------------------------------

HCoSV-1         TCAGTTGAAGATGCAATTCTTGGAATTCCCGGACTTGACAGACTTGACCCGAATACTGCT
HCoSV-A-6344    TCAGTTGAAGATGCAATTCTTGGAATTCCCGGACTCGACAGGCTTGACCCGAACACTGCT
HCoSV-B-2263    ------------------------------------------------------------
HCoSV-D-5004    ACTGTAGAGGAAGCAATTCTTGGAATTCCAGGACTTGACCGGATGGACCCCAATACTGCT
HCoSV-C-5152-2  ACTGTGGAAGAGGCAATTTTGGGAATACCTGGCTTGGACAGGATGGATCCTAATACATCA
HCoSV-C2-5005   ------------------------------------------------------------

HCoSV-1         TCTGGATTGCCCTACACTAAAACCAGACGACAGATGATTGACTTCAACACAGGACAGATT
HCoSV-A-6344    TCTGGATTGCCCTACACAAAAACCAGACGCCAGATGATTGACTTCAACACAGGACAGATT
HCoSV-B-2263    ------------------------------------------------------------
HCoSV-D-5004    TCAGGATTACCCTATACTAAAAACTAGAAGACAGATGATTGATTTTCAGGAAGGGAAATA
HCoSV-C-5152-2  TCTGGCCTGCCTTATACTAAAAACAAGAAGACAGCTCATAGATTTTGTCAATGGAAAATT
HCoSV-C2-5005   ------------------------------------------------------------

HCoSV-1         TTGGACGACACTCTTAAGTGTCGACTTGGACAATGGCTTGCAGGACGACCCCCCCAGGAA
HCoSV-A-6344    TTGGACGACACTCTCAAGTGCCGACTAGGACAATGGCTTGCTGGACGGCCCCCACAGGAT
HCoSV-B-2263    ------------------------------------------------------------
HCoSV-D-5004    CTTGACCCAGAACTCCAATCCAGACTTGACACTTGGCTTTCAAATAAACAACCA---GAA
HCoSV-C-5152-2  TTGGACACACAATTACAGGAAAGACTCGACATGTGGCTGAGTGGAAAACAACCT---GAA
HCoSV-C2-5005   ------------------------------------------------------------

HCoSV-1         GTACATTACCAGACATTTCTTAAGGATGAAATCAGGCCCATTGAAAAGGTCAAAGCAGGA
HCoSV-A-6344    GTGCACTACCAGACTTTCCTCAAGGATGAGATTAGGCCCATTGAAAAGGTCAAAGCAGGA
HCoSV-B-2263    ------------------------------------------------------------
HCoSV-D-5004    ATGCTCTACCAAACATTTTTAAAAGATGAAATCAGACCAATTGAAAAAGTAAAAGCTGGT
HCoSV-C-5152-2  ACTTATTACCAAACTTTCCTAAAAGATGAAATTAGGCATATTGACAAAGTGAGAAGAGGG
HCoSV-C2-5005   ------------------------------------------------------------
```

FIG. 12-16

```
HCoSV-1        AAGACTAGAATAATTGATGTTCCTCCTCTTGATCATGTCATCGCTTTTAGAATGCTCTTT
HCoSV-A-6344   AAGACTAGAATAATTGATGTTCCTCCTCTTGACCATGTCATCGCTTTCAGAATGCTATTT
HCoSV-B-2263   ------------------------------GATCACGTGTTGGCCTTCAGAATGCTTTTT
HCoSV-D-5004   AAAACCAGAATTATTGATGTGACCCCCCTTGACCATGTTTTGGCATTCAGAATTGTTCTA
HCoSV-C-5152-2 AAAACTCGCATTATCGATGTGACTCCCTTAGATCATGTTTTGGCTTTCAGAATTCTATTT
HCoSV-C2-5005  ------------------------------GATCATGTGATTGCTTTTCGTGTGTTGTTT
                                             **  ** **   * **  **    *   *     *

HCoSV-1        GGCAGATTCATTGCCCACTACCACTTAAACTTTGGCTTCAAAACAGGCTCTGCTATTGGT
HCoSV-A-6344   GGCAGATTCATTGCCCATTACCACTTAAATTTTGGTTTCAAGACAGGATCCGCTATTGGC
HCoSV-B-2263   GGAAGATTTATGGCTTATTACCACCTCAACCCAGGATTCAAAATTGGCTCAGCAATTGGT
HCoSV-D-5004   GGCAGATTCATGGCTCATTTTCACAATAATTATGGTTTTAATCTTGGTTCTGCTGTTGGA
HCoSV-C-5152-2 GGCAGATTCATGGCACATTACCACCTAAACCCTGGCTTTGATTTAGGCAGCGCTATTGGA
HCoSV-C2-5005  GGCAGATTCATGGCTTACTATCATCTAAATCCCGGCTTTGAACTCGGAAGCGCCATAGGG
               ** *****  ** **   *   **    **       ** **  *    **     **   * **

HCoSV-1        TGTGACCCAGATGTCGCTTGGGCTTCTTTTGGCTTTGAACTCAGTGGCTTTCCTTATCTG
HCoSV-A-6344   TGTGACCCAGATGTTGCTTGGGCTTCTTTTGGCTTTGAACTCAGTGGTTTTCCCTATCTG
HCoSV-B-2263   TGTGACCCAGAAACTGCTTGGAATGGATTTGGTTACACGCTCTCTAGCAAACAATACAAA
HCoSV-D-5004   TGCGATCCCGACGTTGCTGGGCCAACTTTGGCTTTGCTCTTTCTTCTAAGAAGTACCAG
HCoSV-C-5152-2 TGTGACCCAGAAGTTGCTTGGAATCAGTTTGGTTATCATCTTACTAAGTATAAAAATCTC
HCoSV-C2-5005  TGCGATCCTGAAATTGCCTGGACTCATTTCGGTTACCACCTCAGTGGTTTCCGGAATCTT
               ** **  ** **       **  ***       ** **  *      **   *             *

HCoSV-1        TATGATTTTGATTACTCAAACTTTGATGCTTCTCACAGTACTTCAATATTTGAAATCTTA
HCoSV-A-6344   TATGATTTTGATTACTCAAATTTTGATGCTTCACACAGTACTTCAATTTTTGAAATCATA
HCoSV-B-2263   TATGACTTTGACTATTCAAACTTTGATGCAAGTCATTCCACTTCCATATTTGAAATCTTG
HCoSV-D-5004   TATGACTTTGATTACTCAAACTTTGATGCTTCTCATTCAGAGTCCATCTTTGAACTTCTT
HCoSV-C-5152-2 TATGACTTTGATTACTCAAACTTTGATTCTTCTCATTCTAAGTCTATCTTTGAGATTCTG
HCoSV-C2-5005  TATGACTTTGACTATTCTAACTTTGATTCTAGTCACTCTGTGTCTATTTTCAAAATCCTC
               ***** *****  ** **  ** ****** *      **       ** ** **  *   *   *

HCoSV-1        GAACAGAAATTCTTTTCCCCAGAATTAGGTTTTGATCCTAGATGCTCACTTCTCTTGAAA
HCoSV-A-6344   GAACAGAAATTCTTTTCTCCAGAATTAGGTTTTGATCCTAGATGCTCACTTCTCTTGAAA
HCoSV-B-2263   GAAGAGGAATTCTTTACCCCAAAAAATGGTTTTGATGTGAGATGCTCTCTACTGCTAAAA
HCoSV-D-5004   AAACAGTTTGTTTTCACCAAAGACAATGGTTTTGATCACAGATGCTCTCTCATGATTGAT
HCoSV-C-5152-2 AAAGATCATTTCTTCACCACAACCAACGGTTTTGATTCTCGTTGCGCCTTGCTACTAGAT
HCoSV-C2-5005  AAAGATCATTTCTTTACCCCTTCCAACGGTTTTGATTCTCGTTGCACCTTACTTTTAGAT
               **  *     * **   *              ********   * ***  *    *     *  *

HCoSV-1        TCCCTTGCAGTTTCAACCCACTGTTATGAGAACAAGAGACTCCAGATTGCTGGAGGACTT
HCoSV-A-6344   TCTCTTGCAGTTTCGACCCACTGTTACGAGAACAAGAGACTCCAGAT-------------
HCoSV-B-2263   TCTTTATCTTGTTCTACTCACTGTTATGAAAACAAACGGTTTACCAT-------------
HCoSV-D-5004   TCTCTGGTTACCTCGACCCACTGCTATGAGCAACAAAGAATGACCATTCGCGGCGGCCTC
HCoSV-C-5152-2 TCTCTGGCTGTCTCCAAACACAAATATGACAACAAAGTGATGACTATAGTGGGCGGCCTC
HCoSV-C2-5005  TCACTGGCTGTTTCAAAACACAAGTATGACAACAAGGTTATGACTAT-------------
               **   *       * *   ** *  ** **  **  *            *    **

HCoSV-1        CCCTCTGGCACGGCAGGTACCTCAGTACTGAACACCGTGATAAACAACATTATCTTTCAC
HCoSV-A-6344   ------------------------------------------------------------
HCoSV-B-2263   ------------------------------------------------------------
HCoSV-D-5004   CC----------------------------------------------------------
HCoSV-C-5152-2 ------------------------------------------------------------
HCoSV-C2-5005  ------------------------------------------------------------
```

FIG. 12-17

| | |
|---|---|
| HCoSV-1 | GGTGCACTATACCACACTTACACTAATTTTGAGCGGGATGACATCAGTATGTTAGCCTAT |
| HCoSV-A-6344 | ------------------------------------------------------------ |
| HCoSV-B-2263 | ------------------------------------------------------------ |
| HCoSV-D-5004 | ------------------------------------------------------------ |
| HCoSV-C-5152-2 | ------------------------------------------------------------ |
| HCoSV-C2-5005 | ------------------------------------------------------------ |
| | |
| HCoSV-1 | GGCGACGACATTGTTGTTGCCTCCAAATTTGAACTTGACTTGGTTATGGTTAAGGCTTTC |
| HCoSV-A-6344 | ------------------------------------------------------------ |
| HCoSV-B-2263 | ------------------------------------------------------------ |
| HCoSV-D-5004 | ------------------------------------------------------------ |
| HCoSV-C-5152-2 | ------------------------------------------------------------ |
| HCoSV-C2-5005 | ------------------------------------------------------------ |
| | |
| HCoSV-1 | ATGAACCGGATTGGCTATAAGATTACCCCTGCAGACAAAAGTGATGAATTCAGACCAAAG |
| HCoSV-A-6344 | ------------------------------------------------------------ |
| HCoSV-B-2263 | ------------------------------------------------------------ |
| HCoSV-D-5004 | ------------------------------------------------------------ |
| HCoSV-C-5152-2 | ------------------------------------------------------------ |
| HCoSV-C2-5005 | ------------------------------------------------------------ |
| | |
| HCoSV-1 | TGTATGGATGACATTTGCTTCTTAAAGAGGCGTTTTGTTAAAGTTGCTGGAGTTTGGGCT |
| HCoSV-A-6344 | ------------------------------------------------------------ |
| HCoSV-B-2263 | ------------------------------------------------------------ |
| HCoSV-D-5004 | ------------------------------------------------------------ |
| HCoSV-C-5152-2 | ------------------------------------------------------------ |
| HCoSV-C2-5005 | ------------------------------------------------------------ |
| | |
| HCoSV-1 | CCAGTGATGGAAACTGAAAACCTCGAGGCAATGTTGTCTTGGTACAAACCAGGAACTCTT |
| HCoSV-A-6344 | ------------------------------------------------------------ |
| HCoSV-B-2263 | ------------------------------------------------------------ |
| HCoSV-D-5004 | ------------------------------------------------------------ |
| HCoSV-C-5152-2 | ------------------------------------------------------------ |
| HCoSV-C2-5005 | ------------------------------------------------------------ |
| | |
| HCoSV-1 | AATGAAAAGCTCCAGAGTGTCTCAAGACTTGCCCACTTCTCAGGACGTGACGTGTATGAC |
| HCoSV-A-6344 | ------------------------------------------------------------ |
| HCoSV-B-2263 | ------------------------------------------------------------ |
| HCoSV-D-5004 | ------------------------------------------------------------ |
| HCoSV-C-5152-2 | ------------------------------------------------------------ |
| HCoSV-C2-5005 | ------------------------------------------------------------ |
| | |
| HCoSV-1 | CACCTTTTCAAGCCCTTCATTCGTGATGGGTTTGATGTCACACCTTGGAAACAGTTACAC |
| HCoSV-A-6344 | ------------------------------------------------------------ |
| HCoSV-B-2263 | ------------------------------------------------------------ |
| HCoSV-D-5004 | ------------------------------------------------------------ |
| HCoSV-C-5152-2 | ------------------------------------------------------------ |
| HCoSV-C2-5005 | ------------------------------------------------------------ |

FIG. 12-18

```
HCoSV-1         TTGGAATGGCTTAATAAGTTATCAGCTTAAAGAATTTTGAATTGGCATTTCAGATTTATT
HCoSV-A-6344    ------------------------------------------------------------
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         TTGAATTTGGCTTTTAATTCGGCTTTAATTTGGTTATTTATTGGGTATATTCAAATCTAA
HCoSV-A-6344    ------------------------------------------------------------
HCoSV-B-2263    ------------------------------------------------------------
HCoSV-D-5004    ------------------------------------------------------------
HCoSV-C-5152-2  ------------------------------------------------------------
HCoSV-C2-5005   ------------------------------------------------------------

HCoSV-1         TGACC
HCoSV-A-6344    -----
HCoSV-B-2263    -----
HCoSV-D-5004    -----
HCoSV-C-5152-2  -----
HCoSV-C2-5005   -----
```

FIG. 12-19

| | | |
|---|---|---|
| HCoSV-1 | TTCTGAGACCGGCACGGTCAACCCGACTCATTTACGAGTTACTCATTTATTTTGAAACAT | 60 |
| HCoSV-C-5152-1 | ------------------------------------------------------------ | |
| | | |
| HCoSV-1 | CATAAAGAACGTGAACCGCTCTTTGTTTCTTTAAGGAATTTAGAGTAGAAAACATTTGAG | 120 |
| HCoSV-C-5152-1 | ------------------------------------------------------------ | |
| | | |
| HCoSV-1 | ATGAGGCCCGGTTGAACTCCGGGCGCTTTCCATCCGCTGTGATGGGCTCACTCCTGTACA | 180 |
| HCoSV-C-5152-1 | ------------------------------------------------------------ | |
| | | |
| HCoSV-1 | CCGTGAGTCCGCGCAGTGCTGACTTAACACTTAAGTAATGTATAGGCCGAGGATTACACC | 240 |
| HCoSV-C-5152-1 | ------------------------------------------------------------ | |
| | | |
| HCoSV-1 | GCTCGGCTCCCACCTTTCACCACCGTGGGATTAACAGGTTCAATGCACAAATTCCTGTCC | 300 |
| HCoSV-C-5152-1 | ------------------------------------------------------------ | |
| | | |
| HCoSV-1 | TTGGCTATGTCAAAGCAATACAGTGTGTACATGGCGTGCACGCTCAAAGCGGAGACTTAG | 360 |
| HCoSV-C-5152-1 | ------------------------------------------------------------ | |
| | | |
| HCoSV-1 | GCCTCACAGATTGTGTTTTGTGTTATTGGATGCTGGATGGTCACGTTGGAGACTGCATGT | 420 |
| HCoSV-C-5152-1 | ------------------------------------------------------------ | |
| | | |
| HCoSV-1 | GGCAGTCTTGAAACGTGTGGTTTGACGTCTATCCATTATGGCAGTGGGTGGAGTACTGCA | 480 |
| HCoSV-C-5152-1 | ------------------------------------------------------------ | |
| | | |
| HCoSV-1 | AAGATGTCACCGTGCTTTACACGGTTTTTGAACCCCACACCGGCTGTTTGGCGCTTGCAG | 540 |
| HCoSV-C-5152-1 | ------------------------------------------------------------ | |
| | | |
| HCoSV-1 | GACAGCAGGTTTATTTTCTTATGTTCTCCATTTCTAGCCAACAGGGTTCTATCCTGTTGG | 600 |
| HCoSV-C-5152-1 | ------------------------------------------------------------ | |
| | | |
| HCoSV-1 | GCGGAGTGATACTCCCGTTCCTTCTTGGACAGATTGCCTCCACGTTCTTTGTGGATCTCA | 660 |
| HCoSV-C-5152-1 | ------------------------------------------------------------ | |
| | | |
| HCoSV-1 | AGGTGATCAAGTCACTGGTGAATAGAGCGAAGGTTGAGGAGACCTGAGGAATTTCCATGT | 720 |
| HCoSV-C-5152-1 | ------------------------------------------------------------ | |
| | | |
| HCoSV-1 | GGCTTTGCCAGGAGTTGTAGCGATGCTGTGTGTGTGTGCGGATTTCCCCTCATGGCAACA | 780 |
| HCoSV-C-5152-1 | ------------------------------------------------------------ | |
| | | |
| HCoSV-1 | TGAGCCTCACAGGCCAAAAGCCCTGTCCGAAAGGACCCACACAGTGGAGCAACCCCAGCT | 840 |
| HCoSV-C-5152-1 | ------------------------------------------------------------ | |
| | | |
| HCoSV-1 | CCCTCCTACAAAGCTTTGTGAGAATGAACTCAAGTTTATTCTACTTTATTCTCTATTTAC | 900 |
| HCoSV-C-5152-1 | ------------------------------------------------------------ | |

FIG. 13-1

```
HCoSV-1        ATCAGGCCCCAAAGATGTCCTGAAGGTACCTTGTGTATCTGGGCACGAGCACCATCAGCT 960
HCoSV-C-5152-1 ------------------------------------------------------------

HCoSV-1        ACCCGGACTTGTATTTCGG--TACAGACACATGTGGTGACCCAGCCCCTCTGCT--TCGG 1016
HCoSV-C-5152-1 ----GGACTTACAGTTTAAGCTGTAGACACATGTGGTAACCCAGCCCCTTCCCTGACGGG 56
                   ******  * **      * ************* *********  **    **

HCoSV-1        CAGGGGGGCTTTCGCTCGCTCAGCACGAGATCTGATCAGGAGCCCCTCCCAGTGTGCTTT 1076
HCoSV-C-5152-1 AGAGGGGGCTTTTGCTCACCTAGCACAGGATCTGATCAGGAGACTCCCTCACAGTGCTTT 116
                * ********* ****  * ***** ************* * ****** ******

HCoSV-1        ACACC-TGGCGAGGGGTTAAAAATTGCCCAAGGCCTGGCAAAACAACCTAGGGG-ACTAG 1134
HCoSV-C-5152-1 ACACTGTTGTGGGAGTTTAAAAATTGCCCAAGGCCTGGCACA-CAACCTAGGGGGACTAG 175
               ****  *  *  * * *  ************************ * ************ *****

HCoSV-1        GTTTTCCTTTTATTAATAATATCTGTCATTATGGGTGCAAATAATAGCAAAGAATCTGTG 1194
HCoSV-C-5152-1 GTTTTCCTTTTATT--TTGAAGTTGTCAATATGGGTGCAAACAACAGCAAAGAGAGTGTT 233
               **************  *  *   ***** ************ ** ********   ***

HCoSV-1        TCCAGCAATGGCAACGAGGGAACAATTGTTAATAACTTTTATTCAAACCAGTATTATGCT 1254
HCoSV-C-5152-1 TCTAGCAATGGCAATCAGGGTACTATTGTTAACAATTTTTATGCTAATTCTTACTATGCT 293
               ** ***********  **** **  ******** **  *****  **    ** ******

HCoSV-1        TCTATTGATGCTTCTGCCCAAGGTGTTGGGACCTCTACTACTCCTGAAAACGGCAACGTA 1314
HCoSV-C-5152-1 TCTATTGACGCTTCTGCCTCCTCGGTCGGGGGCGACACTCCTGCTGAAAACGGTACTGTC 353
               ********  ********      ** ***   *  *  *** ** ********* * **

HCoSV-1        TCTGGCTTTCTTGGACTTGCAGGTAGTGCTTTTAATGCTCTCTCTCTTCTCGCCTCACCA 1374
HCoSV-C-5152-1 ACTGGTCTTCTGGGAAATATTGCTTCTGCTTTCACTTCCGCTGCACTCTTGGCCAAACCA 413
                ****  **** ***       *    ******  *   **   * *** * *** ****

HCoSV-1        CGAACCGAGACAGGAATGATGATGGAAGATCGTGTCCTTTCCCGTACTGCCGGTAATACA 1434
HCoSV-C-5152-1 ACTGTAGAAAATGAAACCGGTATGGAAGATAGGGTAATTTCTCTCAAGGCAGGCAATACT 473
                 * * *  *       *  *****************   ***  ** ** *****

HCoSV-1        TCTGTAAACTCTCAAGCTGCTGAAGGGGTTTTGCAGGCATATGGGACTGAGACAGACAGC 1494
HCoSV-C-5152-1 TTGGTTAACTCACAGGCTTCAGAAGGGCTGTTATATGGATATGGCAAGGAAAGTGATAAA 533
                * ** ***** ** ***  * ****** *  * *  ****** ** * *  ** *

HCoSV-1        AATTCGCCCACTTCGTGTGGCGACGATCCTAGCAAGGGTACACACGCAACAGACAGAGCC 1554
HCoSV-C-5152-1 AACCCCCCAACATCATGCGGTGATGATCCATCTGAAACACAACACTGCATACAGAGAGGT 593
               **  * ** ** ** ** ** ** ** *****     *    ****  * * * ****

HCoSV-1        TTTGTAATACAATTGCTTCCATGGAAACAGACAACAAATTCATACTTTGCTCAATGGGTA 1614
HCoSV-C-5152-1 TTTACTATTCCTTTGACTGATTGGACCAGAACCCAAGATCCATGGCAAGCTCT-TGTATA 652
               ***   ** *  *** *  *    ****   * *** **  ***    ****  ** **

HCoSV-1        -AGACTCACACAGAAACTGTCAAACAATTTGCATGGAAATGTTATGGCCAAAAACATTAA 1673
HCoSV-C-5152-1 CAAACTTTCAGATCAGTTTAAAAATGAAAGCAAGGGAAACATGTTTCCAAGGGAATGAA 712
                * *** ** *  *  * *  *  ***  *   * ****  ** *  ****   ** **

HCoSV-1        ATCACATGCTTTTGCCAAAATGGGCTTTGAAGTAATGTTACAGGCAAACACCTCGCCTTT 1733
HCoSV-C-5152-1 AACACATGCTTTTACCAAAACTGGCTACAGGGTATCTCTTCAGGTTAACACTTCTCCTTT 772
               * *********** ******  *****    ****   *  ****  * **** ** *****
```

FIG. 13-2

```
HCoSV-1        CCATAATGGCATACTGGGTCTTTTCTTGGTACCGGAGTTTGTTAGAAAGGGTGAAATTAC 1793
HCoSV-C-5152-1 CCACTCTGGCCTTTTAGGCCTATTTCTTGTCCCAGAGTGTAGTATACCTGCATCTACGTC 832
               ***  ****  *  *  **  **  **    *  **  ** ****  *  **  *     *        *    *

HCoSV-1        AGATGAGTGGATTGACCTCACACCTACCTCTTCTTTAGTTTCAAACACTGAGTTGTACAA 1853
HCoSV-C-5152-1 ACTGGATTGGATTGACTTGAAGACAGATGCTCCTCTTTTAAAGAGCACAAACTATTACAR 892
                *   **  *********  *  *       *    **  **    *   *     * ***  *  *   ****

HCoSV-1        C--CCCCAGACTTATGCAA-ATTTTCCATTTG------------ATGC---TAAACATAG 1895
HCoSV-C-5152-1 GGGTCTTGGACTACAGCAACAATCTTCAGCCGCTGGAAACAAGTATGCAGACAACTGTAT 952
                *   ****   **** * *  **    *               ****     **      **

HCoSV-1        TTTTGATTATTCTGATATTACACCAGAACAATTTATGATTTTCCCTCACCAACTTATAAA 1955
HCoSV-C-5152-1 CATAGACTCCTCAGCAATAACTCCTCAGCAGCTCTTTATATATCCTCACCAACTTATAAA 1012
                 *  **   **  *   **  **  **       *   *   **  *    *****************

HCoSV-1        TCCTAAAGACACAAATGTTGCCACAGTACGTGTGCCGTACATTAATATTGCTCCAACAAA 2015
HCoSV-C-5152-1 CCCCAAAGAAACTAACATTGCCTCAGTTGCAGTTCCTTATGTGAACTGTGCTCCAACATC 1072
                 ** *****  **  **   *****  ****      **  **  **    *  **     **********

HCoSV-1        TGATACTACAGTACATACAGTATGGACAGCTGTTGTTATGGTTCTTGTACCTCTTAACTT 2075
HCoSV-C-5152-1 TGATCCTCAGATCCACAACATCTGGACTGCCTTGGTAGTGATAATTTCACCCCTCCAGTT 1132
               ****  **        *  **   *  ***** **    *  **    **  *    **    ***  **     *  **

HCoSV-1        TTCTTCTGGTGCTTCACCAACTGTATCTTTAACATTAACTATAACTCCAATAAACTCAGT 2135
HCoSV-C-5152-1 TGCTAATGGTGCTTCTCCTAATGTAACCATGTCACTTACAGTAACCCCTCTTAACACTGT 1192
                 *  **  *********  **  *  ****  *   *   **  *  **   ****  **       *  ***  *  **

HCoSV-1        TTTTAATGGATTACATCACACC---------GCACAGGGGCCTATCCCTGTGCGACCTTT 2186
HCoSV-C-5152-1 TTTCAATGGCTTACGCCATGCTCTGCCTGCTACGCAAGGCCCTATACCAGTTAGGTGTAT 1252
               ***  *****  ****    **    *          *   **  **  *****  **  **     *     * *

HCoSV-1        CCATAATTTCCAGCAGTTTAGCACTACTGTCCCTCTGCGCACTGAACCATGTTACGGCAT 2246
HCoSV-C-5152-1 GCAGAATTCTTACCAGTTCTCAACCACACTTCCCGCAACCGCAGAACCGTGTTACGGTTG 1312
                 **  ****    *  ******   **  **   *  **          *  *  ***** ********

HCoSV-1        GACAGTGACTCCTCCAGTTGATTACATGCCCTTACCCATTACAGATTTAGTTGAGCTTGC 2306
HCoSV-C-5152-1 CACAGTGAACCCGCCCAGAGACTACTTGCCTCCTGCTATCGAGGATTTGCTTTCTTTGGC 1372
                *******  **  **    **  ***  ****      *  **     *****  **      *  **

HCoSV-1        TAAAGTGCCCAGTTTTGTTACTGTGGCAAACAGTGACACGACTAGCGAGCGTAGTTTCCC 2366
HCoSV-C-5152-1 TAAAGTTCCTTCTTTT-CTGCTTTGT--AGCGAAGACACCGCTAAACAGG------TGCC 1423
               ******  **   ****  *  **  **    *  *   *****  ***    **        *  **

HCoSV-1        TTATTTCTCTGTTAGTAACACA-GAACAAGGCAGAA----ATCTTTTCAAATCCAGTGTA 2421
HCoSV-C-5152-1 ATATGTGAAGGTTACAAACACTCAAACACAGCACAACTCTATCTTTTCAA--TGAATGTA 1481
                ***  *     ****  *****     ****  ***  **   **********       *  ****

HCoSV-1        GTTCTCAGCGACT-TACACTACCAGCACACTCTTGTAGCAAATTTGGCCCGTTACTTTTG 2480
HCoSV-C-5152-1 GTTTTGTCAGATTATGCACT-TCAGAGGACCATGGTTTCACAGCTGGGAACATTTTTCTG 1540
               ***  *    **  *  *  *  ****  ***    **  *  **  *  **  *    ***        *    **  **

HCoSV-1        CAACTACAGAGGTAGTCTACAGTTTGATTTTATAGCTGCAACAACTGCAATGACAAGAGG 2540
HCoSV-C-5152-1 TAATTATAGAGGAAGCATTCAGATA--------------------------------- 1565
                **  **  *****  **   * ***  *

HCoSV-1        CAAATTGCTCATTAGCTACACCCCACCAGGGGCTGGTGAGCCACAATCAATTGATCAGGC 2600
HCoSV-C-5152-1 ------------------------------------------------------------
```

FIG. 13-3

```
HCoSV-1        AATGATGGGAACTTATGCTATCTGGGATTTGGGATTACAATCAACCTTCAATTTTGTAGT 2660
HCoSV-C-5152-1 ------------------------------------------------------------

HCoSV-1        CCCTTTTATATCTGCTTCTGACTTCAGATTTAACACCTCTTCTGTATCTAATGCTTTGAA 2720
HCoSV-C-5152-1 ------------------------------------------------------------

HCoSV-1        CTCTGATGGTTGGATCACAGTGTGGCTTATGAACCCTCTAACATATCCTCCCAGTACACC 2780
HCoSV-C-5152-1 ------------------------------------------------------------

HCoSV-1        TCCTACCCAACAGATATTGATGTTGATGTCAGCTGGCAGTGACTTTTCTTACCGGTTGCC 2840
HCoSV-C-5152-1 ------------------------------------------------------------

HCoSV-1        CATTTCGCCCGGTTTCGCCGAGGGGGAAACGAGCGAACATCCAATGGACAACGCTGAGTG 2900
HCoSV-C-5152-1 ------------------------------------------------------------

HCoSV-1        CGGGAAAATTGATGACAAAGACGCAGGAATGTTTTCCGGACACTCTGTTGGGCTGCCTAC 2960
HCoSV-C-5152-1 ------------------------------------------------------------

HCoSV-1        TCCCCACACCTCGACTTCTTTCTTCTATGACAGGTACAGATTCGTAGGAATTGTAAAGAG 3020
HCoSV-C-5152-1 ------------------------------------------------------------

HCoSV-1        TGTAGTGAATAATACTCCCAAACCAGTCAACATTTATGATGATACAGGAAAAGTTAAGAA 3080
HCoSV-C-5152-1 ------------------------------------------------------------

HCoSV-1        CCTACAACAGGTTTTTCCAACTTCAGACACACTACTGCCCCACTCTTTGATGTCCCTTTC 3140
HCoSV-C-5152-1 ------------------------------------------------------------

HCoSV-1        TCCCTGTGCGTCAGTGTGTGGCCAGCCTATCTCTTCCTTCCTGTTTGCTCAACGAGCGAA 3200
HCoSV-C-5152-1 ------------------------------------------------------------

HCoSV-1        TCCCAAGAAAACTCTAAAGCTGCGCTCAGGTGATGAATTCTTGTATAGATGTTGCCCTTT 3260
HCoSV-C-5152-1 ------------------------------------------------------------

HCoSV-1        TTCTTACATTAAATGTGACCTTGAGTTTACTGTGGTCCCCCCTGCGAATTCTACTAGAGA 3320
HCoSV-C-5152-1 ------------------------------------------------------------

HCoSV-1        TTATATTGTGCACTGGTACCCGCCAGGGGCCACCCTGGATGCTGGAGAAGTAGCCGTGGG 3380
HCoSV-C-5152-1 ------------------------------------------------------------

HCoSV-1        TAATACATCAGGTAGCAATGGCTTTGATGATAATGGGATGAACGCTGGTTCTAGTCTGTT 3440
HCoSV-C-5152-1 ------------------------------------------------------------
```

FIG. 13-4

| | | |
|---|---|---|
| HCoSV-1 | TTCTTACAATCCTACTTTCCACGCAAGAGCTCCGTCAAAAGTCTCAGCTGTTATACCTTT | 3500 |
| HCoSV-C-5152-1 | ------------------------------------------------------------ | |
| HCoSV-1 | TTGCTTACCCGTTTCTCTATTACCTCTATATTTTGATGGCTTTCCCGATTACAGTACTAC | 3560 |
| HCoSV-C-5152-1 | ------------------------------------------------------------ | |
| HCoSV-1 | AAAAGGAATGTATGGATGCTCCCCTTCTTTTAGTTTTGGAACCATATACATTGAATCTGG | 3620 |
| HCoSV-C-5152-1 | ------------------------------------------------------------ | |
| HCoSV-1 | ACTCCAAGAAACTTATTCAGTTTACATTAGATACAAGGATTTTAAGGGTTATGCTCCCAG | 3680 |
| HCoSV-C-5152-1 | ------------------------------------------------------------ | |
| HCoSV-1 | ACCGCTCATTCGGACACCACACATTAGGCTATCAGAAAGAGCTAGATATATTATGGCAGA | 3740 |
| HCoSV-C-5152-1 | ------------------------------------------------------------ | |
| HCoSV-1 | CTCGGTGCTTCCACGCCCTCTCACACGCGCTGAACGTGATGTGGCGCGTGATTTGCTGCT | 3800 |
| HCoSV-C-5152-1 | ------------------------------------------------------------ | |
| HCoSV-1 | CATTGCTGGGGATATTGAATCAAATCCAGGACCTGCATTTAATCCAGAATATACAGCTCA | 3860 |
| HCoSV-C-5152-1 | ------------------------------------------------------------ | |
| HCoSV-1 | TGGCCCAGTTACTGAATTGATTCAATTGGCAAGGAAACCAGAAACTGTAGATAATGTAAA | 3920 |
| HCoSV-C-5152-1 | ------------------------------------------------------------ | |
| HCoSV-1 | TAGGCTTCTCACAACCCTGAATACTCTTATGGCTAAATGGAACAATCTCAAGGATACTGT | 3980 |
| HCoSV-C-5152-1 | ------------------------------------------------------------ | |
| HCoSV-1 | TACAGATGCTGTGTTTCTTAGAGACATGGTATGTCTTCTTGTGAAGCTTACTTCTCTTAT | 4040 |
| HCoSV-C-5152-1 | ------------------------------------------------------------ | |
| HCoSV-1 | GTACTTGGTTCATGGACAGGGACCAGGTGCTTACTTTGCTGCTGCCTCCATTCTTCTTGC | 4100 |
| HCoSV-C-5152-1 | ------------------------------------------------------------ | |
| HCoSV-1 | TGATGGCATAACTTTCTTTGATTGGTACGAGAAAATCAAGATTTTCATGGCTAGAAAACT | 4160 |
| HCoSV-C-5152-1 | ------------------------------------------------------------ | |
| HCoSV-1 | CAGAGTTTCCCCTCCCTTCTTCCCCGCTGCCCAGGGGCCGGACCTTAGAGACTTTGTGAC | 4220 |
| HCoSV-C-5152-1 | ------------------------------------------------------------ | |
| HCoSV-1 | CTTTTTCAACGCAGCGCGCGGAGCGCAATGGATGATTGATTCTCTCAAATCCCTTATAAC | 4280 |
| HCoSV-C-5152-1 | ------------------------------------------------------------ | |
| HCoSV-1 | TTGTATCAAACAATGGCTTGAACTTGAAGAGGAAAATGAAGCAGTACAACTTGAAAAGAT | 4340 |
| HCoSV-C-5152-1 | ------------------------------------------------------------ | |

FIG. 13-5

| | | |
|---|---|---|
| HCoSV-1 | GTTAATAGACTCTCCCAGACATTGCAAGGCAATAAATGACTACAACAGAGGTGACTCCTT | 4400 |
| HCoSV-C-5152-1 | ------------------------------------------------------------ | |

| | | |
|---|---|---|
| HCoSV-1 | TCAGAGACCGACCAACTCTTTTGAATTCATGGACAGACTTGTGGAATGTGCTACCAAGCT | 4460 |
| HCoSV-C-5152-1 | ------------------------------------------------------------ | |

| | | |
|---|---|---|
| HCoSV-1 | TGGGAAAGTCCAAATTGCAACTTATTTCAGAAATTTTACTACAGCTGATTCTGATACAAG | 4520 |
| HCoSV-C-5152-1 | ------------------------------------------------------------ | |

| | | |
|---|---|---|
| HCoSV-1 | CAGACCAGAGCCAGTTGTTGTTGTTTTGCGCGGGAAACCAGGCGTAGGCAAATCTGCTGC | 4580 |
| HCoSV-C-5152-1 | ------------------------------------------------------------ | |

| | | |
|---|---|---|
| HCoSV-1 | AGCTACTGTTATGGCAGCTGCAGTATCTAAATTGTTGGTAGGAAGTCAATCAGTGTACAC | 4640 |
| HCoSV-C-5152-1 | ------------------------------------------------------------ | |

| | | |
|---|---|---|
| HCoSV-1 | CCTTTCCCCAGATACGGAACATATGGATGGATATCACGGACAGTTTGTGACTTTGATGGA | 4700 |
| HCoSV-C-5152-1 | ------------------------------------------------------------ | |

| | | |
|---|---|---|
| HCoSV-1 | TGACCTTGGACAAAACCCAGACGGAGAAGACTTCAGATGTTTCTGTCAAATGGTTTCTTG | 4760 |
| HCoSV-C-5152-1 | ------------------------------------------------------------ | |

| | | |
|---|---|---|
| HCoSV-1 | TGCTCAGTACAGACCTGCTATGGCTGACCTTAAAGACAAAGGAATCCTGTTTACATCCAG | 4820 |
| HCoSV-C-5152-1 | ------------------------------------------------------------ | |

| | | |
|---|---|---|
| HCoSV-1 | ACTGTTGATTGCTACTACTAATCTCCCAGATTTTAACCCTGTTACTATCTCTGATCCGCG | 4880 |
| HCoSV-C-5152-1 | ------------------------------------------------------------ | |

| | | |
|---|---|---|
| HCoSV-1 | AGCTTTAGATCGTCGGATCACTTTTGATATTCTTGTCACTCCAGGTTCTGCCGCCACCAA | 4940 |
| HCoSV-C-5152-1 | ------------------------------------------------------------ | |

| | | |
|---|---|---|
| HCoSV-1 | GAATGGGAAACTTGACTTGGCCGCTGCTCTCAAACCAGATGGACCGGGAGAACACCCTTA | 5000 |
| HCoSV-C-5152-1 | ------------------------------------------------------------ | |

| | | |
|---|---|---|
| HCoSV-1 | CACTTCTGATTGCCCTATTCTCCACACCACTGGACTCCTCCTGAAGAACCTCAGAAACAA | 5060 |
| HCoSV-C-5152-1 | ------------------------------------------------------------ | |

| | | |
|---|---|---|
| HCoSV-1 | CCAGACCATGAACTTGAAAGACCTAGTGGACATGATTGTTAAGAGAATTAAACACAAGAA | 5120 |
| HCoSV-C-5152-1 | ------------------------------------------------------------ | |

| | | |
|---|---|---|
| HCoSV-1 | AGAAGTTGGAAATATGCTTGACTCTCTTGTTGCTCAGGGACCTACTATGATTGTTGGCTA | 5180 |
| HCoSV-C-5152-1 | ------------------------------------------------------------ | |

FIG. 13-6

| | | |
|---|---|---|
| HCoSV-1 | TACCAAAGACGATGATGGTATCGCTATTGTGGACTGCTTGGAAGAATGGAACAAGATAAA | 5240 |
| HCoSV-C-5152-1 | ------------------------------------------------------------ | |
| | | |
| HCoSV-1 | GGACAAGAAGAAGAAACAGCTTGCTTTGGAAATGGTTGCTCAAGAACTTAAGGACAAACA | 5300 |
| HCoSV-C-5152-1 | ------------------------------------------------------------ | |
| | | |
| HCoSV-1 | TGAAGAACATAAAGGCACAATCAAATTACTCAAAATGTTTGTTACTGGCCTTGGAGTGGT | 5360 |
| HCoSV-C-5152-1 | ------------------------------------------------------------ | |
| | | |
| HCoSV-1 | TGCCGCTGTTGCAGGCGCGTATGCCACAATGAAATACTTTACAAAGGACAAACCCAAGGA | 5420 |
| HCoSV-C-5152-1 | ------------------------------------------------------------ | |
| | | |
| HCoSV-1 | AGAAGAAGAAGAGCCAGAAGAAAAGAAAGAGAAGAAAACAGAAGAATCCAAAGAGGCTGC | 5480 |
| HCoSV-C-5152-1 | ------------------------------------------------------------ | |
| | | |
| HCoSV-1 | AGGACCATACAACGGACCTACAAAGAAAGAAATTAAAACATTGAAGTTAAAGGCCCAGAG | 5540 |
| HCoSV-C-5152-1 | ------------------------------------------------------------ | |
| | | |
| HCoSV-1 | TCCACTTATGGATATGGAAAAGAAAATTGCCCAGAATGTCATGCCCTTCCAGATTTTCTA | 5600 |
| HCoSV-C-5152-1 | ------------------------------------------------------------ | |
| | | |
| HCoSV-1 | TAATGGAAAAAGATACACCCAGTCTTGTCTGGCAATTGGAAAAAGAGTTATTCTTGTGAA | 5660 |
| HCoSV-C-5152-1 | ------------------------------------------------------------ | |
| | | |
| HCoSV-1 | CAAACATGCTTTTGAATCAGTTGAACACAAATTTGTTGTTGACCAAAAGGAATACACATT | 5720 |
| HCoSV-C-5152-1 | ------------------------------------------------------------ | |
| | | |
| HCoSV-1 | GGACCAGGTTACAGCTATTTCCCTTGACTGCGGATCAGGTGTCACGGATGTGTGTGCTGT | 5780 |
| HCoSV-C-5152-1 | ------------------------------------------------------------ | |
| | | |
| HCoSV-1 | ATGTTTGCCCCCAGGCCCAGACTTCAAATCAATAAAGAAACATTTCCTACCCTTCAACAC | 5840 |
| HCoSV-C-5152-1 | ------------------------------------------------------------ | |
| | | |
| HCoSV-1 | TACCATGTTTCCAGGAACCAGACTGACCATCCTCTCGAATGACCACTACCCTATGTCCAG | 5900 |
| HCoSV-C-5152-1 | ------------------------------------------------------------ | |
| | | |
| HCoSV-1 | AGAAGGCTCTTTCCTCAGATTTGAGGATGAGGTACCGACTAATGTAGGTAACATGCCCTT | 5960 |
| HCoSV-C-5152-1 | ------------------------------------------------------------ | |
| | | |
| HCoSV-1 | TGTAATGCTTTACAAATCAACCTCTTATTTTGGAATGTGTGGCTCAGTTGTATGTAGCAG | 6020 |
| HCoSV-C-5152-1 | ------------------------------------------------------------ | |
| | | |
| HCoSV-1 | ATTTGTTGATGGTGGAGGAATAATTGGAATGCACTGCGCAGGTGGAGGCGGAGTCAGTGT | 6080 |
| HCoSV-C-5152-1 | ------------------------------------------------------------ | |

FIG. 13-7

```
HCoSV-1       TGGAACTCGTTTGACTGCTAGAATGATTGAATCAGTTTTTGATTACTTCTACCCCCCAGT  6140
HCoSV-C-5152-1 ------------------------------------------------------------

HCoSV-1       AGCCCAGGGAATAATTGAAAACACAGAGACAGGACCCCGTGTACATGTGCCCAGAACTTC  6200
HCoSV-C-5152-1 ------------------------------------------------------------

HCoSV-1       CAAACTCAAAAGAACAAACGCCACTTATCCGGCAACGGAAAAGTATGGCCCAGCTGCTCT  6260
HCoSV-C-5152-1 ------------------------------------------------------------

HCoSV-1       TTCGCGGTATGATCCGCGATTAAATGAGGGAGTCAACTTGGATGAGGTGATCTTCTCAAA  6320
HCoSV-C-5152-1 ------------------------------------------------------------

HCoSV-1       ACATACTCAAAACACTCTTGTTGAGAAAGGATCCACTTTCAGAAGCGCCCTTGACATGGC  6380
HCoSV-C-5152-1 ------------------------------------------------------------

HCoSV-1       AGCAGAAATTTATGGTGAAAAGTTTAGAGGAAATGATTTCTCTCCCCTTTCAGTTGAAGA  6440
HCoSV-C-5152-1 ------------------------------------------------------------

HCoSV-1       TGCAATTCTTGGAATTCCCGGACTTGACAGACTTGACCCGAATACTGCTTCTGGATTGCC  6500
HCoSV-C-5152-1 ------------------------------------------------------------

HCoSV-1       CTACACTAAAACCAGACGACAGATGATTGACTTCAACACAGGACAGATTTTGGACGACAC  6560
HCoSV-C-5152-1 ------------------------------------------------------------

HCoSV-1       TCTTAAGTGTCGACTTGGACAATGGCTTGCAGGACGACCCCCCCAGGAAGTACATTACCA  6620
HCoSV-C-5152-1 ------------------------------------------------------------

HCoSV-1       GACATTTCTTAAGGATGAAATCAGGCCCATTGAAAAGGTCAAAGCAGGAAAGACTAGAAT  6680
HCoSV-C-5152-1 ------------------------------------------------------------

HCoSV-1       AATTGATGTTCCTCCTCTTGATCATGTCATCGCTTTTAGAATGCTCTTTGGCAGATTCAT  6740
HCoSV-C-5152-1 ------------------------------------------------------------

HCoSV-1       TGCCCACTACCACTTAAACTTTGGCTTCAAAACAGGCTCTGCTATTGGTTGTGACCCAGA  6800
HCoSV-C-5152-1 ------------------------------------------------------------

HCoSV-1       TGTCGCTTGGGCTTCTTTTGGCTTTGAACTCAGTGGCTTTCCTTATCTGTATGATTTTGA  6860
HCoSV-C-5152-1 ------------------------------------------------------------

HCoSV-1       TTACTCAAACTTTGATGCTTCTCACAGTACTTCAATATTTGAAATCTTAGAACAGAAATT  6920
HCoSV-C-5152-1 ------------------------------------------------------------
```

FIG. 13-8

```
HCoSV-1        CTTTTCCCCAGAATTAGGTTTTGATCCTAGATGCTCACTTCTCTTGAAATCCCTTGCAGT 6980
HCoSV-C-5152-1 ------------------------------------------------------------

HCoSV-1        TTCAACCCACTGTTATGAGAACAAGAGACTCCAGATTGCTGGAGGACTTCCCTCTGGCAC 7040
HCoSV-C-5152-1 ------------------------------------------------------------

HCoSV-1        GGCAGGTACCTCAGTACTGAACACCGTGATAAACAACATTATCTTTCACGGTGCACTATA 7100
HCoSV-C-5152-1 ------------------------------------------------------------

HCoSV-1        CCACACTTACACTAATTTTGAGCGGGATGACATCAGTATGTTAGCCTATGGCGACGACAT 7160
HCoSV-C-5152-1 ------------------------------------------------------------

HCoSV-1        TGTTGTTGCCTCCAAATTTGAACTTGACTTGGTTATGGTTAAGGCTTTCATGAACCGGAT 7220
HCoSV-C-5152-1 ------------------------------------------------------------

HCoSV-1        TGGCTATAAGATTACCCCTGCAGACAAAAGTGATGAATTCAGACCAAAGTGTATGGATGA 7280
HCoSV-C-5152-1 ------------------------------------------------------------

HCoSV-1        CATTTGCTTCTTAAAGAGGCGTTTTGTTAAAGTTGCTGGAGTTTGGGCTCCAGTGATGGA 7340
HCoSV-C-5152-1 ------------------------------------------------------------

HCoSV-1        AACTGAAAACCTCGAGGCAATGTTGTCTTGGTACAAACCAGGAACTCTTAATGAAAAGCT 7400
HCoSV-C-5152-1 ------------------------------------------------------------

HCoSV-1        CCAGAGTGTCTCAAGACTTGCCCACTTCTCAGGACGTGACGTGTATGACCACCTTTTCAA 7460
HCoSV-C-5152-1 ------------------------------------------------------------

HCoSV-1        GCCCTTCATTCGTGATGGGTTTGATGTCACACCTTGGAAACAGTTACACTTGGAATGGCT 7520
HCoSV-C-5152-1 ------------------------------------------------------------

HCoSV-1        TAATAAGTTATCAGCTTAAAGAATTTTGAATTGGCATTTCAGATTTATTTTGAATTTGGC 7580
HCoSV-C-5152-1 ------------------------------------------------------------

HCoSV-1        TTTTAATTCGGCTTTAATTTGGTTATTTATTGGGTATATTCAAATCTAATGACC 7634
HCoSV-C-5152-1 ------------------------------------------------------
```

FIG. 13-9

>HCoSV-E-5-UTR-246
AACCCCACACCGGCGGTTTGACGCTTGTAGGACCGTAGGTTTATCTTCACAACAAAGACTCTTA
GTTTCTAGTCCCATTGGCTCTATCAATGGGAGCGGAGAGGTGGCTCCCCGTTTCTTCTTGAACA
GGTTACACCCACGCCCTTTGTGGAATTCTTAGTGTGACCAATGCCTGGTGATATAATGATACAG
TAGTTTGGTGCTGCGGACGGGTTTGGGAAGGAAATGTAGCGTCGTAGCGGTGCTGTGTGTGTGA
GCGGAACTCCCCACGTGGTGACACGTGCCTCTCAGACCGAAAGTCACGCCGAAAGGCCCACACA
GTTGGACAACCCCAGTCCACGTCACATTTCAGTCTCACTCCTGGAAACAGTTAGTGAACTATTC
ACCCATTTATCACCCTGGACCCCAAAGATGCCCTGAAGGTACCCCGTGTATTCTACTATGGAAA
CATCAACTACCCGGACAGTTCTTCGGAACGACGCATGTGGTAATCCGGCCCCCGTTCTTGGGAC
GGGGGCCTGTCCATAAGTAGACACTGGATCTGATCAGGGGAGAGGTCGCTGCTTTACGGCCCTC
TTTAAAAATTGCCCAAGGTCCGGCCACCCAACCTAGGGGACTAGGTTTTCCTTTTATTTCATCA
CTGTCATCATGGGTG

>HCoSV-E-RdRp-246
ATTCTCAAGGATGAAATCAGACCGATAGAAAAGGTAAAGGCTGGCAAAACAAGAATAATTGATG
TGCCTCCTTTGGATCACGTCATAGTGTTCAGAATGATGTTTGGTAAATTCATGGCCCATTACCA
CCTAAATCCAGGATTTGAGACAGGGTCGGCTATAGGGTGCGACCCTGATATAGCCTGGGCTTCC
TTTGGCTTTAGTCTTGATCAGTGTAGTTATAAATATGATTTTGATTACTCTAACTTTGATTCTT
GCCATTCAGTTTCTATTTTTAAAATAATTGAAGAATACTTTTTCAATGAAGAAAATGGTTTTGA
TCCCAGATGCTCACTTCTGCTTCGCTCTTTAGCTATTTCAAAACATGCTTATGAGGACAAGCAG
ATTATTGTCGAGGGCGGCCTCCCCTC

>HCoSV-E-RdRp-246
ILKDEIRPIEKVKAGKTRIIDVPPLDHVIVFRMMFGKFMAHYHLNPGFETGSAIGCDPDIAWAS
FGFSLDQCSYKYDFDYSNFDSCHSVSIFKIIEEYFFNEENGFDPRCSLLLRSLAISKHAYEDKQ
IIVEGGLP

DIVERGENT PICORNAVIRUS: COSAVIRUS

RELATED APPLICATIONS

This application is a utility application and claims priority under 35 U.S.C. §119(e) of U.S. Provisional application Ser. No. 61/038,375 filed Mar. 20, 2008, the entire content of which is incorporated herein by reference.

GRANT INFORMATION

This invention was made in part with government support under NIH Grant No. R01 HL083254-01A1 awarded by the National Institutes of Health. The United States government has certain rights in this invention.

BACKGROUND OF THE INVENTION

1. Field of the Invention

The present invention relates generally to the discovery of a new human picornavirus virus and more specifically, to methods of detecting the virus and diagnosing viral infection, methods of treating or preventing virus infection, and methods for identifying anti-viral compounds.

2. Background Information

Picornaviridae are a large family of non-enveloped, positive-sense RNA animal viruses, comprised of six genera capable of infecting human (Enterovirus, Parechovirus, Rhinovirus, Hepatovirus, Cardiovirus, and Aphthovirus) that contain more than 200 viral species known to cause important diseases of humans and animals, including type A viral hepatitis, aseptic meningitis, chronic heart disease and the common cold.

Acute flaccid paralysis (AFP) is a term that is often used to describe a sudden onset of generalized or symmetric limb weakness. AFP is associated with a number of pathogenic agents including enteroviruses, echoviruses, and adenoviruses, among others. However, existing molecular reagents frequently fail to identify the causative agent if it is a highly divergent variant of a known virus or if it is a novel virus.

Despite the known pathogenicity of picornaviruses and the urgent need for methods to prevent, diagnose and treat picornavirus infections, other divergent human picornaviruses have not yet been identified. Therefore, a need exists to detect divergent human picornaviruses and to provide a method to diagnose, prevent and treat divergent picornavirus infection. Moreover, there exists a need to provide methods to identify divergent picornavirus antiviral compounds.

SUMMARY OF THE INVENTION

The present invention relates to the identification of a new human picornavirus, Dekavirus (DKV), and recently re-named Cosavirus (for Human Common Stool Associated (or South Asia) picornavirus; HCoSV) in the scientific literature. Accordingly, the name of the virus as used herein has been updated to Cosavirus to reflect this change in name. The total nucleotide sequence of Cosavirus is greater than 70% divergent from all described picornaviruses. The complete amino acid sequence of Cosavirus type-1 (HCoSV-1) exhibits greater than 60% diversity with known picornaviruses. Cosavirus type-1 is divergent enough from known picornaviruses to be assigned as the prototype member of a new genus in the Picornaviridae family. Also identified is the genomic sequence of a species of Cosavirus, as well as partial genomic sequences of several other species of Cosavirus, and the open-reading frame encoding viral proteins. Five species of Cosavirus have been identified; A, B, C, D, and E. The present invention therefore provides methods of detecting the Cosavirus and diagnosing Cosavirus infection in biological samples, methods of treating or preventing Cosavirus infection, and methods for identifying antiviral compounds.

Accordingly, in one embodiment of the present invention there are provided isolated nucleic acid molecules isolated from Cosavirus. In certain embodiments, the nucleic acid molecule is from Cosavirus species A, B, C, D, or E, or variants thereof. In particular embodiments, the nucleic acid molecule comprises a nucleotide sequence at least 80% identical to SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16. In some embodiments, the nucleotide sequence comprises a nucleotide sequence at least 90% identical to SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16. In other embodiments, the nucleotide sequence comprises a nucleotide sequence at least 95% identical to SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16. In one aspect, the nucleotide sequence is selected from the group consisting of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO:16, and a complement thereof. In still other embodiments, the nucleotide sequence a fragment of at least 12 nucleotides in length of any of the above nucleic acids.

In certain embodiments, the nucleic acid molecule comprises a sequence that hybridizes under stringent conditions to at least 12 contiguous nucleotides of the nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO:16, or a complement thereof. In particular embodiments, the nucleic acid sequence hybridizes under stringent conditions to at least 25, or at least 50, or at least 100, or at least 150 contiguous nucleotides of the nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO:16, or a complement thereof. In one aspect, the nucleotide sequence hybridizes under highly stringent conditions over the full length of the nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16, or a complement thereof.

In another embodiment, the nucleotide sequence hybridizes to at least 12 contiguous nucleotides of an open reading frame of a nucleotide sequence selected from the group consisting of SEQ ID NO:1, SEQ ID NO:3, SEQ ID NO:5, SEQ ID NO:6, SEQ ID NO:9, SEQ ID NO:10, SEQ ID NO:11, SEQ ID NO:15, and SEQ ID NO:16. In one aspect, the nucleotide sequence comprises an open reading frame encoding SEQ ID NO: 2, SEQ ID NO:4, SEQ ID NO:7, SEQ ID NO:8, SEQ ID NO:12, SEQ ID NO:13, SEQ ID NO:14, or SEQ ID NO:17.

In another embodiment of the invention, there are provided substantially purified proteins encoded by Cosavirus nucleic acid molecules of the invention. In some embodiments, the protein is encoded by a nucleic acid sequence that hybridizes under stringent conditions to at least 12 contiguous nucleotides of the nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO:16, or a complement thereof. In certain embodiments, the protein is encoded by a nucleic acid sequence that hybridizes under stringent conditions to at least 25, or at least 50, or at least 100, or at least 150 contiguous nucleotides of the nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO:16, or a complement thereof. In particular embodiments, the invention includes a protein encoded by a nucleotide sequence selected from the group consisting of SEQ ID NO:1, SEQ ID NO:3, SEQ ID NO:5, SEQ ID NO:6, SEQ ID NO:9, SEQ ID NO:10, SEQ ID NO:11, SEQ ID NO:15, and SEQ ID NO:16. In other embodiments, the protein comprises a sequence having about 80%, or 90%, or 95% identity to a sequence selected from the group consisting of SEQ ID NO: 2, SEQ ID NO:4, SEQ ID NO:7, SEQ ID NO:8, SEQ ID NO:12, SEQ ID NO:13, SEQ ID NO:14, SEQ ID NO:17, and fragments thereof. In some embodiments, the protein comprises a sequence selected from the group consisting of SEQ ID NO: 2, SEQ ID NO:4, SEQ ID NO:7, SEQ ID NO:8, SEQ ID NO:12, SEQ ID NO:13, SEQ ID NO:14, SEQ ID NO:17, and fragments thereof. In certain embodiments the fragment is an antigen or immunogenic fragment.

In another embodiment, there is provided a composition containing a protein of the invention.

The invention also provides an isolated antibody that specifically binds to a protein of the invention. In one aspect, the antibody is a polyclonal antibody. In another aspect, the antibody is a monoclonal antibody.

In another embodiment, the invention includes purified serum containing polyclonal antibodies that specifically bind to a protein of the invention.

The invention also provides an isolated Cosavirus comprising a nucleic acid of the invention. In certain embodiments, the Cosavirus genome comprises a nucleic acid that hybridizes under stringent conditions to at least 12 contiguous nucleotides of the nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO:16, or a complement thereof.

In still another embodiment, there are provided expression vectors comprising the nucleic acids disclosed herein. Also provided are host cells comprising such an expression vector.

In another embodiment, the invention includes a substantially pure preparation of Cosavirus which induces acute flaccid paralysis (AFP).

In still another embodiment of the invention, there is provided a method of detecting a Cosavirus nucleic acid by hybridization to a probe. In some embodiments, the method includes contacting, under highly stringent hybridization conditions, a sample suspected of containing a Cosavirus nucleic acid with a nucleotide sequence that hybridizes to a nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO: 16, and detecting the presence or absence of hybridization. In one aspect, the stringent hybridization conditions comprise hybridizing at 42° C. in a solution comprising 50% formamide, 5×SSC, and 1% SDS and washing at 65° C. in a solution comprising 0.2×SSC and 0.1% SDS.

Another method contemplated by the invention is a method of detecting a Cosavirus nucleic acid by detection of a amplification product. In one aspect the method includes amplifying the nucleic acid of a sample suspected of containing the Cosavirus nucleic acid with at least one primer that hybridizes to a nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO: 16, or a complement thereof to produce an amplification product; and detecting the presence of an amplification product, thereby detecting the presence of Cosavirus nucleic acid. In one aspect, the amplifying includes a denaturation phase of 90° C.-95° C. for 30 sec-2 min., an annealing phase of 50° C. to about 65° C. lasting 30 sec.-2 min., and an extension phase of about 72° C. for 1-2 min., and an extension phase of about 72° C. for 1-2 min for 20-40 cycles.

In one embodiment, a method of detecting a Cosavirus infection in a sample is detecting a protein of the invention in a sample using an antibody. In one aspect the method includes contacting a sample suspected of comprising a Cosavirus protein with an antibody that specifically binds a polypeptide encoded by SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO: 16 to form a protein/antibody complex; and detecting the presence of the protein/antibody complex, thereby detecting the presence of the Cosavirus protein.

The invention also contemplates a kit for detecting a Cosavirus nucleic acid molecule, containing a polynucleotide having a nucleotide sequence that hybridizes under highly stringent conditions to a nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO: 16, or a complement thereof.

The invention also contemplates a kit for detecting a Cosavirus nucleic acid molecule, containing at least one primer that hybridizes to a nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO: 16, or a complement thereof.

In another embodiment, the invention describes a kit for detecting a Cosavirus in a sample, where the kit contains an antibody that detects a polypeptide encoded by SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO: 16. In one aspect, the kit contains a monoclonal antibody. In another aspect, the kit contains a polyclonal antibody.

The invention contemplates a method of assaying for an anti-Cosavirus compound, the method including contacting a sample suspected of containing a Cosavirus with a test compound, where the Cosavirus encodes a genome that hybridizes under highly stringent conditions to a nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO: 16, wherein the highly stringent conditions comprise hybridizing at 42° C. in a solution comprising 50% formamide, 5×SSC, and 1% SDS and washing at 65° C. in a solution comprising 0.2×SSC and 0.1% SDS; and determining whether the test compound inhibits Cosavirus replication, wherein inhibition of Cosavirus replication indicates that the test compound is the anti-Cosavirus compound.

In one embodiment, the invention describes a method of treating or preventing a Cosavirus infection in a subject by administering to the subject an antigen encoded by a Cosavirus, the Cosavirus comprising a genome that hybridizes under highly stringent conditions to a nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO: 16, thereby treating or prevention infection in the subject.

Another embodiment of the invention provides a vaccine for the prevention of acute flaccid paralysis (AFP) in a subject, comprising: a virus which induces AFP in a subject and a pharmacologically acceptable carrier wherein said virus has AFP inducing characteristics. In one aspect, the virus of the vaccine is in a killed form. In another aspect, the virus of the vaccine is in a live but attenuated form.

In one embodiment of the invention, a method for detecting and serotyping Cosavirus in a sample is provided by 1) contacting a first portion of the sample with a first pair of primers in a first amplification protocol, wherein the first pair of primers have an associated first characteristic amplification product if a Cosavirus is present in the sample; 2) determining whether or not the first characteristic amplification product is present; 3) contacting a second portion of the sample with a second pair of primers in a second amplification protocol, wherein the second pair of primers have an associated second characteristic amplification product if a Cosavirus is present in the sample and wherein the second pair of primers are different from the first pair of primers; 4) determining whether or not the second characteristic amplification product is present; 5) based on whether or not the first and second characteristic amplification product are present, selecting one or more subsequent pair of primers and contacting the one or more subsequent pair of primers with additional portions of the sample in subsequent amplification protocols, wherein each subsequent pair of primers is different from each pair of primers already used and wherein each subsequent pair of primers has an associated subsequent characteristic amplification product if a Cosavirus is present in the sample; 6) determining whether or not the associated characteristic amplification product for each subsequent pair of primers used is present; 7) repeating steps 5 and 6 for one or more subsequent pairs of primers if the Cosavirus cannot be serotyped based on the determinations of steps 2, 4, and 6 until the Cosavirus can be serotyped, wherein the one or more subsequent pairs of primers are different from all pairs of primers used in earlier amplification protocols; and determining the serotype or groups of serotypes of the Cosavirus that may be present in the sample. In one aspect, the sample is a biological sample. In another aspect, the sample is whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, semen, cerebrospinal fluid, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal. In one aspect, the first, second, and any subsequent amplification protocols are polymerase chain reactions or reverse-transcription polymerase chain reactions. In another aspect, detecting and serotyping of the Cosavirus in the sample is used to diagnose a viral disease or medical condition. In yet another aspect, the viral disease or medical condition is acute flaccid paralysis (AFP).

The present invention also contemplates a method for detecting the presence of a Cosavirus in a sample by 1) purifying RNA contained in the sample; 2) reverse transcribing the RNA with primers effective to reverse transcribe Cosavirus RNA to provide a cDNA; 3) contacting at least a portion of the cDNA with (i) a composition that promotes amplification of a nucleic acid and (ii) an oligonucleotide mixture wherein the mixture comprises at least one oligonucleotide that hybridizes to a highly conserved sequence of the sense strand of a Cosavirus nucleic acid and at least one oligonucleotide that hybridizes to a highly conserved sequence of the antisense strand of a Cosavirus nucleic acid; 4) carrying out an amplification procedure on the amplification mixture such that, if a Cosavirus is present in the sample, a Cosavirus amplicon is produced whose sequence comprises a nucleotide sequence of at least a portion of the Cosavirus genome; and 5) detecting whether an amplicon is present; wherein the presence of the amplicon indicates that a Cosavirus is present in the sample. In one aspect, the amplification procedure comprises a polymerase chain reaction. In another aspect, the sample is chosen from the group consisting of whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, semen, cerebrospinal fluid, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal. In another aspect, the detection is carried out by a procedure chosen from the group consisting of gel electrophoresis and visualization of amplicons contained in a resulting gel, size separation matrix, capillary electrophoresis and detection of the emerging amplicon, probing for the presence of the amplicon using a labeled probe, sequencing the amplicon, and labeling a PCR primer employed in the method and detecting the label.

BRIEF DESCRIPTION OF THE DRAWINGS

FIG. 1 shows the nucleotide sequence of new human picornavirus, Cosavirus type-1 (HCoSV-1) (SEQ ID NO:1).

FIG. 2 shows the derived amino acid sequence of new human picornavirus, Cosavirus type-1 (HCoSV-1) (SEQ ID NO:2).

FIG. 3 shows the predicted cleavage sites of the viral polyprotein (SEQ ID NO'S 18-82).

FIG. 4 shows the partial genome of a novel Cosavirus variant HCoSV-D-5004 (SEQ ID NO:3).

FIG. 5 shows the partial amino acid sequence of HCoSV-D-5004 (SEQ ID NO:4).

FIG. 6 shows the partial genome of a novel Cosavirus variant HCoSV-C-5152-1 (SEQ ID NO:5) and HCoSV-C-5152-2 (SEQ ID NO:6).

FIG. 7 shows the partial amino acid sequence of HCoSV-C-5152-1 (SEQ ID NO:7), and HCoSV-C-5152-2 (SEQ ID NO:8).

FIG. 8 shows an amino acid sequence alignment between a portion of the sequence of HCoSV-1 (SEQ ID NO:83) and HCoSV-D-5004 (SEQ ID NO:4).

FIG. 9 shows an amino acid sequence alignment between a portion of the sequence of HCoSV-1 (84) and HCoSV-C-5152-1 (7).

FIG. 10 shows an amino acid sequence alignment between a portion of the sequence of HCoSV-1 (SEQ ID NO:85) and a portion of the sequence of HCoSV-C-5152-2 (SEQ ID NO:86).

FIG. 11 shows an amino acid sequence alignment between HCoSV-C2-5005 (SEQ ID NO.:12), HCoSV-C-5152-2 (SEQ ID NO:8), HCoSV-B-2263 (SEQ ID NO.:13), HCoSV-1 (SEQ ID NO:2), HCoSV-A-6344 (SEQ ID NO.:14), a portion of the sequence of HCoSV-C-5152-1 (SEQ ID NO:87) and HCoSV-D-5004 (SEQ ID NO:4).

FIG. 12 shows a nucleotide sequence alignment between HCoSV-1 (SEQ ID NO:1), HCoSV-A-6344 (SEQ ID NO.:9), HCoSV-B-2263 (SEQ ID NO.:10), HCoSV-D-5004 (SEQ ID NO:3), HCoSV-C-5152-2 (SEQ ID NO:6), and HCoSV-C2-5005 (SEQ ID NO.:11).

FIG. 13 shows a nucleotide sequence alignment between HCoSV-1 (SEQ ID NO:1) and a portion of the sequence of HCoSV-C-5152-1 (SEQ ID NO:88).

FIG. 14 shows a portion of the 5'UTR nucleotide sequence of cosavirus species E (HCoSV-E-5-UTR-246; SEQ ID NO:15), a portion of the nucleotide sequence of the RNA dependent RNA polymerase gene (HCoSV-E-RdRp-246; SEQ ID NO:16), and the amino acid sequence encoded by the partial nucleotide sequence of the RNA dependent RNA polymerase gene (SEQ ID NO:17).

DETAILED DESCRIPTION OF THE INVENTION

The present invention is based on the discovery of a novel virus, Cosavirus, previously termed Dekavirus, which is associated with acute flaccid paralysis (AFP). There are various molecular methods for discovery of novel human viruses including immunoreactive cDNA expression library screening, representational difference analysis (RDA), DNA microarrays and use of degenerate PCR primers. Other methods include sequence independent single primer amplification of nucleic acids in serum (DNase-SISPA), or "metagenomics shotgun sequencing." For these approaches, DNA can be isolated directly from environmental samples and sequenced, without attempting to culture the organisms from which it comes. The DNase-SISPA method first removes contaminating human DNA in plasma or serum by DNase digestion. Viral nucleic acids protected from DNase digestion by their viral coats are then converted into double stranded DNA (dsDNA) using random primers. The dsDNA is then digested by a 4 base pair specific restriction endonuclease resulting in two overhanging bases to which are ligated a complementary oligonucleotide linker. A PCR primer complementary to the ligated linker is then used to PCR amplify the sequences between the restriction sites. The PCR products are analyzed by PAGE and distinct DNA bands are extracted, subcloned and sequenced. Similarity to known viruses is then tested using BLASTn (for nucleic acid similarity) and tBLASTx (for protein similarity). The DNase-SISPA method does not require foreknowledge of the viral sequences being amplified and can therefore theoretically amplify more divergent members of known viral families than nucleic acid sequence similarity-dependent approaches using degenerate primers or microarrays.

A metagenomic shotgun sequencing approach was used to identify known and previously uncharacterized viruses in the stool samples of children presenting with acute flaccid paralysis (AFP). Large scale sequencing and Rapid Amplification of cDNA Ends (RACE) were used to acquire the complete genome of a new virus, Cosavirus. Phylogenetic analysis of Cosavirus establishes it as an outlier virus, with mean protein identity of only 16-32% to other genera of Picornaviridae. The Cosavirus genome codes for a single polyprotein flanked by 5' and 3' non-translated regions, similar to all Picornaviruses.

Accordingly, the present invention provides a new human virus, Cosavirus (previously termed Dekavirus), as well as the genomic sequence of the virus and open reading frames encoding viral proteins. The results described herein indicate that Cosavirus is a unique virus, most closely related to the Picornaviridae family. The genome encodes the structural proteins of the virus and non-structural proteins involved in viral replication.

As provided herein, PCR primers targeting conserved non-structural genes were used to determine the prevalence of Cosavirus in stool samples from children with AFP. Six genetic variants of Cosavirus were found in 14 stool samples from AFP children, suggesting a high prevalence among this disease group.

The genomic sequence of an exemplary Cosavirus, Cosavirus type 1 (termed herein HCoSV-1), is provided herein (SEQ ID NO:1). The complete genome sequence was also acquired from another divergent Cosavirus variant, termed Cosavirus type-2. This variant has an 82% amino acid identity to Cosavirus type-1. Five species (termed A, B, C, D, and E) of Cosavirus have been identified. Other Cosavirus isolates include HCoSV-D-5004 (FIGS. 4 and 5), HCoSV-C-5152 (FIGS. 6 and 7), HCoSV-C2-5005 (FIGS. 11 and 12), HCoSV-B-2263 (FIGS. 11 and 12), HCoSV-A-6344 (FIGS. 11 and 12), and HCoSV-E (FIG. 14).

The terms "Cosavirus" and "Dekavirus" are used interchangeably herein and refer to both the genetic components of the virus, e.g., the genome (positive or negative) and RNA transcripts thereof (either sense or antisense), proteins encoded by the genome (including structural and nonstructural proteins), and viral particles. This description includes Cosavirus nucleic acids that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleic acids, up to the full length sequence, to the nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16; (2) encodes a protein that bind to antibodies, e.g., polyclonal or monoclonal antibodies, raised against an antigen or an immunogen from an amino acid sequence selected from the group consisting of SEQ ID NO: 2, SEQ ID NO:4, SEQ ID NO:7, SEQ ID NO:8, SEQ ID NO:12, SEQ ID NO:13, SEQ ID NO:14, SEQ ID NO:17, and conservatively modified variants thereof; (3) specifically hybridize under stringent hybridization conditions to a nucleic acid sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO:16, or complement thereof, or conservatively modified variants thereof; or (4) encode a protein having an amino acid sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more amino acids, an amino acid sequence selected from the group consisting of SEQ ID NO: 2, SEQ ID NO:4, SEQ ID NO:7, SEQ ID NO:8, SEQ ID NO:12, SEQ ID NO:13, and SEQ ID NO:14. The nucleic acids and proteins of the invention include both naturally occurring and recombinant molecules.

Cosavirus nucleic acids can be used to produce infectious clones, e.g., for production of recombinant viral particles, including empty capsids or capsids containing a recombinant (e.g., wild type or further comprising a heterologous nucleic acid) or modified (e.g., mutated) Cosavirus genome, which may be replication competent or incompetent, using the methods disclosed in U.S. Pat. Nos. 6,558,676; 6,132,732; 6,001,371; 5,916,563; 5,827,647; 5,508,186; 6,379,885; 6,287,815; 6,204,044; and 5,449,608. Such particles are useful as gene transfer vehicles, and as vaccines, and for use in diagnostic applications and for drug discovery assays for antiviral compounds, as discussed below.

The Cosavirus virus, nucleic acids and proteins of the invention can be used to assay for antiviral compounds, including compounds that inhibit (1) viral interactions at the cell surface, e.g., viral transduction (e.g., block viral cell receptor binding or internalization); (2) viral replication and gene expression, e.g., viral replication (e.g., by inhibiting non-structural protein activity, origin activity, or primer binding), viral transcription (promoter or splicing inhibition, non-structural protein inhibition), viral protein translation, protein processing (e.g., cleavage or phosphorylation); and (3) viral assembly and egress, e.g., viral packaging, and virus release.

"Protein encoded by Cosavirus" or "protein encoded by Cosavirus open reading frame (ORF)" refers to a structural or a non-structural Cosavirus protein that (1) is encoded by a nucleotide sequence of the invention such as a nucleic acid having a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleic acids, up to the full length sequence, to the nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16; (2) binds to an antibody, e.g., polyclonal or monoclonal, raised against an antigen or an immunogen from an amino acid sequence selected from the group consisting of SEQ ID NO: 2, SEQ ID NO:4, SEQ ID NO:7, SEQ ID NO:8, SEQ ID NO:12, SEQ ID NO:13, SEQ ID NO:14, SEQ ID NO:17, and conservatively modified variants thereof; (3) is encoded by a nucleotide sequence that hybridizes under stringent hybridization conditions to complementary nucleotide sequence corresponding to a nucleic acid sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16, and conservatively modified variants thereof; or (4) has an amino acid sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more amino acids, of a sequence selected from the group consisting of SEQ ID NO: 2, SEQ ID NO:4, SEQ ID NO:7, SEQ ID NO:8, SEQ ID NO:12, SEQ ID NO:13, SEQ ID NO:14, and SEQ ID NO:17.

The identification of the new Cosavirus provides methods of detecting the virus, its genome, transcripts, and proteins including structural and non-structural proteins. Antibodies (polyclonal and monoclonal) generated against an antigen derived from any of these proteins, may be used to detect the presence of that viral protein, as well as to isolate the protein or antigen and to remove virus, proteins, or nucleic acids from a sample, e.g., a blood sample. Antibodies to Cosavirus antigens can be used in diagnostic assays to detect viral infection. Any suitable sample, including blood, saliva, sputum, stool, etc., can be used in a diagnostic assay of the invention. Such antibodies can also be used in therapeutic applications to inhibit or prevent viral infection.

The Cosavirus antigens of the invention can also be used in diagnostic applications to detect anti-Cosavirus antigen antibodies in infected or exposed subjects. Cosavirus antigens of the invention can also be used therapeutically, as prophylactic vaccines or vaccines for acute or latent infections, e.g., whole virus vaccines, protein or subunit vaccines, and nucleic acid vaccines encoding viral proteins, ORFs or genomes for intracellular expression and secretion or cell surface display, or can be targeted to specific cell types using promoters and vectors.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence (FIG. 1) or amino acid sequence of HCoSV-1 (FIG. 2) corresponding to SEQ ID NO:1 and SEQ ID NO:2, respectively), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

There are several methods available and well known to those skilled in the art to obtain full-length DNAs, or extend short DNAs, for example those based on the method of Rapid Amplification of cDNA Ends (RACE). Another sequencing method is based on detecting the activity of DNA polymerase with a chemiluminescent enzyme. Essentially, the method allows sequencing of a single strand of DNA by synthesizing the complementary strand along it, one base pair at a time, and detecting which base was actually added at each step. The template DNA is immobilized, and solutions of A, C, G, and T nucleotides are added sequentially. Light is produced only when the nucleotide solution compliments the first unpaired base of the template. The sequence of solutions which produce chemiluminescent signals allows the determination of the sequence of the template.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith &

Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1). Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The antibody can be conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a Cosavirus, polymorphic variants, alleles, orthologs, and conservatively modified variants, or splice variants, or portions thereof, can be selected to obtain only those polyclonal antibodies that are specifically immunoreactive with Cosavirus and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The phrase "functional effects" in the context of assays for testing compounds that modulate activity of a Cosavirus includes the determination of a parameter that is indirectly or directly under the influence of a Cosavirus, e.g., a phenotypic or chemical effect, such as the ability to increase or decrease viral genome replication, viral RNA and protein production, virus packaging, viral particle production (particularly replication competent viral particle production), cell receptor binding, viral transduction, cellular infection, antibody binding, inducing a cellular or humoral immune response, viral protein enzymatic activity, etc. "Functional effects" include in vitro, in vivo, and ex vivo activities. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for a protein; measuring inducible markers or transcriptional activation of a protein; measuring binding activity or binding assays, e.g. binding to antibodies; measuring changes in ligand or substrate binding activity; measuring viral replication; measuring cell surface marker expression; measurement of changes in protein levels; measurement of RNA stability; identification of downstream or reporter gene expression (CAT, luciferase, β-gal, GFP and the like), e.g., via chemiluminescence, fluorescence, colorimetric reactions, antibody binding, and inducible markers.

"Inhibitors," "activators," and "modulators" of Cosavirus nucleic acid and polypeptide sequences are used to refer to activating, inhibitory, or modulating molecules identified using in vitro and in vivo assays of the Cosavirus nucleic acid and polypeptide sequences. Inhibitors are compounds that, e.g., bind to, partially or totally block activity, decrease, prevent, delay activation, inactivate, desensitize, or down regulate the activity or expression of Cosavirus, e.g., antagonists. "Activators" are compounds that increase, open, activate, facilitate, enhance activation, sensitize, agonize, or up regulate Cosavirus activity, e.g., agonists. Inhibitors, activators, or modulators also include genetically modified versions of Cosavirus, e.g., versions with altered activity, as well as naturally occurring and synthetic ligands, substrates, antagonists, agonists, antibodies, peptides, cyclic peptides, nucleic acids, antisense molecules, ribozymes, small chemical molecules and the like. Such assays for inhibitors and activators include, e.g., expressing Cosavirus in vitro, in cells, or cell membranes, applying putative modulator compounds, and then determining the functional effects on activity, as described above.

Samples or assays comprising Cosavirus that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of Cosavirus is achieved when the activity value relative to the control is about 80%, preferably 50%, more preferably 25-0%. Activation of Cosavirus is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

An "siRNA" molecule or an "RNAi molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety.

An siRNA molecule or RNAi molecule is "specific" for a target nucleic acid if it reduces expression of the nucleic acid by at least about 10% when the siRNA or RNAi is expressed in a cell that expresses the target nucleic acid.

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Cosavirus, polymorphic variants, orthologs, and alleles that are substantially identical to an amino acid sequence encoded by nucleic acids of SEQ ID NO:1 (FIG. 1) can be isolated using nucleic acid probes and oligonucleotides under stringent hybridization conditions, by screening DNA libraries or by using PCR. Genes encoding Cosavirus proteins can be isolated using cDNA libraries. Alternatively, expression libraries can be used to clone the Cosavirus, polymorphic variants, orthologs, and alleles by detecting expressed homologs immunologically with antisera or purified antibodies made against Cosavirus or portions thereof.

Other techniques that can be used to identify known and previously uncharacterized Cosavirus isolates, including representational difference analysis (RDA), DNA microarrays and use of degenerate PCR primers or other methods well known to those of skill in the art. Other methods for determining the sequence of a Cosavirus, are, for example, sequence independent single primer amplification of nucleic acids in serum (DNase-SISPA) can be used. In this method, DNA is isolated directly from environmental samples and sequenced. This method first removes contaminating human DNA in plasma or serum by DNase digestion. Viral nucleic acids protected from DNase digestion by their viral coats are then converted into double stranded DNA (dsDNA) using random primers. The dsDNA is then digested by a 4 base pair specific restriction endonuclease resulting in two overhanging bases to which are ligated a complementary oligonucleotide linker. A PCR primer complementary to the ligated linker is then used to PCR amplify the sequences between the restriction sites. The PCR products are analyzed by PAGE and distinct DNA bands are extracted, subcloned and sequenced. Similarity to known viruses is then tested using BLASTn (for nucleic acid similarity) and tBLASTx (for protein similarity). The DNase-SISPA method does not require foreknowledge of the viral sequences being amplified and can therefore theoretically amplify more divergent members of known viral families than nucleic acid sequence similarity-dependent approaches using degenerate primers or microarrays. There are several methods available and well known to those skilled in the art to obtain full-length DNAs, or extend short DNAs, for example, those based on the method of Rapid Amplification of cDNA Ends (RACE) and large scale sequencing.

To make a cDNA library to clone Cosavirus genes expressed by the genome, the source used should be rich in the RNA of choice. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and optionally mechanically sheared or enzymatically digested. The fragments are then separated by gradient centrifugation from undesired sizes and are constructed in suitable vectors. These vectors are packaged in vitro. Recombinant vectors can be analyzed, e.g., by plaque hybridization as described in Benton & Davis, *Science* 196:180-182 (1977). Colony hybridization is carried out as generally described in Grunstein et al., *Proc. Natl. Acad. Sci. USA.,* 72:3961-3965 (1975).

A preferred method of isolating Cosavirus and orthologs, alleles, mutants, polymorphic variants, splice variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR and RT-PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Cosavirus encoding mRNA in physiological samples, for nucleic acid sequencing, or for other purposes. Genes amplified by the PCR reaction can be purified from agarose gels and cloned into an appropriate vector.

Gene expression of Cosavirus can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding a Cosavirus genome or protein can be used with high density oligonucleotide array technology to identify Cosavirus, orthologs, alleles, conservatively modified variants, and polymorphic variants in this invention. In the case where the homologs being identified are linked to modulation of the cell cycle, they can be used with oligonucleotide array as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224: 110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene of choice is typically cloned into intermediate vectors before transformation into prokaryotic or eukaryotic cells for replication and/or expression. These intermediate vectors are typically prokaryote vectors, e.g., plasmids, or shuttle vectors.

To obtain high level expression of a cloned gene or genome, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing Cosavirus proteins and nucleic acids.

After the expression vector is introduced into the cells, the transfected cells are cultured under conditions favoring expression of the protein of choice, which is recovered from the culture using standard techniques identified below.

Either naturally occurring or recombinant Cosavirus proteins can be purified for use in diagnostic assays, for making antibodies (for diagnosis and therapy) and vaccines, and for assaying for anti-viral compounds. As described above, SEQ ID NO: 2 encodes structural proteins. Naturally occurring proteins can be purified, e.g., from human tissue samples. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

Methods for production and purification of recombinant protein from a bacterial or eukaryotic (e.g., yeast, mammalian cell, and the like) system are well known in the art. Recombinant proteins are expressed by transformed host cells, (e.g., bacteria) in large amounts, typically after promoter induction; but expression can be constitutive. Promoter induction with IPTG is one example of an inducible promoter system. Host cells are grown according to standard procedures in the art. Where the host cell is a bacterial cell, fresh or frozen bacteria cells are used for isolation of protein.

Recombinant proteins, particularly when expressed in bacterial host cells, may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, where the host cell is a bacterium, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard protein separation techniques for purifying proteins are also contemplated in the present invention. Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The protein can also be separated from other proteins on the basis of its size, net surface charge, hydrophobicity, and affinity for ligands or substrates. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

In addition to the detection of a Cosavirus gene and gene expression using nucleic acid hybridization technology, one can also use immunoassays to detect Cosavirus proteins, virus, and nucleic acids of the invention. Such assays are useful for, e.g., therapeutic and diagnostic applications. Immunoassays can be used to qualitatively or quantitatively analyze protein, virus, and nucleic acids. A general overview of the applicable technology can be found in Harlow & Lane, *Antibodies: A Laboratory Manual* (1988).

Methods of producing polyclonal and monoclonal antibodies that react specifically with Cosavirus protein, virus and nucleic acids are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of a Cosavirus protein, virus or nucleic acid may be used to produce antibodies specifically reactive with the Cosavirus. For example, a recombinant Cosavirus protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-Cosavirus proteins and nucleic acids, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular Cosavirus protein can also be made by subtracting out other cross-reacting proteins, e.g., from other human Cosaviruses or other non-human Cosaviruses. In this manner, antibodies that bind only to the protein of choice may be obtained.

Once the specific antibodies against a Cosavirus protein, virus or nucleic acid in are available, the antigen can be detected by a variety of immunoassay methods. In addition, the antibody can be used therapeutically. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

Protein, in this case Cosavirus protein which is either associated with or separate from a Cosavirus viral particle, can be detected and/or quantified using any of a number of well recognized immunological binding assays (see, e.g., U.S. Pat. Nos. 4,366,241; 4,376,110; 4,517,288; and 4,837,168). Cosavirus viral particles may be detected based on an epitope defined by the viral proteins as presented in a viral particle and/or an epitope defined by a viral protein that is separate from a viral particle (e.g., such as may be present in an infected cell). As used in this context, then, "antigen" is meant to refer to a Cosavirus polypeptide as well as Cosavirus viral particles. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice. The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled Cosavirus protein nucleic acid or a labeled anti-Cosavirus antibody. Alternatively, the labeling agent may be a third moiety, such a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Immunoassays for detecting Cosavirus protein, virus and nucleic acid in samples may be either competitive or noncompetitive, and may be either quantitative or non-quantitative. Noncompetitive immunoassays are assays in which antigen is directly detected and, in some instances the amount of antigen directly measured. In a "sandwich" assay, for example, the anti-Cosavirus antibodies can be bound directly to a solid substrate on which they are immobilized. These immobilized antibodies then capture the Cosavirus antigen present in the test sample. Proteins thus immobilized are then bound by a labeling agent, such as a second anti-Cosavirus antigen antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

In competitive assays, Cosavirus antigen present in a sample is detected indirectly by detecting a decrease in a detectable signal associated with a known, added (exogenous) Cosavirus antigen displaced (competed away) from an anti-Cosavirus antigen antibody by the unknown Cosavirus antigen present in a sample. In this manner, such assays can also be adapted to provide for an indirect measurement of the amount of Cosavirus antigen present in the sample. In one competitive assay, a known amount of Cosavirus antigen is added to a sample and the sample is then contacted with an antibody that specifically binds to the Cosavirus antigen. The amount of exogenous Cosavirus antigen bound to the antibody is inversely proportional to the concentration of Cosavirus antigen present in the sample. In a particularly preferred embodiment, the antibody is immobilized on a solid substrate. The amount of Cosavirus antigen bound to the antibody may be determined either by measuring the amount of Cosavirus antigen present in Cosavirus antigen/antibody complex, or alternatively by measuring the amount of remaining uncomplexed protein. The amount of Cosavirus antigen may be detected by providing a labeled Cosavirus antigen.

A hapten inhibition assay is another competitive assay. In this assay the known Cosavirus antigen is immobilized on a solid substrate. A known amount of anti-Cosavirus antigen antibody is added to the sample, and the sample is then contacted with the immobilized Cosavirus antigen. The amount of anti-Cosavirus antigen bound to the known immobilized Cosavirus antigen is inversely proportional to the amount of Cosavirus antigen present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can also be used for crossreactivity determinations. For example, a Cosavirus antigen can be immobilized to a solid support. Proteins are added to the assay that compete for binding of the antisera to the immobilized antigen. The ability of the added proteins to compete for binding of the antisera to the immobilized protein is compared to the ability of the Cosavirus antigen to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a Cosavirus antigen, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the Cosavirus antigen that is required to inhibit 50% of binding, then the second protein is said to specifically bind to the polyclonal antibodies generated to Cosavirus antigen.

Western blot (immunoblot) analysis can be used to detect and quantify the presence of Cosavirus antigen in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the Cosavirus antigen. The anti-Cosavirus antigen antibodies specifically bind to the Cosavirus antigen on the solid support. These antibodies may be directly labeled or alternatively may be subsequently detected using labeled antibodies (e.g., labeled sheep anti-mouse antibodies) that specifically bind to the anti-Cosavirus antigen antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize Cosavirus antigen, or secondary antibodies that recognize anti-Cosavirus antigen.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The present invention provides diagnostic assays to detect Cosavirus, Cosavirus nucleic acids (genome and genes), Cosavirus antibodies in an infected subject, and Cosavirus proteins. In one embodiment, Cosavirus nucleic acid is detected using a nucleic acid amplification-based assay, such as a PCR assay, e.g., in a quantitative assay to determine viral load. In another embodiment, Cosavirus antigens are detected using a serological assay with antibodies (either monoclonal or polyclonal) to antigens encoded by Cosavirus.

In one embodiment of the present invention, the presence of Cosavirus, Cosavirus nucleic acid, or Cosavirus protein in a sample is determined by an immunoassay. Enzyme mediated immunoassays such as immunofluorescence assays (IFA), enzyme linked immunosorbent assays (ELISA) and immunoblotting (western) assays can be readily adapted to accomplish the detection of the Cosavirus or Cosavirus proteins. An ELISA method effective for the detection of the virus can, for example, be as follows: (1) bind an anti-Cosavirus antibody or antigen to a substrate; (2) contact the bound receptor with a fluid or tissue sample containing the virus, a viral antigen, or antibodies to the virus; (3) contact the above with an antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect presence of an anti-Cosavirus antibody in the sample or a specific Cosavirus protein as well as the virus.

Another immunologic technique that can be useful in the detection of Cosaviruses is the competitive inhibition assay, utilizing monoclonal antibodies (MABs) specifically reactive with the virus. Briefly, serum or other body fluids from the subject is reacted with an antibody bound to a substrate (e.g. an ELISA 96-well plate). Excess serum is thoroughly washed away. A labeled (enzyme-linked, fluorescent, radioactive, etc.) monoclonal antibody is then reacted with the previously reacted Cosavirus virus-antibody complex. The amount of inhibition of monoclonal antibody binding is measured relative to a control. MABs can also be used for detection directly in samples by IFA for MABs specifically reactive for the antibody-virus complex.

Alternatively, a Cosavirus antigen and/or a patient's antibodies to the virus can be detected utilizing a capture assay. Briefly, to detect antibodies to Cosavirus in a patient sample, antibodies to the patient's immunoglobulin, e.g., anti-IgG (or IgM) are bound to a solid phase substrate and used to capture the patient's immunoglobulin from serum. A Cosavirus, or reactive fragments of a Cosavirus, are then contacted with the solid phase followed by addition of a labeled antibody. The amount of patient Cosavirus specific antibody can then be quantitated by the amount of labeled antibody binding.

Additionally, a micro-agglutination test can also be used to detect the presence of Cosavirus in test samples. Briefly, latex beads are coated with an antibody and mixed with a test sample, such that Cosavirus in the tissue or body fluids that are specifically reactive with the antibody crosslink with the receptor, causing agglutination. The agglutinated antibody-virus complexes form a precipitate, visible with the naked eye or by spectrophotometer. Other assays include serologic assays, in which the relative concentrations of IgG and IgM are measured.

In the diagnostic methods described above, the sample can be taken directly from the patient or in a partially purified form. The antibody specific for a particular Cosavirus (the primary reaction) reacts by binding to the virus. Thereafter, a secondary reaction with an antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the virus will be selected for its ability to react with multiple sites on the complex of antibody and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, (1988)).

As described herein, a Cosavirus infection may also, or alternatively, be detected based on the level of a Cosavirus RNA or DNA in a biological sample. Primers from Cosavirus can be used for detection of Cosavirus, diagnosis, and determination of Cosavirus viral load. Any suitable primer can be used to detect the genome, nucleic acid sub sequence, ORF, or protein of choice, using, e.g., methods described in US 20030104009. For example, the subject nucleic acid compositions can be used as single- or double-stranded probes or primers for the detection of Cosavirus mRNA or cDNA generated from such mRNA, as obtained may be present in a biological sample (e.g., extracts of human cells). The Cosavirus polynucleotides of the invention can also be used to generate additional copies of the polynucleotides, to generate antisense oligonucleotides, and as triple-strand forming oligonucleotides. For example, two oligonucleotide primers may be employed in a polymerase chain reaction (PCR) based assay to amplify a portion of Cosavirus cDNA derived from a biological sample, wherein at least one of the oligonucleotide primers is specific for (i.e., hybridizes to) the Cosavirus polynucleotide. The amplified cDNA is then separated and detected using techniques well known in the art, such as gel electrophoresis. Similarly, oligonucleotide probes that specifically hybridize to a Cosavirus polynucleotide may be used in a hybridization assay to detect the presence of the Cosavirus polynucleotide in a biological sample. These and other uses are described in more detail below.

The polynucleotides of the invention, particularly where used as a probe in a diagnostic assay, can be detectably labeled. Exemplary detectable labels include, but are not limited to, radiolabels, fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N,N'-tetramethyl-6-carboxyrho-damine (TAMRA)), radioactive labels, (e.g. $^{32}P$, $^{35}S$, and $^{3}H$), and the like. The detectable label can involve two stage systems (e.g., biotin-avidin, hapten-anti-hapten antibody, and the like).

The invention also includes solid substrates, such as arrays, comprising any of the polynucleotides described herein. The polynucleotides are immobilized on the arrays using methods known in the art. An array may have one or more different polynucleotides.

Any suitable qualitative or quantitative methods known in the art for detecting specific Cosavirus nucleic acid (e.g., RNA or DNA) can be used. Cosavirus nucleic acid can be detected by, for example, in situ hybridization in tissue sections, using methods that detect single base pair differences between hybridizing nucleic acid (e.g., using the technology described in U.S. Pat. No. 5,846,717), by reverse transcriptase-PCR, or in Northern blots containing poly A+ mRNA, and other methods well known in the art. For detection of Cosavirus polynucleotides in blood or blood-derived samples, the use of methods that allow for detection of single base pair mismatches is preferred.

Nucleic acid probes specific to Cosavirus can be generated using the polynucleotide sequences disclosed herein. The probes may be at least about 12, 15, 16, 18, 20, 22, 24, or 25 nucleotide fragments of a contiguous sequence of SEQ ID NO: 1 or other polynucleotide sequence encoding a Cosavirus polypeptide. Nucleic acid probes can be less than about 200, 150, 100, 75, 60, 50, 40, 30, or 25 nucleotides in length; or may be up to about 2 kb, 1.5 kb, 1 kb, 0.5 kb, 0.25 kb, 0.1 kb, or 0.05 kb in length. Probes may be 5 to 40 nucleotides in length, or 8 to 35 nucleotides, or 10 to 25 nucleotides. The probes can be produced by, for example, chemical synthesis, PCR amplification, generation from longer polynucleotides using restriction enzymes, or other methods well known in the art.

Using the Cosavirus nucleic acid as a basis, nucleic acid probes (e.g., including oligomers of at least about 8 nucleotides or more) can be prepared, either by excision from recombinant polynucleotides or synthetically, which probes hybridize with the Cosavirus nucleic acid, and thus are useful in detection of Cosavirus virus in a sample, and identification of infected individuals, as well as further characterization of the viral genome(s). The probes for Cosavirus polynucleotides (natural or derived) are of a length or have a sequence which allows the detection of unique viral sequences by hybridization. While about 6-8 nucleotides may be useful, longer sequences may be preferred, e.g., sequences of about 10-12 nucleotides, or about 20 nucleotides or more. Preferably, these sequences will derive from regions which lack heterogeneity among Cosavirus viral isolates.

Nucleic acid probes can be prepared using routine methods, including automated oligonucleotide synthetic methods. A complement to any unique portion of the Cosavirus genome may be used, e.g., a portion of the Cosavirus genome that allows for distinguishing Cosavirus from other viruses that may be present in the sample. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled with a detectable label. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the Cosavirus genome or portion thereof. Therefore, usually high stringency conditions are desirable in order to prevent or at least minimize false positives. However, conditions of high stringency should only be used if the probes are complementary to regions of the viral genome which lack heterogeneity among Cosavirus viral isolates. The stringency of hybridization is determined by a number of factors during hybridization and during the washing procedure, including temperature, ionic strength, length of time, and concentration of formamide. These factors are outlined in, for example, Sambrook et al. (1989), "Molecular Cloning; A Laboratory Manual", Second Edition (Cold Spring Harbor Press, Cold Spring Harbor, N.Y.).

Generally, it is expected that the Cosavirus sequences will be present in a biological sample (e.g., blood, cells, and the liked) obtained from an infected individual at relatively low levels, e.g., at approximately $10^2$-$10^4$ Cosavirus sequences per $10^6$ cells. This level may require that amplification techniques be used in hybridization assays. Such techniques are known in the art.

For example, the Enzo Biochemical Corporation "BioBridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT Publication No. WO84/03520 and European application no. EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands.

Non-PCR-based, sequence specific DNA amplification techniques can also be used in the invention to detect Cosavirus sequences. An example of such techniques include, but are not necessarily limited to the Invader assay, see, e.g., Kwiatkowski et al. *Mol Diagn*. December 1999; 4(4):353-64. See also U.S. Pat. No. 5,846,717.

A particularly desirable technique may first involve amplification of the target Cosavirus sequences in sera approximately 10,000 fold, e.g., to approximately 10 sequences/mL. This may be accomplished, for example, by the polymerase chain reactions (PCR) technique described which is by Saiki et al. (1986), by Mullis, U.S. Pat. No. 4,683,195, and by Mullis et al. U.S. Pat. No. 4,683,202. Other amplification methods are well known in the art. In a preferred embodiment, a sample suspected of comprising the Cosavirus nucleic acid is contacted with at least one primer that hybridizes to a nucleotide sequence of SEQ ID NO:1, said contacting being under conditions suitable for amplification of an amplification product from a Cosavirus nucleic acid in the sample.

In one embodiment, there is provided a method of detecting a Cosavirus nucleic acid by 1) contacting a sample suspected of containing a Cosavirus nucleic acid with a nucleotide sequence that hybridizes under highly stringent conditions to a nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16, incubating the hybridization reaction at 42° C. in a solution comprising 50% formamide, 5×SSC, and 1% SDS and washed at 65° C. in a solution comprising 0.2×SSC and 0.1% SDS; and 2) detecting the presence or absence of hybridization.

In another embodiment, there is provided a method of detecting a Cosavirus nucleic acid by performing the steps of: 1) contacting a sample suspected of containing the Cosavirus nucleic acid with at least one primer that hybridizes to a nucleotide sequence of SEQ ID NO:1, SEQ ID NO:3, SEQ ID NO:5, SEQ ID NO:6, SEQ ID NO:9, SEQ ID NO:10, SEQ ID NO:11, SEQ ID NO:15, or SEQ ID NO:16; 2) performing an amplification reaction with a denaturation phase of 90° C.-95° C. for 30 sec-2 min., an annealing phase of 50° C. to about 65° C. lasting 30 sec.-2 min., and an extension phase of about 72° C. for 1-2 min., and an extension phase of about 72° C. for 1-2 min for 20-40 cycles; and 3) detecting the presence or absence of the Cosavirus nucleic acid.

The probes, or alternatively nucleic acid from the samples, may be provided in solution for such assays, or may be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads.

In one embodiment, the probe (or sample nucleic acid) is provided on an array for detection. Arrays can be created by, for example, spotting polynucleotide probes onto a substrate (e.g., glass, nitrocellulose, and the like) in a two-dimensional matrix or array. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734. Arrays are particularly useful where, for example a single sample is to be analyzed for the presence of two or more nucleic acid target regions, as the probes for each of the target regions, as well as controls (both positive and negative) can be provided on a single array. Arrays thus facilitate rapid and convenience analysis.

The invention further provides diagnostic reagents and kits comprising one or more such reagents for use in a variety of diagnostic assays, including for example, immunoassays such as ELISA and "sandwich"-type immunoassays, as well as nucleic acid assay, e.g., PCR assays. In a related embodiment, the assay is performed in a flow-through or strip test format, wherein the binding agent is immobilized on a membrane, such as nitrocellulose. Such kits may preferably include at least a first peptide, or a first antibody or antigen binding fragment of the invention, a functional fragment thereof, or a cocktail thereof, or a first oligo pair, and means for signal generation. The kit's components may be pre-attached to a solid support, or may be applied to the surface of a solid support when the kit is used. The signal generating means may come pre-associated with an antibody or nucleic acid of the invention or may require combination with one or more components, e.g., buffers, nucleic acids, antibody-enzyme conjugates, enzyme substrates, or the like, prior to use.

Kits may also include additional reagents, e.g., blocking reagents for reducing nonspecific binding to the solid phase surface, washing reagents, enzyme substrates, enzymes, and the like. The solid phase surface may be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorigenic, or other type of detectable label or detecting means is included within the kit, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery. Kits may further include instructions for use.

Assays for modulators of Cosavirus are also contemplated in the present invention. Modulation of a Cosavirus, and corresponding modulation of the cell cycle, e.g., tumor cell, proliferation, can be assessed using a variety of in vitro and in vivo assays, including cell-based models. Such assays can be used to test for inhibitors and activators of Cosavirus. Modulators of Cosavirus are tested using either recombinant or naturally occurring protein of choice, preferably human Cosavirus.

Preferably, the Cosavirus will have a sequence as shown in SEQ ID NO:1, SEQ ID NO:3, SEQ ID NO:5, SEQ ID NO:6, SEQ ID NO:9, SEQ ID NO:10, SEQ ID NO:11, SEQ ID NO:15, SEQ ID NO:16 or conservatively modified variants thereof. Alternatively, the Cosavirus of the assay will be derived from a eukaryote and include an amino acid subsequence having substantial amino acid sequence identity to a sequence as shown in SEQ ID NO: 2, SEQ ID NO:4, SEQ ID NO:7, or SEQ ID NO:8, SEQ ID NO:12, SEQ ID NO:13, SEQ ID NO:14, or SEQ ID NO:17. Generally, the amino acid sequence identity will be at least 60%, preferably at least 65%, 70%, 75%, 80%, 85%, or 90%, most preferably at least 95%.

Measurement of modulation of a Cosavirus or a cell expressing Cosavirus, either recombinant or naturally occurring, can be performed using a variety of assays, in vitro, in vivo, and ex vivo, as described herein. A suitable physical, chemical or phenotypic change that affects activity, e.g., enzymatic activity, cell surface marker expression, viral replication and proliferation can be used to assess the influence of a test compound on the polypeptide of this invention. When the functional effects are determined using intact cells or animals, one can also measure a variety of effects.

Assays to identify compounds with Cosavirus modulating activity can be performed in vitro. Such assays can used full length Cosavirus or a variant thereof, or a mutant thereof, or a fragment thereof, such as a RING domain. Purified recombinant or naturally occurring protein can be used in the in vitro methods of the invention. In addition to purified Cosavirus, the recombinant or naturally occurring protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, etc. A wide variety of assays can be used to identify Cosavirus-modulator binding, including labeled protein-protein binding assays, electrophoretic mobility shifts, immunoassays, enzymatic assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the protein is washed, interference with binding, either of the potential modulator or of the known ligand or substrate, is determined. Often, either the potential modulator or the known ligand or substrate is labeled.

In another embodiment, the Cosavirus is expressed in a cell, and functional, e.g., physical and chemical or phenotypic, changes are assayed to identify modulators of the cell cycle. Any suitable functional effect can be measured, as described herein. The Cosavirus can be naturally occurring or recombinant. Also, fragments of the Cosavirus or chimeric proteins can be used in cell based assays. In addition, point mutants in essential residues required by the catalytic site can be used in these assays.

The compounds tested as modulators of Cosavirus can be any small organic molecule, or a biological entity, such as a protein, e.g., an antibody or peptide, a sugar, a nucleic acid, e.g., an antisense oligonucleotide or a ribozyme or RNAi, or a lipid. Alternatively, modulators can be genetically altered versions of a Cosavirus. Typically, test compounds will be small organic molecules, peptides, circular peptides, RNAi, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment the invention, soluble assays using a Cosavirus, or a cell or tissue expressing an Cosavirus, either naturally occurring or recombinant are provided. In another embodiment, the invention provides solid phase based in vitro assays in a high throughput format, where the Cosavirus is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for Cosavirus in vitro, or for cell-based or membrane-based assays comprising a Cosavirus. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Within certain aspects, Cosavirus, proteins or peptides and immunogenic fragments thereof, and/or polynucleotides, as well as anti-Cosavirus antibodies and/or T cells, may be incorporated into pharmaceutical compositions or immunogenic compositions (e.g., vaccines). Whole virus vaccine (live and attenuated, or replication incompetent, or killed) or subunit vaccines, such as structural or non-structural Cosavirus proteins or immunogenic fragments thereof, encoded by SEQ ID NO: 2, SEQ ID NO:4, SEQ ID NO:7, or SEQ ID NO:8, can be used to treat or prevent Cosavirus infections by eliciting an immune response in a subject. Alternatively, a pharmaceutical composition may comprise an antigen-presenting cell (e.g., a dendritic cell) transfected with a Cosavirus polynucleotide such that the antigen-presenting cell expresses a Cosavirus peptide.

Pharmaceutical compositions comprise one or more such vaccine compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Vaccine preparation is generally described in, for example, Powell and Newman, eds., *Vaccine Design* (the subunit and adjuvant approach), Plenum Press (NY, 1995). Vaccines may be designed to generate antibody immunity and/or cellular immunity such as that arising from CTL or CD4+ T cells.

Pharmaceutical compositions and vaccines within the scope of the present invention may also contain other compounds, which may be biologically active or inactive. For example, one or more immunogenic portions of other antigens may be present, either incorporated into a fusion polypeptide or as a separate compound, within the composition or vaccine. Polypeptides may, but need not, be conjugated to other macromolecules as described, for example, within U.S. Pat. Nos. 4,372,945 and 4,474,757. Pharmaceutical compositions and vaccines may generally be used for prophylactic and therapeutic purposes.

Nucleic acid vaccines encoding a genome, structural protein or non-structural protein or a fragment thereof of Cosavirus can also be used to elicit an immune response to treat or prevent Cosavirus infection. Numerous gene delivery techniques are well known in the art, such as those described by Rolland (1998) *Crit. Rev. Therap. Drug Carrier Systems* 15:143-198, and references cited therein. Appropriate nucleic acid expression systems contain the necessary DNA sequences for expression in the patient (such as a suitable promoter and terminating signal). In a preferred embodiment, the DNA may be introduced using a viral expression system (e.g., vaccinia, pox virus, retrovirus, or adenovirus), which may involve the use of a non-pathogenic (defective), replication competent virus. Suitable systems are disclosed, for example, in Fisher-Hoch et al. (1989) *Proc. Natl. Acad. Sei. USA* 86:317-321; Flexner et al. (1989) *Ann. N.Y. Acad. Sci.* 569:86-103; Flexner et al. (1990) *Vaccine* 8:17-21; U.S. Pat. Nos. 4,603,112, 4,769,330, 4,777,127 and 5,017,487; WO 89/01973; GB 2,200,651; EP 0,345,242; WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al. (1993) *Circulation* 88:2838-2848; and Guzman et al. (1993) *Cir. Res.* 73:1202-1207. Techniques for incorporating DNA into such expression systems are well known to those of ordinary skill in the art. The DNA may also be "naked," as described, for example, in Ulmer et al. (1993) *Science* 259:1745-1749 and reviewed by Cohen (1993) *Science* 259:1691-1692. The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* $17^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

The following examples are intended to illustrate but not limit the invention.

Examples

Stool samples from children presenting with acute flaccid paralysis (AFP) were used for virus isolation in cell culture. A metagenomic shotgun sequencing approach was used to determine if known and previously uncharacterized viruses could be identified. Large scale sequencing and Rapid Amplification of cDNA Ends (RACE) were used to acquire the complete genome of a new virus, Cosavirus.

Phylogenetic analysis of Cosavirus established it as an outlier showing mean protein identity of 16-32% to other genera of Picornaviridae. The Cosavirus genome codes for a single polyprotein flanked by 5' and 3' non-translated regions, similar to all Picornaviruses.

The complete genome sequence was also acquired from another divergent Cosavirus variant, termed Cosavirus type-2. This variant had an 82% amino acid identity to Cosavirus type-1.

PCR primers targeting conserved nonstructural genes were used to determine the prevalence of Cosavirus in stool samples from children with AFP. Six genetic variants of Cosavirus were found in 14 stool samples from AFP children, suggesting a high prevalence among this disease group.

Although the invention has been described with reference to the above example, it will be understood that modifications and variations are encompassed within the spirit and scope of the invention. Accordingly, the invention is limited only by the following claims.

What is claimed is:

1. An isolated nucleic acid molecule comprising a sequence that comprises 50 or more contiguous nucleic acids of SEQ ID NO:1, or the complement thereof in a recombinant expression vector.

2. The nucleic acid of claim 1, which comprises SEQ ID NO:1.

3. The nucleic acid of claim 1, which comprises SEQ ID NO:9.

4. An isolated and detectably labeled nucleic acid molecule comprising a sequence that comprises 50 or more contiguous nucleic acids of SEQ ID NO:1, or the complement thereof which hybridizes to SEQ ID NO:1 under conditions of hybridization at 42° C. in a solution comprising 50% formamide, 5×SSC, and 1% SDS, and washing at 65° C. in a solution comprising 0.2×SSC and 0.1% SDS.

5. A kit for detecting a Cosavirus nucleic acid that comprises the nucleic acid of claim 4.

6. A method of detecting a Cosavirus nucleic acid comprising:
   (a) contacting a sample suspected of comprising a Cosavirus nucleic acid with a detectably labeled fragment of 12 or more contiguous nucleic acids of SEQ ID NO:1 or the complement thereof bound to a solid support, and
   (b) detecting the presence or absence of hybridization.

7. A method of detecting a Cosavirus nucleic acid comprising:
   (a) amplifying nucleic acid of a sample suspected of containing a Cosavirus with a primer pair that is a fragment of 12 or more contiguous nucleic acids of SEQ ID NO:1 or the complement thereof producing a partially double stranded nucleic acid molecule prior to amplification followed by producing, an amplification product; and
   (b) detecting the presence of an amplification product, thereby detecting the presence of the Cosavirus nucleic acid.

8. An isolated nucleic acid that consists of 25 or more contiguous nucleic acids of SEQ ID NO:1, or the complement thereof in a recombinant vector.

9. An isolated nucleic acid molecule comprising SEQ ID NO:1, or the complement thereof in a recombinant vector.

10. The expression vector of any of claims 8 to 9, which encodes the protein of SEQ ID NO:2.

11. An isolated host cell comprising the expression vector of any of claims 8 to 9.

12. An isolated nucleic acid molecule comprising a nucleotide sequence at least 80% identical to SEQ ID NO:1, or the complement thereof in a recombinant vector.

13. An isolated nucleic acid molecule comprising a nucleotide sequence at least 90% identical to SEQ ID NO:1, or the complement thereof in a recombinant vector.

14. An isolated nucleic acid molecule comprising a nucleotide sequence at least 95% identical to SEQ ID NO:1, or the complement thereof in a recombinant vector.

* * * * *

SEQUENCE LISTING

```
<160> NUMBER OF SEQ ID NOS: 88

<210> SEQ ID NO 1
<211> LENGTH: 7634
<212> TYPE: DNA
<213> ORGANISM: Cosavirus

<400> SEQUENCE: 1
ttctgagacc ggcacggtca acccgactca tttacgagtt actcatttat tttgaaacat      60
cataaagaac gtgaaccgct ctttgtttct ttaaggaatt tagagtagaa aacatttgag     120
atgaggcccg gttgaactcc gggcgctttc catccgctgt gatgggctca ctcctgtaca     180
ccgtgagtcc gcgcagtgct gacttaacac ttaagtaatg tataggccga ggattacacc     240
gctcggctcc cacctttcac caccgtggga ttaacaggtt caatgcacaa attcctgtcc     300
ttggctatgt caaagcaata cagtgtgtac atggcgtgca cgctcaaagc ggagacttag     360
gcctcacaga ttgtgttttg tgttattgga tgctggatgg tcacgttgga gactgcatgt     420
ggcagtcttg aaacgtgtgg tttgacgtct atccattatg gcagtgggtg gagtactgca     480
aagatgtcac cgtgctttac acggtttttg aaccccacac cggctgtttg gcgcttgcag     540
gacagcaggt ttattttctt atgttctcca tttctagcca acagggttct atcctgttgg     600
gcggagtgat actcccgttc cttcttggac agattgcctc cacgttcttt gtggatctca     660
aggtgatcaa gtcactggtg aatagagcga aggttgagga gacctgagga atttccatgt     720 ggcttttgcca ggagttgtag cgatgctgtg tgtgtgtgcg gatttcccct catggcaaca     780
tgagcctcac aggccaaaag ccctgtccga aaggaccac acagtggagc aacccccagct     840
```

```
ccctcctaca aagctttgtg agaatgaact caagtttatt ctactttatt ctctatttac    900
atcaggcccc aaagatgtcc tgaaggtacc ttgtgtatct gggcacgagc accatcagct    960
acccggactt gtatttcggt acagacacat gtggtgaccc agcccctctg cttcggcagg   1020
ggggctttcg ctcgctcagc acgagatctg atcaggagcc cctcccagtg tgctttacac   1080
ctggcgaggg gttaaaaatt gcccaaggcc tggcaaaaca acctagggga ctaggttttc   1140
cttttattaa taatatctgt cattatgggt gcaataata gcaaagaatc tgtgtccagc   1200
aatggcaacg agggaacaat tgttaataac ttttattcaa accagtatta tgcttctatt   1260
gatgcttctg cccaaggtgt tgggacctct actactcctg aaaacggcaa cgtatctggc   1320
tttcttggac ttgcaggtag tgcttttaat gctctctctc ttctcgcctc accacgaacc   1380
gagacaggaa tgatgatgga agatcgtgtc ctttcccgta ctgccggtaa tacatctgta   1440
aactctcaag ctgctgaagg ggttttgcag gcatatggga ctgagacaga cagcaattcg   1500
cccacttcgt gtggcgacga tcctagcaag ggtacacacg caacagacag agcctttgta   1560
atacaattgc ttccatggaa acagacaaca aattcatact ttgctcaatg ggtaagactc   1620
acacagaaac tgtcaaacaa tttgcatgga aatgttatgg ccaaaaacat aaatcacat   1680
gcttttgcca aaatgggctt tgaagtaatg ttacaggcaa cacctcgcc tttccataat   1740
ggcatactgg tcttttcttt ggtaccggag tttgttagaa agggtgaaat tacagatgag   1800
tggattgacc tcacacctac ctcttcttta gtttcaaaca ctgagttgta caaccccag   1860
acttatgcaa atttt ccatt tgatgctaaa catagttttg attattctga tattacacca   1920
gaacaattta tgattttccc tcaccaactt ataaatccta aagacacaaa tgttgccaca   1980
gtacgtgtgc cgtacattaa tattgctcca acaaatgata ctacagtaca tacagtatgg   2040
acagctgttg ttatggttct tgtacctctt aactttttctt ctggtgcttc accaactgta   2100
tctttaacat taactataac tccaataaac tcagttttta atggattaca tcacaccgca   2160
caggggccta tccctgtgcg acctttccat aatttccagc agtttagcac tactgtccct   2220
ctgcgcactg aaccatgtta cggcatgaca gtgactcctc cagttgatta catgcccta   2280
cccattacag atttagttga gcttgctaaa gtgcccagtt tgttactgt ggcaaacagt   2340
gacacgacta gcgagcgtag tttcccttat ttctctgtta gtaacacaga acaaggcaga   2400
aatcttttca aatccagtgt agttctcagc gacttacact accagcacac tcttgtagca   2460
aatttggccc gttacttttg caactacaga ggtagtctac agtttgattt tatagctgca   2520
acaactgcaa tgacaagagg caaattgctc attagctaca ccccaccagg ggctggtgag   2580
ccacaatcaa ttgatcaggc aatgatggga acttatgcta tctgggattt gggattacaa   2640
tcaaccttca attttgtagt cccttttata tctgcttctg acttcagatt taacacctct   2700
tctgtatcta atgctttgaa ctctgatggt tggatcacag tgtggcttat gaaccctcta   2760
acatatcctc ccagtacacc tcctacccaa cagatattga tgttgatgtc agctggcagt   2820
gacttttctt accggttgcc catttcgccc ggtttcgccg agggggaaac gagcgaacat   2880
ccaatggaca acgctgagtg cgggaaaatt gatgacaaag acgcaggaat gttttccgga   2940
cactctgttg ggctgcctac tccccacacc tcgacttctt tcttctatga caggtacaga   3000
ttcgtaggaa ttgtaaagag tgtagtgaat aatactccca aaccagtcaa catttatgat   3060
gatacaggaa aagttaagaa cctacaacag gttttttccaa cttcagacac actactgccc   3120
cactctttga tgtccctttc tcctgtgcg tcagtgtgtg gccagcctat ctcttccttc   3180
```

```
ctgtttgctc aacgagcgaa tcccaagaaa actctaaagc tgcgctcagg tgatgaattc   3240
ttgtatagat gttgcccttt ttcttacatt aaatgtgacc ttgagtttac tgtggtcccc   3300
cctgcgaatt ctactagaga ttatattgtg cactggtacc cgccagggc caccctggat    3360 gctggagaag tagccgtggg taatacatca ggtagcaatg gctttgatga taatgggatg   3420
aacgctggtt ctagtctgtt ttcttacaat cctactttcc acgcaagagc tccgtcaaaa   3480
gtctcagctg ttatacccttt ttgcttaccc gtttctctat tacctctata ttttgatggc  3540
tttcccgatt acagtactac aaaaggaatg tatggatgct cccccttcttt tagttttgga  3600 accatataca ttgaatctgg actccaagaa acttattcag tttacattag atacaaggat   3660
tttaagggtt atgctcccag accgctcatt cggacaccac acattaggct atcagaaaga   3720
gctagatata ttatggcaga ctcggtgctt ccacgccctc tcacacgcgc tgaacgtgat   3780
gtggcgcgtg atttgctgct cattgctggg gatattgaat caaatccagg acctgcattt   3840
aatccagaat atacagctca tggcccagtt actgaattga ttcaattggc aaggaaacca   3900
gaaactgtag ataatgtaaa taggcttctc acaaccctga atactcttat ggctaaatgg   3960
aacaatctca aggatactgt tacagatgct gtgtttctta gagacatggt atgtcttctt   4020
gtgaagctta cttctcttat gtacttggtt catggacagg gaccaggtgc ttactttgct   4080
gctgcctcca ttcttcttgc tgatggcata acttctcttg attggtacga gaaaatcaag   4140
attttcatgg ctagaaaact cagagtttcc cctcccttct tccccgctgc ccaggggccg   4200
gaccttagag actttgtgac cttttttcaac gcagcgcgcg gagcgcaatg gatgattgat   4260
tctctcaaat cccttataac ttgtatcaaa caatggcttg aacttgaaga ggaaaatgaa   4320
gcagtacaac ttgaaaagat gttaatagac tctcccagac attgcaaggc aataaatgac   4380
tacaacagag gtgactcctt tcagagaccg accaactctt ttgaattcat ggacagactt   4440
gtggaatgtg ctaccaagct tgggaaagtc caaattgcaa cttatttcag aaattttact   4500
acagctgatt ctgatacaag cagaccgag ccagttgttg ttgttttgcg cgggaaacca    4560
ggcgtaggca atctgctgc agctactgtt atggcagctg cagtatctaa attgttggta    4620
ggaagtcaat cagtgtacac cctttccca gatacgaaac atatggatgg atatcacgga    4680
cagtttgtga cttttgatgga tgaccttgga caaaacccag acggagaaga cttcagatgt   4740
ttctgtcaaa tggtttcttg tgctcagtac agacctgcta tggctgacct taaagacaaa   4800
ggaatcctgt ttacatccag actgttgatt gctactacta atctcccaga ttttaaccct   4860
gttactatct ctgatccgcg agctttagat cgtcggatca cttttgatat tcttgtcact   4920
ccaggttctg ccgccaccaa gaatgggaaa cttgacttgg ccgctgctct caaaccagat   4980
ggaccgggag aacaccctta cacttctgat tgccctattc tccacaccac tggactcctc   5040
ctgaagaacc tcagaaacaa ccagaccatg aacttgaaag acctagtgga catgattgtt   5100
aagagaatta acacaagaa agaagttgga aatatgcttg actctcttgt tgctcaggga   5160
cctactatga ttgttggcta taccaaagac gatgatggta tcgctattgt ggactgcttg   5220
gaagaatgga acaagataaa ggacaagaag aagaaacagc ttgctttgga atggttgct    5280 caagaactta aggacaaaca tgaagaacat aaaggcacaa tcaaattact caaaatgttt   5340
gttactggcc ttggagtggt tgccgctgtt gcaggcgcgt atgccacaat gaaatacttt   5400
acaaaggaca aacccaagga agaagaagaa gagccagaag aaaagaaaga gaagaaaaca   5460
gaagaatcca agaggctgc aggaccatac aacggaccta caaagaaaga aattaaaaca   5520
ttgaagttaa aggcccagag tccacttatg gatatggaaa agaaaattgc ccagaatgtc   5580
```

```
atgcccttcc agattttcta taatggaaaa agatacaccc agtcttgtct ggcaattgga    5640
aaaagagtta ttcttgtgaa caaacatgct tttgaatcag ttgaacacaa atttgttgtt    5700
gaccaaaagg aatacacatt ggaccaggtt acagctattt cccttgactg cggatcaggt    5760
gtcacggatg tgtgtgctgt atgtttgccc ccaggcccag acttcaaatc aataaagaaa    5820
catttcctac ccttcaacac taccatgttt ccaggaacca gactgaccat cctctcgaat    5880
gaccactacc ctatgtccag agaaggctct ttcctcagat tgaggatgaa ggtaccgact    5940
aatgtaggta acatgcccct tgtaatgctt acaaatcaa cctcttattt tggaatgtgt    6000
ggctcagttg tatgtagcag atttgttgat ggtggaggaa taattggaat gcactgcgca    6060
ggtggaggcg gagtcagtgt tggaactcgt ttgactgcta aatgattga atcagttttt    6120 gattacttct acccccagt agcccaggga ataattgaaa acacagagac aggaccccgt    6180
gtacatgtgc ccagaacttc caaactcaaa agaacaaacg ccacttatcc ggcaacggaa    6240
aagtatggcc cagctgctct ttcgcggtat gatccgcgat taaatgaggg agtcaacttg    6300
gatgaggtga tcttctcaaa acatactcaa aacactcttg ttgagaaagg atccactttc    6360
agaagcgccc ttgacatggc agcagaaatt tatggtgaaa agtttagagg aaatgatttc    6420
tctccccttt cagttgaaga tgcaattctt ggaattcccg acttgacag acttgacccg    6480 aatactgctt ctggattgcc ctacactaaa accagacgac agatgattga cttcaacaca    6540
ggacagattt tggacgacac tcttaagtgt cgacttggac aatggcttgc aggacgaccc    6600
ccccaggaag tacattacca gacatttctt aaggatgaaa tcaggcccat tgaaaaggtc    6660
aaagcaggaa agactagaat aattgatgtt cctcctcttg atcatgtcat cgcttttaga    6720
atgctctttg gcagattcat tgcccactac cacttaaact ttggcttcaa aacaggctct    6780
gctattggtt gtgacccaga tgtcgcttgg gcttctttg ctttgaact cagtggcttt    6840 ccttatctgt atgattttga ttactcaaac tttgatgctt ctcacagtac ttcaatatttt   6900 gaaatcttag aacagaaatt cttttcccca gaattaggtt ttgatcctag atgctcactt    6960
ctcttgaaat cccttgcagt ttcaaccac tgttatgaga caagagact ccagattgct    7020 ggaggacttc cctctggcac ggcaggtacc tcagtactga acaccgtgat aaacaacatt    7080
atctttcacg gtgcactata ccacacttac actaattttg agcgggatga catcagtatg    7140
ttagcctatg cgacgacat tgttgttgcc tccaaatttg aacttgactt ggttatggtt    7200
aaggctttca tgaaccggat tggctataag attacccctg cagacaaaag tgatgaattc    7260
agaccaaagt gtatggatga catttgcttc ttaaagaggc gttttgttaa agttgctgga    7320
gtttgggctc cagtgatgga aactgaaaac ctcgaggcaa tgttgtcttg gtacaaacca    7380
ggaactctta tgaaaagct ccagagtgtc tcaagacttg cccacttctc aggacgtgac    7440
gtgtatgacc acctttcaa gcccttcatt cgtgatgggt tgatgtcac accttggaaa    7500 cagttacact tggaatggct taataagtta tcagcttaaa gaattttgaa ttggcatttc    7560 agatttatt tgaatttggc ttttaattcg gctttaattt ggttatttat tgggtatatt    7620
caaatctaat gacc                                                     7634
```

<210> SEQ ID NO 2
<211> LENGTH: 2124
<212> TYPE: PRT
<213> ORGANISM: Cosavirus

<400> SEQUENCE: 2

```
Met Gly Ala Asn Asn Ser Lys Glu Ser Val Ser Ser Asn Gly Asn Glu
1               5                   10                  15

Gly Thr Ile Val Asn Asn Phe Tyr Ser Asn Gln Tyr Tyr Ala Ser Ile
            20                  25                  30

Asp Ala Ser Ala Gln Gly Val Gly Thr Ser Thr Pro Glu Asn Gly
            35                  40                  45

Asn Val Ser Gly Phe Leu Gly Leu Ala Gly Ser Ala Phe Asn Ala Leu
    50                  55                  60

Ser Leu Leu Ala Ser Pro Arg Thr Glu Thr Gly Met Met Met Glu Asp
65                  70                  75                  80

Arg Val Leu Ser Arg Thr Ala Gly Asn Thr Ser Val Asn Ser Gln Ala
                85                  90                  95

Ala Glu Gly Val Leu Gln Ala Tyr Gly Thr Glu Thr Asp Ser Asn Ser
                100                 105                 110

Pro Thr Ser Cys Gly Asp Asp Pro Ser Lys Gly Thr His Ala Thr Asp
            115                 120                 125

Arg Ala Phe Val Ile Gln Leu Leu Pro Trp Lys Gln Thr Thr Asn Ser
            130                 135                 140

Tyr Phe Ala Gln Trp Val Arg Leu Thr Gln Lys Leu Ser Asn Asn Leu
145                 150                 155                 160

His Gly Asn Val Met Ala Lys Asn Ile Lys Ser His Ala Phe Ala Lys
                165                 170                 175

Met Gly Phe Glu Val Met Leu Gln Ala Asn Thr Ser Pro Phe His Asn
                180                 185                 190

Gly Ile Leu Gly Leu Phe Leu Val Pro Glu Phe Val Arg Lys Gly Glu
            195                 200                 205

Ile Thr Asp Glu Trp Ile Asp Leu Thr Pro Thr Ser Ser Leu Val Ser
            210                 215                 220

Asn Thr Glu Leu Tyr Asn Pro Gln Thr Tyr Ala Asn Phe Pro Phe Asp
225                 230                 235                 240

Ala Lys His Ser Phe Asp Tyr Ser Asp Ile Thr Pro Glu Gln Phe Met
                245                 250                 255

Ile Phe Pro His Gln Leu Ile Asn Pro Lys Asp Thr Asn Val Ala Thr
            260                 265                 270

Val Arg Val Pro Tyr Ile Asn Ile Ala Pro Thr Asn Asp Thr Thr Val
    275                 280                 285

His Thr Val Trp Thr Ala Val Val Met Val Leu Val Pro Leu Asn Phe
    290                 295                 300

Ser Ser Gly Ala Ser Pro Thr Val Ser Leu Thr Leu Thr Ile Thr Pro
305                 310                 315                 320

Ile Asn Ser Val Phe Asn Gly Leu His His Thr Ala Gln Gly Pro Ile
                325                 330                 335

Pro Val Arg Pro Phe His Asn Phe Gln Gln Phe Ser Thr Thr Val Pro
            340                 345                 350

Leu Arg Thr Glu Pro Cys Tyr Gly Met Thr Val Thr Pro Pro Val Asp
            355                 360                 365

Tyr Met Pro Leu Pro Ile Thr Asp Leu Val Glu Leu Ala Lys Val Pro
    370                 375                 380

Ser Phe Val Thr Val Ala Asn Ser Asp Thr Thr Ser Glu Arg Ser Phe
385                 390                 395                 400

Pro Tyr Phe Ser Val Ser Asn Thr Glu Gln Gly Arg Asn Leu Phe Lys
                405                 410                 415

Ser Ser Val Val Leu Ser Asp Leu His Tyr Gln His Thr Leu Val Ala
```

```
                420             425             430
Asn Leu Ala Arg Tyr Phe Cys Asn Tyr Arg Gly Ser Leu Gln Phe Asp
            435                 440             445
Phe Ile Ala Ala Thr Thr Ala Met Thr Arg Gly Lys Leu Leu Ile Ser
            450                 455             460
Tyr Thr Pro Pro Gly Ala Gly Glu Pro Gln Ser Ile Asp Gln Ala Met
465                 470                 475                 480
Met Gly Thr Tyr Ala Ile Trp Asp Leu Gly Leu Gln Ser Thr Phe Asn
                485                 490             495
Phe Val Val Pro Phe Ile Ser Ala Ser Asp Phe Arg Phe Asn Thr Ser
                500                 505             510
Ser Val Ser Asn Ala Leu Asn Ser Asp Gly Trp Ile Thr Val Trp Leu
            515                 520             525
Met Asn Pro Leu Thr Tyr Pro Pro Ser Thr Pro Thr Gln Gln Ile
            530                 535             540
Leu Met Leu Met Ser Ala Gly Ser Asp Phe Ser Tyr Arg Leu Pro Ile
545                 550                 555                 560
Ser Pro Gly Phe Ala Glu Gly Glu Thr Ser Glu His Pro Met Asp Asn
                565                 570                 575
Ala Glu Cys Gly Lys Ile Asp Asp Lys Asp Ala Gly Met Phe Ser Gly
                580                 585                 590
His Ser Val Gly Leu Pro Thr Pro His Thr Ser Thr Ser Phe Phe Tyr
            595                 600                 605
Asp Arg Tyr Arg Phe Val Gly Ile Val Lys Ser Val Asn Asn Thr
            610                 615             620
Pro Lys Pro Val Asn Ile Tyr Asp Asp Thr Gly Lys Val Lys Asn Leu
625                 630                 635                 640
Gln Gln Val Phe Pro Thr Ser Asp Thr Leu Leu Pro His Ser Leu Met
                645                 650                 655
Ser Leu Ser Pro Cys Ala Ser Val Cys Gly Gln Pro Ile Ser Ser Phe
                660                 665                 670
Leu Phe Ala Gln Arg Ala Asn Pro Lys Lys Thr Leu Lys Leu Arg Ser
            675                 680             685
Gly Asp Glu Phe Leu Tyr Arg Cys Cys Pro Phe Ser Tyr Ile Lys Cys
            690                 695             700
Asp Leu Glu Phe Thr Val Val Pro Pro Ala Asn Ser Thr Arg Asp Tyr
705                 710                 715                 720
Ile Val His Trp Tyr Pro Pro Gly Ala Thr Leu Asp Ala Gly Glu Val
                725                 730                 735
Ala Val Gly Asn Thr Ser Gly Ser Asn Gly Phe Asp Asp Asn Gly Met
                740                 745                 750
Asn Ala Gly Ser Ser Leu Phe Ser Tyr Asn Pro Thr Phe His Ala Arg
            755                 760             765
Ala Pro Ser Lys Val Ser Ala Val Ile Pro Phe Cys Leu Pro Val Ser
            770                 775             780
Leu Leu Pro Leu Tyr Phe Asp Gly Phe Pro Asp Tyr Ser Thr Thr Lys
785                 790                 795                 800
Gly Met Tyr Gly Cys Ser Pro Ser Phe Ser Gly Thr Ile Tyr Ile
                805                 810                 815
Glu Ser Gly Leu Gln Glu Thr Tyr Ser Val Tyr Ile Arg Tyr Lys Asp
            820                 825             830
Phe Lys Gly Tyr Ala Pro Arg Pro Leu Ile Arg Thr Pro His Ile Arg
            835                 840             845
```

```
Leu Ser Glu Arg Ala Arg Tyr Ile Met Ala Asp Ser Val Leu Pro Arg
850                 855                 860

Pro Leu Thr Arg Ala Glu Arg Asp Val Ala Arg Asp Leu Leu Leu Ile
865                 870                 875                 880

Ala Gly Asp Ile Glu Ser Asn Pro Gly Pro Ala Phe Asn Pro Glu Tyr
            885                 890                 895

Thr Ala His Gly Pro Val Thr Glu Leu Ile Gln Leu Ala Arg Lys Pro
            900                 905                 910

Glu Thr Val Asp Asn Val Asn Arg Leu Leu Thr Thr Leu Asn Thr Leu
        915                 920                 925

Met Ala Lys Trp Asn Asn Leu Lys Asp Thr Val Thr Asp Ala Val Phe
930                 935                 940

Leu Arg Asp Met Val Cys Leu Val Lys Leu Thr Ser Leu Met Tyr
945                 950                 955                 960

Leu Val His Gly Gln Gly Pro Gly Ala Tyr Phe Ala Ala Ser Ile
            965                 970                 975

Leu Leu Ala Asp Gly Ile Thr Phe Phe Asp Trp Tyr Glu Lys Ile Lys
            980                 985                 990

Ile Phe Met Ala Arg Lys Leu Arg Val Ser Pro Pro Phe Phe Pro Ala
        995                 1000                1005

Ala Gln Gly Pro Asp Leu Arg Asp Phe Val Thr Phe Phe Asn Ala
    1010                1015                1020

Ala Arg Gly Ala Gln Trp Met Ile Asp Ser Leu Lys Ser Leu Ile
    1025                1030                1035

Thr Cys Ile Lys Gln Trp Leu Glu Leu Glu Glu Asn Glu Ala
    1040                1045                1050

Val Gln Leu Glu Lys Met Leu Ile Asp Ser Pro Arg His Cys Lys
    1055                1060                1065

Ala Ile Asn Asp Tyr Asn Arg Gly Asp Ser Phe Gln Arg Pro Thr
    1070                1075                1080

Asn Ser Phe Glu Phe Met Asp Arg Leu Val Glu Cys Ala Thr Lys
    1085                1090                1095

Leu Gly Lys Val Gln Ile Ala Thr Tyr Phe Arg Asn Phe Thr Thr
    1100                1105                1110

Ala Asp Ser Asp Thr Ser Arg Pro Glu Pro Val Val Val Leu
    1115                1120                1125

Arg Gly Lys Pro Gly Val Gly Lys Ser Ala Ala Ala Thr Val Met
    1130                1135                1140

Ala Ala Ala Val Ser Lys Leu Leu Val Gly Ser Gln Ser Val Tyr
    1145                1150                1155

Thr Leu Ser Pro Asp Thr Glu His Met Asp Gly Tyr His Gly Gln
    1160                1165                1170

Phe Val Thr Leu Met Asp Asp Leu Gly Gln Asn Pro Asp Gly Glu
    1175                1180                1185

Asp Phe Arg Cys Phe Cys Gln Met Val Ser Cys Ala Gln Tyr Arg
    1190                1195                1200

Pro Ala Met Ala Asp Leu Lys Asp Lys Gly Ile Leu Phe Thr Ser
    1205                1210                1215

Arg Leu Leu Ile Ala Thr Thr Asn Leu Pro Asp Phe Asn Pro Val
    1220                1225                1230

Thr Ile Ser Asp Pro Arg Ala Leu Asp Arg Arg Ile Thr Phe Asp
    1235                1240                1245
```

```
Ile Leu Val Thr Pro Gly Ser Ala Ala Thr Lys Asn Gly Lys Leu
    1250            1255            1260

Asp Leu Ala Ala Ala Leu Lys Pro Asp Gly Pro Gly Glu His Pro
    1265            1270            1275

Tyr Thr Ser Asp Cys Pro Ile Leu His Thr Thr Gly Leu Leu Leu
    1280            1285            1290

Lys Asn Leu Arg Asn Asn Gln Thr Met Asn Leu Lys Asp Leu Val
    1295            1300            1305

Asp Met Ile Val Lys Arg Ile Lys His Lys Lys Glu Val Gly Asn
    1310            1315            1320

Met Leu Asp Ser Leu Val Ala Gln Gly Pro Thr Met Ile Val Gly
    1325            1330            1335

Tyr Thr Lys Asp Asp Asp Gly Ile Ala Ile Val Asp Cys Leu Glu
    1340            1345            1350

Glu Trp Asn Lys Ile Lys Asp Lys Lys Lys Gln Leu Ala Leu
    1355            1360            1365

Glu Met Val Ala Gln Glu Leu Lys Asp Lys His Glu Glu His Lys
    1370            1375            1380

Gly Thr Ile Lys Leu Leu Lys Met Phe Val Thr Gly Leu Gly Val
    1385            1390            1395

Val Ala Ala Val Ala Gly Ala Tyr Ala Thr Met Lys Tyr Phe Thr
    1400            1405            1410

Lys Asp Lys Pro Lys Glu Glu Glu Glu Pro Glu Lys Lys
    1415            1420            1425

Glu Lys Lys Thr Glu Glu Ser Lys Glu Ala Ala Gly Pro Tyr Asn
    1430            1435            1440

Gly Pro Thr Lys Lys Glu Ile Lys Thr Leu Lys Leu Lys Ala Gln
    1445            1450            1455

Ser Pro Leu Met Asp Met Glu Lys Lys Ile Ala Gln Asn Val Met
    1460            1465            1470

Pro Phe Gln Ile Phe Tyr Asn Gly Lys Arg Tyr Thr Gln Ser Cys
    1475            1480            1485

Leu Ala Ile Gly Lys Arg Val Ile Leu Val Asn Lys His Ala Phe
    1490            1495            1500

Glu Ser Val Glu His Lys Phe Val Val Asp Gln Lys Glu Tyr Thr
    1505            1510            1515

Leu Asp Gln Val Thr Ala Ile Ser Leu Asp Cys Gly Ser Gly Val
    1520            1525            1530

Thr Asp Val Cys Ala Val Cys Leu Pro Pro Gly Pro Asp Phe Lys
    1535            1540            1545

Ser Ile Lys Lys His Phe Leu Pro Phe Asn Thr Thr Met Phe Pro
    1550            1555            1560

Gly Thr Arg Leu Thr Ile Leu Ser Asn Asp His Tyr Pro Met Ser
    1565            1570            1575

Arg Glu Gly Ser Phe Leu Arg Phe Glu Asp Glu Val Pro Thr Asn
    1580            1585            1590

Val Gly Asn Met Pro Phe Val Met Leu Tyr Lys Ser Thr Ser Tyr
    1595            1600            1605

Phe Gly Met Cys Gly Ser Val Val Cys Ser Arg Phe Val Asp Gly
    1610            1615            1620

Gly Gly Ile Ile Gly Met His Cys Ala Gly Gly Gly Val Ser
    1625            1630            1635

Val Gly Thr Arg Leu Thr Ala Arg Met Ile Glu Ser Val Phe Asp
```

-continued

```
               1640                1645                1650

Tyr Phe Tyr Pro Pro Val Ala Gln Gly Ile Ile Glu Asn Thr Glu
        1655                1660                1665

Thr Gly Pro Arg Val His Val Pro Arg Thr Ser Lys Leu Lys Arg
        1670                1675                1680

Thr Asn Ala Thr Tyr Pro Ala Thr Glu Lys Tyr Gly Pro Ala Ala
        1685                1690                1695

Leu Ser Arg Tyr Asp Pro Arg Leu Asn Glu Gly Val Asn Leu Asp
        1700                1705                1710

Glu Val Ile Phe Ser Lys His Thr Gln Asn Thr Leu Val Glu Lys
        1715                1720                1725

Gly Ser Thr Phe Arg Ser Ala Leu Asp Met Ala Ala Glu Ile Tyr
        1730                1735                1740

Gly Glu Lys Phe Arg Gly Asn Asp Phe Ser Pro Leu Ser Val Glu
        1745                1750                1755

Asp Ala Ile Leu Gly Ile Pro Gly Leu Asp Arg Leu Asp Pro Asn
        1760                1765                1770

Thr Ala Ser Gly Leu Pro Tyr Thr Lys Thr Arg Arg Gln Met Ile
        1775                1780                1785

Asp Phe Asn Thr Gly Gln Ile Leu Asp Asp Thr Leu Lys Cys Arg
        1790                1795                1800

Leu Gly Gln Trp Leu Ala Gly Arg Pro Pro Gln Glu Val His Tyr
        1805                1810                1815

Gln Thr Phe Leu Lys Asp Glu Ile Arg Pro Ile Glu Lys Val Lys
        1820                1825                1830

Ala Gly Lys Thr Arg Ile Ile Asp Val Pro Pro Leu Asp His Val
        1835                1840                1845

Ile Ala Phe Arg Met Leu Phe Gly Arg Phe Ile Ala His Tyr His
        1850                1855                1860

Leu Asn Phe Gly Phe Lys Thr Gly Ser Ala Ile Gly Cys Asp Pro
        1865                1870                1875

Asp Val Ala Trp Ala Ser Phe Gly Phe Glu Leu Ser Gly Phe Pro
        1880                1885                1890

Tyr Leu Tyr Asp Phe Asp Tyr Ser Asn Phe Asp Ala Ser His Ser
        1895                1900                1905

Thr Ser Ile Phe Glu Ile Leu Glu Gln Lys Phe Phe Ser Pro Glu
        1910                1915                1920

Leu Gly Phe Asp Pro Arg Cys Ser Leu Leu Lys Ser Leu Ala
        1925                1930                1935

Val Ser Thr His Cys Tyr Glu Asn Lys Arg Leu Gln Ile Ala Gly
        1940                1945                1950

Gly Leu Pro Ser Gly Thr Ala Gly Thr Ser Val Leu Asn Thr Val
        1955                1960                1965

Ile Asn Asn Ile Ile Phe His Gly Ala Leu Tyr His Thr Tyr Thr
        1970                1975                1980

Asn Phe Glu Arg Asp Asp Ile Ser Met Leu Ala Tyr Gly Asp Asp
        1985                1990                1995

Ile Val Val Ala Ser Lys Phe Glu Leu Asp Leu Val Met Val Lys
        2000                2005                2010

Ala Phe Met Asn Arg Ile Gly Tyr Lys Ile Thr Pro Ala Asp Lys
        2015                2020                2025

Ser Asp Glu Phe Arg Pro Lys Cys Met Asp Asp Ile Cys Phe Leu
        2030                2035                2040
```

| | | | | | | | | | | |
|---|---|---|---|---|---|---|---|---|---|---|
|Lys|Arg|Arg|Phe|Val|Lys|Val|Ala|Gly|Val|Trp|Ala|Pro|Val|Met|
| |2045| | | |2050| | | |2055| |

Lys Arg Arg Phe Val Lys Val Ala Gly Val Trp Ala Pro Val Met
    2045              2050              2055

Glu Thr Glu Asn Leu Glu Ala Met Leu Ser Trp Tyr Lys Pro Gly
    2060              2065              2070

Thr Leu Asn Glu Lys Leu Gln Ser Val Ser Arg Leu Ala His Phe
    2075              2080              2085

Ser Gly Arg Asp Val Tyr Asp His Leu Phe Lys Pro Phe Ile Arg
    2090              2095              2100

Asp Gly Phe Asp Val Thr Pro Trp Lys Gln Leu His Leu Glu Trp
    2105              2110              2115

Leu Asn Lys Leu Ser Ala
    2120

```
<210> SEQ ID NO 3
<211> LENGTH: 5861
<212> TYPE: DNA
<213> ORGANISM: Cosavirus

<400> SEQUENCE: 3
aatagcaagg agagtgtgtc cagcaatggc aatcagggta ctattgtcaa taatttttat      60
gctaactcat attatgcttc tattgacgct tctgcctcct cagtcggggg cgatactcct     120
gctgaaaatg gtactgtatc tggcattctc ggaagttttg cttctgcttt cacttccgct     180
gcactactag caaaaccaaa agttgaaaat gacacaaaca tggaagacag agtaataaca     240
ctcaaagcag gaaatacaat tgtcaattct caggcttctg aaggtgttct acatggttat     300
ggcattggaa caaacacaca gagaccctct tcatgtggtg atgacccctc aattgcgacg     360
cactgtattg agcgagggtt taccatcaat ttggctgact gggacaaatc caaggaatca     420
tggcaggcac ttgtttacag actctcagat catttgaaag atgatacagt aggtaacatg     480
ttttccaaga ctttgggaac ccacgcttat actaagtgtg ttacagagt cagtctgcaa     540
attaacacat ctcccttca ctccggtctt attggcttat tcttagttcc agagtgttgt     600
atacctgcta gcttgaatat ggattggatt gatttaaaaa ctcagctacc attactgaca     660
agcagctcgc actaccaggg tttaggtctt tcaacaggtc aagggacaat atctgaaaag     720
ggttctattg atgctgctgg tacaattcct caacaactct tcatatatcc acaccagttg     780
attaacccaa aagcacacaa catagcctca gttgaagttc cttatgtaaa ttgtgctccc     840
acctcagatc caatgataca caacatttgg actgctcttg tagtagttat agctcctctc     900
cagtctaatg catcagcttc tcctactgta gcaatgtcta tgactgtaac tccagtgggt     960
gctgtcttta cggactaag acaccctgct cctaatgtac aaacagcaat acctgttaga    1020
atgacacaaa attctggaca gttttccaca actcttcctg ctagaatgga accatgttat    1080
ggcttaactc ccaaccccac cagagacttt cttccccag tagtcgaaga tttactcagc    1140
atagcaaaag tcccttgttt cctgctggca gatgaagata ccacaaaaca gaaaccctat    1200
tttcttattt caaatgcctc ttcaactcaa acagctgttt ttgaaatgaa tgtcatactc    1260
agtgaatatg cgctccagcg caccttttgtg tcaatgtttg aaagtttttt ctgtaactac    1320
agaggcagta tacagattac cgcctgggca gctgtgacag caatgactag ggaaagttg    1380
ctcttctctt acacaccacc aggtgcaggt aaaccacaaa acataaaaca agcaatgatg    1440
ggtacctaca ccatatggga cttgggtctc aatccactc ttaatttcac cattccttac    1500
atctccagtg tagactttag aattaactct agggctgttg cttctgcctt gaatgctgac    1560
```

```
gggtggctta ctatttggat cctcaatcct ataacttatc ctccacagac tcctccacaa    1620
caagccattt tgttaatggc ttctgcaggt tctgattttt catacagatt gcctataaac    1680
cctcccttcg tccaaggaga tatccatgac aacgcagaaa agggactcac tgaaacaact    1740
gatgcaaccc agtctgtgg tgccgctgtt gggtacacaa caaatcattc aaattgtgaa     1800
ttcttctttg atagatatag atttgtaggt tttatagatg ctgttagaaa caacaaaaga    1860
agtgtgattt ctgtttttga ctcaaacaac aaagtcaaga gaattgctga attgtttaaa    1920
gaaccaaaca aaccaggtaa ttatttcact ttatcaccaa acccagcaat tcgacaact     1980 cctatgtcag cttacattgt catagatcat ccttcttcaa cttcaagccc ttacactcag    2040
tatgctattg caacaactgg tgatcccttc tttctaagat cttgcccctt cacatacttt    2100
cactgtgatt tagaggtaac aataaaacca gaaaatgcag tttcaggtgt ttggcgcgcc    2160
acttggtatc caccaggctc ggacttaaaa gaagatgagg ttgttccaag ttttaggact    2220
acaggtgaat ctggtaatat gtctcttact gtaaacaata gagagaggtc aacaatatat    2280
aatacttatc ccaccttta ctctagggat ggtcagtgtg tttcttttaa catacctac      2340 acctcacctc ttagtgttat tcctaccaga tttgatggtt atcctgacta ttcaaggact    2400
gttggtgcat acggtgtggc ccctgcaaac cactttggca ctttgactgt agctgctaat    2460
gatgaaggtt acaaattctt tgtttatgtt agatacaaaa acttcaaagg gtatgtcccc    2520
aagaccctac ctccacaacc actgttttta aagaattcca gaagtttgac taatgaaaca    2580
ataatagcaa gaccttacat tagagagagc agcaatgtct ctagattaaa gctcctactt    2640
tcaggtgaca ttgaaacaaa tcctggacct aatcactcta aatttcaggt acaaggatcc    2700
atgtcagatt ttttaaatgt ggccagaaaa ccagaaacat tggataatgt gaccaggctt    2760
ttaactactt taaataatct aatgaataaa tggacaatg ttaaacatat gtgtactgat      2820
tcttattttc taagagatat tctgtgcttg cttgttaagc ttacatcact ctcataccttt    2880 gttgcaggac agggaccttc tgcttactta gctgcttccg ctgtgctcat gcggacggc     2940 atttctttcc ttgactggta tgaaaaaata aaaagatttc ttggttctcg ttttcgagtt    3000
ccacctccta tcttcactct tgcccaagga ccagatctta gagacttagt tactttctt     3060 aatgctgcta ggggcgcaca gtggatggtt gattccatcc gtggactgat ttcatggatc    3120
aaacaatggc ttgaactgga agaagcaaac gaagctgtcc aattcgaaag actgttgata    3180
gaaagtccca agcactgcaa ggcaataaat gactacaatg ttggaaaaag ctttattaga    3240
ccagagaact cctttgactt catggaaaaa cttgtggatt ctgccacaaa acttggaaaa    3300
gtgaacattg caggttattt cagatctttt acctcggttg acacagatac agcaagaatg    3360
gaaccagttg tcttggtact acgtggcaaa ccaggagctg aaaatcagc agcagctact    3420 atcatcacag ctgctgtctc caaaattttg acaggaactc aatctgttta ttctctctcc    3480
cctgacactg aacacatgga cggatatcac ggccagtttg caatgatcat ggatgattta    3540
ggacaaaacc cagatggaga agactttaga actttctgtc aaatgatttc agttgcacaa    3600
tacagacctt caatggctga cttaaaggac aaaggcattt tgtttaaatc ccagtttatt    3660
gttgcaacaa caaatttacc agagtttaga cctttgactt tttctgatcg cggagctgtt    3720
gaccgcagaa taacatttga tattggtgtg accccaggta ctgctgtaac aaaaaatgga    3780
aagcttgacc ttgccatggc tttgaaacca gacggtgagg gagagttccc ttactcgtgt    3840
gattgccaga tattacacac tactggactt gctctacaga acctcagaac aggcaaaaca    3900
atgaacatca aggaattagt tgatttaatt gtaaagaaaa tcaagagcaa aaggactaca    3960
```

```
agcggaatgc ttgaaggact ggtggtgcag tcgcccaaaa ttgtaggcta caccaaggac   4020
gacgagggcg tcgtcattgt tgactgtctc gaggattggc acagaattcg agacaagaaa   4080
agaaagcaac aggctcttga gatggttgca gaggagatgc aaattcaaca tgacaaacat   4140
tctcagacca tttccttgat aaaacagttt ctctcagggc tcggtgtggt ggctgctgtt   4200
ggagccgcct ttgccgcagg caaggtactg aaaaacatga tgacctcaga ccgggcacag   4260
gatgaaccag actctgaatc ccaggagaag actgaagaaa acaaaaagc tgaaggacca   4320 tacaatggac caacaaagaa ggaactgaaa actctaaagc tgaaagccca gggcccttg   4380 ttggatcttg aaaagaaggt cctcgctaac gtgcagcctt tcattttgcg cgttgctggt   4440
agagactaca ttcaatcttg tctctttgtt ggaaaaaggg ttttccttgt gaacaaacat   4500
gcaattgact cagttgaaca aaaatttcaa gttgcaggaa aaacatatga cttggatgat   4560
gttgatgtgg caattcttga cacggaatat ggacttacgg atgttgcagc tgtcaagctc   4620
aacacaggcc cagaatggaa aaacctttca aaactctttg tttcactgga cacgactcta   4680
cacccaggaa ccaggataac gattttgtct aacgaccaac ttaacatggt gagagagggt   4740
agttttctca gaaatgagga tgacataccc accaatattg cccaatacc ttttgtcatg   4800 ctttataagg cttcctctta ctttggtatg tgtggttctg ctgttgtgac cagaattggt   4860
gattgtcccg gaattcttgg tctccattgt gctggcggtg ggggtgtgtg tgtggcttcc   4920
agagttacaa aaagaatggt agaaactgtc ctaaaatact tttatccacc tcaggtacag   4980
ggacaaatta taaacacaga aaatggaccc cgtgtgcatg ttcccagaca gtctaagctc   5040
aaaagaacaa atgctgttta tcctgctact ccaaaatatg gacctgctgt gctttctaag   5100
aatgatccca ggcttgaccc agatgtggac tttgacaaag taattttctc aaaacatgtt   5160
gccaacgtgg ttattgatga ggacactagt ttctggaatg ccctaaaaat gtctgcccaa   5220
atatacgcag aaaaattcaa aggtgttgac ttctcccctc tcactgtaga ggaagcaatt   5280
cttggaattc caggacttga ccggatggac cccaatactg cttcaggatt accctatact   5340
aaaactagaa gacagatgat tgattttcag gaagggaaaa tacttgaccc agaactccaa   5400
tccagacttg acacttggct ttcaaataaa caaccagaaa tgctctacca acatttta   5460 aaagatgaaa tcagaccaat tgaaaaagta aaagctggta aaaccagaat tattgatgtg   5520
accccccttg accatgtttt ggcattcaga attgttctag cagattcat ggctcatttt   5580 cacaataatt atggttttaa tcttggttct gctgttggat gcgatcccga cgttgcttgg   5640
gccaactttg gctttgctct tcttctaag aagtaccagt atgactttga ttactcaaac   5700
tttgatgctt ctcattcaga gtccatcttt gaacttctta acagtttgt tttcaccaaa   5760 gacaatggtt ttgatcacag atgctctctc atgattgatt ctctggttac ctcgacccac   5820
tgctatgagc aacaaagaat gaccattcgc ggcggcctcc c                        5861
```

<210> SEQ ID NO 4
<211> LENGTH: 1953
<212> TYPE: PRT
<213> ORGANISM: Cosavirus

<400> SEQUENCE: 4

Asn Ser Lys Glu Ser Val Ser Ser Asn Gly Asn Gln Gly Thr Ile Val
1               5                   10                  15

Asn Asn Phe Tyr Ala Asn Ser Tyr Tyr Ala Ser Ile Asp Ala Ser Ala
            20                  25                  30

```
Ser Ser Val Gly Gly Asp Thr Pro Ala Glu Asn Gly Thr Val Ser Gly
         35                  40                  45

Ile Leu Gly Ser Phe Ala Ser Ala Phe Thr Ser Ala Ala Leu Leu Ala
 50                  55                  60

Lys Pro Lys Val Glu Asn Asp Thr Asn Met Glu Asp Arg Val Ile Thr
 65                  70                  75                  80

Leu Lys Ala Gly Asn Thr Ile Val Asn Ser Gln Ala Ser Glu Gly Val
                 85                  90                  95

Leu His Gly Tyr Gly Ile Gly Thr Asn Thr Gln Arg Pro Ser Ser Cys
                100                 105                 110

Gly Asp Asp Pro Ser Ile Ala Thr His Cys Ile Glu Arg Gly Phe Thr
            115                 120                 125

Ile Asn Leu Ala Asp Trp Asp Lys Ser Lys Glu Ser Trp Gln Ala Leu
        130                 135                 140

Val Tyr Arg Leu Ser Asp His Leu Lys Asp Asp Thr Val Gly Asn Met
145                 150                 155                 160

Phe Ser Lys Thr Leu Gly Thr His Ala Tyr Thr Lys Cys Gly Tyr Arg
                165                 170                 175

Val Ser Leu Gln Ile Asn Thr Ser Pro Phe His Ser Gly Leu Ile Gly
            180                 185                 190

Leu Phe Leu Val Pro Glu Cys Cys Ile Pro Ala Ser Leu Asn Met Asp
        195                 200                 205

Trp Ile Asp Leu Lys Thr Gln Leu Pro Leu Leu Thr Ser Ser Ser His
    210                 215                 220

Tyr Gln Gly Leu Gly Leu Ser Thr Gly Gln Gly Thr Ile Ser Glu Lys
225                 230                 235                 240

Gly Ser Ile Asp Ala Ala Gly Thr Ile Pro Gln Gln Leu Phe Ile Tyr
                245                 250                 255

Pro His Gln Leu Ile Asn Pro Lys Asp Thr Asn Ile Ala Ser Val Glu
            260                 265                 270

Val Pro Tyr Val Asn Cys Ala Pro Thr Ser Asp Pro Met Ile His Asn
        275                 280                 285

Ile Trp Thr Ala Leu Val Val Val Ile Ala Pro Leu Gln Ser Asn Ala
    290                 295                 300

Ser Ala Ser Pro Thr Val Ala Met Ser Met Thr Val Thr Pro Val Gly
305                 310                 315                 320

Ala Val Phe Asn Gly Leu Arg His Pro Ala Pro Asn Val Gln Thr Ala
                325                 330                 335

Ile Pro Val Arg Met Thr Gln Asn Ser Gly Gln Phe Ser Thr Thr Leu
            340                 345                 350

Pro Ala Arg Met Glu Pro Cys Tyr Gly Leu Thr Pro Asn Pro Thr Arg
        355                 360                 365

Asp Phe Leu Pro Pro Val Val Glu Asp Leu Leu Ser Ile Ala Lys Val
    370                 375                 380

Pro Cys Phe Leu Leu Ala Asp Glu Asp Thr Thr Lys Gln Lys Pro Tyr
385                 390                 395                 400

Phe Leu Ile Ser Asn Ala Ser Ser Thr Gln Thr Ala Val Phe Glu Met
                405                 410                 415

Asn Val Ile Leu Ser Glu Tyr Ala Leu Gln Arg Thr Phe Val Ser Met
            420                 425                 430

Phe Gly Lys Phe Phe Cys Asn Tyr Arg Gly Ser Ile Gln Ile Thr Ala
        435                 440                 445

Trp Ala Ala Val Thr Ala Met Thr Arg Gly Lys Leu Leu Phe Ser Tyr
```

-continued

```
            450                 455                 460
Thr Pro Pro Gly Ala Gly Lys Pro Gln Asn Ile Lys Gln Ala Met Met
465                 470                 475                 480

Gly Thr Tyr Thr Ile Trp Asp Leu Gly Leu Gln Ser Thr Leu Asn Phe
                485                 490                 495

Thr Ile Pro Tyr Ile Ser Ser Val Asp Phe Arg Ile Asn Ser Arg Ala
            500                 505                 510

Val Ala Ser Ala Leu Asn Ala Asp Gly Trp Leu Thr Ile Trp Ile Leu
        515                 520                 525

Asn Pro Ile Thr Tyr Pro Pro Gln Thr Pro Gln Gln Ala Ile Leu
        530                 535                 540

Leu Met Ala Ser Ala Gly Ser Asp Phe Ser Tyr Arg Leu Pro Ile Asn
545                 550                 555                 560

Pro Pro Phe Val Gln Gly Asp Ile His Asp Asn Ala Glu Lys Gly Leu
                565                 570                 575

Thr Glu Thr Thr Asp Ala Thr Gln Phe Cys Gly Ala Ala Val Gly Tyr
                580                 585                 590

Thr Thr Asn His Ser Asn Cys Glu Phe Phe Asp Arg Tyr Arg Phe
            595                 600                 605

Val Gly Phe Ile Asp Ala Val Arg Asn Asn Lys Arg Ser Val Ile Ser
        610                 615                 620

Val Phe Asp Ser Asn Asn Lys Val Lys Arg Ile Ala Glu Leu Phe Lys
625                 630                 635                 640

Glu Pro Asn Lys Pro Gly Asn Tyr Phe Thr Leu Ser Pro Asn Pro Ala
                645                 650                 655

Ile Ser Thr Thr Pro Met Ser Ala Tyr Ile Val Ile Asp His Pro Ser
                660                 665                 670

Ser Thr Ser Ser Pro Tyr Thr Gln Tyr Ala Ile Ala Thr Thr Gly Asp
        675                 680                 685

Pro Phe Phe Leu Arg Ser Cys Pro Phe Thr Tyr Phe His Cys Asp Leu
        690                 695                 700

Glu Val Thr Ile Lys Pro Glu Asn Ala Val Ser Gly Val Trp Arg Ala
705                 710                 715                 720

Thr Trp Tyr Pro Pro Gly Ser Asp Leu Lys Glu Asp Glu Val Val Pro
                725                 730                 735

Ser Phe Arg Thr Thr Gly Glu Ser Gly Asn Met Ser Leu Thr Val Asn
                740                 745                 750

Asn Arg Glu Arg Ser Thr Ile Tyr Asn Thr Tyr Pro Thr Phe Tyr Ser
            755                 760                 765

Arg Asp Gly Gln Cys Val Ser Phe Asn Ile Pro Tyr Thr Ser Pro Leu
        770                 775                 780

Ser Val Ile Pro Thr Arg Phe Asp Gly Tyr Pro Asp Tyr Ser Arg Thr
785                 790                 795                 800

Val Gly Ala Tyr Gly Val Ala Pro Ala Asn His Phe Gly Thr Leu Thr
                805                 810                 815

Val Ala Ala Asn Asp Glu Gly Tyr Lys Phe Phe Val Tyr Val Arg Tyr
                820                 825                 830

Lys Asn Phe Lys Gly Tyr Val Pro Lys Thr Leu Pro Pro Gln Pro Leu
            835                 840                 845

Phe Leu Lys Asn Ser Arg Ser Leu Thr Asn Glu Thr Ile Ile Ala Arg
        850                 855                 860

Pro Tyr Ile Arg Glu Ser Ser Asn Val Ser Arg Leu Lys Leu Leu Leu
865                 870                 875                 880
```

Ser Gly Asp Ile Glu Thr Asn Pro Gly Pro Asn His Ser Lys Phe Gln
            885                 890                 895

Val Gln Gly Ser Met Ser Asp Phe Leu Asn Val Ala Arg Lys Pro Glu
            900                 905                 910

Thr Leu Asp Asn Val Thr Arg Leu Leu Thr Thr Leu Asn Asn Leu Met
            915                 920                 925

Asn Lys Trp Asn Asn Val Lys His Met Cys Thr Asp Ser Tyr Phe Leu
            930                 935                 940

Arg Asp Ile Leu Cys Leu Leu Val Lys Leu Thr Ser Leu Ser Tyr Leu
945                 950                 955                 960

Val Ala Gly Gln Gly Pro Ser Ala Tyr Leu Ala Ala Ser Ala Val Leu
            965                 970                 975

Ile Ala Asp Gly Ile Ser Phe Leu Asp Trp Tyr Glu Lys Ile Lys Arg
            980                 985                 990

Phe Leu Gly Ser Arg Phe Arg Val Pro Pro Pro Ile Phe Thr Leu Ala
            995                 1000                1005

Gln Gly Pro Asp Leu Arg Asp Leu Val Thr Phe Phe Asn Ala Ala
            1010                1015                1020

Arg Gly Ala Gln Trp Met Val Asp Ser Ile Arg Gly Leu Ile Ser
            1025                1030                1035

Trp Ile Lys Gln Trp Leu Glu Leu Glu Glu Ala Asn Glu Ala Val
            1040                1045                1050

Gln Phe Glu Arg Leu Leu Ile Glu Ser Pro Lys His Cys Lys Ala
            1055                1060                1065

Ile Asn Asp Tyr Asn Val Gly Lys Ser Phe Ile Arg Pro Glu Asn
            1070                1075                1080

Ser Phe Asp Phe Met Glu Lys Leu Val Asp Ser Ala Thr Lys Leu
            1085                1090                1095

Gly Lys Val Asn Ile Ala Gly Tyr Phe Arg Ser Phe Thr Ser Val
            1100                1105                1110

Asp Thr Asp Thr Ala Arg Met Glu Pro Val Val Leu Val Leu Arg
            1115                1120                1125

Gly Lys Pro Gly Ala Gly Lys Ser Ala Ala Ala Thr Ile Ile Thr
            1130                1135                1140

Ala Ala Val Ser Lys Ile Leu Thr Gly Thr Gln Ser Val Tyr Ser
            1145                1150                1155

Leu Ser Pro Asp Thr Glu His Met Asp Gly Tyr His Gly Gln Phe
            1160                1165                1170

Ala Met Ile Met Asp Asp Leu Gly Gln Asn Pro Asp Gly Glu Asp
            1175                1180                1185

Phe Arg Thr Phe Cys Gln Met Ile Ser Val Ala Gln Tyr Arg Pro
            1190                1195                1200

Ser Met Ala Asp Leu Lys Asp Lys Gly Ile Leu Phe Lys Ser Gln
            1205                1210                1215

Phe Ile Val Ala Thr Thr Asn Leu Pro Glu Phe Arg Pro Leu Thr
            1220                1225                1230

Val Ser Asp Arg Gly Ala Val Asp Arg Arg Ile Thr Phe Asp Ile
            1235                1240                1245

Gly Val Thr Pro Gly Thr Ala Val Thr Lys Asn Gly Lys Leu Asp
            1250                1255                1260

Leu Ala Met Ala Leu Lys Pro Asp Gly Glu Gly Glu Phe Pro Tyr
            1265                1270                1275

-continued

```
Ser Cys Asp Cys Gln Ile Leu His Thr Thr Gly Leu Ala Leu Gln
    1280                1285                1290

Asn Leu Arg Thr Gly Lys Thr Met Asn Ile Lys Glu Leu Val Asp
    1295                1300                1305

Leu Ile Val Lys Lys Ile Lys Ser Lys Arg Thr Thr Ser Gly Met
    1310                1315                1320

Leu Glu Gly Leu Val Val Gln Ser Pro Lys Ile Val Gly Tyr Thr
    1325                1330                1335

Lys Asp Asp Glu Gly Val Val Ile Val Asp Cys Leu Glu Asp Trp
    1340                1345                1350

His Arg Ile Arg Asp Lys Lys Arg Lys Gln Gln Ala Leu Glu Met
    1355                1360                1365

Val Ala Glu Glu Met Gln Ile Gln His Asp Lys His Ser Gln Thr
    1370                1375                1380

Ile Ser Leu Ile Lys Gln Phe Leu Ser Gly Leu Gly Val Val Ala
    1385                1390                1395

Ala Val Gly Ala Ala Phe Ala Ala Gly Lys Val Leu Lys Asn Met
    1400                1405                1410

Met Thr Ser Asp Arg Ala Gln Asp Glu Pro Asp Ser Glu Ser Gln
    1415                1420                1425

Glu Lys Thr Glu Lys Gln Lys Ala Glu Gly Pro Tyr Asn Gly
    1430                1435                1440

Pro Thr Lys Lys Glu Leu Lys Thr Leu Lys Leu Lys Ala Gln Gly
    1445                1450                1455

Pro Leu Leu Asp Leu Glu Lys Lys Val Leu Ala Asn Val Gln Pro
    1460                1465                1470

Phe Ile Leu Arg Val Ala Gly Arg Asp Tyr Ile Gln Ser Cys Leu
    1475                1480                1485

Phe Val Gly Lys Arg Val Phe Leu Val Asn Lys His Ala Ile Asp
    1490                1495                1500

Ser Val Glu Gln Lys Phe Gln Val Ala Gly Lys Thr Tyr Asp Leu
    1505                1510                1515

Asp Asp Val Asp Val Ala Ile Leu Asp Thr Glu Tyr Gly Leu Thr
    1520                1525                1530

Asp Val Ala Ala Val Lys Leu Asn Thr Gly Pro Glu Trp Lys Asn
    1535                1540                1545

Leu Ser Lys Leu Phe Val Ser Leu Asp Thr Thr Leu His Pro Gly
    1550                1555                1560

Thr Arg Ile Thr Ile Leu Ser Asn Asp Gln Leu Asn Met Val Arg
    1565                1570                1575

Glu Gly Ser Phe Leu Arg Asn Glu Asp Asp Ile Pro Thr Asn Ile
    1580                1585                1590

Gly Pro Ile Pro Phe Val Met Leu Tyr Lys Ala Ser Ser Tyr Phe
    1595                1600                1605

Gly Met Cys Gly Ser Ala Val Val Thr Arg Ile Gly Asp Cys Pro
    1610                1615                1620

Gly Ile Leu Gly Leu His Cys Ala Gly Gly Gly Val Cys Val
    1625                1630                1635

Ala Ser Arg Val Thr Lys Arg Met Val Glu Thr Val Leu Lys Tyr
    1640                1645                1650

Phe Tyr Pro Pro Gln Val Gln Gly Gln Ile Ile Asn Thr Glu Asn
    1655                1660                1665

Gly Pro Arg Val His Val Pro Arg Gln Ser Lys Leu Lys Arg Thr
```

```
              1670             1675             1680
Asn Ala Val Tyr Pro Ala Thr Pro Lys Tyr Gly Pro Ala Val Leu
        1685            1690            1695

Ser Lys Asn Asp Pro Arg Leu Asp Pro Asp Val Asp Phe Asp Lys
    1700            1705            1710

Val Ile Phe Ser Lys His Val Ala Asn Val Val Ile Asp Glu Asp
        1715            1720            1725

Thr Ser Phe Trp Asn Ala Leu Lys Met Ser Ala Gln Ile Tyr Ala
    1730            1735            1740

Glu Lys Phe Lys Gly Val Asp Phe Ser Pro Leu Thr Val Glu Glu
    1745            1750            1755

Ala Ile Leu Gly Ile Pro Gly Leu Asp Arg Met Asp Pro Asn Thr
    1760            1765            1770

Ala Ser Gly Leu Pro Tyr Thr Lys Thr Arg Arg Gln Met Ile Asp
    1775            1780            1785

Phe Gln Glu Gly Lys Ile Leu Asp Pro Glu Leu Gln Ser Arg Leu
    1790            1795            1800

Asp Thr Trp Leu Ser Asn Lys Gln Pro Glu Met Leu Tyr Gln Thr
    1805            1810            1815

Phe Leu Lys Asp Glu Ile Arg Pro Ile Glu Lys Val Lys Ala Gly
    1820            1825            1830

Lys Thr Arg Ile Ile Asp Val Thr Pro Leu Asp His Val Leu Ala
    1835            1840            1845

Phe Arg Ile Val Leu Gly Arg Phe Met Ala His Phe His Asn Asn
    1850            1855            1860

Tyr Gly Phe Asn Leu Gly Ser Ala Val Gly Cys Asp Pro Asp Val
    1865            1870            1875

Ala Trp Ala Asn Phe Gly Phe Ala Leu Ser Ser Lys Lys Tyr Gln
    1880            1885            1890

Tyr Asp Phe Asp Tyr Ser Asn Phe Asp Ala Ser His Ser Glu Ser
    1895            1900            1905

Ile Phe Glu Leu Leu Lys Gln Phe Val Phe Thr Lys Asp Asn Gly
    1910            1915            1920

Phe Asp His Arg Cys Ser Leu Met Ile Asp Ser Leu Val Thr Ser
    1925            1930            1935

Thr His Cys Tyr Glu Gln Gln Arg Met Thr Ile Arg Gly Gly Leu
    1940            1945            1950

<210> SEQ ID NO 5
<211> LENGTH: 1595
<212> TYPE: DNA
<213> ORGANISM: Cosavirus

<400> SEQUENCE: 5
cgtgtatcta gggatgagca acccaccaac taccgggact tacagtttaa gctgtagaca      60
catgtggtaa cccagcccct tccctgacgg gagaggggggc ttttgctcac ctagcacagg    120
atctgatcag gagactccct cacagtgctt tacactgttg tgggagttta aaaattgccc     180
aaggcctggc acacaaccta ggggactag gttttccttt tattttgaag ttgtcaatat      240
gggtgcaaac aacagcaaag agagtgtttc tagcaatggc aatcagggta ctattgttaa     300
caatttttat gctaattctt actatgcttc tattgacgct tctgcctcct cggtcggggg     360
cgacactcct gctgaaaacg gtactgtcac tggtcttctg ggaaatattg cttctgcttt     420
cacttccgct gcactcttgg ccaaaccaac tgtagaaaat gaaaccggta tggaagatag     480
```

```
ggtaatttct ctcaaggcag gcaatacttt ggttaactca caggcttcag aagggctgtt      540
atatggatat ggcaaggaaa gtgataaaaa cccccaaca tcatgcggtg atgatccatc       600
tgaaacacaa cactgcatac agagaggttt tactattcct ttgactgatt ggaccagaac      660
ccaagatcca tggcaagctc ttgtatacaa actttcagat cagtttaaaa atgaaagcaa      720
gggaaacatg ttttccaagg gaatgaaaac acatgctttt accaaaactg ctacagggt       780 atctcttcag gttaacactt tcctttcca ctctggcctt ttaggcctat ttcttgtccc       840
agagtgtagt ataccctgcat ctacgtcact ggattggatt gacttgaaga cagatgctcc     900
tcttttaaag agcacaaact attacarggg tcttggacta cagcaacaat cttcagccgc      960
tggaaacaag tatgcagaca actgtatcat agactcctca gcaataactc ctcagcagct      1020
ctttatatat cctcaccaac ttataaaccc caaagaaact aacattgcct cagttgcagt      1080
tccttatgtg aactgtgctc caacatctga tcctcagatc cacaacatct ggactgcctt      1140
ggtagtgata atttcacccc tccagtttgc taatggtgct tctcctaatg taaccatgtc      1200
acttacagta accctctta acactgtttt caatggctta cgccatgctc tgcctgctac       1260
gcaaggccct ataccagtta ggtgtatgca gaattcttac cagttctcaa ccacacttcc      1320
cgcaaccgca gaaccgtgtt acggttgcac agtgaaccg cccagagact acttgcctcc      1380
tgctatcgag gatttgcttt cttttggctaa agttccttct tttctgcttt gtagcgaaga     1440
caccgctaaa caggtgccat atgtgaaggt tacaaacact caaacacagc acaactctat      1500
cttttcaatg aatgtagttt tgtcagatta tgcacttcag aggaccatgg tttcacagct      1560
gggaacattt ttctgtaatt atagaggaag cattc                                 1595
```

<210> SEQ ID NO 6
<211> LENGTH: 2273
<212> TYPE: DNA
<213> ORGANISM: Cosavirus

<400> SEQUENCE: 6

```
tttcagtcac acagtacaga cctgctatgg cttcccttga ggacaaagga atacttttct      60
cttctagatt aataattgca caacaaatc ttgtagattt caaccccgtc accatttctg       120
accctcgtgc tttagacaga agaataacat ttgatttgtg tgttacccct ggttctgccg      180
caacaacatc taagggcaaa cttgacctta agaaggcatt acaacctgat ggacctggct      240
ttggacctta cacaacagac tgctctctcc tgcatacgac tgggctaaat ctcaagaatc      300
tcagaaacaa tagggtttac agcatagttg atttggttga agaggtagtg gccaatatga      360
acaagaaaaa agctgtgaat gtcatgctag aaggacttgt ggcacagact ggaaaagtag      420
ttggttatac caaagatgac gatggagttg tcatcgtaga ttcaatggat gaatggcaca      480
aaatactaga caagaaaagg aaacaggaag tgttagaagt gattgcccaa gaaatacagg      540
taagacatga tgaacacaag gagtttactc agattgtcac caaattttta acagccctag      600
gcgtaattgt tgctgtaggt gctgctttaa ttggatacaa gtatttgaca tccggccctg      660
acaaagaaaa ggaatcaact gaggagccag aaaacaaga agagaaagaa gaacaaaaga      720
aagctgaggg accttacgag ggaccctcca agaaagagct aaaacactc aaactgcgca      780 ttcagtgccc agttaaagac tgtgagaaaa actttttgaa tgcaatacac ccctttgtaa      840
ttcactatga taaagaaaag tacacacagt catgtatagc tctaggtaaa aggttaataa      900
tggtaaacaa acatgcaatg gaaacactgg acagatatgt taccatagct ggaaagatgt      960
```

-continued

```
atgagattga tgatttggac tgggttaacc ttgaaacctc ccatggagaa actgacgtct    1020
ccatagtgaa actgccccc ggaccggaat tcaagaatat agttagaaat ttttgttcac    1080
aagacataac tctcatgcct ggcactagaa tgatgatctt gtctaatgat gactttcta    1140 tggttaggga aggctctttt ctgagatttg aggattctgt accaacaaat atcggaccta    1200
ttccatttac cttactatac aagtcctcct cttatttcgg aatgtgtggc tcggctgttg    1260
tgtgcagaac atctggcgaa actggcatag tgggaatgca ctgtgcaggt ggaggcggag    1320
tttctgtcgc atgtcgcgtc actagaaaaa tggtagaagc tgctgtcatg tattttttaa    1380
tccttctaat agttcaaggc atgattgtgt caactgaaac atgtgaccca attcacgttc    1440
ctagaaaaac aaagtacaag agaactaatg ctgattatcc ttctactaag aattatgccc    1500
cagctgtttt atctagaaat gaccccagac ttgaccctga tgttgatttt gatactgttt    1560
tgttctccaa acacactgaa aatgtcatca tccctcctga cacactggct tacgatagtc    1620
tcctgaaggc tacacaggtt tacgcttgta agtttaatgg caattttgaa cctttaactg    1680
tggaagaggc aattttggga atacctggct tggacaggat ggatcctaat acatcatctg    1740
gcctgcctta tactaaaaca agaagacagc tcatagattt tgtcaatgga aaaattttgg    1800
acacacaatt acaggaaaga ctcgacatgt ggctgagtgg aaaacaacct gaaacttatt    1860
accaaacttt cctaaaagat gaaattaggc atattgacaa agtgagaaga gggaaaactc    1920
gcattatcga tgtgactccc ttagatcatg ttttggcttt cagaattcta tttggcagat    1980
tcatggcaca ttaccaccta aaccctggct tgatttagg cagcgctatt ggatgtgacc    2040
cagaagttgc ttggaatcag tttggttatc atcttactaa gtataaaaat ctctatgact    2100
ttgattactc aaactttgat tcttctcatt ctaagtctat ctttgagatt ctgaaagatc    2160
atttcttcac cacaaccaac ggttttgatt ctcgttgcgc cttgctacta gattctctgg    2220
ctgtctccaa acacaaatat gacaacaaag tgatgactat agtgggcggc ctc          2273
```

<210> SEQ ID NO 7
<211> LENGTH: 452
<212> TYPE: PRT
<213> ORGANISM: Cosavirus
<220> FEATURE:
<221> NAME/KEY: misc_feature
<222> LOCATION: (230)..(230)
<223> OTHER INFORMATION: Xaa can be any naturally occurring amino acid

<400> SEQUENCE: 7

Met Gly Ala Asn Asn Ser Lys Glu Ser Val Ser Ser Asn Gly Asn Gln
1               5                   10                  15

Gly Thr Ile Val Asn Asn Phe Tyr Ala Asn Ser Tyr Tyr Ala Ser Ile
            20                  25                  30

Asp Ala Ser Ala Ser Ser Val Gly Gly Asp Thr Pro Ala Glu Asn Gly
        35                  40                  45

Thr Val Thr Gly Leu Leu Gly Asn Ile Ala Ser Ala Phe Thr Ser Ala
    50                  55                  60

Ala Leu Leu Ala Lys Pro Thr Val Glu Asn Glu Thr Gly Met Glu Asp
65                  70                  75                  80

Arg Val Ile Ser Leu Lys Ala Gly Asn Thr Leu Val Asn Ser Gln Ala
                85                  90                  95

Ser Glu Gly Leu Leu Tyr Gly Tyr Gly Lys Glu Ser Asp Lys Asn Pro
            100                 105                 110

Pro Thr Ser Cys Gly Asp Asp Pro Ser Glu Thr Gln His Cys Ile Gln
        115                 120                 125

Arg Gly Phe Thr Ile Pro Leu Thr Asp Trp Thr Arg Thr Gln Asp Pro
            130                 135                 140

Trp Gln Ala Leu Val Tyr Lys Leu Ser Asp Gln Phe Lys Asn Glu Ser
145                 150                 155                 160

Lys Gly Asn Met Phe Ser Lys Gly Met Lys Thr His Ala Phe Thr Lys
                165                 170                 175

Thr Gly Tyr Arg Val Ser Leu Gln Val Asn Thr Ser Pro Phe His Ser
            180                 185                 190

Gly Leu Leu Gly Leu Phe Leu Val Pro Glu Cys Ser Ile Pro Ala Ser
        195                 200                 205

Thr Ser Leu Asp Trp Ile Asp Leu Lys Thr Asp Ala Pro Leu Leu Lys
210                 215                 220

Ser Thr Asn Tyr Tyr Xaa Gly Leu Gly Leu Gln Gln Gln Ser Ser Ala
225                 230                 235                 240

Ala Gly Asn Lys Tyr Ala Asp Asn Cys Ile Ile Asp Ser Ser Ala Ile
                245                 250                 255

Thr Pro Gln Gln Leu Phe Ile Tyr Pro His Gln Leu Ile Asn Pro Lys
            260                 265                 270

Glu Thr Asn Ile Ala Ser Val Ala Val Pro Tyr Val Asn Cys Ala Pro
        275                 280                 285

Thr Ser Asp Pro Gln Ile His Asn Ile Trp Thr Ala Leu Val Val Ile
290                 295                 300

Ile Ser Pro Leu Gln Phe Ala Asn Gly Ala Ser Pro Asn Val Thr Met
305                 310                 315                 320

Ser Leu Thr Val Thr Pro Leu Asn Thr Val Phe Asn Gly Leu Arg His
                325                 330                 335

Ala Leu Pro Ala Thr Gln Gly Pro Ile Pro Val Arg Cys Met Gln Asn
            340                 345                 350

Ser Tyr Gln Phe Ser Thr Thr Leu Pro Ala Thr Ala Glu Pro Cys Tyr
        355                 360                 365

Gly Cys Thr Val Asn Pro Pro Arg Asp Tyr Leu Pro Pro Ala Ile Glu
370                 375                 380

Asp Leu Leu Ser Leu Ala Lys Val Pro Ser Phe Leu Leu Cys Ser Glu
385                 390                 395                 400

Asp Thr Ala Lys Gln Val Pro Tyr Val Lys Val Thr Asn Thr Gln Thr
                405                 410                 415

Gln His Asn Ser Ile Phe Ser Met Asn Val Val Leu Ser Asp Tyr Ala
            420                 425                 430

Leu Gln Arg Thr Met Val Ser Gln Leu Gly Thr Phe Phe Cys Asn Tyr
        435                 440                 445

Arg Gly Ser Ile
    450

<210> SEQ ID NO 8
<211> LENGTH: 757
<212> TYPE: PRT
<213> ORGANISM: Cosavirus

<400> SEQUENCE: 8

Ser Val Thr Gln Tyr Arg Pro Ala Met Ala Ser Leu Glu Asp Lys Gly
1               5                   10                  15

Ile Leu Phe Ser Ser Arg Leu Ile Ile Ala Thr Thr Asn Leu Val Asp
            20                  25                  30

Phe Asn Pro Val Thr Ile Ser Asp Pro Arg Ala Leu Asp Arg Arg Ile

-continued

```
                 35                  40                  45
Thr Phe Asp Leu Cys Val Thr Pro Gly Ser Ala Ala Thr Ser Lys
 50                  55                  60
Gly Lys Leu Asp Leu Lys Lys Ala Leu Gln Pro Asp Gly Pro Phe
 65                  70                  75                  80
Gly Pro Tyr Thr Thr Asp Cys Ser Leu Leu His Thr Thr Gly Leu Asn
                 85                  90                  95
Leu Lys Asn Leu Arg Asn Asn Arg Val Tyr Ser Ile Val Asp Leu Val
                100                 105                 110
Glu Glu Val Val Ala Asn Met Asn Lys Lys Ala Val Asn Val Met
                115                 120                 125
Leu Glu Gly Leu Val Ala Gln Thr Gly Lys Val Val Gly Tyr Thr Lys
                130                 135                 140
Asp Asp Asp Gly Val Val Ile Val Asp Ser Met Asp Glu Trp His Lys
145                 150                 155                 160
Ile Leu Asp Lys Lys Arg Lys Gln Glu Val Leu Glu Val Ile Ala Gln
                165                 170                 175
Glu Ile Gln Val Arg His Asp Glu His Lys Glu Phe Thr Gln Ile Val
                180                 185                 190
Thr Lys Phe Leu Thr Ala Leu Gly Val Ile Val Ala Val Gly Ala Ala
                195                 200                 205
Leu Ile Gly Tyr Lys Tyr Leu Thr Ser Gly Pro Asp Lys Glu Lys Glu
210                 215                 220
Ser Thr Glu Glu Pro Glu Lys Gln Glu Glu Lys Glu Gln Lys Lys
225                 230                 235                 240
Ala Glu Gly Pro Tyr Glu Gly Pro Ser Lys Lys Glu Leu Lys Thr Leu
                245                 250                 255
Lys Leu Arg Ile Gln Cys Pro Val Lys Asp Cys Glu Lys Lys Leu Leu
                260                 265                 270
Asn Ala Ile His Pro Phe Val Ile His Tyr Asp Lys Arg Lys Tyr Thr
                275                 280                 285
Gln Ser Cys Ile Ala Leu Gly Lys Arg Leu Ile Met Val Asn Lys His
                290                 295                 300
Ala Met Glu Thr Leu Asp Arg Tyr Val Thr Ile Ala Gly Lys Met Tyr
305                 310                 315                 320
Glu Ile Asp Asp Leu Asp Trp Val Asn Leu Glu Thr Ser His Gly Glu
                325                 330                 335
Thr Asp Val Ser Ile Val Lys Leu Pro Pro Gly Pro Glu Phe Lys Asn
                340                 345                 350
Ile Val Arg Asn Phe Cys Ser Gln Asp Ile Thr Leu Met Pro Gly Thr
                355                 360                 365
Arg Met Met Ile Leu Ser Asn Asp Phe Ser Met Val Arg Glu Gly
                370                 375                 380
Ser Phe Leu Arg Phe Glu Asp Ser Val Pro Thr Asn Ile Gly Pro Ile
385                 390                 395                 400
Pro Phe Thr Leu Leu Tyr Lys Ser Ser Ser Tyr Phe Gly Met Cys Gly
                405                 410                 415
Ser Ala Val Val Cys Arg Thr Ser Gly Glu Thr Gly Ile Val Gly Met
                420                 425                 430
His Cys Ala Gly Gly Gly Gly Val Ser Val Ala Cys Arg Val Thr Arg
                435                 440                 445
Lys Met Val Glu Ala Ala Val Met Tyr Phe Leu Ile Leu Leu Ile Val
450                 455                 460
```

Gln Gly Met Ile Val Ser Thr Glu Thr Cys Asp Pro Ile His Val Pro
465                 470                 475                 480

Arg Lys Thr Lys Tyr Lys Arg Thr Asn Ala Asp Tyr Pro Ser Thr Lys
                485                 490                 495

Asn Tyr Ala Pro Ala Val Leu Ser Arg Asn Asp Pro Arg Leu Asp Pro
            500                 505                 510

Asp Val Asp Phe Asp Thr Val Leu Phe Ser Lys His Thr Glu Asn Val
        515                 520                 525

Ile Ile Pro Pro Asp Thr Leu Ala Tyr Asp Ser Leu Leu Lys Ala Thr
    530                 535                 540

Gln Val Tyr Ala Cys Lys Phe Asn Gly Asn Phe Glu Pro Leu Thr Val
545                 550                 555                 560

Glu Glu Ala Ile Leu Gly Ile Pro Gly Leu Asp Arg Met Asp Pro Asn
                565                 570                 575

Thr Ser Ser Gly Leu Pro Tyr Thr Lys Thr Arg Arg Gln Leu Ile Asp
            580                 585                 590

Phe Val Asn Gly Lys Ile Leu Asp Thr Gln Leu Gln Glu Arg Leu Asp
        595                 600                 605

Met Trp Leu Ser Gly Lys Gln Pro Glu Thr Tyr Tyr Gln Thr Phe Leu
    610                 615                 620

Lys Asp Glu Ile Arg His Ile Asp Lys Val Arg Arg Gly Lys Thr Arg
625                 630                 635                 640

Ile Ile Asp Val Thr Pro Leu Asp His Val Leu Ala Phe Arg Ile Leu
                645                 650                 655

Phe Gly Arg Phe Met Ala His Tyr His Leu Asn Pro Gly Phe Asp Leu
            660                 665                 670

Gly Ser Ala Ile Gly Cys Asp Pro Glu Val Ala Trp Asn Gln Phe Gly
        675                 680                 685

Tyr His Leu Thr Lys Tyr Lys Asn Leu Tyr Asp Phe Asp Tyr Ser Asn
    690                 695                 700

Phe Asp Ser Ser His Ser Lys Ser Ile Phe Glu Ile Leu Lys Asp His
705                 710                 715                 720

Phe Phe Thr Thr Thr Asn Gly Phe Asp Ser Arg Cys Ala Leu Leu Leu
                725                 730                 735

Asp Ser Leu Ala Val Ser Lys His Lys Tyr Asp Asn Lys Val Met Thr
            740                 745                 750

Ile Val Gly Gly Leu
        755

<210> SEQ ID NO 9
<211> LENGTH: 6719
<212> TYPE: DNA
<213> ORGANISM: Cosavirus

<400> SEQUENCE: 9
atgtcaaagc aatacagtat gtacacagtg tacacgctca aggcggagat ttaggcctca      60
cagattgtgt tttgtgttat tggatgctgg atggtcacgt tggagactgc atgtggcagt     120
cttgaaacgt gtggtttgac gtctatccgt tatggcagtg ggtggagcac tgcaaagacg     180
tcaccgtgct ttacacggtt tttgaacccc acaccggctg tttggcgctt gcaggacagc     240
aggtttattt tcatatgttc tttatttcta gccaacaggg ttctatcctg ttgggcggag     300
tgatactccc gttccttctt ggacagattg cctccacgat ctttgtggac cttaaggtga     360
tcaagtcact ggtgaattga gcgaaggttg aggaagcctg aggaatttcc atgtggcttt     420

```
gccaggagtt gtagcgatgc tgtgtgtgtg tgcggatttc ccctcatggc aacatgagcc      480
tcacaggcca aaagcccgt ccgaaaggac ccacacagtg gagcaacccc agctccctcc      540
tacaaagctt tgtgtgaatg aactcatgtt tattcttctt tattctctat ttacatcagg    600
ccccaaagat gtcctgaagg taccttgtgt atctgggcgt gagcaccatc aactacccgg    660
acttgcactt tggtgcagac gcatgtggtg acccagcccc tctgcttcgg cggaggggct    720
tttgctcgct cagcacgaga tctgatcagg agtccctccc agtgtgcttt acacctggcg    780
aggggttaaa aattgcccaa ggcctggcac aacaacctag gggactaggt tttccttta    840 ttaacaatgt ctgtcaatat gggtgcaaac aacagcaaag aatcagtgtc tagcaatggc    900
aacgagggaa ctattgttaa taactttat tcaaaccagt actatgcttc tattgatgct    960
tctgcccaag tgttgggac ctctactact cctgaaaatg gtaatgtttc tggctttctt    1020
ggacttgcaa gtagtgcttt taatgctctc tctcttctcg cctctcccag agtagaaaac   1080
agtagatacc aggaagatcg actcttgact cgcaaagcag gcaatacatc tataaactca   1140
caagctgcag aagggttt gtgtgcttat ggtaaagagt cagattctag aagtcccacc     1200
tcatgtggcg atgcaccaag caacggtaca cctgccactg atagaggttt tgttttttcaa   1260 ttactaccat ggcaaaagac aaacaaggcc tatgacgcac aatggatcag aattacagct   1320
ggtttgctac agaacaataa ggcaaatgtg tttgcaaaga acttaaaagc acattcatac   1380
ctgcgggcag gctatgaggt tactctccag gtaaatacat cccctttcca cattggttta   1440
attggccttt tccttgttcc agaatttacc cgacctggac ccgaaaactt ggaatggaga   1500
gatttgactg aaatgaaaag gatattaaat gacacaaaca tttataactc tcagactcta    1560
cctggctcct tttcttttga ttcggaccat tcttttgatc ttggtgactt tacacctgaa    1620
cagttcttgc ttttccctca tcagctgatt aacccaaaag acaacaacat tgccactgtt    1680
cgcgtcccgt acgtaaatat agcacccacc agtgacacta ctgtacacaa catctggaca    1740
gctgtggtga tggttgttc ccctcttgat tttgctactg gtgcatctcc ccaggtaggt     1800
atggtgttga ctatcacacc tgtaaactct gtattcaatg gttacacca caccgctcag    1860 ggtcctatcc ccactcgtcc tttccacaac ttcaatcagt ttaacactac tgtgcctctc    1920
agaactgaac cttgttatgg aatgactctc actccgcyag tagactacat gcccaaacct    1980
attgatgatt tagtttctttt ggtcaaggtg cccagctta ttactaattc tggttctgac    2040
actccgactg gtaggtcatt tccatattt tcagttagtt cctctactca aggtgaaaaa    2100
ttgttttcca gtggcgttgt gttgagtgac aaacattacc agcacacact cctctccaat    2160
ctggccgatt tcttttgtaa ttacagaggt agcttacagt ttgatttggt tgcagtaaca   2220
actgccatga cccgtggcaa gcttttactg gcctacgcc ctcctggtgc tggtgaacca    2280
acaacgattg accaggctat gatgggaaca taccaccatat gggatttagg tcttcagtca    2340
actgtaaatt ttgtgtggtg cc tttcatatca gctagtgatt ttagatacaa tagtgttagt   2400
gtgtcctcag ctctgaattc ggatggatgg tttactgtat ggctgcttaa ccccttgact    2460
tatccaccgg gttctccccc gacccagcaa attgtagtga tgctttctgc cggggaagac    2520
ttctcttaca ggttgcctat ttctcccggt atggcccaaa cagatggagc ttcaggtccc    2580
catgacaacg tcgagtgcgg cgtgacagac gacgctgatg ctgatctcaa ctctggtcat    2640
agtgtgtctc ttcctacccc gcacacccat actggcttct tctatgatag atatagattc    2700
attggagcta tgaaatccaa tgctttagat ggccccaaac cagtttctta tcttgatact    2760
```

```
agcaagaagg taaaaactct taacaaagtt ttccagacta taatgaact  gaaaccttat   2820 tcagttcttt cccttccccc ctacccaagc atttgtggtg tccctatatc cagctttgtc   2880
tacggcaagg catccaccag gaaatacatc aggataatga caggtgatga cttgctttac   2940
aaatcatgtc cctttaccta ctataagtgt gatctagaat ttactgtagt acccccccct   3000
ggctttgata gggattacgt ggttcattgg tatcctccag gttccacgtt ggattcggca   3060
aaagttatgt atggaatgac aggaaatcca gacaatggtt ttgatgacaa tggtgagaat   3120
cacggctctg gcatgcttaa tgtgaatcca tctttctatg cccgcggtac cacgaaagtt   3180
agcgcagtgg tcccgttctg tgcacctaca tctcttttac ctttgtactt tgatggctat   3240
cctgattatt ctcgcacccc gggctactac ggggtatctc cagctacatc tttcggctca   3300
ctcactgttg aaacaactgc aggtaatgag gatctgtttt cagtctacat taggtacaaa   3360
aattttaaag gctatcttcc tcgaccagtg attcggcgtc cacacactgc agtttctggc   3420
cgttctaaac ttgtcatgtc tgactctgtc ttgccccgaa gtctaacacg agaggagcga   3480
gaggttgcac gtctcctcct gaaaatatca ggtgatgtag aatccaatcc aggccctgca   3540
tttaacccag aatatactgc tcatggtccc gttactgaac tgattcaatt ggccagaaaa   3600
ccagaaactg tagataatgt aaacaggctt ttgacaactc tcaatactct tatggcaaaa   3660
tggaacaacc ttaaggatac tgttacagac gctgtgtttc tcagggacat ggtatgtctt   3720
cttgtaaagc tcacttctct catgtacctg gttcacggac aaggaccagg tgcttacttt   3780
gctgctgcct ctatccttct tgctgacggc ataaccttct tgattggta  cgagaaaatt   3840 aaaatcttca tggccagaaa actcagagtt tctcccccctt tctttcccgc cgcccaagga   3900
ccggacctca gagactttgt gaccttcttc aatgctgcgc gcggagcgca atggatgatt   3960
gattctctca gtccctcat  aacttggatc aaacaatggc ttgaacttga agaagaaat   4020 gaagcagtgc aacttgaaaa gatgctaata gactctccta gacactgcaa ggcaataaat   4080
gactacaaca gaggtgattc tttccagaga ccgaccaact ctttcgaatt catggacagg   4140
cttgtggaat gtgctactaa acttgggaaa gttcaaattg caacttattt cagaaatttc   4200
accacagctg attctgacac aagtagacca gaaccagttg ttgttgtcct gcgtggaaaa   4260
ccaggcgcag gtaaatctgc tgcagctact gttatggcgg ctgcagtatc taaattgtta   4320
gtaggaagtc aatcagtata tactctttcc ccagacacgg aacacatgga tggatatcat   4380
ggacagtttg tgaccttgat ggatgacctt ggacaaaacc cagacggtga agatttcaga   4440 tgttctgcc  aaatggtttc ttgtgctcag tatagacctg ctatggctga ccttaaagac   4500
aaaggaatcc tgtttacatc cagattgttg attgctacta ctaatctccc agattttaac   4560
cctgttacta tctctgatcc acgagcttta gatcgtcgga tcacttttga cgttcttgtc   4620
actccaggtt ctgccgctac caagaatggg aaacttgact tggctgctgc tctcaaacca   4680
gatggaccag gagaacaccc ttatacttct gattgcccta ttctccacac cactggactc   4740
ctcctgaaga atctcagaaa caaccagacc atgaacttga agacctagt  ggacatgatt   4800 gttaagagaa ttaaacacaa gaaggaagtt ggaaacatgc ttgactctct tgttgctcaa   4860
ggacctacca tgattgttgg ctacactaaa atgacgatg  gcattgctat tgtgactgc   4920 ttggaagaat ggaacaagat aaaggacaag aagaagaaac agcttgcttt ggaaatggtt   4980
gctcaagaac tcaaggacaa acatgaagaa cacaaaggaa ctataaagct gctcaagatg   5040
tttgttactg gccttggagt ggttgccgct gttgcaggcg cgtatgccac gatgaagtac   5100
ttcacaaaag acaaacccaa ggaagaagaa gaagagccag aggaaaagaa agaaaagaaa   5160
```

```
acagaagaat ccaaagaagc tgcaggacca tacaatggtc ccacaaagaa agaaattaag    5220
actttgaagt tgaaagccca gagtccactt atggatatgg agaagaagat tgctcagaat    5280
gtcatgccat ttcagatttt ctacaatggc aaaaggtaca cccagtcttg cttggcaatt    5340
ggcaaaagag ttattcttgt aaacaaacat gcctttgaat cagttgagca caaatttgtt    5400
gttgaccaaa gagaatacac attggaccag ttacagcta tttcccttga ctgtggatca     5460
ggtgttacag atgtgtgtgc tgtttgtttg cccccaggcc cagacttcaa atcaataaag    5520
aaacatttcc taccttcaa cactaccatg tcccaggaa ctagattgac tattctgtca      5580
aatgaccact accctatgtc cagagaaggc tctttcctca gatttgagga cgaagtgccg    5640
actaatgtag gtaacatgcc ctttgtaatg ctttataaat caacttctta ctttggtatg    5700
tgtggttcag ttgtgtgtag tagatttgtt gatggtggag gaataattgg aatgcactgt    5760
gcaggtggag gcggagtcag tgttggtacc cgtttgactg ctagaatggt tgaatcagtg    5820
ttcgactact tctacccccc aatagctcag ggaataattg aaaacacaga cacggaccc     5880 cgtgtgcatg tgcccagaac ttccaaactc aaaagaacaa atgctactta ccggcaacg     5940 gataagtacg gcccagctgc tctttcgcgt tatgatccgc gattaaatga aggagtcaat    6000
ttggatgagg tgattttctc aaaacacact caaaacaccc ttgttgagaa aggatccact    6060
ttcagaagcg ctcttgacat ggcagcagaa atttatggtg aaaagtttag aggaaatgat    6120
ttctctcccc tttcagttga agatgcaatt cttggaattc ccggactcga caggcttgac    6180
ccgaacactg cttctggatt gccctacaca aaaaccagac gccagatgat tgacttcaac    6240
acaggacaga ttttggacga cactctcaag tgccgactag acaatggct tgctggacgg    6300 cccccacagg atgtgcacta ccagactttc ctcaaggatg agattaggcc cattgaaaag    6360
gtcaaagcag gaaagactag aataattgat gttcctcctc ttgaccatgt catcgctttc    6420
agaatgctat ttggcagatt cattgcccat taccacttaa attttggttt caagacagga    6480
tccgctattg gctgtgaccc agatgttgct tgggcttctt ttggctttga actcagtggt    6540
tttccctatc tgtatgattt tgattactca aattttgatg cttccacacag tacttcaatt    6600 tttgaaatca tagaacagaa attcttttct ccagaattag gttttgatcc tagatgctca    6660
cttctcttga aatctcttgc agtttcgacc cactgttacg agaacaagag actccagat     6719
```

<210> SEQ ID NO 10
<211> LENGTH: 318
<212> TYPE: DNA
<213> ORGANISM: Cosavirus

<400> SEQUENCE: 10

```
agatcacgtg ttggccttca gaatgctttt tggaagattt atggcttatt accacctcaa      60
cccaggattc aaaattggct cagcaattgg ttgtgaccca gaaactgctt ggaatggatt     120
tggttacacg ctctctagca aacaatacaa atatgacttt gactattcaa actttgatgc     180
aagtcattcc acttccatat ttgaaatctt ggaagaggaa ttctttaccc caaaaaatgg     240
ttttgatgtg agatgctctc tactgctaaa atctttatct tgttctactc actgttatga     300
aaacaaacgg tttaccat                                                    318
```

<210> SEQ ID NO 11
<211> LENGTH: 317
<212> TYPE: DNA
<213> ORGANISM: Cosavirus

<400> SEQUENCE: 11

```
gatcatgtga ttgcttttcg tgtgttgttt ggcagattca tggcttacta tcatctaaat     60
cccggctttg aactcggaag cgccataggg tgcgatcctg aaattgcctg gactcatttc    120
ggttaccacc tcagtggttt ccggaatctt tatgactttg actattctaa ctttgattct    180
agtcactctg tgtctatttt caaaatcctc aaagatcatt tctttacccc ttccaacggt    240
tttgattctc gttgcacctt acttttagat tcactggctg tttcaaaaca caagtatgac    300
aacaaggtta tgactat                                                    317
```

<210> SEQ ID NO 12
<211> LENGTH: 105
<212> TYPE: PRT
<213> ORGANISM: Cosavirus

<400> SEQUENCE: 12

```
Asp His Val Ile Ala Phe Arg Val Leu Phe Gly Arg Phe Met Ala Tyr
1               5                   10                  15
Tyr His Leu Asn Pro Gly Phe Glu Leu Gly Ser Ala Ile Gly Cys Asp
                20                  25                  30
Pro Glu Ile Ala Trp Thr His Phe Gly Tyr His Leu Ser Gly Phe Arg
            35                  40                  45
Asn Leu Tyr Asp Phe Asp Tyr Ser Asn Phe Asp Ser Ser His Ser Val
        50                  55                  60
Ser Ile Phe Lys Ile Leu Lys Asp His Phe Phe Thr Pro Ser Asn Gly
65                  70                  75                  80
Phe Asp Ser Arg Cys Thr Leu Leu Leu Asp Ser Leu Ala Val Ser Lys
                85                  90                  95
His Lys Tyr Asp Asn Lys Val Met Thr
            100                 105
```

<210> SEQ ID NO 13
<211> LENGTH: 105
<212> TYPE: PRT
<213> ORGANISM: Cosavirus

<400> SEQUENCE: 13

```
Asp His Val Leu Ala Phe Arg Met Leu Phe Gly Arg Phe Met Ala Tyr
1               5                   10                  15
Tyr His Leu Asn Pro Gly Phe Lys Ile Gly Ser Ala Ile Gly Cys Asp
                20                  25                  30
Pro Glu Thr Ala Trp Asn Gly Phe Gly Tyr Thr Leu Ser Ser Lys Gln
            35                  40                  45
Tyr Lys Tyr Asp Phe Asp Tyr Ser Asn Phe Asp Ala Ser His Ser Thr
        50                  55                  60
Ser Ile Phe Glu Ile Leu Glu Glu Phe Phe Thr Pro Lys Asn Gly
65                  70                  75                  80
Phe Asp Val Arg Cys Ser Leu Leu Leu Lys Ser Leu Ser Cys Ser Thr
                85                  90                  95
His Cys Tyr Glu Asn Lys Arg Phe Thr
            100                 105
```

<210> SEQ ID NO 14
<211> LENGTH: 1953
<212> TYPE: PRT
<213> ORGANISM: Cosavirus
<220> FEATURE:
<221> NAME
<222> LOCATION: (367)..(367)
<223> OTHER INFORMATION: Xaa can be any naturally occurring amino acid

<400> SEQUENCE: 14

```
Met Gly Ala Asn Asn Ser Lys Glu Ser Val Ser Asn Gly Asn Glu
1               5                   10                  15

Gly Thr Ile Val Asn Asn Phe Tyr Ser Asn Gln Tyr Tyr Ala Ser Ile
                20                  25                  30

Asp Ala Ser Ala Gln Gly Val Gly Thr Ser Thr Pro Glu Asn Gly
            35                  40                  45

Asn Val Ser Gly Phe Leu Gly Leu Ala Ser Ser Ala Phe Asn Ala Leu
    50                  55                  60

Ser Leu Leu Ala Ser Pro Arg Val Glu Asn Ser Arg Tyr Gln Glu Asp
65                  70                  75                  80

Arg Leu Leu Thr Arg Lys Ala Gly Asn Thr Ser Ile Asn Ser Gln Ala
                85                  90                  95

Ala Glu Gly Val Leu Cys Ala Tyr Gly Lys Glu Ser Asp Ser Arg Ser
            100                 105                 110

Pro Thr Ser Cys Gly Asp Ala Pro Ser Asn Gly Thr Pro Ala Thr Asp
        115                 120                 125

Arg Gly Phe Val Phe Gln Leu Leu Pro Trp Gln Lys Thr Asn Lys Ala
    130                 135                 140

Tyr Asp Ala Gln Trp Ile Arg Ile Thr Ala Gly Leu Leu Gln Asn Asn
145                 150                 155                 160

Lys Ala Asn Val Phe Ala Lys Asn Leu Lys Ala His Ser Tyr Leu Arg
                165                 170                 175

Ala Gly Tyr Glu Val Thr Leu Gln Val Asn Thr Ser Pro Phe His Ile
            180                 185                 190

Gly Leu Ile Gly Leu Phe Leu Val Pro Glu Phe Thr Arg Pro Gly Pro
        195                 200                 205

Glu Asn Leu Glu Trp Arg Asp Leu Thr Glu Met Lys Arg Ile Leu Asn
    210                 215                 220

Asp Thr Asn Ile Tyr Asn Ser Gln Thr Leu Pro Gly Ser Phe Ser Phe
225                 230                 235                 240

Asp Ser Asp His Ser Phe Asp Leu Gly Asp Phe Thr Pro Glu Gln Phe
                245                 250                 255

Leu Leu Phe Pro His Gln Leu Ile Asn Pro Lys Asp Asn Asn Ile Ala
            260                 265                 270

Thr Val Arg Val Pro Tyr Val Asn Ile Ala Pro Thr Ser Asp Thr Thr
        275                 280                 285

Val His Asn Ile Trp Thr Ala Val Val Met Val Val Ser Pro Leu Asp
    290                 295                 300

Phe Ala Thr Gly Ala Ser Pro Gln Val Gly Met Val Leu Thr Ile Thr
305                 310                 315                 320

Pro Val Asn Ser Val Phe Asn Gly Leu His His Thr Ala Gln Gly Pro
                325                 330                 335

Ile Pro Thr Arg Pro Phe His Asn Phe Asn Gln Phe Asn Thr Thr Val
            340                 345                 350

Pro Leu Arg Thr Glu Pro Cys Tyr Gly Met Thr Leu Thr Pro Xaa Val
        355                 360                 365

Asp Tyr Met Pro Lys Pro Ile Asp Asp Leu Val Ser Leu Val Lys Val
    370                 375                 380

Pro Ser Phe Ile Thr Asn Ser Gly Ser Asp Thr Pro Thr Gly Arg Ser
385                 390                 395                 400
```

```
Phe Pro Tyr Phe Ser Val Ser Ser Thr Gln Gly Glu Lys Leu Phe
            405                 410                 415

Ser Ser Gly Val Val Leu Ser Asp Lys His Tyr Gln His Thr Leu Leu
        420                 425                 430

Ser Asn Leu Ala Asp Phe Phe Cys Asn Tyr Arg Gly Ser Leu Gln Phe
        435                 440                 445

Asp Leu Val Ala Val Thr Thr Ala Met Thr Arg Gly Lys Leu Leu Leu
    450                 455                 460

Ala Tyr Thr Pro Pro Gly Ala Gly Glu Pro Thr Thr Ile Asp Gln Ala
465                 470                 475                 480

Met Met Gly Thr Tyr Thr Ile Trp Asp Leu Gly Leu Gln Ser Thr Val
                485                 490                 495

Asn Phe Val Val Pro Phe Ile Ser Ala Ser Asp Phe Arg Tyr Asn Ser
                500                 505                 510

Val Ser Val Ser Ser Ala Leu Asn Ser Asp Gly Trp Phe Thr Val Trp
            515                 520                 525

Leu Leu Asn Pro Leu Thr Tyr Pro Pro Gly Ser Pro Pro Thr Gln Gln
        530                 535                 540

Ile Val Val Met Leu Ser Ala Gly Glu Asp Phe Ser Tyr Arg Leu Pro
545                 550                 555                 560

Ile Ser Pro Gly Met Ala Gln Thr Asp Gly Ala Ser Gly Pro His Asp
                565                 570                 575

Asn Val Glu Cys Gly Val Thr Asp Asp Ala Asp Ala Asp Leu Asn Ser
                580                 585                 590

Gly His Ser Val Ser Leu Pro Thr Pro His Thr His Thr Gly Phe Phe
            595                 600                 605

Tyr Asp Arg Tyr Arg Phe Ile Gly Ala Met Lys Ser Asn Ala Leu Asp
        610                 615                 620

Gly Pro Lys Pro Val Ser Tyr Leu Asp Thr Ser Lys Lys Val Lys Thr
625                 630                 635                 640

Leu Asn Lys Val Phe Gln Thr Asn Asn Glu Leu Lys Pro Tyr Ser Val
                645                 650                 655

Leu Ser Leu Ser Pro Tyr Pro Ser Ile Cys Gly Val Pro Ile Ser Ser
            660                 665                 670

Phe Val Tyr Gly Lys Ala Ser Thr Arg Lys Tyr Ile Arg Ile Met Thr
        675                 680                 685

Gly Asp Asp Leu Leu Tyr Lys Ser Cys Pro Phe Thr Tyr Tyr Lys Cys
    690                 695                 700

Asp Leu Glu Phe Thr Val Val Pro Pro Gly Phe Asp Arg Asp Tyr
705                 710                 715                 720

Val Val His Trp Tyr Pro Pro Gly Ser Thr Leu Asp Ser Ala Lys Val
                725                 730                 735

Met Tyr Gly Met Thr Gly Asn Pro Asp Asn Gly Phe Asp Asp Asn Gly
            740                 745                 750

Glu Asn His Gly Ser Gly Met Leu Asn Val Asn Pro Ser Phe Tyr Ala
        755                 760                 765

Arg Gly Thr Thr Lys Val Ser Ala Val Val Pro Phe Cys Ala Pro Thr
    770                 775                 780

Ser Leu Leu Pro Leu Tyr Phe Asp Gly Tyr Pro Asp Tyr Ser Arg Thr
785                 790                 795                 800

Pro Gly Tyr Tyr Gly Val Ser Pro Ala Thr Ser Phe Gly Ser Leu Thr
                805                 810                 815
```

Val Glu Thr Thr Ala Gly Asn Glu Asp Leu Phe Ser Val Tyr Ile Arg
820 825 830

Tyr Lys Asn Phe Lys Gly Tyr Leu Pro Arg Pro Val Ile Arg Arg Pro
835 840 845

His Thr Ala Val Ser Gly Arg Ser Lys Leu Val Met Ser Asp Ser Val
850 855 860

Leu Pro Arg Ser Leu Thr Arg Glu Glu Arg Glu Val Ala Arg Leu Leu
865 870 875 880

Leu Lys Ile Ser Gly Asp Val Glu Ser Asn Pro Gly Pro Ala Phe Asn
885 890 895

Pro Glu Tyr Thr Ala His Gly Pro Val Thr Glu Leu Ile Gln Leu Ala
900 905 910

Arg Lys Pro Glu Thr Val Asp Asn Val Asn Arg Leu Leu Thr Thr Leu
915 920 925

Asn Thr Leu Met Ala Lys Trp Asn Asn Leu Lys Asp Thr Val Thr Asp
930 935 940

Ala Val Phe Leu Arg Asp Met Val Cys Leu Leu Val Lys Leu Thr Ser
945 950 955 960

Leu Met Tyr Leu Val His Gly Gln Gly Pro Gly Ala Tyr Phe Ala Ala
965 970 975

Ala Ser Ile Leu Leu Ala Asp Gly Ile Thr Phe Phe Asp Trp Tyr Glu
980 985 990

Lys Ile Lys Ile Phe Met Ala Arg Lys Leu Arg Val Ser Pro Pro Phe
995 1000 1005

Phe Pro Ala Ala Gln Gly Pro Asp Leu Arg Asp Phe Val Thr Phe
1010 1015 1020

Phe Asn Ala Ala Arg Gly Ala Gln Trp Met Ile Asp Ser Leu Lys
1025 1030 1035

Ser Leu Ile Thr Trp Ile Lys Gln Trp Leu Glu Leu Glu Glu Glu
1040 1045 1050

Asn Glu Ala Val Gln Leu Glu Lys Met Leu Ile Asp Ser Pro Arg
1055 1060 1065

His Cys Lys Ala Ile Asn Asp Tyr Asn Arg Gly Asp Ser Phe Gln
1070 1075 1080

Arg Pro Thr Asn Ser Phe Glu Phe Met Asp Arg Leu Val Glu Cys
1085 1090 1095

Ala Thr Lys Leu Gly Lys Val Gln Ile Ala Thr Tyr Phe Arg Asn
1100 1105 1110

Phe Thr Thr Ala Asp Ser Asp Thr Ser Arg Pro Glu Pro Val Val
1115 1120 1125

Val Val Leu Arg Gly Lys Pro Gly Ala Gly Lys Ser Ala Ala Ala
1130 1135 1140

Thr Val Met Ala Ala Ala Val Ser Lys Leu Leu Val Gly Ser Gln
1145 1150 1155

Ser Val Tyr Thr Leu Ser Pro Asp Thr Glu His Met Asp Gly Tyr
1160 1165 1170

His Gly Gln Phe Val Thr Leu Met Asp Asp Leu Gly Gln Asn Pro
1175 1180 1185

Asp Gly Glu Asp Phe Arg Cys Phe Cys Gln Met Val Ser Cys Ala
1190 1195 1200

Gln Tyr Arg Pro Ala Met Ala Asp Leu Lys Asp Lys Gly Ile Leu
1205 1210 1215

Phe Thr Ser Arg Leu Leu Ile Ala Thr Thr Asn Leu Pro Asp Phe

```
                1220                1225                1230
Asn Pro Val Thr Ile Ser Asp Pro Arg Ala Leu Asp Arg Arg Ile
                1235                1240                1245
Thr Phe Asp Val Leu Val Thr Pro Gly Ser Ala Ala Thr Lys Asn
                1250                1255                1260
Gly Lys Leu Asp Leu Ala Ala Ala Leu Lys Pro Asp Gly Pro Gly
                1265                1270                1275
Glu His Pro Tyr Thr Ser Asp Cys Pro Ile Leu His Thr Thr Gly
                1280                1285                1290
Leu Leu Leu Lys Asn Leu Arg Asn Asn Gln Thr Met Asn Leu Lys
                1295                1300                1305
Asp Leu Val Asp Met Ile Val Lys Arg Ile Lys His Lys Lys Glu
                1310                1315                1320
Val Gly Asn Met Leu Asp Ser Leu Val Ala Gln Gly Pro Thr Met
                1325                1330                1335
Ile Val Gly Tyr Thr Lys Asp Asp Gly Ile Ala Ile Val Asp
                1340                1345                1350
Cys Leu Glu Glu Trp Asn Lys Ile Lys Asp Lys Lys Lys Gln
                1355                1360                1365
Leu Ala Leu Glu Met Val Ala Gln Glu Leu Lys Asp Lys His Glu
                1370                1375                1380
Glu His Lys Gly Thr Ile Lys Leu Leu Lys Met Phe Val Thr Gly
                1385                1390                1395
Leu Gly Val Val Ala Ala Val Ala Gly Ala Tyr Ala Thr Met Lys
                1400                1405                1410
Tyr Phe Thr Lys Asp Lys Pro Lys Glu Glu Glu Glu Pro Glu
                1415                1420                1425
Glu Lys Lys Glu Lys Lys Thr Glu Glu Ser Lys Glu Ala Ala Gly
                1430                1435                1440
Pro Tyr Asn Gly Pro Thr Lys Lys Glu Ile Lys Thr Leu Lys Leu
                1445                1450                1455
Lys Ala Gln Ser Pro Leu Met Asp Met Glu Lys Lys Ile Ala Gln
                1460                1465                1470
Asn Val Met Pro Phe Gln Ile Phe Tyr Asn Gly Lys Arg Tyr Thr
                1475                1480                1485
Gln Ser Cys Leu Ala Ile Gly Lys Arg Val Ile Leu Val Asn Lys
                1490                1495                1500
His Ala Phe Glu Ser Val Glu His Lys Phe Val Asp Gln Arg
                1505                1510                1515
Glu Tyr Thr Leu Asp Gln Val Thr Ala Ile Ser Leu Asp Cys Gly
                1520                1525                1530
Ser Gly Val Thr Asp Val Cys Ala Val Cys Leu Pro Pro Gly Pro
                1535                1540                1545
Asp Phe Lys Ser Ile Lys Lys His Phe Leu Pro Phe Asn Thr Thr
                1550                1555                1560
Met Phe Pro Gly Thr Arg Leu Thr Ile Leu Ser Asn Asp His Tyr
                1565                1570                1575
Pro Met Ser Arg Glu Gly Ser Phe Leu Arg Phe Glu Asp Glu Val
                1580                1585                1590
Pro Thr Asn Val Gly Asn Met Pro Phe Val Met Leu Tyr Lys Ser
                1595                1600                1605
Thr Ser Tyr Phe Gly Met Cys Gly Ser Val Val Cys Ser Arg Phe
                1610                1615                1620
```

| | | | | | | | | | | |
|---|---|---|---|---|---|---|---|---|---|---|
| Val | Asp | Gly | Gly | Gly | Ile | Ile | Gly | Met | His | Cys | Ala | Gly | Gly | Gly |
| | 1625 | | | | 1630 | | | | 1635 | |

Val Asp Gly Gly Gly Ile Ile Gly Met His Cys Ala Gly Gly Gly
 1625                1630               1635

Gly Val Ser Val Gly Thr Arg Leu Thr Ala Arg Met Val Glu Ser
 1640                1645               1650

Val Phe Asp Tyr Phe Tyr Pro Pro Ile Ala Gln Gly Ile Ile Glu
 1655                1660               1665

Asn Thr Glu Thr Gly Pro Arg Val His Val Pro Arg Thr Ser Lys
 1670                1675               1680

Leu Lys Arg Thr Asn Ala Thr Tyr Pro Ala Thr Asp Lys Tyr Gly
 1685                1690               1695

Pro Ala Ala Leu Ser Arg Tyr Asp Pro Arg Leu Asn Glu Gly Val
 1700                1705               1710

Asn Leu Asp Glu Val Ile Phe Ser Lys His Thr Gln Asn Thr Leu
 1715                1720               1725

Val Glu Lys Gly Ser Thr Phe Arg Ser Ala Leu Asp Met Ala Ala
 1730                1735               1740

Glu Ile Tyr Gly Glu Lys Phe Arg Gly Asn Asp Phe Ser Pro Leu
 1745                1750               1755

Ser Val Glu Asp Ala Ile Leu Gly Ile Pro Gly Leu Asp Arg Leu
 1760                1765               1770

Asp Pro Asn Thr Ala Ser Gly Leu Pro Tyr Thr Lys Thr Arg Arg
 1775                1780               1785

Gln Met Ile Asp Phe Asn Thr Gly Gln Ile Leu Asp Asp Thr Leu
 1790                1795               1800

Lys Cys Arg Leu Gly Gln Trp Leu Ala Gly Arg Pro Pro Gln Asp
 1805                1810               1815

Val His Tyr Gln Thr Phe Leu Lys Asp Glu Ile Arg Pro Ile Glu
 1820                1825               1830

Lys Val Lys Ala Gly Lys Thr Arg Ile Ile Asp Val Pro Pro Leu
 1835                1840               1845

Asp His Val Ile Ala Phe Arg Met Leu Phe Gly Arg Phe Ile Ala
 1850                1855               1860

His Tyr His Leu Asn Phe Gly Phe Lys Thr Gly Ser Ala Ile Gly
 1865                1870               1875

Cys Asp Pro Asp Val Ala Trp Ala Ser Phe Gly Phe Glu Leu Ser
 1880                1885               1890

Gly Phe Pro Tyr Leu Tyr Asp Phe Asp Tyr Ser Asn Phe Asp Ala
 1895                1900               1905

Ser His Ser Thr Ser Ile Phe Glu Ile Ile Glu Gln Lys Phe Phe
 1910                1915               1920

Ser Pro Glu Leu Gly Phe Asp Pro Arg Cys Ser Leu Leu Leu Lys
 1925                1930               1935

Ser Leu Ala Val Ser Thr His Cys Tyr Glu Asn Lys Arg Leu Gln
 1940                1945               1950

<210> SEQ ID NO 15
<211> LENGTH: 655
<212> TYPE: DNA
<213> ORGANISM: Cosavirus

<400> SEQUENCE: 15
aaccccacac cggcggtttg acgcttgtag gaccgtaggt ttatcttcac aacaaagact      60
cttagtttct agtcccattg gctctatcaa tgggagcgga gaggtggctc cccgtttctt     120

```
cttgaacagg ttacacccac gcctttgtg gaattcttag tgtgaccaat gcctggtgat    180
ataatgatac agtagtttgg tgctgcggac gggtttggga aggaaatgta gcgtcgtagc    240
ggtgctgtgt gtgtgagcgg aactccccac gtggtgacac gtgcctctca gaccgaaagt    300
cacgccgaaa ggcccacaca gttggacaac cccagtccac gtcacatttc agtctcactc    360
ctggaaacag ttagtgaact attcacccat ttatcaccct ggaccccaaa gatgccctga    420
aggtaccccg tgtattctac tatggaaaca tcaactaccc ggacagttct tcggaacgac    480
gcatgtggta atccggcccc cgttcttggg acggggcct gtccataagt agacactgga    540
tctgatcagg ggagaggtcg ctgctttacg gccctcttta aaaattgccc aaggtccggc    600
cacccaacct aggggactag ttttccttt tatttcatca ctgtcatcat gggtg         655
```

```
<210> SEQ ID NO 16
<211> LENGTH: 410
<212> TYPE: DNA
<213> ORGANISM: Cosavirus

<400> SEQUENCE: 16
attctcaagg atgaaatcag accgatagaa aaggtaaagg ctggcaaaac aagaataatt    60
gatgtgcctc ctttggatca cgtcatagtg ttcagaatga tgtttggtaa attcatggcc   120
cattaccacc taaatccagg atttgagaca gggtcggcta tagggtgcga ccctgatata   180
gcctgggctt cctttggctt tagtcttgat cagtgtagtt ataaatatga ttttgattac   240
tctaactttg attcttgcca ttcagtttct attttaaaa taattgaaga atacttttc    300 aatgaagaaa atggttttga tcccagatgc tcacttctgc ttcgctcttt agctatttca   360
aaacatgctt atgaggacaa gcagattatt gtcgagggcg gcctcccctc               410
```

```
<210> SEQ ID NO 17
<211> LENGTH: 136
<212> TYPE: PRT
<213> ORGANISM: Cosavirus

<400> SEQUENCE: 17

Ile Leu Lys Asp Glu Ile Arg Pro Ile Glu Lys Val Lys Ala Gly Lys
1               5                   10                  15

Thr Arg Ile Ile Asp Val Pro Pro Leu Asp His Val Ile Val Phe Arg
            20                  25                  30

Met Met Phe Gly Lys Phe Met Ala His Tyr His Leu Asn Pro Gly Phe
        35                  40                  45

Glu Thr Gly Ser Ala Ile Gly Cys Asp Pro Asp Ile Ala Trp Ala Ser
    50                  55                  60

Phe Gly Phe Ser Leu Asp Gln Cys Ser Tyr Lys Tyr Asp Phe Asp Tyr
65                  70                  75                  80

Ser Asn Phe Asp Ser Cys His Ser Val Ser Ile Phe Lys Ile Ile Glu
                85                  90                  95

Glu Tyr Phe Phe Asn Glu Glu Asn Gly Phe Asp Pro Arg Cys Ser Leu
            100                 105                 110

Leu Leu Arg Ser Leu Ala Ile Ser Lys His Ala Tyr Glu Asp Lys Gln
        115                 120                 125

Ile Ile Val Glu Gly Gly Leu Pro
    130                 135
```

```
<210> SEQ ID NO 18
<211> LENGTH: 12
<212> TYPE: PRT
```

<213> ORGANISM: Encephalomyocarditis

<400> SEQUENCE: 18

Val Val Phe Glu Leu Gln Gly Asn Ser Thr Ser Ser
1               5                   10

<210> SEQ ID NO 19
<211> LENGTH: 12
<212> TYPE: PRT
<213> ORGANISM: Mengo virus

<400> SEQUENCE: 19

Val Val Phe Glu Thr Gln Gly Asn Ser Thr Ser Ser
1               5                   10

<210> SEQ ID NO 20
<211> LENGTH: 12
<212> TYPE: PRT
<213> ORGANISM: Saffold virus

<400> SEQUENCE: 20

Val Leu Met Glu Pro Gln Gly Asn Ser Asn Ser Ser
1               5                   10

<210> SEQ ID NO 21
<211> LENGTH: 12
<212> TYPE: PRT
<213> ORGANISM: Foot and mouth disease virus

<400> SEQUENCE: 21

Ala Gly Leu Phe Leu Arg Gly Ala Gly His Ser Ser
1               5                   10

<210> SEQ ID NO 22
<211> LENGTH: 12
<212> TYPE: PRT
<213> ORGANISM: Equine rhinovirus 2

<400> SEQUENCE: 22

Arg Asp Ser Gln Cys Arg Gly Ala Gly His Ser Arg
1               5                   10

<210> SEQ ID NO 23
<211> LENGTH: 12
<212> TYPE: PRT
<213> ORGANISM: Encephalomyocarditis

<400> SEQUENCE: 23

Met Leu Pro Leu Leu Ala Asp Gln Asn Thr Glu Glu
1               5                   10

<210> SEQ ID NO 24
<211> LENGTH: 12
<212> TYPE: PRT
<213> ORGANISM: Mengo virus

<400> SEQUENCE: 24

Met Leu Pro Leu Leu Ala Asp Gln Asn Thr Glu Glu
1               5                   10

<210> SEQ ID NO 25
<211> LENGTH: 12
<212> TYPE: PRT
<213> ORGANISM: Saffold virus

<400> SEQUENCE: 25

Ile Ala Pro Leu Leu Met Asp Gln Asn Thr Glu Glu
1               5                   10

<210> SEQ ID NO 26
<211> LENGTH: 12
<212> TYPE: PRT
<213> ORGANISM: Cosavirus

<400> SEQUENCE: 26

Ala Leu Ser Leu Leu Ala Ser Pro Arg Thr Glu Thr
1               5                   10

<210> SEQ ID NO 27
<211> LENGTH: 12
<212> TYPE: PRT
<213> ORGANISM: Foot and mouth disease virus

<400> SEQUENCE: 27

Phe Gly Ala Leu Leu Ala Asp Lys Lys Thr Glu Glu
1               5                   10

<210> SEQ ID NO 28
<211> LENGTH: 12
<212> TYPE: PRT
<213> ORGANISM: Equine rhinovirus 2

<400> SEQUENCE: 28

Gln Ser Leu Ala Leu Leu Asp Gln Asp Thr Glu Glu
1               5                   10

<210> SEQ ID NO 29
<211> LENGTH: 12
<212> TYPE: PRT
<213> ORGANISM: Encephalomyocarditis

<400> SEQUENCE: 29

Glu Thr Leu Ser Arg Gln Ser Pro Ile Pro Val Thr
1               5                   10

<210> SEQ ID NO 30
<211> LENGTH: 12
<212> TYPE: PRT
<213> ORGANISM: Mengo virus

<400> SEQUENCE: 30

Glu Val Leu Ser Arg Gln Ser Pro Ile Pro Val Thr
1               5                   10

<210> SEQ ID NO 31
<211> LENGTH: 12
<212> TYPE: PRT
<213> ORGANISM: Saffold virus

<400> SEQUENCE: 31

Ser Val Leu Glu Ala Asp Ser Pro Ile Pro Val Thr
1               5                   10

<210> SEQ ID NO 32
<211> LENGTH: 12
<212> TYPE: PRT
<213> ORGANISM: Cosavirus

<400> SEQUENCE: 32

```
Leu His His Thr Ala Gln Gly Pro Ile Pro Val Arg
1               5                   10
```

<210> SEQ ID NO 33
<211> LENGTH: 12
<212> TYPE: PRT
<213> ORGANISM: Foot and mouth disease virus

<400> SEQUENCE: 33

```
Glu Lys Pro Ala Lys Gln Gly Ile Ile Pro Val Ala
1               5                   10
```

<210> SEQ ID NO 34
<211> LENGTH: 12
<212> TYPE: PRT
<213> ORGANISM: Equine rhinovirus 2

<400> SEQUENCE: 34

```
Arg Gln Thr Val Ser Glu Gly Ile Pro Gly Thr Gln
1               5                   10
```

<210> SEQ ID NO 35
<211> LENGTH: 12
<212> TYPE: PRT
<213> ORGANISM: Encephalomyocarditis

<400> SEQUENCE: 35

```
Ala Pro Trp Ser Pro Gln Gly Val Glu Asn Ala Glu
1               5                   10
```

<210> SEQ ID NO 36
<211> LENGTH: 12
<212> TYPE: PRT
<213> ORGANISM: Mengo virus

<400> SEQUENCE: 36

```
Ala Pro Trp Ser Pro Gln Gly Val Glu Asn Ala Glu
1               5                   10
```

<210> SEQ ID NO 37
<211> LENGTH: 12
<212> TYPE: PRT
<213> ORGANISM: Saffold virus

<400> SEQUENCE: 37

```
Thr Lys Tyr Thr Pro Gln Gly Val Asp Asn Ala Glu
1               5                   10
```

<210> SEQ ID NO 38
<211> LENGTH: 12
<212> TYPE: PRT
<213> ORGANISM: Cosavirus

<400> SEQUENCE: 38

```
Gly Phe Ala Glu Gly Glu Thr Ser Glu His Pro Met
1               5                   10
```

<210> SEQ ID NO 39
<211> LENGTH: 12
<212> TYPE: PRT
<213> ORGANISM: Foot and mouth disease virus

<400> SEQUENCE: 39

```
Val Asp Pro Val Arg Gln Thr Thr Ser Ser Gly Glu
1               5                   10
```

<210> SEQ ID NO 40
<211> LENGTH: 12
<212> TYPE: PRT
<213> ORGANISM: Equine rhinovirus 2

<400> SEQUENCE: 40

Thr Tyr Pro Arg Val Glu Gly Thr Glu Asn Met Glu
1               5                   10

<210> SEQ ID NO 41
<211> LENGTH: 12
<212> TYPE: PRT
<213> ORGANISM: Encephalomyocarditis

<400> SEQUENCE: 41

Gly Val Leu Met Leu Glu Ser Pro Asn Ala Leu Asp
1               5                   10

<210> SEQ ID NO 42
<211> LENGTH: 12
<212> TYPE: PRT
<213> ORGANISM: Mengo virus

<400> SEQUENCE: 42

Gly Val Leu Met Leu Glu Ser Pro Asn Pro Leu Asp
1               5                   10

<210> SEQ ID NO 43
<211> LENGTH: 12
<212> TYPE: PRT
<213> ORGANISM: Saffold virus

<400> SEQUENCE: 43

Gln Ile Leu Glu Leu Gln Asp Pro Ile Ser Ile Tyr
1               5                   10

<210> SEQ ID NO 44
<211> LENGTH: 12
<212> TYPE: PRT
<213> ORGANISM: Cosavirus

<400> SEQUENCE: 44

Arg Tyr Ile Met Ala Asp Ser Val Leu Pro Arg Pro
1               5                   10

<210> SEQ ID NO 45
<211> LENGTH: 12
<212> TYPE: PRT
<213> ORGANISM: Foot and mouth disease virus

<400> SEQUENCE: 45

Val Lys Lys Gln Leu Cys Asn Phe Asp Leu Leu Lys
1 5 10

<210> SEQ ID NO 46
<211> LENGTH: 12
<212> TYPE: PRT
<213> ORGANISM: Equine rhinovirus 2

<400> SEQUENCE: 46

Leu Ser Gln Gly Ala Thr Asn Phe Asp Leu Leu Lys
1 5 10

-continued

```
<210> SEQ ID NO 47
<211> LENGTH: 12
<212> TYPE: PRT
<213> ORGANISM: Encephalomyocarditis

<400> SEQUENCE: 47

Ile Glu Thr Asn Pro Gly Pro Phe Met Phe Arg Pro
1               5                   10

<210> SEQ ID NO 48
<211> LENGTH: 12
<212> TYPE: PRT
<213> ORGANISM: Mengo virus

<400> SEQUENCE: 48

Val Glu Thr Asn Pro Gly Pro Phe Thr Phe Lys Pro
1               5                   10

<210> SEQ ID NO 49
<211> LENGTH: 12
<212> TYPE: PRT
<213> ORGANISM: Saffold virus

<400> SEQUENCE: 49

Val Glu Thr Asn Pro Gly Pro Val Gln Ser Val Phe
1               5                   10

<210> SEQ ID NO 50
<211> LENGTH: 12
<212> TYPE: PRT
<213> ORGANISM: Cosavirus

<400> SEQUENCE: 50

Ile Glu Ser Asn Pro Gly Pro Ala Phe Asn Pro Glu
1               5                   10

<210> SEQ ID NO 51
<211> LENGTH: 12
<212> TYPE: PRT
<213> ORGANISM: Foot and mouth disease virus

<400> SEQUENCE: 51

Val Glu Ser Asn Pro Gly Pro Phe Phe Phe Ser Asp
1               5                   10

<210> SEQ ID NO 52
<211> LENGTH: 12
<212> TYPE: PRT
<213> ORGANISM: Equine rhinovirus 2

<400> SEQUENCE: 52

Val Glu Ser Asn Pro Gly Pro Thr Ile Trp Ser Met
1               5                   10

<210> SEQ ID NO 53
<211> LENGTH: 12
<212> TYPE: PRT
<213> ORGANISM: Encephalomyocarditis

<400> SEQUENCE: 53

Ser Leu Phe Gln Gln Gln Ser Pro Leu Lys Gln Val
1               5                   10

<210> SEQ ID NO 54
<211> LENGTH: 12
```

```
<212> TYPE: PRT
<213> ORGANISM: Mengo virus

<400> SEQUENCE: 54

Ser Leu Phe Gln Gln Gln Ser Pro Leu Lys Gln Val
1               5                   10

<210> SEQ ID NO 55
<211> LENGTH: 12
<212> TYPE: PRT
<213> ORGANISM: Saffold virus

<400> SEQUENCE: 55

Pro Leu Leu Gln Gln Gln Ser Pro Ile Arg Glu Ala
1               5                   10

<210> SEQ ID NO 56
<211> LENGTH: 12
<212> TYPE: PRT
<213> ORGANISM: Cosavirus

<400> SEQUENCE: 56

Phe Phe Pro Ala Ala Gln Gly Pro Asp Leu Arg Asp
1               5                   10

<210> SEQ ID NO 57
<211> LENGTH: 12
<212> TYPE: PRT
<213> ORGANISM: Foot and mouth disease virus

<400> SEQUENCE: 57

Glu Arg Ala Glu Lys Gln Leu Lys Ala Arg Asp Ile
1               5                   10

<210> SEQ ID NO 58
<211> LENGTH: 12
<212> TYPE: PRT
<213> ORGANISM: Equine rhinovirus 2

<400> SEQUENCE: 58

Gln Ala Leu Leu Ser Glu Gly Ile Ser Ser Thr Leu
1               5                   10

<210> SEQ ID NO 59
<211> LENGTH: 12
<212> TYPE: PRT
<213> ORGANISM: Encephalomyocarditis

<400> SEQUENCE: 59

Gln Thr Leu Val Ala Gln Ala Pro Val Asp Glu Val
1               5                   10

<210> SEQ ID NO 60
<211> LENGTH: 12
<212> TYPE: PRT
<213> ORGANISM: Mengo virus

<400> SEQUENCE: 60

Gln Thr Leu Val Ala Gln Gly Pro Val Asp Glu Val
1               5                   10

<210> SEQ ID NO 61
<211> LENGTH: 12
<212> TYPE: PRT
<213> ORGANISM: Saffold virus
```

```
<400> SEQUENCE: 61

Asn Thr Leu Val Ala Gln Ser Pro Gly Asn Asp Met
1               5                   10

<210> SEQ ID NO 62
<211> LENGTH: 12
<212> TYPE: PRT
<213> ORGANISM: Cosavirus

<400> SEQUENCE: 62

Asp Ser Leu Val Ala Gln Gly Pro Thr Met Ile Val
1               5                   10

<210> SEQ ID NO 63
<211> LENGTH: 12
<212> TYPE: PRT
<213> ORGANISM: Foot and mouth disease virus

<400> SEQUENCE: 63

His Pro Ile Phe Lys Gln Ile Ser Ile Pro Ser Gln
1               5                   10

<210> SEQ ID NO 64
<211> LENGTH: 12
<212> TYPE: PRT
<213> ORGANISM: Equine rhinovirus 2

<400> SEQUENCE: 64

Gly Gly Ile Phe Ala Gln Ser Arg Asp Arg Tyr Tyr
1               5                   10

<210> SEQ ID NO 65
<211> LENGTH: 13
<212> TYPE: PRT
<213> ORGANISM: Encephalomyocarditis

<400> SEQUENCE: 65

Leu Asp Glu Gln Glu Gln Gly Pro Tyr Asn Glu Thr Ala
1               5                   10

<210> SEQ ID NO 66
<211> LENGTH: 13
<212> TYPE: PRT
<213> ORGANISM: Mengo virus

<400> SEQUENCE: 66

Leu Asp Glu Gln Glu Gln Gly Pro Tyr Asn Glu Thr Thr
1               5                   10

<210> SEQ ID NO 67
<211> LENGTH: 13
<212> TYPE: PRT
<213> ORGANISM: Saffold virus

<400> SEQUENCE: 67

Leu Ser Glu Gly Glu Gln Ala Ala Tyr Ser Gly Gly Lys
1               5                   10

<210> SEQ ID NO 68
<211> LENGTH: 13
<212> TYPE: PRT
<213> ORGANISM: Cosavirus

<400> SEQUENCE: 68
```

Glu Ser Lys Glu Ala Ala Gly Pro Tyr Asn Gly Pro Thr
1               5                   10

<210> SEQ ID NO 69
<211> LENGTH: 13
<212> TYPE: PRT
<213> ORGANISM: Foot and mouth disease virus

<400> SEQUENCE: 69

Glu Lys Pro Gln Ala Glu Gly Pro Tyr Ala Gly Pro Leu
1               5                   10

<210> SEQ ID NO 70
<211> LENGTH: 13
<212> TYPE: PRT
<213> ORGANISM: Equine rhinovirus 2

<400> SEQUENCE: 70

Asp Ser Ile Phe Glu Gln Ser Arg Ala Tyr Asn Ile Pro
1               5                   10

<210> SEQ ID NO 71
<211> LENGTH: 12
<212> TYPE: PRT
<213> ORGANISM: Encephalomyocarditis

<400> SEQUENCE: 71

Gln Leu Leu Asp Ile Gln Gly Pro Asn Pro Val Met
1               5                   10

<210> SEQ ID NO 72
<211> LENGTH: 12
<212> TYPE: PRT
<213> ORGANISM: Mengo virus

<400> SEQUENCE: 72

Gln Leu Leu Asp Val Gln Gly Pro Asn Pro Thr Met
1               5                   10

<210> SEQ ID NO 73
<211> LENGTH: 12
<212> TYPE: PRT
<213> ORGANISM: Saffold virus

<400> SEQUENCE: 73

Gln Val Leu Asp Val Gln Gly Gly Gly Lys Ile Val
1               5                   10

<210> SEQ ID NO 74
<211> LENGTH: 12
<212> TYPE: PRT
<213> ORGANISM: Cosavirus

<400> SEQUENCE: 74

Leu Lys Leu Lys Ala Gln Ser Pro Leu Met Asp Met
1               5                   10

<210> SEQ ID NO 75
<211> LENGTH: 12
<212> TYPE: PRT
<213> ORGANISM: Foot and mouth disease virus

<400> SEQUENCE: 75

Ala Pro Ile Val Thr Glu Ser Gly Cys Pro Pro Thr

-continued

```
1               5                   10

<210> SEQ ID NO 76
<211> LENGTH: 12
<212> TYPE: PRT
<213> ORGANISM: Equine rhinovirus 2

<400> SEQUENCE: 76

Glu Ala His Ile Pro Gln Gly Pro Val Cys Glu Val
1               5                   10

<210> SEQ ID NO 77
<211> LENGTH: 12
<212> TYPE: PRT
<213> ORGANISM: Encephalomyocarditis

<400> SEQUENCE: 77

Asn Ala Phe Glu Pro Gln Gly Ala Leu Glu Arg Leu
1               5                   10

<210> SEQ ID NO 78
<211> LENGTH: 12
<212> TYPE: PRT
<213> ORGANISM: Mengo virus

<400> SEQUENCE: 78

Gln Ala Phe Glu Pro Gln Gly Ala Leu Glu Arg Leu
1               5                   10

<210> SEQ ID NO 79
<211> LENGTH: 12
<212> TYPE: PRT
<213> ORGANISM: Saffold virus

<400> SEQUENCE: 79

Asp Cys Leu Thr Pro Gln Gly Ala Ile Val Glu Ile
1               5                   10

<210> SEQ ID NO 80
<211> LENGTH: 12
<212> TYPE: PRT
<213> ORGANISM: Cosavirus

<400> SEQUENCE: 80

Tyr Pro Pro Val Ala Gln Gly Ile Ile Glu Asn Thr
1               5                   10

<210> SEQ ID NO 81
<211> LENGTH: 12
<212> TYPE: PRT
<213> ORGANISM: Foot and mouth disease virus

<400> SEQUENCE: 81

Pro Pro Pro His Thr Glu Gly Leu Val Val Asp Thr
1               5                   10

<210> SEQ ID NO 82
<211> LENGTH: 12
<212> TYPE: PRT
<213> ORGANISM: Equine rhinovirus 2

<400> SEQUENCE: 82

Gly Glu Pro Val Ala Gln Gly Trp Thr Tyr Phe Asp
1               5                   10
```

-continued

```
<210> SEQ ID NO 83
<211> LENGTH: 1964
<212> TYPE: PRT
<213> ORGANISM: Cosavirus

<400> SEQUENCE: 83

Met Gly Ala Asn Asn Ser Lys Glu Ser Val Ser Ser Asn Gly Asn Glu
1               5                   10                  15

Gly Thr Ile Val Asn Asn Phe Tyr Ser Asn Gln Tyr Tyr Ala Ser Ile
            20                  25                  30

Asp Ala Ser Ala Gln Gly Val Gly Thr Ser Thr Thr Pro Glu Asn Gly
        35                  40                  45

Asn Val Ser Gly Phe Leu Gly Leu Ala Gly Ser Ala Phe Asn Ala Leu
    50                  55                  60

Ser Leu Leu Ala Ser Pro Arg Thr Glu Thr Gly Met Met Met Glu Asp
65                  70                  75                  80

Arg Val Leu Ser Arg Thr Ala Gly Asn Thr Ser Val Asn Ser Gln Ala
                85                  90                  95

Ala Glu Gly Val Leu Gln Ala Tyr Gly Thr Glu Thr Asp Ser Asn Ser
            100                 105                 110

Pro Thr Ser Cys Gly Asp Asp Pro Ser Lys Gly Thr His Ala Thr Asp
        115                 120                 125

Arg Ala Phe Val Ile Gln Leu Leu Pro Trp Lys Gln Thr Thr Asn Ser
    130                 135                 140

Tyr Phe Ala Gln Trp Val Arg Leu Thr Gln Lys Leu Ser Asn Asn Leu
145                 150                 155                 160

His Gly Asn Val Met Ala Lys Asn Ile Lys Ser His Ala Phe Ala Lys
                165                 170                 175

Met Gly Phe Glu Val Met Leu Gln Ala Asn Thr Ser Pro Phe His Asn
            180                 185                 190

Gly Ile Leu Gly Leu Phe Leu Val Pro Glu Phe Val Arg Lys Gly Glu
        195                 200                 205

Ile Thr Asp Glu Trp Ile Asp Leu Thr Pro Thr Ser Ser Leu Val Ser
    210                 215                 220

Asn Thr Glu Leu Tyr Asn Pro Gln Thr Tyr Ala Asn Phe Pro Phe Asp
225                 230                 235                 240

Ala Lys His Ser Phe Asp Tyr Ser Asp Ile Thr Pro Glu Gln Phe Met
                245                 250                 255

Ile Phe Pro His Gln Leu Ile Asn Pro Lys Asp Thr Asn Val Ala Thr
            260                 265                 270

Val Arg Val Pro Tyr Ile Asn Ile Ala Pro Thr Asn Asp Thr Thr Val
        275                 280                 285

His Thr Val Trp Thr Ala Val Val Met Val Leu Val Pro Leu Asn Phe
    290                 295                 300

Ser Ser Gly Ala Ser Pro Thr Val Ser Leu Thr Leu Thr Ile Thr Pro
305                 310                 315                 320

Ile Asn Ser Val Phe Asn Gly Leu His His Thr Ala Gln Gly Pro Ile
                325                 330                 335

Pro Val Arg Pro Phe His Asn Phe Gln Gln Phe Ser Thr Thr Val Pro
            340                 345                 350

Leu Arg Thr Glu Pro Cys Tyr Gly Met Thr Val Thr Pro Pro Val Asp
        355                 360                 365

Tyr Met Pro Leu Pro Ile Thr Asp Leu Val Glu Leu Ala Lys Val Pro
    370                 375                 380
```

-continued

```
Ser Phe Val Thr Val Ala Asn Ser Asp Thr Thr Ser Glu Arg Ser Phe
385                 390                 395                 400

Pro Tyr Phe Ser Val Ser Asn Thr Glu Gln Gly Arg Asn Leu Phe Lys
            405                 410                 415

Ser Ser Val Val Leu Ser Asp Leu His Tyr Gln His Thr Leu Val Ala
        420                 425                 430

Asn Leu Ala Arg Tyr Phe Cys Asn Tyr Arg Gly Ser Leu Gln Phe Asp
            435                 440                 445

Phe Ile Ala Ala Thr Thr Ala Met Thr Arg Gly Lys Leu Leu Ile Ser
        450                 455                 460

Tyr Thr Pro Pro Gly Ala Gly Glu Pro Gln Ser Ile Asp Gln Ala Met
465                 470                 475                 480

Met Gly Thr Tyr Ala Ile Trp Asp Leu Gly Leu Gln Ser Thr Phe Asn
            485                 490                 495

Phe Val Val Pro Phe Ile Ser Ala Ser Asp Phe Arg Phe Asn Thr Ser
            500                 505                 510

Ser Val Ser Asn Ala Leu Asn Ser Asp Gly Trp Ile Thr Val Trp Leu
        515                 520                 525

Met Asn Pro Leu Thr Tyr Pro Pro Ser Thr Pro Thr Gln Gln Ile
530                 535                 540

Leu Met Leu Met Ser Ala Gly Ser Asp Phe Ser Tyr Arg Leu Pro Ile
545                 550                 555                 560

Ser Pro Gly Phe Ala Glu Gly Glu Thr Ser Glu His Pro Met Asp Asn
            565                 570                 575

Ala Glu Cys Gly Lys Ile Asp Asp Lys Asp Ala Gly Met Phe Ser Gly
            580                 585                 590

His Ser Val Gly Leu Pro Thr Pro His Thr Ser Thr Ser Phe Phe Tyr
            595                 600                 605

Asp Arg Tyr Arg Phe Val Gly Ile Val Lys Ser Val Asn Asn Thr
    610                 615                 620

Pro Lys Pro Val Asn Ile Tyr Asp Asp Thr Gly Lys Val Lys Asn Leu
625                 630                 635                 640

Gln Gln Val Phe Pro Thr Ser Asp Thr Leu Pro His Ser Leu Met
            645                 650                 655

Ser Leu Ser Pro Cys Ala Ser Val Cys Gly Gln Pro Ile Ser Ser Phe
            660                 665                 670

Leu Phe Ala Gln Arg Ala Asn Pro Lys Lys Thr Leu Lys Leu Arg Ser
        675                 680                 685

Gly Asp Glu Phe Leu Tyr Arg Cys Cys Pro Phe Ser Tyr Ile Lys Cys
    690                 695                 700

Asp Leu Glu Phe Thr Val Val Pro Pro Ala Asn Ser Thr Arg Asp Tyr
705                 710                 715                 720

Ile Val His Trp Tyr Pro Pro Gly Ala Thr Leu Asp Ala Gly Glu Val
            725                 730                 735

Ala Val Gly Asn Thr Ser Gly Ser Asn Gly Phe Asp Asp Asn Gly Met
            740                 745                 750

Asn Ala Gly Ser Ser Leu Phe Ser Tyr Asn Pro Thr Phe His Ala Arg
            755                 760                 765

Ala Pro Ser Lys Val Ser Ala Val Ile Pro Phe Cys Leu Pro Val Ser
        770                 775                 780

Leu Leu Pro Leu Tyr Phe Asp Gly Phe Pro Asp Tyr Ser Thr Thr Lys
785                 790                 795                 800
```

-continued

```
Gly Met Tyr Gly Cys Ser Pro Ser Phe Ser Phe Gly Thr Ile Tyr Ile
                805                 810                 815
Glu Ser Gly Leu Gln Glu Thr Tyr Ser Val Tyr Ile Arg Tyr Lys Asp
            820                 825                 830
Phe Lys Gly Tyr Ala Pro Arg Pro Leu Ile Arg Thr Pro His Ile Arg
        835                 840                 845
Leu Ser Glu Arg Ala Arg Tyr Ile Met Ala Asp Ser Val Leu Pro Arg
    850                 855                 860
Pro Leu Thr Arg Ala Glu Arg Asp Val Ala Arg Asp Leu Leu Leu Ile
865                 870                 875                 880
Ala Gly Asp Ile Glu Ser Asn Pro Gly Pro Ala Phe Asn Pro Glu Tyr
                885                 890                 895
Thr Ala His Gly Pro Val Thr Glu Leu Ile Gln Leu Ala Arg Lys Pro
            900                 905                 910
Glu Thr Val Asp Asn Val Asn Arg Leu Leu Thr Thr Leu Asn Thr Leu
        915                 920                 925
Met Ala Lys Trp Asn Asn Leu Lys Asp Thr Val Thr Asp Ala Val Phe
    930                 935                 940
Leu Arg Asp Met Val Cys Leu Leu Val Lys Leu Thr Ser Leu Met Tyr
945                 950                 955                 960
Leu Val His Gly Gln Gly Pro Gly Ala Tyr Phe Ala Ala Ala Ser Ile
                965                 970                 975
Leu Leu Ala Asp Gly Ile Thr Phe Phe Asp Trp Tyr Glu Lys Ile Lys
            980                 985                 990
Ile Phe Met Ala Arg Lys Leu Arg  Val Ser Pro Pro Phe  Phe Pro Ala
        995                 1000                1005
Ala Gln  Gly Pro Asp Leu Arg  Asp Phe Val Thr Phe  Phe Asn Ala
    1010                1015                1020
Ala Arg  Gly Ala Gln Trp Met  Ile Asp Ser Leu Lys  Ser Leu Ile
    1025                1030                1035
Thr Cys  Ile Lys Gln Trp Leu  Glu Leu Glu Glu Glu  Asn Glu Ala
    1040                1045                1050
Val Gln  Leu Glu Lys Met Leu  Ile Asp Ser Pro Arg  His Cys Lys
    1055                1060                1065
Ala Ile  Asn Asp Tyr Asn Arg  Gly Asp Ser Phe Gln  Arg Pro Thr
    1070                1075                1080
Asn Ser  Phe Glu Phe Met Asp  Arg Leu Val Glu Cys  Ala Thr Lys
    1085                1090                1095
Leu Gly  Lys Val Gln Ile Ala  Thr Tyr Phe Arg Asn  Phe Thr Thr
    1100                1105                1110
Ala Asp  Ser Asp Thr Ser Arg  Pro Glu Pro Val Val  Val Val Leu
    1115                1120                1125
Arg Gly  Lys Pro Gly Val Gly  Lys Ser Ala Ala Ala  Thr Val Met
    1130                1135                1140
Ala Ala  Ala Val Ser Lys Leu  Leu Val Gly Ser Gln  Ser Val Tyr
    1145                1150                1155
Thr Leu  Ser Pro Asp Thr Glu  His Met Asp Gly Tyr  His Gly Gln
    1160                1165                1170
Phe Val  Thr Leu Met Asp Asp  Leu Gly Gln Asn Pro  Asp Gly Glu
    1175                1180                1185
Asp Phe  Arg Cys Phe Cys Gln  Met Val Ser Cys Ala  Gln Tyr Arg
    1190                1195                1200
Pro Ala  Met Ala Asp Leu Lys  Asp Lys Gly Ile Leu  Phe Thr Ser
```

-continued

```
            1205                1210               1215
Arg  Leu  Leu  Ile  Ala  Thr  Thr  Asn  Leu  Pro  Asp  Phe  Asn  Pro  Val
            1220                1225               1230

Thr  Ile  Ser  Asp  Pro  Arg  Ala  Leu  Asp  Arg  Arg  Ile  Thr  Phe  Asp
            1235                1240               1245

Ile  Leu  Val  Thr  Pro  Gly  Ser  Ala  Ala  Thr  Lys  Asn  Gly  Lys  Leu
            1250                1255               1260

Asp  Leu  Ala  Ala  Ala  Leu  Lys  Pro  Asp  Gly  Pro  Gly  Glu  His  Pro
            1265                1270               1275

Tyr  Thr  Ser  Asp  Cys  Pro  Ile  Leu  His  Thr  Thr  Gly  Leu  Leu  Leu
            1280                1285               1290

Lys  Asn  Leu  Arg  Asn  Asn  Gln  Thr  Met  Asn  Leu  Lys  Asp  Leu  Val
            1295                1300               1305

Asp  Met  Ile  Val  Lys  Arg  Ile  Lys  His  Lys  Lys  Glu  Val  Gly  Asn
            1310                1315               1320

Met  Leu  Asp  Ser  Leu  Val  Ala  Gln  Gly  Pro  Thr  Met  Ile  Val  Gly
            1325                1330               1335

Tyr  Thr  Lys  Asp  Asp  Asp  Gly  Ile  Ala  Ile  Val  Asp  Cys  Leu  Glu
            1340                1345               1350

Glu  Trp  Asn  Lys  Ile  Lys  Asp  Lys  Lys  Lys  Gln  Leu  Ala  Leu
            1355                1360               1365

Glu  Met  Val  Ala  Gln  Glu  Leu  Lys  Asp  Lys  His  Glu  Glu  His  Lys
            1370                1375               1380

Gly  Thr  Ile  Lys  Leu  Leu  Lys  Met  Phe  Val  Thr  Gly  Leu  Gly  Val
            1385                1390               1395

Val  Ala  Ala  Val  Ala  Gly  Ala  Tyr  Ala  Thr  Met  Lys  Tyr  Phe  Thr
            1400                1405               1410

Lys  Asp  Lys  Pro  Lys  Glu  Glu  Glu  Glu  Pro  Glu  Glu  Lys  Lys
            1415                1420               1425

Glu  Lys  Lys  Thr  Glu  Glu  Ser  Lys  Glu  Ala  Ala  Gly  Pro  Tyr  Asn
            1430                1435               1440

Gly  Pro  Thr  Lys  Lys  Glu  Ile  Lys  Thr  Leu  Lys  Leu  Lys  Ala  Gln
            1445                1450               1455

Ser  Pro  Leu  Met  Asp  Met  Glu  Lys  Lys  Ile  Ala  Gln  Asn  Val  Met
            1460                1465               1470

Pro  Phe  Gln  Ile  Phe  Tyr  Asn  Gly  Lys  Arg  Tyr  Thr  Gln  Ser  Cys
            1475                1480               1485

Leu  Ala  Ile  Gly  Lys  Arg  Val  Ile  Leu  Val  Asn  Lys  His  Ala  Phe
            1490                1495               1500

Glu  Ser  Val  Glu  His  Lys  Phe  Val  Val  Asp  Gln  Lys  Glu  Tyr  Thr
            1505                1510               1515

Leu  Asp  Gln  Val  Thr  Ala  Ile  Ser  Leu  Asp  Cys  Gly  Ser  Gly  Val
            1520                1525               1530

Thr  Asp  Val  Cys  Ala  Val  Cys  Leu  Pro  Pro  Gly  Pro  Asp  Phe  Lys
            1535                1540               1545

Ser  Ile  Lys  Lys  His  Phe  Leu  Pro  Phe  Asn  Thr  Thr  Met  Phe  Pro
            1550                1555               1560

Gly  Thr  Arg  Leu  Thr  Ile  Leu  Ser  Asn  Asp  His  Tyr  Pro  Met  Ser
            1565                1570               1575

Arg  Glu  Gly  Ser  Phe  Leu  Arg  Phe  Glu  Asp  Glu  Val  Pro  Thr  Asn
            1580                1585               1590

Val  Gly  Asn  Met  Pro  Phe  Val  Met  Leu  Tyr  Lys  Ser  Thr  Ser  Tyr
            1595                1600               1605
```

Phe Gly Met Cys Gly Ser Val Val Cys Ser Arg Phe Val Asp Gly
    1610                1615                1620

Gly Gly Ile Ile Gly Met His Cys Ala Gly Gly Gly Val Ser
    1625                1630                1635

Val Gly Thr Arg Leu Thr Ala Arg Met Ile Glu Ser Val Phe Asp
    1640                1645                1650

Tyr Phe Tyr Pro Pro Val Ala Gln Gly Ile Ile Glu Asn Thr Glu
    1655                1660                1665

Thr Gly Pro Arg Val His Val Pro Arg Thr Ser Lys Leu Lys Arg
    1670                1675                1680

Thr Asn Ala Thr Tyr Pro Ala Thr Glu Lys Tyr Gly Pro Ala Ala
    1685                1690                1695

Leu Ser Arg Tyr Asp Pro Arg Leu Asn Glu Gly Val Asn Leu Asp
    1700                1705                1710

Glu Val Ile Phe Ser Lys His Thr Gln Asn Thr Leu Val Glu Lys
    1715                1720                1725

Gly Ser Thr Phe Arg Ser Ala Leu Asp Met Ala Ala Glu Ile Tyr
    1730                1735                1740

Gly Glu Lys Phe Arg Gly Asn Asp Phe Ser Pro Leu Ser Val Glu
    1745                1750                1755

Asp Ala Ile Leu Gly Ile Pro Gly Leu Asp Arg Leu Asp Pro Asn
    1760                1765                1770

Thr Ala Ser Gly Leu Pro Tyr Thr Lys Thr Arg Arg Gln Met Ile
    1775                1780                1785

Asp Phe Asn Thr Gly Gln Ile Leu Asp Asp Thr Leu Lys Cys Arg
    1790                1795                1800

Leu Gly Gln Trp Leu Ala Gly Arg Pro Pro Gln Glu Val His Tyr
    1805                1810                1815

Gln Thr Phe Leu Lys Asp Glu Ile Arg Pro Ile Glu Lys Val Lys
    1820                1825                1830

Ala Gly Lys Thr Arg Ile Ile Asp Val Pro Pro Leu Asp His Val
    1835                1840                1845

Ile Ala Phe Arg Met Leu Phe Gly Arg Phe Ile Ala His Tyr His
    1850                1855                1860

Leu Asn Phe Gly Phe Lys Thr Gly Ser Ala Ile Gly Cys Asp Pro
    1865                1870                1875

Asp Val Ala Trp Ala Ser Phe Gly Phe Glu Leu Ser Gly Phe Pro
    1880                1885                1890

Tyr Leu Tyr Asp Phe Asp Tyr Ser Asn Phe Asp Ala Ser His Ser
    1895                1900                1905

Thr Ser Ile Phe Glu Ile Leu Glu Gln Lys Phe Phe Ser Pro Glu
    1910                1915                1920

Leu Gly Phe Asp Pro Arg Cys Ser Leu Leu Lys Ser Leu Ala
    1925                1930                1935

Val Ser Thr His Cys Tyr Glu Asn Lys Arg Leu Gln Ile Ala Gly
    1940                1945                1950

Gly Leu Pro Ser Gly Thr Ala Gly Thr Ser Val
    1955                1960

<210> SEQ ID NO 84
<211> LENGTH: 470
<212> TYPE: PRT
<213> ORGANISM: Cosavirus

-continued

```
<400> SEQUENCE: 84

Met Gly Ala Asn Asn Ser Lys Glu Ser Val Ser Ser Asn Gly Asn Glu
1               5                   10                  15

Gly Thr Ile Val Asn Asn Phe Tyr Ser Asn Gln Tyr Tyr Ala Ser Ile
            20                  25                  30

Asp Ala Ser Ala Gln Gly Val Gly Thr Ser Thr Thr Pro Glu Asn Gly
        35                  40                  45

Asn Val Ser Gly Phe Leu Gly Leu Ala Gly Ser Ala Phe Asn Ala Leu
    50                  55                  60

Ser Leu Leu Ala Ser Pro Arg Thr Glu Thr Gly Met Met Met Glu Asp
65                  70                  75                  80

Arg Val Leu Ser Arg Thr Ala Gly Asn Thr Ser Val Asn Ser Gln Ala
                85                  90                  95

Ala Glu Gly Val Leu Gln Ala Tyr Gly Thr Glu Thr Asp Ser Asn Ser
            100                 105                 110

Pro Thr Ser Cys Gly Asp Asp Pro Ser Lys Gly Thr His Ala Thr Asp
        115                 120                 125

Arg Ala Phe Val Ile Gln Leu Leu Pro Trp Lys Gln Thr Thr Asn Ser
130                 135                 140

Tyr Phe Ala Gln Trp Val Arg Leu Thr Gln Lys Leu Ser Asn Asn Leu
145                 150                 155                 160

His Gly Asn Val Met Ala Lys Asn Ile Lys Ser His Ala Phe Ala Lys
                165                 170                 175

Met Gly Phe Glu Val Met Leu Gln Ala Asn Thr Ser Pro Phe His Asn
            180                 185                 190

Gly Ile Leu Gly Leu Phe Leu Val Pro Glu Phe Val Arg Lys Gly Glu
        195                 200                 205

Ile Thr Asp Glu Trp Ile Asp Leu Thr Pro Thr Ser Ser Leu Val Ser
    210                 215                 220

Asn Thr Glu Leu Tyr Asn Pro Gln Thr Tyr Ala Asn Phe Pro Phe Asp
225                 230                 235                 240

Ala Lys His Ser Phe Asp Tyr Ser Asp Ile Thr Pro Glu Gln Phe Met
                245                 250                 255

Ile Phe Pro His Gln Leu Ile Asn Pro Lys Asp Thr Asn Val Ala Thr
            260                 265                 270

Val Arg Val Pro Tyr Ile Asn Ile Ala Pro Thr Asn Asp Thr Thr Val
        275                 280                 285

His Thr Val Trp Thr Ala Val Val Met Val Leu Val Pro Leu Asn Phe
    290                 295                 300

Ser Ser Gly Ala Ser Pro Thr Val Ser Leu Thr Leu Thr Ile Thr Pro
305                 310                 315                 320

Ile Asn Ser Val Phe Asn Gly Leu His His Thr Ala Gln Gly Pro Ile
                325                 330                 335

Pro Val Arg Pro Phe His Asn Phe Gln Gln Phe Ser Thr Thr Val Pro
            340                 345                 350

Leu Arg Thr Glu Pro Cys Tyr Gly Met Thr Val Thr Pro Pro Val Asp
        355                 360                 365

Tyr Met Pro Leu Pro Ile Thr Asp Leu Val Glu Leu Ala Lys Val Pro
    370                 375                 380

Ser Phe Val Thr Val Ala Asn Ser Asp Thr Thr Ser Glu Arg Ser Phe
385                 390                 395                 400

Pro Tyr Phe Ser Val Ser Asn Thr Glu Gln Gly Arg Asn Leu Phe Lys
                405                 410                 415
```

Ser Ser Val Val Leu Ser Asp Leu His Tyr Gln His Thr Leu Val Ala
            420                 425                 430

Asn Leu Ala Arg Tyr Phe Cys Asn Tyr Arg Gly Ser Leu Gln Phe Asp
        435                 440                 445

Phe Ile Ala Ala Thr Thr Ala Met Thr Arg Gly Lys Leu Leu Ile Ser
450                 455                 460

Tyr Thr Pro Pro Gly Ala
465                 470

<210> SEQ ID NO 85
<211> LENGTH: 778
<212> TYPE: PRT
<213> ORGANISM: Cosavirus

<400> SEQUENCE: 85

Gln Tyr Arg Pro Ala Met Ala Asp Leu Lys Asp Lys Gly Ile Leu Phe
1               5                   10                  15

Thr Ser Arg Leu Leu Ile Ala Thr Thr Asn Leu Pro Asp Phe Asn Pro
            20                  25                  30

Val Thr Ile Ser Asp Pro Arg Ala Leu Asp Arg Arg Ile Thr Phe Asp
        35                  40                  45

Ile Leu Val Thr Pro Gly Ser Ala Ala Thr Lys Asn Gly Lys Leu Asp
50                  55                  60

Leu Ala Ala Ala Leu Lys Pro Asp Gly Pro Gly Glu His Pro Tyr Thr
65                  70                  75                  80

Ser Asp Cys Pro Ile Leu His Thr Thr Gly Leu Leu Leu Lys Asn Leu
            85                  90                  95

Arg Asn Asn Gln Thr Met Asn Leu Lys Asp Leu Val Asp Met Ile Val
            100                 105                 110

Lys Arg Ile Lys His Lys Lys Glu Val Gly Asn Met Leu Asp Ser Leu
        115                 120                 125

Val Ala Gln Gly Pro Thr Met Ile Val Gly Tyr Thr Lys Asp Asp Asp
    130                 135                 140

Gly Ile Ala Ile Val Asp Cys Leu Glu Glu Trp Asn Lys Ile Lys Asp
145                 150                 155                 160

Lys Lys Lys Lys Gln Leu Ala Leu Glu Met Val Ala Gln Glu Leu Lys
                165                 170                 175

Asp Lys His Glu Glu His Lys Gly Thr Ile Lys Leu Leu Lys Met Phe
            180                 185                 190

Val Thr Gly Leu Gly Val Val Ala Ala Val Ala Gly Ala Tyr Ala Thr
        195                 200                 205

Met Lys Tyr Phe Thr Lys Asp Lys Pro Lys Glu Glu Glu Glu Glu Pro
    210                 215                 220

Glu Glu Lys Lys Glu Lys Lys Thr Glu Glu Ser Lys Glu Ala Ala Gly
225                 230                 235                 240

Pro Tyr Asn Gly Pro Thr Lys Lys Glu Ile Lys Thr Leu Lys Leu Lys
                245                 250                 255

Ala Gln Ser Pro Leu Met Asp Met Glu Lys Lys Ile Ala Gln Asn Val
            260                 265                 270

Met Pro Phe Gln Ile Phe Tyr Asn Gly Lys Arg Tyr Thr Gln Ser Cys
        275                 280                 285

Leu Ala Ile Gly Lys Arg Val Ile Leu Val Asn Lys His Ala Phe Glu
    290                 295                 300

Ser Val Glu His Lys Phe Val Val Asp Gln Lys Glu Tyr Thr Leu Asp

```
305             310             315             320
Gln Val Thr Ala Ile Ser Leu Asp Cys Gly Ser Gly Val Thr Asp Val
                325             330             335
Cys Ala Val Cys Leu Pro Pro Gly Pro Asp Phe Lys Ser Ile Lys Lys
                340             345             350
His Phe Leu Pro Phe Asn Thr Thr Met Phe Pro Gly Thr Arg Leu Thr
                355             360             365
Ile Leu Ser Asn Asp His Tyr Pro Met Ser Arg Glu Gly Ser Phe Leu
        370             375             380
Arg Phe Glu Asp Glu Val Pro Thr Asn Val Gly Asn Met Pro Phe Val
385             390             395             400
Met Leu Tyr Lys Ser Thr Ser Tyr Phe Gly Met Cys Gly Ser Val Val
                405             410             415
Cys Ser Arg Phe Val Asp Gly Gly Ile Ile Gly Met His Cys Ala
                420             425             430
Gly Gly Gly Gly Val Ser Val Gly Thr Arg Leu Thr Ala Arg Met Ile
            435             440             445
Glu Ser Val Phe Asp Tyr Phe Tyr Pro Pro Val Ala Gln Gly Ile Ile
        450             455             460
Glu Asn Thr Glu Thr Gly Pro Arg Val His Val Pro Arg Thr Ser Lys
465             470             475             480
Leu Lys Arg Thr Asn Ala Thr Tyr Pro Ala Thr Glu Lys Tyr Gly Pro
            485             490             495
Ala Ala Leu Ser Arg Tyr Asp Pro Arg Leu Asn Glu Gly Val Asn Leu
            500             505             510
Asp Glu Val Ile Phe Ser Lys His Thr Gln Asn Thr Leu Val Glu Lys
            515             520             525
Gly Ser Thr Phe Arg Ser Ala Leu Asp Met Ala Ala Glu Ile Tyr Gly
            530             535             540
Glu Lys Phe Arg Gly Asn Asp Phe Ser Pro Leu Ser Val Glu Asp Ala
545             550             555             560
Ile Leu Gly Ile Pro Gly Leu Asp Arg Leu Asp Pro Asn Thr Ala Ser
                565             570             575
Gly Leu Pro Tyr Thr Lys Thr Arg Arg Gln Met Ile Asp Phe Asn Thr
            580             585             590
Gly Gln Ile Leu Asp Asp Thr Leu Lys Cys Arg Leu Gly Gln Trp Leu
        595             600             605
Ala Gly Arg Pro Pro Gln Glu Val His Tyr Gln Thr Phe Leu Lys Asp
        610             615             620
Glu Ile Arg Pro Ile Glu Lys Val Lys Ala Gly Lys Thr Arg Ile Ile
625             630             635             640
Asp Val Pro Pro Leu Asp His Val Ile Ala Phe Arg Met Leu Phe Gly
                645             650             655
Arg Phe Ile Ala His Tyr His Leu Asn Phe Gly Phe Lys Thr Gly Ser
                660             665             670
Ala Ile Gly Cys Asp Pro Asp Val Ala Trp Ala Ser Phe Gly Phe Glu
            675             680             685
Leu Ser Gly Phe Pro Tyr Leu Tyr Asp Phe Asp Tyr Ser Asn Phe Asp
        690             695             700
Ala Ser His Ser Thr Ser Ile Phe Glu Ile Leu Glu Gln Lys Phe Phe
705             710             715             720
Ser Pro Glu Leu Gly Phe Asp Pro Arg Cys Ser Leu Leu Leu Lys Ser
            725             730             735
```

-continued

```
Leu Ala Val Ser Thr His Cys Tyr Glu Asn Lys Arg Leu Gln Ile Ala
                740                 745                 750

Gly Gly Leu Pro Ser Gly Thr Ala Gly Thr Ser Val Leu Asn Thr Val
            755                 760                 765

Ile Asn Asn Ile Ile Phe His Gly Ala Leu
        770                 775

<210> SEQ ID NO 86
<211> LENGTH: 754
<212> TYPE: PRT
<213> ORGANISM: Cosavirus

<400> SEQUENCE: 86

Gln Tyr Arg Pro Ala Met Ala Ser Leu Glu Asp Lys Gly Ile Leu Phe
1               5                   10                  15

Ser Ser Arg Leu Ile Ile Ala Thr Thr Asn Leu Val Asp Phe Asn Pro
            20                  25                  30

Val Thr Ile Ser Asp Pro Arg Ala Leu Asp Arg Arg Ile Thr Phe Asp
        35                  40                  45

Leu Cys Val Thr Pro Gly Ser Ala Ala Thr Thr Ser Lys Gly Lys Leu
    50                  55                  60

Asp Leu Lys Lys Ala Leu Gln Pro Asp Gly Pro Gly Phe Gly Pro Tyr
65                  70                  75                  80

Thr Thr Asp Cys Ser Leu Leu His Thr Thr Gly Leu Asn Leu Lys Asn
                85                  90                  95

Leu Arg Asn Asn Arg Val Tyr Ser Ile Val Asp Leu Val Glu Glu Val
            100                 105                 110

Val Ala Asn Met Asn Lys Lys Ala Val Asn Val Met Leu Glu Gly
        115                 120                 125

Leu Val Ala Gln Thr Gly Lys Val Val Gly Tyr Thr Lys Asp Asp Asp
    130                 135                 140

Gly Val Val Ile Val Asp Ser Met Asp Glu Trp His Lys Ile Leu Asp
145                 150                 155                 160

Lys Lys Arg Lys Gln Glu Val Leu Glu Val Ile Ala Gln Glu Ile Gln
                165                 170                 175

Val Arg His Asp Glu His Lys Glu Phe Thr Gln Ile Val Thr Lys Phe
            180                 185                 190

Leu Thr Ala Leu Gly Val Ile Val Ala Val Gly Ala Ala Leu Ile Gly
        195                 200                 205

Tyr Lys Tyr Leu Thr Ser Gly Pro Asp Lys Glu Lys Glu Ser Thr Glu
    210                 215                 220

Glu Pro Glu Lys Gln Glu Glu Lys Glu Gln Lys Lys Ala Glu Gly
225                 230                 235                 240

Pro Tyr Glu Gly Pro Ser Lys Lys Glu Leu Lys Thr Leu Lys Leu Arg
                245                 250                 255

Ile Gln Cys Pro Val Lys Asp Cys Glu Lys Lys Leu Leu Asn Ala Ile
            260                 265                 270

His Pro Phe Val Ile His Tyr Asp Lys Arg Lys Tyr Thr Gln Ser Cys
        275                 280                 285

Ile Ala Leu Gly Lys Arg Leu Ile Met Val Asn Lys His Ala Met Glu
    290                 295                 300

Thr Leu Asp Arg Tyr Val Thr Ile Ala Gly Lys Met Tyr Glu Ile Asp
305                 310                 315                 320

Asp Leu Asp Trp Val Asn Leu Glu Thr Ser His Gly Glu Thr Asp Val
```

```
                 325                 330                 335
Ser Ile Val Lys Leu Pro Pro Gly Pro Glu Phe Lys Asn Ile Val Arg
            340                 345                 350

Asn Phe Cys Ser Gln Asp Ile Thr Leu Met Pro Gly Thr Arg Met Met
            355                 360                 365

Ile Leu Ser Asn Asp Asp Phe Ser Met Val Arg Glu Gly Ser Phe Leu
            370                 375                 380

Arg Phe Glu Asp Ser Val Pro Thr Asn Ile Gly Pro Ile Pro Phe Thr
385                 390                 395                 400

Leu Leu Tyr Lys Ser Ser Ser Tyr Phe Gly Met Cys Gly Ser Ala Val
                405                 410                 415

Val Cys Arg Thr Ser Gly Glu Thr Gly Ile Val Gly Met His Cys Ala
            420                 425                 430

Gly Gly Gly Gly Val Ser Val Ala Cys Arg Val Thr Arg Lys Met Val
                435                 440                 445

Glu Ala Ala Val Met Tyr Phe Leu Ile Leu Leu Ile Val Gln Gly Met
            450                 455                 460

Ile Val Ser Thr Glu Thr Cys Asp Pro Ile His Val Pro Arg Lys Thr
465                 470                 475                 480

Lys Tyr Lys Arg Thr Asn Ala Asp Tyr Pro Ser Thr Lys Asn Tyr Ala
                485                 490                 495

Pro Ala Val Leu Ser Arg Asn Asp Pro Arg Leu Asp Pro Asp Val Asp
            500                 505                 510

Phe Asp Thr Val Leu Phe Ser Lys His Thr Glu Asn Val Ile Ile Pro
            515                 520                 525

Pro Asp Thr Leu Ala Tyr Asp Ser Leu Leu Lys Ala Thr Gln Val Tyr
            530                 535                 540

Ala Cys Lys Phe Asn Gly Asn Phe Glu Pro Leu Thr Val Glu Glu Ala
545                 550                 555                 560

Ile Leu Gly Ile Pro Gly Leu Asp Arg Met Asp Pro Asn Thr Ser Ser
                565                 570                 575

Gly Leu Pro Tyr Thr Lys Thr Arg Arg Gln Leu Ile Asp Phe Val Asn
            580                 585                 590

Gly Lys Ile Leu Asp Thr Gln Leu Gln Glu Arg Leu Asp Met Trp Leu
            595                 600                 605

Ser Gly Lys Gln Pro Glu Thr Tyr Tyr Gln Thr Phe Leu Lys Asp Glu
            610                 615                 620

Ile Arg His Ile Asp Lys Val Arg Arg Gly Lys Thr Arg Ile Ile Asp
625                 630                 635                 640

Val Thr Pro Leu Asp His Val Leu Ala Phe Arg Ile Leu Phe Gly Arg
                645                 650                 655

Phe Met Ala His Tyr His Leu Asn Pro Gly Phe Asp Leu Gly Ser Ala
            660                 665                 670

Ile Gly Cys Asp Pro Glu Val Ala Trp Asn Gln Phe Gly Tyr His Leu
            675                 680                 685

Thr Lys Tyr Lys Asn Leu Tyr Asp Phe Asp Tyr Ser Asn Phe Asp Ser
            690                 695                 700

Ser His Ser Lys Ser Ile Phe Glu Ile Leu Lys Asp His Phe Phe Thr
705                 710                 715                 720

Thr Thr Asn Gly Phe Asp Ser Arg Cys Ala Leu Leu Leu Asp Ser Leu
                725                 730                 735

Ala Val Ser Lys His Lys Tyr Asp Asn Lys Val Met Thr Ile Val Gly
            740                 745                 750
```

Gly Leu

<210> SEQ ID NO 87
<211> LENGTH: 454
<212> TYPE: PRT
<213> ORGANISM: Cosavirus
<220> FEATURE:
<221> NAME/KEY: misc_feature
<222> LOCATION: (230)..(230)
<223> OTHER INFORMATION: Xaa can be any naturally occurring amino acid

<400> SEQUENCE: 87

Met Gly Ala Asn Asn Ser Lys Glu Ser Val Ser Ser Asn Gly Asn Gln
1               5                   10                  15

Gly Thr Ile Val Asn Asn Phe Tyr Ala Asn Ser Tyr Tyr Ala Ser Ile
            20                  25                  30

Asp Ala Ser Ala Ser Ser Val Gly Gly Asp Thr Pro Ala Glu Asn Gly
        35                  40                  45

Thr Val Thr Gly Leu Leu Gly Asn Ile Ala Ser Ala Phe Thr Ser Ala
    50                  55                  60

Ala Leu Leu Ala Lys Pro Thr Val Glu Asn Glu Thr Gly Met Glu Asp
65                  70                  75                  80

Arg Val Ile Ser Leu Lys Ala Gly Asn Thr Leu Val Asn Ser Gln Ala
                85                  90                  95

Ser Glu Gly Leu Leu Tyr Gly Tyr Gly Lys Glu Ser Asp Lys Asn Pro
            100                 105                 110

Pro Thr Ser Cys Gly Asp Asp Pro Ser Glu Thr Gln His Cys Ile Gln
        115                 120                 125

Arg Gly Phe Thr Ile Pro Leu Thr Asp Trp Thr Arg Thr Gln Asp Pro
    130                 135                 140

Trp Gln Ala Leu Val Tyr Lys Leu Ser Asp Gln Phe Lys Asn Glu Ser
145                 150                 155                 160

Lys Gly Asn Met Phe Ser Lys Gly Met Lys Thr His Ala Phe Thr Lys
                165                 170                 175

Thr Gly Tyr Arg Val Ser Leu Gln Val Asn Thr Ser Pro Phe His Ser
            180                 185                 190

Gly Leu Leu Gly Leu Phe Leu Val Pro Glu Cys Ser Ile Pro Ala Ser
        195                 200                 205

Thr Ser Leu Asp Trp Ile Asp Leu Lys Thr Asp Ala Pro Leu Leu Lys
    210                 215                 220

Ser Thr Asn Tyr Tyr Xaa Gly Leu Gly Leu Gln Gln Gln Ser Ser Ala
225                 230                 235                 240

Ala Gly Asn Lys Tyr Ala Asp Asn Cys Ile Ile Asp Ser Ser Ala Ile
                245                 250                 255

Thr Pro Gln Gln Leu Phe Ile Tyr Pro His Gln Leu Ile Asn Pro Lys
            260                 265                 270

Glu Thr Asn Ile Ala Ser Val Ala Val Pro Tyr Val Asn Cys Ala Pro
        275                 280                 285

Thr Ser Asp Pro Gln Ile His Asn Ile Trp Thr Ala Leu Val Val Ile
    290                 295                 300

Ile Ser Pro Leu Gln Phe Ala Asn Gly Ala Ser Pro Asn Val Thr Met
305                 310                 315                 320

Ser Leu Thr Val Thr Pro Leu Asn Thr Val Phe Asn Gly Leu Arg His
                325                 330                 335

Ala Leu Pro Ala Thr Gln Gly Pro Ile Pro Val Arg Cys Met Gln Asn

```
                340               345               350
Ser Tyr Gln Phe Ser Thr Thr Leu Pro Ala Thr Ala Glu Pro Cys Tyr
            355                 360                 365

Gly Cys Thr Val Asn Pro Pro Arg Asp Tyr Leu Pro Pro Ala Ile Glu
        370                 375                 380

Asp Leu Leu Ser Leu Ala Lys Val Pro Ser Phe Leu Leu Cys Ser Glu
385                 390                 395                 400

Asp Thr Ala Lys Gln Val Pro Tyr Val Lys Val Thr Asn Thr Gln Thr
                405                 410                 415

Gln His Asn Ser Ile Phe Ser Met Asn Val Val Leu Ser Asp Tyr Ala
            420                 425                 430

Leu Gln Arg Thr Met Val Ser Gln Leu Gly Thr Phe Phe Cys Asn Tyr
        435                 440                 445

Arg Gly Ser Ile Gln Ile
    450

<210> SEQ ID NO 88
<211> LENGTH: 1565
<212> TYPE: DNA
<213> ORGANISM: Cosavirus

<400> SEQUENCE: 88
ggacttacag tttaagctgt agacacatgt ggtaacccag cccctteeet gacgggagag      60 ggggcttttg ctcacctagc acaggatctg atcaggagac tecctcacag tgctttacac     120 tgttgtggga gtttaaaaat tgcccaaggc ctggcacaca acctagggg actaggtttt      180 cctttatttt tgaagttgtc aatatgggtg caaacaacag caaagagagt gtttctagca     240
atggcaatca gggtactatt gttaacaatt tttatgctaa ttcttactat gcttctattg     300
acgcttctgc ctcctcggtc gggggcgaca ctcctgctga aaacggtact gtcactggtc     360
ttctgggaaa tattgcttct gctttcactt ccgctgcact cttggccaaa ccaactgtag     420
aaaatgaaac cggtatggaa gatagggtaa tttctctcaa ggcaggcaat actttggtta     480
actcacaggc ttcagaaggg ctgttatatg gatatggcaa ggaaagtgat aaaaaccccc     540
caacatcatg cggtgatgat ccatctgaaa cacaacactg catacagaga ggttttacta     600 ttccttttgac tgattggacc agaacccaag atccatggca agctcttgta tacaaacttt     660
cagatcagtt taaaaatgaa agcaagggaa acatgttttc caagggaatg aaaacacatg     720
cttttaccaa aactggctac agggtatctc ttcaggttaa cacttctcct ttccactctg     780
gccttttagg cctatttctt gtcccagagt gtagtatacc tgcatctacg tcactggatt     840
ggattgactt gaagacagat gctcctcttt taaagagcac aaactattac argggtcttg     900
gactacagca acaatcttca gccgctggaa acaagtatgc agacaactgt atcatagact     960
cctcagcaat aactcctcag cagctcttta tatatcctca ccaacttata aaccccaaag    1020
aaactaacat tgcctcagtt gcagttcctt atgtgaactg tgctccaaca tctgatcctc    1080
agatccacaa catctggact gccttggtag tgataatttc accctccag tttgctaatg     1140 gtgcttctcc taatgtaacc atgtcactta cagtaacccc tcttaacact gttttcaatg    1200
gcttacgcca tgctctgcct gctacgcaag gccctatacc agttaggtgt atgcagaatt    1260
cttaccagtt ctcaaccaca cttcccgcaa ccgcagaacc gtgttacggt tgcacagtga    1320
acccgcccag agactacttg cctcctgcta tcgaggattt gctttctttg gctaaagttc    1380
cttcttttct gctttgtagc gaagacaccg ctaaacaggt gccatatgtg aaggttacaa    1440
```

| | | |
|---|---|---|
| acactcaaac acagcacaac tctatctttt caatgaatgt agttttgtca gattatgcac | 1500 |
| ttcagaggac catggtttca cagctgggaa catttttctg taattataga ggaagcattc | 1560 |
| agata | 1565 |